United States Patent
Gentry et al.

(10) Patent No.: US 11,155,643 B2
(45) Date of Patent: Oct. 26, 2021

(54) GLUCAN KINASES AND METHODS FOR PROCESSING STARCH USING THE SAME

(71) Applicant: University of Kentucky Research Foundation, Lexington, KY (US)

(72) Inventors: Matthew Gentry, Lexington, KY (US); Craig VanderKooi, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/940,727

(22) Filed: Mar. 29, 2018

(65) Prior Publication Data

US 2018/0291120 A1    Oct. 11, 2018

Related U.S. Application Data

(60) Provisional application No. 62/478,404, filed on Mar. 29, 2017.

(51) Int. Cl.
| | |
|---|---|
| *C12P 19/04* | (2006.01) |
| *C08B 30/12* | (2006.01) |
| *C12N 9/12* | (2006.01) |
| *C12N 15/82* | (2006.01) |

(52) U.S. Cl.
CPC ............ *C08B 30/12* (2013.01); *C12N 9/1294* (2013.01); *C12N 15/8245* (2013.01); *C12N 15/8257* (2013.01); *C12P 19/04* (2013.01); *C12N 2330/50* (2013.01); *C12Y 207/09004* (2013.01)

(58) Field of Classification Search
CPC .................................................... C12P 19/04
See application file for complete search history.

(56) References Cited

U.S. PATENT DOCUMENTS

| | | | |
|---|---|---|---|
| 8,076,534 B2 * | 12/2011 | Basu ................. | C12N 15/8245 435/320.1 |
| 9,222,114 B1 | 12/2015 | Gentry et al. | |
| 9,410,133 B1 | 8/2016 | Gentry et al. | |

OTHER PUBLICATIONS

Sayaslan A. Wet-milling of wheat flour: industrial processes and small-scale test methods. LWT—Food Science and Technology. 2004;37(5):499-515.
Seetharaman K, Bertoft E. Perspectives on the history of research on starch Part I: On the linkages in starch. Starch-Starke. 2012;64(9):677-82.
Seetharaman K, Bertoft E. Perspectives on the history of research on starch Part II: On the discovery of the constitution of diastase. Starch-Starke. 2012;64(10):765-9.
Singh J, Kaur L, McCarthy OJ. Factors influencing the physico-chemical, morphological, thermal and rheological properties of some chemically modified starches for food applications—A review. Food Hydrocolloids. 2007;21(1):1-22.
Vander Kooi CW, Taylor AO, Pace RM, Meekins DA, Guo HF, Kim Y, Gentry MS. Structural basis for the glucan phosphatase activity of Starch Excess4. Proc Natl Acad Sci U S A 2010;107(35):15379-84.
Volkov VV, Svergun DI. Uniqueness of ab initio shape determination in small-angle scattering. Journal of Applied Crystallography. 2003;36:860-4.
Vu WW, Beeson WT, Span EA, Farquhar ER, Marietta, MA. A family of starch-active polysaccharide monooxygenases. Proceedings of the National Academy of Sciences. 2014;111(38).
Walker JA, Takasuka TE, Deng K, Bianchetti CM, Udell HS, Prom BM, Fox BG. Multifunctional cellulase catalysis targeted by fusion to different carbohydrate-binding modules. Biotechnology for Biofuels, 2015; 8(1).
Weise SE, Aung K, Jarou ZJ, Mehrshahi P, Li Z, Hardy AC, Carr DJ, Sharkey TD. Engineering starch accumulation by manipulation of phosphate metabolism of starch. Plant biotechnology journal. 2012;10(5):545-54.
Worby CA, Gentry MS, Dixon JE. Laforin: A dual specificity phosphatase that dephosphorylates complex carbohydrates. J Biol Chem. 2006;281(41):30412-8.
Yu TS, Kofler H, Hausler RE, Hille D, Flugge UI, Zeeman SC, Smith AM, Kossmann J, Lloyd J, Ritte G, Steup M, Lue WL, Chen J, Weber A. The *Arabidopsis* sex1 mutant is defective in the R1 protein, a general regulator of starch degradation in plants, and not in the chloroplast hexose transporter. Plant Cell. 2001;13(8):1907-18.
Zeeman SC, Kossmann J, Smith Am. Starch: Its Metabolism, Evolution, and Biotechnological Modification in Plants. Annu Rev Plant Biol. 2010;61:209-34.
Baslam M, Baroja-Fernández E, Ricarte-Bermejo A, Sánchez-López ÁM, Aranjuelo I, Bahaji A, et al. Genetic and Isotope ratio mass spectrometric evidence for the occurrence of starch degradation and cycling in illuminated *Arabidopsis* leaves. PLOS ONE. 2017;12(2):e0171245.
Blennow A. Phosphorylation of the Starch Granule. In: Nakamura Y, editor. Starch: Metabolism and Structure. Tokyo: Springer Japan; 2015. p. 399-424.

(Continued)

*Primary Examiner* — Tekchand Saidha
(74) *Attorney, Agent, or Firm* — Stites & Harbison PLLC; Sean P. Ritchie

(57) ABSTRACT

Provided herein are a glucan kinase polypeptide, an isolated polynucleotide, and a method for processing starch. The glucan kinase polypeptide comprises an isolated polypeptide including a sequence selected from the group consisting of SEQ ID NO: 2, SEQ ID NO:22, fragments thereof, variants thereof, and combinations thereof. The isolated polynucleotide comprises a nucleotide sequence selected from the group consisting of SEQ ID NO: 1, SEQ ID NO: 21, a fragment thereof, a variant thereof, and a combination thereof. The method for processing starch comprises providing a glucan dikinase; exposing a starch to the glucan dikinase; and collecting the starch that has been exposed to the glucan dikinase.

13 Claims, 14 Drawing Sheets
Specification includes a Sequence Listing.

(56) References Cited

OTHER PUBLICATIONS

Botticella E, Sestili F, Sparla F, Moscatello S, Marri L, Cuesta-Seijo JA, et al. Combining mutations at genes encoding key enzymes involved in starch synthesis affects the amylose content, carbohydrate allocation and hardness in the wheat grain. Plant biotechnology journal. 2018.
Bowerman AF, Newberry M, Dielen A-S, Whan A, Larroque O, Pritchard J, et al. Suppression of glucan, water dikinase in the endosperm alters wheat grain properties, germination and coleoptile growth. Plant Biotechnology Journal. 2015;14(1):398-408.
Carpenter MA, Joyce NI, Genet RA, Cooper RD, Murray SR, Noble AD, et al. Starch phosphorylation in potato tubers is influenced by allelic variation in the genes encoding glucan water dikinase, starch branching enzymes I and II, and starch synthase III. Frontiers in Plant Science. 2015;6:143.
Chen Y, Sun X, Zhou X, Hebelstrup KH, Blennow A, Bao J. Highly phosphorylated functionalized rice starch produced by transgenic rice expressing the potato GWD1 gene. Scientific Reports. 2017;7:3339.
Emanuelle S, Brewer MK, Meekins DA, Gentry MS. Unique carbohydrate binding platforms employed by the glucan phosphatases. Cellular and molecular life sciences : CMLS. 2016;73(14):2765-78.
Gentry MS, Brewer MK, Vander Kooi CW. Structural biology of glucan phosphatases from humans to plants. Current opinion in structural biology. 2016;40:62-9.
Hejazi M, Mahlow S, Fettke J. The glucan phosphorylation mediated by α-glucan, water dikinase (GWD) is also essential in the light phase for a functional transitory starch turn-over. Plant signaling & behavior. 2014;9(7):e28892.
Hirose T, Aoki N, Harada Y, Okamura M, Hashida Y, Ohsugi R, et al. Disruption of a rice gene for α-glucan water dikinase, OsGWD1, leads to hyperaccumulation of starch in leaves but exhibits limited effects on growth. Frontiers in Plant Science. 2013;4:147.
Mahlow S, Hejazi M Fau—Kuhnert F, Kuhnert F Fau—Garz A, Garz A Fau—Brust H, Brust H Fau—Baumann O, Baumann O Fau—Fettke J, et al. Phosphorylation of transitory starch by alpha-glucan, water dikinase during starch turnover affects the surface properties and morphology of starch granules, New Phytologist (2014) 203: 495-507.
Mahlow S, Orzechowski S, Fettke J. Starch phosphorylation: insights and perspectives. Cellular and molecular life sciences. 2016;73(14):2753-64.
Malinova I, Mahto H, Brandt F, Al-Rawi S, Qasim H, Brust H, et al. Early STARVATION1 specifically affects the phosphorylation action of starch-related dikinases. The Plant Journal. 2018;95(1):126-37.
Meekins DA, Raththagala M, Husodo S, White CJ, Guo H-F, Kötting O, et al. Phosphoglucan-bound structure of starch phosphatase Starch Excess4 reveals the mechanism for C6 specificity. Proceedings of the National Academy of Sciences. 2014;111(20):7272.
Meekins DA, Vander Kooi CW, Gentry MS. Structural Mechanisms of Plant Glucan Phosphatases in Starch Metabolism. The FEBS journal. 2016;283(13):2427-47.
Orzechowski S, Grabowska A, Sitnicka D, Siminska J, Felus M, Dudkiewicz M, et al. Analysis of the expression, subcellular and tissue localisation of phosphoglucan, water dikinase (PWD/GWD3) in Solanum tuberosum L: a bioinformatics approach for the comparative analysis of two a-glucan, water dikinases (GWDs) from Solanum .uberosum L. Acta Physiologiae Plantarum. 2013;35(2):483-500.
Pfister B, Zeeman SC. Formation of starch in plant cells. Cellular and Molecular Life Sciences. 2016;73(14):2781-807.
Pirone C, Gurrieri L, Gaiba I, Adamiano A, Valle F, Trost P, et al. The analysis of the different functions of starch-phosphorylating enzymes during the development of Arabidopsis thaliana plants discloses an unexpected role for the cytosolic isoform GWD2. Physiologia Plantarum. 2017;160(4):447-57.

Shaik SS, Obata T, Hebelstrup KH, Schwahn K, Fernie AR, Mateiu RV, et al. Starch Granule Re-Structuring by Starch Branching Enzyme and Glucan Water Dikinase Modulation Affects Caryopsis Physiology and Metabolism. PLOS ONE. 2016;11(2):e0149613.
Skeffington AW, Graf A, Duxbury Z, Gruissem W, Smith AM. Glucan, Water Dikinase Exerts Little Control over Starch Degradation in Arabidopsis Leaves at Night. Plant Physiology. 2014;165(2):866-79.
Skryhan K, Gurrieri L, Sparla F, Trost PB, Blennow A. Redox regulation of starch metabolism. Frontiers in Plant Science. 2018;9:1344.
Xu X, Dees D, Dechesne A, Huang X-F, G.F. Visser R, Trindade L. Starch phosphorylation plays an important role in starch biosynthesis. Carbohydrate Polymers. 2017;157, 1628-1637. PubMed PMID: 27987877.
Zhou W, He S, Naconsie M, Ma Q, Zeeman SC, Gruissem W, et al. Alpha-Glucan, Water Dikinase 1 Affects Starch Metabolism and Storage Root Growth in Cassava (Manihot esculenta Crantz). Scientific Reports. 2017;7:9863.
Baunsgaard L, Lutken H, Mikkelsen R, Glaring MA, Pham TT, Blennow A. A novel isoform of glucan, water dikinase phosphorylates pre-phosphorylated alpha-glucans and is involved in starch degradation in Arabidopsis. Plant J. 2005;41(4):595-605.
Brewer MK, Husodo S, Dukhande VV, Johnson MB, Gentry MS. Expression, purification and characterization of soluble red rooster laforin as a fusion protein in Escherichia coli. BMX biochemistry. 2014;15:8.
Caspar T, Lin T-P, Kakefuda G, Benbow L, Preiss J, Somerville C. Mutants of Arabidopsis with Altered Regulation of Starch Degradation. Plant Physiol. 1991;95(4):1181-8.
Castanheira P, Moreira S, Gama M, Faro C. Escherichia coli expression, refolding and characterization of human laforin. Protein expression and purification. 2010;71(2):195-9.
Dukhande VV, Rogers DM, Roma-Mateo C, Donderis J, Marina A, Taylor AO, Sanz P, Gentry MS. Laforin, a dual specificity phosphatase involved in Lafora disease, is present mainly as monomeric form with full phosphatase activity. PLoS One. 2011;6(8):e24040.
Edner C, Li J, Albrecht T, Mahlow S, Hejazi M, Hussain H, Kaplan F, Guy C, Smith Sm, Steup M, Ritte G. Glucan, water dikinase activity stimulates breakdown of starch granules by plastidial beta-amylases. Plant Physiol. 2007;145 (1):17-28.
Gentry MS, Dowen RH, 3rd, Worby CA, Mattoo S, Ecker JR, Dixon JE. The phosphatase laforin crosses evolutionary boundaries and links carbohydrate metabolism to neuronal disease. J Cell Biol. 2007;178(3):477-88.
Gentry MS, Pace RM. Conservation of the glucan phosphatase laforin is linked to rates of molecular evolution and the glycogen metabolism of the organism. BMC Evol Biol. 2009;9(1):138.
Hejazi M, Fettke J, Haebel S, Edner C, Paris O, Frohberg C, Steup M, Ritte G. Glucan, water dikinase phosphorylates crystalline maltodextrins and thereby initiates solubilization. Plant J. 2008;55(2):323-34.
Hejazi M, Fettke J, Paris O, Steup M. The two plastidial starch-related dikinases sequentially phosphorylate glucosyl residues at the surface of both the A- and B-type allomorphs of crystallized maltodextrins but the mode of action differs. Plant physiology. 2009;150(2):962-76.
Imberty A, Chanzy H, Perez S, Buleon A, Tran V. The double-helical nature of the crystalline part of A-starch. J Mol Biol. 1988;201(2):365-78.
Kelly RM, Dijkhuizen L, Leemhuis H. Starch and α-glucan acting enzymes, modulating their properties by directed evolution. Journal of Biotechnology. 2009;140(3-4):184-93.
Kotting O, Pusch K, Tiessen A, Geigenberger P, Steup M, Ritte G. Identification of a novel enzyme required for starch metabolism in Arabidopsis leaves. The phosphoglucan, water dikinase. Plant Physiol. 2005;137(1):242-52.
Kotting O, Santelia D, Edner C, Eicke S, Marthaler T, Gentry MS, Comparot-Moss S, Chen J, Smith AM, Steup M, Ritte G, Zeeman SC. Starch-Excess4 Is a Laforin-Like Phosphoglucan Phosphatase Required for Starch Degradation in Arabidopsis thaliana. Plant Cell. 2009;21(1):334-46.

(56) References Cited

OTHER PUBLICATIONS

Kumar R, Singh S, Singh OV. Bioconversion of lignocellulosic biomass: biochemical and molecular perspectives. Journal of Industrial Microbiology & Biotechnology 2008;(35.5): 377-91.

Lorberth R, Rile G, Willmitzer L, Kossmann J. Inhibition of a starch-granule-bound protein leads to modified starch and repression of cold sweetening. Nat Biotechnol. 1998;16(5):473-7.

Malcata FX. Microalgae and biofuels: a promising partnership? Trends in biotechnology. 2011;29(11):542-9.

Meekins DA, Guo HF, Husodo S, Paasch BC, Bridges TM, Santelia D, Kotting O, Vander Kooi CW, Gentry MS. Structure of the *Arabidopsis* glucan phosphatase like sex four2 reveals a unique mechanism for starch Dephosphorylation. Plant Cell. 2013;25(6):2302-14.

Michalik, et al., Fibroblast-to-myofibroblast transition in bronchial asthma, Cellular and Molecular Life Sciences (2018) 15:3943-3961.

Mikkelsen R, Mutenda KE, Mant A, Schurmann P, Blennow A. Alpha-glucan, water dikinase (GWD): a plastidic enzyme with redox-regulated and coordinated catalytic activity and binding affinity. Proc Natl Acad Sci U S A. 2005;102(5):1785-90.

Moreira S, Castanheira P, Casal M, Faro C, Gama M. Expression of the functional carbohydrate-binding module (CBM) of human laforin. Protein expression and purification. 2010;74(2)169-74.

Rai JP, Bowerman AF, Li Z, Sirault X, Furbank R, Pritchard JR, Bloemsma M, Cavanagh CR, Howitt CA, Morell MK. Down-regulation of Glucan, Water-Dikinase activity in wheat endosperm increases vegetative biomass and yield. Plant biotechnology journal. 2012.

Ritte G, Lloyd JR, Eckermann N, Rottmann A, Kossmann J, Steup M. The starch-related R1 protein is an alpha-glucan, water dikinase. Proc Natl Acad Sci U S A. 2002;99(10):7166-71.

Ritte G, Steup M, Kossmann J, Lloyd JR. Determination of the starch-phosphorylating enzyme activity in plant extracts Planta. 2003;216(5):798-801.

Ritte G, Heydenreich M, Mahlow S, Haebel S, Kotting O, Steup M. Phosphorylation of C6- and C3-positions of glucosyl residues in starch is catalysed by distinct dikinases. FEBS Lett. 2006;580(20):4872-6.

Robyt JF, Choe J-y, Fox JD, Hahn RS, Fuchs EB. Acid modification of starch granules in alcohols: reactions in mixtures of two alcohols combined in different ratios. Carbohydrate Research. 1996;283(0):141-50.

Santelia D, Kotting O, Seung D, Schubert M, Thalmann M, Bischof S, Meekins DA, Lutz A, Patron N, Gentry MS, Allain FH, Zeeman SC. The phosphoglucan phosphatase like sex Four2 dephosphorylates starch at the C3-position in *Arabidopsis*. Plant Cell. 2011;23(11):4096-111.

\* cited by examiner

SEQUENCE LISTING

```
<160> NUMBER OF SEQ ID NOS: 58

<210> SEQ ID NO 1
<211> LENGTH: 4719
<212> TYPE: DNA
<213> ORGANISM: Cyanidioschyzon merolae

<400> SEQUENCE: 1
atgtcggatc aaccgtcggt ctcggtgaaa gtgccgctgt acgaaaaaat ctatcaactg      60
gatggcttta ttggcgatga agaacgcaat gctctgcaac tgccggaagg tgtggatgaa     120
gcgggcctgt ttgttacggt ctatgtgtca cgcgaatcga cctatccggg cgacgcaccg     180 gccgcggtg cgacgccgca tgaaaacacc ggcgatccgt cagtcgcccg tgaagacatt     240
gtggattggc gtaaagcacg catcgtttgc cgcttcctgc tggtcctgct gagccgtgaa     300
gaagtccgcc acctggatca gctgggcgct agcgtgccga aatctctgaa agaacgtatt     360
gcggaacgta accgctttga atggagccgt attctgcaaa atcgtccgac gtatctgcat     420
tggggcgtgg cccgcgacca cccggatgaa tggaccctgc cggaagcaaa aacgtttccg     480
ccgggcacca ttcgcttcga taaatcgct gtgcgtacgg aatttccggc ggaacatccg     540
cgtattcgca tcaacgttcc gttttttcgaa agcggtaatg aactgcgtac cattcgtggc     600
atcaaagctg tggtttatcg tgcgaaagat cacaaatact ttaaagacgg ccgtcgcgat     660
```

```
attttcgttc cggtctggga cagcgttcgc acctgggtca ttgatggcgc cggtatcgaa    720
gaaaatgtgg cagaactgag tctgacggaa tccgcatttc gcaccgctct gggtgttagt    780
cgttccgact catatatgtc gctgagccgt gaaacctctc cgggcccgga tgcttctggc    840
agtggtcgct ctgcggttcg tcgtagcatt agcctgagca gcgtgcgcaa actgaaaagt    900
tccgcaagtc tggaccgtct ggtgaaagca ggtgctccgc aggatcgctc cctgaaagca    960
gtgcgtcgca tccatacggc ggccaccgtt ctgtttgaag aactgttcgg cggtgtcggt   1020
cgcggcggtt caggtcacct ggacgtcgtg gttgaagaaa tggaaccgca gtcggaatat   1080
catattcaca tggccacgga tatttcaggt ctggcactgc attggggcgt gtcgcgtaaa   1140
aaaccgggtc aatgggttct gccgcgtcgc gactggtggc cggccggcgt gaccagccag   1200
gttgatcaca aagctgtgcg ttctgaattt gaagcggacc aagataatcc gggcgtgtgg   1260
cgcctggata tgtgctttcg tcgcgaaagc gaagatgaca ttgcgaatgg cgaatcatgg   1320
ctgccgtcgg ctctggtgtt tgttctgtat caggcggaat acaacttctg gtctaactac   1380
cataacgaca acttcgtcgt gccggtggca ccgccggccc cgagcgtcct ggaagatgtg   1440
tatgcttctt acctgcacac cctgcaagaa caagaaaaaa tgctgggtga tcgcgcacag   1500
ggcgaagaac cggaaacgct gccggttggc accattctgg gtctggaacg tcgctcactg   1560
gatgacgatg tgaaaccgt gatttgcttt tcggtcgaag aagacggctt cgccctgcgt   1620
gtccatgcgg atctgagtcc gctggtgatt cattggggta tcgcgcgtca ccgcgtgacc   1680
gaatttctgc aaccggatga atccctggct gttgaaacga aaggccgtac ctatcgcttc   1740
gaaaataaag cgatgcgtac ggaatttgtg ccggatgaac atcaccaggg cacctattac   1800
gccgaaattc atctgaaaaa agaacacgca ccgcgcgctg ttacctttgt cctgttcaac   1860
ccggaactga atcgttggta tcgtgcggaa ggcggtggca acttcgtgct gcgtatggac   1920
ctggaatcgt ttagccagct gccgggctca gtgggtaaac atgaagatgt tgcgcaaaaa   1980
atcatcgaag tcgaagtgga atatggctcg tggaccctga tgcaccgcta caacctggcc   2040
aatgatattc tgcgtaattc tatgagtgcg ctggacgcgg atctgctgca aatcgttttt   2100
gtctggctgc gctatagttt cctgcgtcag ctggattggc aacgctccta caacacccag   2160
ccgcgtctgc tggcacatgc acaggaacaa ctgaccacga ccctggcgca agtgttcgtt   2220
agccgtccgg atctgcgcct gtgggtgcgt ctgtgcctgt ctatgctggg tcgtggtggc   2280
ggtaatggcc agcgtattcg cgacgatatt ctgcgcatca tgcataaaca tcacatcccg   2340
gaaacgccgg ccactttat ggaacagtgg catcaaaaac tgcacaacaa tacgaccccg   2400
gacgatgtgg ccatttgcga aagttatctg gcattcctgc gctccaacgg tgataaaaac   2460
gtgttttatg aaacgctgca aaaacatggc gtcaccaaag aacgcctggc cagttatgaa   2520
cgtccgattt tcgcagaagt gcaaacgtac ccgtgtgaca ccaactccct gatccacgat   2580
ttcgaagaat atctgcatgt tctgaaaagc gtccactctg gcacggacct ggccgttgtc   2640
ctggattacg cacgttggac cctggatcag gaactgattt caaaagtcga acatatccaa   2700
tcggtgcgtg cagaactgat ggccagtccg cagggtgccc tggaattttc cttcctgatt   2760
gcagaagctc gcaaaatgct gcaaagtacg ctggaacacg ttgaagaccc gacccgtgtc   2820
cgcgatatgc tgtttctgga cctggcgctg atgaactgg cacgtctggc tgtggaatcc   2880
cagggcctgg cagactatgt ggctgaaacg gatgttcaga aagcgtgcaa cctgctggtt   2940
gtgctggcgc aacatgttgg ttggtcaatg ctgtcatcgg cgttcctgga aacctcgtat   3000
gatctggcag ctctggtgta cggtatccag tctgacgttc agctgcaaga accggatttt   3060
```

```
ggcctgcgcc tgtatgccac gatggaacgt ctgatggact gcgtcggcca tgatgtcgtg    3120
gaacgcctgc atcacgacgt tcagccgaaa gcagtgtaca ttggcgttgg ttgtaatatc    3180
gatcaaaaag ttgtcaccct gttcagcgaa gaactgattc gtggtcaggc agcatttgca    3240
ctggcacaag tgctgcgccc gctgatgcgt aacattcgca acaggccaa cctgggtaat    3300 tggcaagtga tcagtccggg ctcctgcacc ggtcagggtg cagttttga tgaactgctg    3360 tcaatccaat ataaaacgtt tgctgaaccg accgtggcgt tcgttcgtcg catttcgggc    3420
gaagaagaaa tcccgacggg catggtgggt ctgattacga ccgacaccct ggatattctg    3480
agccattgtg cggttcgtgc cgcaacgaa cacgtggttc tggcctgctg ttttctgaa     3540 gaactgttcg atcagctgac ggaacgtttc cgcggtgcat gggtcgctgt cgtagcctg     3600 accgacggct ctctggattt tcagccgatt caagaaggcg cgggtcgcac gaccgcagct    3660
gacacgaccg atggtgcaag cgaacatgca cagcgtcgcg cagtgtcaat gcgttcggat    3720
attgagaaaa aaccggtcaa atctgtgctg ggtatcgccc agtttaacac ccaacgtggc    3780
ggttccaaat caaattcgct ggcaaaactg attcgcgtga tcccggattg gattcatatc    3840
ccgccgtgcg cactgctgcc gttcggtgtc tgtgaacagg tgctggcaga agctcaaaat    3900
agcgacgttg gcgaacgctt tcagcaactg atggccgaac tggatggcaa aggtccgacg    3960
gacgattgca gcgcactgct ggcacgtctg cgtcattgtg tgcgtcagct ggcgccgtct    4020
gataccttca tgaaagaact gcaacaagtt ctgcaacatg aaggctttca cagtattgac    4080
aacctggata tgcgtcgcgc ctgggaatgc atcctggacg tgtgggcatc caaatttaat    4140
gatcgcgcat tcctggctct gcgtaaagcg ggcgccgttg gtaaaccag cctgagcagc     4200 ctgtatatgg cggttctggt ccaggaagtc gtgccggcgg attacgcctt tgtgctgcat    4260
acgaaaaacc cgttcaccgg tgaaccgagc gaaatttatg cgaactggt tcacggcctg     4320 ggtgaagtgc tggttggcaa ctatccgggt cgtgcactgg gcttcacgta cagcaaatct    4380
accggccagg tccgcgtgtg taattacccg agcaaaacca aagcgctgat tccgcgcggc    4440
ggtctgatct ttcgtagtga ctccaacggt gaagacctgg aagatttgc aggcgctggt     4500 ctgttcgatt ctattctgat gcagccggcg gaagaagttg tcgtgcgtta tcgcgaactg    4560
aaaatcctgc aagataaagc ctacctggaa cgtattctga gtaaaatcgg caaatgcggt    4620
attgaaatcg aatccaactg tggtaataaa ccgcaggata ttgaaggctg tatttgtggc    4680
gaagatgttt atgtcgtcca gtcacgcgat caggtttga                          4719
```

<210> SEQ ID NO 2
<211> LENGTH: 1572
<212> TYPE: PRT
<213> ORGANISM: Cyanidioschyzon merolae

<400> SEQUENCE: 2

Met Ser Asp Gln Pro Ser Val Ser Val Lys Val Pro Leu Tyr Glu Lys
1               5                   10                  15

Ile Tyr Gln Leu Asp Gly Phe Ile Gly Asp Glu Glu Arg Asn Ala Leu
            20                  25                  30

Gln Leu Pro Glu Gly Val Asp Glu Ala Gly Leu Phe Val Thr Val Tyr
        35                  40                  45

Val Ser Arg Glu Ser Thr Tyr Pro Gly Asp Ala Pro Ala Gly Gly Ala
    50                  55                  60

Thr Pro His Glu Asn Thr Gly Asp Pro Ser Val Ala Arg Glu Asp Ile
65                  70                  75                  80

```
Val Asp Trp Arg Lys Ala Arg Ile Val Cys Arg Phe Leu Leu Val Leu
             85                  90                  95

Leu Ser Arg Glu Glu Val Arg His Leu Asp Gln Leu Gly Ala Ser Val
            100                 105                 110

Pro Lys Ser Leu Lys Glu Arg Ile Ala Glu Arg Asn Arg Phe Glu Trp
            115                 120                 125

Ser Arg Ile Leu Gln Asn Arg Pro Thr Tyr Leu His Trp Gly Val Ala
130                 135                 140

Arg Asp His Pro Asp Glu Trp Thr Leu Pro Glu Ala Lys Thr Phe Pro
145                 150                 155                 160

Pro Gly Thr Ile Arg Phe Asp Lys Ile Ala Val Arg Thr Glu Phe Pro
                165                 170                 175

Ala Glu His Pro Arg Ile Arg Ile Asn Val Pro Phe Phe Glu Ser Gly
            180                 185                 190

Asn Glu Leu Arg Thr Ile Arg Gly Ile Lys Ala Val Val Tyr Arg Ala
            195                 200                 205

Lys Asp His Lys Tyr Phe Lys Asp Gly Arg Arg Asp Ile Phe Val Pro
210                 215                 220

Val Trp Asp Ser Val Arg Thr Trp Val Ile Asp Gly Ala Gly Ile Glu
225                 230                 235                 240

Glu Asn Val Ala Glu Leu Ser Leu Thr Glu Ser Ala Phe Arg Thr Ala
                245                 250                 255

Leu Gly Val Ser Arg Ser Asp Ser Tyr Met Ser Leu Ser Arg Glu Thr
            260                 265                 270

Ser Pro Gly Pro Asp Ala Ser Gly Ser Gly Arg Ser Ala Val Arg Arg
            275                 280                 285

Ser Ile Ser Leu Ser Ser Val Arg Lys Leu Lys Ser Ser Ala Ser Leu
290                 295                 300

Asp Arg Leu Val Lys Ala Gly Ala Pro Gln Asp Arg Ser Leu Lys Ala
305                 310                 315                 320

Val Arg Arg Ile His Thr Ala Ala Thr Val Leu Phe Glu Glu Leu Phe
                325                 330                 335

Gly Gly Val Gly Arg Gly Gly Ser Gly His Leu Asp Val Val Glu
            340                 345                 350

Glu Met Glu Pro Gln Ser Glu Tyr His Ile His Met Ala Thr Asp Ile
            355                 360                 365

Ser Gly Leu Ala Leu His Trp Gly Val Ser Arg Lys Lys Pro Gly Gln
370                 375                 380

Trp Val Leu Pro Arg Arg Asp Trp Trp Pro Ala Gly Val Thr Ser Gln
385                 390                 395                 400

Val Asp His Lys Ala Val Arg Ser Glu Phe Glu Ala Asp Gln Asp Asn
                405                 410                 415

Pro Gly Val Trp Arg Leu Asp Met Cys Phe Arg Arg Glu Ser Glu Asp
            420                 425                 430

Asp Ile Ala Asn Gly Glu Ser Trp Leu Pro Ser Ala Leu Val Phe Val
            435                 440                 445

Leu Tyr Gln Ala Glu Tyr Asn Phe Trp Ser Asn Tyr His Asn Asp Asn
450                 455                 460

Phe Val Val Pro Val Ala Pro Pro Ala Pro Ser Val Leu Glu Asp Val
465                 470                 475                 480

Tyr Ala Ser Tyr Leu His Thr Leu Gln Glu Gln Glu Lys Met Leu Gly
                485                 490                 495
```

-continued

Asp Arg Ala Gln Gly Glu Glu Pro Glu Thr Leu Pro Val Gly Thr Ile
                500                 505                 510

Leu Gly Leu Glu Arg Arg Ser Leu Asp Asp Gly Glu Thr Val Ile
            515                 520                 525

Cys Phe Ser Val Glu Glu Asp Gly Phe Ala Leu Arg Val His Ala Asp
        530                 535                 540

Leu Ser Pro Leu Val Ile His Trp Gly Ile Ala Arg His Arg Val Thr
545                 550                 555                 560

Glu Phe Leu Gln Pro Asp Glu Ser Leu Ala Val Glu Thr Lys Gly Arg
                565                 570                 575

Thr Tyr Arg Phe Glu Asn Lys Ala Met Arg Thr Glu Phe Val Pro Asp
            580                 585                 590

Glu His His Gln Gly Thr Tyr Tyr Ala Glu Ile His Leu Lys Lys Glu
        595                 600                 605

His Ala Pro Arg Ala Val Thr Phe Val Leu Phe Asn Pro Glu Leu Asn
        610                 615                 620

Arg Trp Tyr Arg Ala Glu Gly Gly Asn Phe Val Leu Arg Met Asp
625                 630                 635                 640

Leu Glu Ser Phe Ser Gln Leu Pro Gly Ser Val Gly Lys His Glu Asp
                645                 650                 655

Val Ala Gln Lys Ile Ile Glu Val Glu Val Glu Tyr Gly Ser Trp Thr
            660                 665                 670

Leu Met His Arg Tyr Asn Leu Ala Asn Asp Ile Leu Arg Asn Ser Met
        675                 680                 685

Ser Ala Leu Asp Ala Asp Leu Leu Gln Ile Val Phe Val Trp Leu Arg
690                 695                 700

Tyr Ser Phe Leu Arg Gln Leu Asp Trp Gln Arg Ser Tyr Asn Thr Gln
705                 710                 715                 720

Pro Arg Leu Leu Ala His Ala Gln Glu Gln Leu Thr Thr Thr Leu Ala
            725                 730                 735

Gln Val Phe Val Ser Arg Pro Asp Leu Arg Leu Trp Val Arg Leu Cys
        740                 745                 750

Leu Ser Met Leu Gly Arg Gly Gly Asn Gly Gln Arg Ile Arg Asp
        755                 760                 765

Asp Ile Leu Arg Ile Met His Lys His His Ile Pro Glu Thr Pro Gly
770                 775                 780

His Phe Met Glu Gln Trp His Gln Lys Leu His Asn Asn Thr Thr Pro
785                 790                 795                 800

Asp Asp Val Ala Ile Cys Glu Ser Tyr Leu Ala Phe Leu Arg Ser Asn
            805                 810                 815

Gly Asp Lys Asn Val Phe Tyr Glu Thr Leu Gln Lys His Gly Val Thr
        820                 825                 830

Lys Glu Arg Leu Ala Ser Tyr Glu Arg Pro Ile Phe Ala Glu Val Gln
    835                 840                 845

Thr Tyr Pro Cys Asp Thr Asn Ser Leu Ile His Asp Phe Glu Glu Tyr
        850                 855                 860

Leu His Val Leu Lys Ser Val His Ser Gly Thr Asp Leu Ala Val Val
865                 870                 875                 880

Leu Asp Tyr Ala Arg Trp Thr Leu Asp Gln Glu Leu Ile Ser Lys Val
                885                 890                 895

Glu His Ile Gln Ser Val Arg Ala Glu Leu Met Ala Ser Pro Gln Gly
            900                 905                 910

Ala Leu Glu Phe Ser Phe Leu Ile Ala Glu Ala Arg Lys Met Leu Gln

```
            915                 920                 925
Ser Thr Leu Glu His Val Glu Asp Pro Thr Arg Val Arg Asp Met Leu
930                 935                 940

Phe Leu Asp Leu Ala Leu Asp Glu Leu Ala Arg Leu Ala Val Glu Ser
945                 950                 955                 960

Gln Gly Leu Ala Asp Tyr Val Ala Glu Thr Asp Val Gln Lys Ala Cys
                965                 970                 975

Asn Leu Leu Val Val Leu Ala Gln His Val Gly Trp Ser Met Leu Ser
            980                 985                 990

Ser Ala Phe Leu Glu Thr Ser Tyr Asp Leu Ala Ala Leu Val Tyr Gly
            995                 1000                1005

Ile Gln Ser Asp Val Gln Leu Gln Glu Pro Asp Phe Gly Leu Arg
    1010                1015                1020

Leu Tyr Ala Thr Met Glu Arg Leu Met Asp Cys Val Gly His Asp
    1025                1030                1035

Val Val Glu Arg Leu His His Asp Val Gln Pro Lys Ala Val Tyr
    1040                1045                1050

Ile Gly Val Gly Cys Asn Ile Asp Gln Lys Val Val Thr Leu Phe
    1055                1060                1065

Ser Glu Glu Leu Ile Arg Gly Gln Ala Ala Phe Ala Leu Ala Gln
    1070                1075                1080

Val Leu Arg Pro Leu Met Arg Asn Ile Arg Lys Gln Ala Asn Leu
    1085                1090                1095

Gly Asn Trp Gln Val Ile Ser Pro Gly Ser Cys Thr Gly Gln Gly
    1100                1105                1110

Ala Val Phe Asp Glu Leu Leu Ser Ile Gln Tyr Lys Thr Phe Ala
    1115                1120                1125

Glu Pro Thr Val Ala Phe Val Arg Arg Ile Ser Gly Glu Glu Glu
    1130                1135                1140

Ile Pro Thr Gly Met Val Gly Leu Ile Thr Thr Asp Thr Leu Asp
    1145                1150                1155

Ile Leu Ser His Cys Ala Val Arg Ala Arg Asn Glu His Val Val
    1160                1165                1170

Leu Ala Cys Cys Phe Ser Glu Glu Leu Phe Asp Gln Leu Thr Glu
    1175                1180                1185

Arg Phe Arg Gly Ala Trp Val Ala Val Arg Ser Leu Thr Asp Gly
    1190                1195                1200

Ser Leu Asp Phe Gln Pro Ile Gln Glu Gly Ala Gly Arg Thr Thr
    1205                1210                1215

Ala Ala Asp Thr Thr Asp Gly Ala Ser Glu His Ala Gln Arg Arg
    1220                1225                1230

Ala Val Ser Met Arg Ser Asp Ile Glu Lys Lys Pro Val Lys Ser
    1235                1240                1245

Val Leu Gly Ile Ala Gln Phe Asn Thr Gln Arg Gly Gly Ser Lys
    1250                1255                1260

Ser Asn Ser Leu Ala Lys Leu Ile Arg Val Ile Pro Asp Trp Ile
    1265                1270                1275

His Ile Pro Pro Cys Ala Leu Leu Pro Phe Gly Val Cys Glu Gln
    1280                1285                1290

Val Leu Ala Glu Ala Gln Asn Ser Asp Val Gly Glu Arg Phe Gln
    1295                1300                1305

Gln Leu Met Ala Glu Leu Asp Gly Lys Gly Pro Thr Asp Asp Cys
    1310                1315                1320
```

| | | | | | | | | | |
|---|---|---|---|---|---|---|---|---|---|
|Ser|Ala|Leu|Leu|Ala|Arg|Leu|Arg|His|Cys|Val|Arg|Gln|Leu|Ala|
|1325| | | |1330| | | |1335| | | | | | |

Ser Ala Leu Leu Ala Arg Leu Arg His Cys Val Arg Gln Leu Ala
    1325            1330            1335

Pro Ser Asp Thr Phe Met Lys Glu Leu Gln Gln Val Leu Gln His
    1340            1345            1350

Glu Gly Phe His Ser Ile Asp Asn Leu Asp Met Arg Arg Ala Trp
    1355            1360            1365

Glu Cys Ile Leu Asp Val Trp Ala Ser Lys Phe Asn Asp Arg Ala
    1370            1375            1380

Phe Leu Ala Leu Arg Lys Ala Gly Ala Val Gly Lys Thr Ser Leu
    1385            1390            1395

Ser Ser Leu Tyr Met Ala Val Leu Val Gln Glu Val Val Pro Ala
    1400            1405            1410

Asp Tyr Ala Phe Val Leu His Thr Lys Asn Pro Phe Thr Gly Glu
    1415            1420            1425

Pro Ser Glu Ile Tyr Gly Glu Leu Val His Gly Leu Gly Glu Val
    1430            1435            1440

Leu Val Gly Asn Tyr Pro Gly Arg Ala Leu Gly Phe Thr Tyr Ser
    1445            1450            1455

Lys Ser Thr Gly Gln Val Arg Val Cys Asn Tyr Pro Ser Lys Thr
    1460            1465            1470

Lys Ala Leu Ile Pro Arg Gly Gly Leu Ile Phe Arg Ser Asp Ser
    1475            1480            1485

Asn Gly Glu Asp Leu Glu Asp Phe Ala Gly Ala Gly Leu Phe Asp
    1490            1495            1500

Ser Ile Leu Met Gln Pro Ala Glu Glu Val Val Val Arg Tyr Arg
    1505            1510            1515

Glu Leu Lys Ile Leu Gln Asp Lys Ala Tyr Leu Glu Arg Ile Leu
    1520            1525            1530

Ser Lys Ile Gly Lys Cys Gly Ile Glu Ile Glu Ser Asn Cys Gly
    1535            1540            1545

Asn Lys Pro Gln Asp Ile Glu Gly Cys Ile Cys Gly Glu Asp Val
    1550            1555            1560

Tyr Val Val Gln Ser Arg Asp Gln Val
    1565            1570

<210> SEQ ID NO 3
<211> LENGTH: 4383
<212> TYPE: DNA
<213> ORGANISM: Artificial Sequence
<220> FEATURE:
<223> OTHER INFORMATION: Fragment of Cyanidioschyzon merolae GWD
      polypeptide

<400> SEQUENCE: 3
atgaaatctc tgaaagaacg tattgcggaa cgtaaccgct ttgaatggag ccgtattctg      60
caaaatcgtc cgacgtatct gcattggggc gtggcccgcg accacccgga tgaatggacc     120
ctgccggaag caaaaacgtt tccgccgggc accattcgct tcgataaaat cgctgtgcgt     180
acggaatttc cggcggaaca tccgcgtatt cgcatcaacg ttccgttttt cgaaagcggt     240
aatgaactgc gtaccattcg tggcatcaaa gctgtggttt atcgtgcgaa agatcacaaa     300
tactttaaag acggccgtcg cgatattttc gttccggtct gggacagcgt tcgcacctgg     360
gtcattgatg cgccggtat cgaagaaaat gtggcagaac tgagtctgac ggaatccgca     420
tttcgcaccg ctctgggtgt tagtcgttcc gactcatata tgtcgctgag ccgtgaaacc     480

```
tctccgggcc cggatgcttc tggcagtggt cgctctgcgg ttcgtcgtag cattagcctg    540
agcagcgtgc gcaaactgaa aagttccgca agtctggacc gtctggtgaa agcaggtgct    600
ccgcaggatc gctccctgaa agcagtgcgt cgcatccata cggcggccac cgttctgttt    660
gaagaactgt tcggcggtgt cggtcgcggc ggttcaggtc acctgacgt cgtggttgaa     720 gaaatggaac cgcagtcgga atatcatatt cacatggcca cggatatttc aggtctggca    780
ctgcattggg gcgtgtcgcg taaaaaaccg ggtcaatggg ttctgccgcg tcgcgactgg    840
tggccggccg gcgtgaccag ccaggttgat cacaaagctg tgcgttctga atttgaagcg    900
gaccaagata tcccgggcgt gtggcgcctg gatatgtgct ttcgtcgcga aagcgaagat    960
gacattgcga atggcgaatc atggctgccg tcggctctgg tgtttgttct gtatcaggcg   1020
gaatacaact tctggtctaa ctaccataac gacaacttcg tcgtgccggt ggcaccgccg   1080
gccccgagcg tcctggaaga tgtgtatgct tcttacctgc acaccctgca agaacaagaa   1140
aaaatgctgg gtgatcgcgc acagggcgaa gaaccggaaa cgctgccggt tggcaccatt   1200
ctgggtctgg aacgtcgctc actggatgac gatggtgaaa ccgtgatttg cttttcggtc   1260
gaagaagacg gcttcgccct gcgtgtccat gcggatctga gtccgctggt gattcattgg   1320
ggtatcgcgc gtcaccgcgt gaccgaattt ctgcaaccgg atgaatccct ggctgttgaa   1380
acgaaaggcc gtacctatcg cttcgaaaat aaagcgatgc gtacggaatt tgtgccggat   1440
gaacatcacc agggcaccta ttacgccgaa attcatctga aaaagaaca cgcaccgcgc    1500 gctgttacct ttgtcctgtt caacccggaa ctgaatcgtt ggtatcgtgc ggaaggcggt   1560
ggcaacttcg tgctgcgtat ggacctggaa tcgtttagcc agctgccggg ctcagtgggt   1620
aaacatgaag atgttgcgca aaaaatcatc gaagtcgaag tggaatatgg ctcgtggacc   1680
ctgatgcacc gctacaacct ggccaatgat attctgcgta attctatgag tgcgctggac   1740
gcggatctgc tgcaaatcgt ttttgtctgg ctgcgctata gtttcctgcg tcagctggat   1800
tggcaacgct cctacaacac ccagccgcgt ctgctggcac atgcacagga acaactgacc   1860
acgaccctgg cgcaagtgtt cgttagccgt ccggatctgc gcctgtgggt gcgtctgtgc   1920
ctgtctatgc tgggtcgtgg tggcggtaat ggccagcgta ttcgcgacga tattctgcgc   1980
atcatgcata acatcacat cccggaaacg ccgggccact ttatggaaca gtggcatcaa    2040
aaactgcaca caatacgac cccggacgat gtggccattt gcgaaagtta tctggcattc     2100
ctgcgctcca acggtgataa aaacgtgttt tatgaaacgc tgcaaaaaca tggcgtcacc   2160
aaagaacgcc tggccagtta tgaacgtccg attttcgcag aagtgcaaac gtacccgtgt   2220
gacaccaact ccctgatcca cgatttcgaa gaatatctgc atgttctgaa aagcgtccac   2280
tctggcacgg acctggccgt tgtcctggat tacgcacgtt ggaccctgga tcaggaactg   2340
atttcaaaag tcgaacatat ccaatcggtg cgtgcagaac tgatggccag tccgcagggt   2400
gccctggaat tttccttcct gattgcagaa gctcgcaaaa tgctgcaaag tacgctggaa   2460
cacgttgaag acccgaccg tgtccgcgat atgctgtttc tggacctggc gctggatgaa   2520
ctggcacgtc tggctgtgga atcccagggc ctggcagact atgtggctga acggatgtt    2580 cagaaagcgt gcaacctgct ggttgtgctg gcgcaacatg ttggttggtc aatgctgtca   2640
tcggcgttcc tggaaacctc gtatgatctg gcagctctgg tgtacggtat ccagtctgac   2700
gttcagctgc aagaaccgga ttttggcctg cgcctgtatg ccacgatgga acgtctgatg   2760
gactgcgtcg gccatgatgt cgtggaacgc ctgcatcacg acgttcagcc gaaagcagtg   2820
tacattggcg ttggttgtaa tatcgatcaa aaagttgtca ccctgttcag cgaagaactg   2880
```

-continued

```
attcgtggtc aggcagcatt tgcactggca caagtgctgc gcccgctgat gcgtaacatt    2940
cgcaaacagg ccaacctggg taattggcaa gtgatcagtc cgggctcctg caccggtcag    3000
ggtgcagttt ttgatgaact gctgtcaatc aatataaaa cgtttgctga accgaccgtg     3060
gcgttcgttc gtcgcatttc gggcgaagaa gaaatcccga cgggcatggt gggtctgatt    3120
acgaccgaca ccctggatat tctgagccat tgtgcggttc gtgcccgcaa cgaacacgtg    3180
gttctggcct gctgttttc tgaagaactg ttcgatcagc tgacggaacg tttccgcggt     3240
gcatgggtcg ctgtgcgtag cctgaccgac ggctctctgg attttcagcc gattcaagaa    3300
ggcgcgggtc gcacgaccgc agctgacacg accgatggtg caagcgaaca tgcacagcgt    3360
cgcgcagtgt caatgcgttc ggatattgag aaaaaaccgg tcaaatctgt gctgggtatc    3420
gcccagttta acacccaacg tggcggttcc aaatcaaatt cgctggcaaa actgattcgc    3480
gtgatcccgg attggattca tatcccgccg tgcgcactgc tgccgttcgg tgtctgtgaa    3540
caggtgctgg cagaagctca aaatagcgac gttggcgaac gctttcagca actgatggcc    3600
gaactggatg gcaaaggtcc gacggacgat tgcagcgcac tgctggcacg tctgcgtcat    3660
tgtgtgcgtc agctggcgcc gtctgatacc ttcatgaaag aactgcaaca agttctgcaa    3720
catgaaggct ttcacagtat tgacaacctg gatatgcgtc gcgcctggga atgcatcctg    3780
gacgtgtggg catccaaatt taatgatcgc gcattcctgg ctctgcgtaa agcgggcgcc    3840
gttggtaaaa ccagcctgag cagcctgtat atggcggttc tggtccagga agtcgtgccg    3900
gcggattacg cctttgtgct gcatacgaaa aacccgttca ccggtgaacc gagcgaaatt    3960
tatggcgaac tggttcacgg cctgggtgaa gtgctggttg caactatcc gggtcgtgca    4020 ctgggcttca cgtacagcaa atctaccggc caggtccgcg tgtgtaatta cccgagcaaa    4080
accaaagcgc tgattccgcg cggcggtctg atctttcgta gtgactccaa cggtgaagac    4140
ctggaagatt ttgcaggcgc tggtctgttc gattctattc tgatgcagcc ggcggaagaa    4200
gttgtcgtgc gttatcgcga actgaaaatc ctgcaagata aagcctacct ggaacgtatt    4260
ctgagtaaaa tcggcaaatg cggtattgaa atcgaatcca actgtggtaa taaaccgcag    4320
gatattgaag ctgtatttg tggcgaagat gtttatgtcg tccagtcacg cgatcaggtt    4380
tga                                                                 4383
```

<210> SEQ ID NO 4
<211> LENGTH: 1460
<212> TYPE: PRT
<213> ORGANISM: Artificial Sequence
<220> FEATURE:
<223> OTHER INFORMATION: Fragment of Cyanidioschyzon merolae GWD polypeptide

<400> SEQUENCE: 4

```
Met Lys Ser Leu Lys Glu Arg Ile Ala Glu Arg Asn Arg Phe Glu Trp
1               5                   10                  15

Ser Arg Ile Leu Gln Asn Arg Pro Thr Tyr Leu His Trp Gly Val Ala
            20                  25                  30

Arg Asp His Pro Asp Glu Trp Thr Leu Pro Glu Ala Lys Thr Phe Pro
        35                  40                  45

Pro Gly Thr Ile Arg Phe Asp Lys Ile Ala Val Arg Thr Glu Phe Pro
    50                  55                  60

Ala Glu His Pro Arg Ile Arg Ile Asn Val Pro Phe Phe Glu Ser Gly
65                  70                  75                  80
```

```
Asn Glu Leu Arg Thr Ile Arg Gly Ile Lys Ala Val Val Tyr Arg Ala
                    85                  90                  95
Lys Asp His Lys Tyr Phe Lys Asp Gly Arg Arg Asp Ile Phe Val Pro
            100                 105                 110
Val Trp Asp Ser Val Arg Thr Trp Val Ile Asp Gly Ala Gly Ile Glu
        115                 120                 125
Glu Asn Val Ala Glu Leu Ser Leu Thr Glu Ser Ala Phe Arg Thr Ala
    130                 135                 140
Leu Gly Val Ser Arg Ser Asp Ser Tyr Met Ser Leu Ser Arg Glu Thr
145                 150                 155                 160
Ser Pro Gly Pro Asp Ala Ser Gly Ser Gly Arg Ser Ala Val Arg Arg
                165                 170                 175
Ser Ile Ser Leu Ser Ser Val Arg Lys Leu Lys Ser Ser Ala Ser Leu
            180                 185                 190
Asp Arg Leu Val Lys Ala Gly Ala Pro Gln Asp Arg Ser Leu Lys Ala
        195                 200                 205
Val Arg Arg Ile His Thr Ala Ala Thr Val Leu Phe Glu Glu Leu Phe
    210                 215                 220
Gly Gly Val Gly Arg Gly Gly Ser Gly His Leu Asp Val Val Val Glu
225                 230                 235                 240
Glu Met Glu Pro Gln Ser Glu Tyr His Ile His Met Ala Thr Asp Ile
                245                 250                 255
Ser Gly Leu Ala Leu His Trp Gly Val Ser Arg Lys Lys Pro Gly Gln
            260                 265                 270
Trp Val Leu Pro Arg Arg Asp Trp Pro Ala Gly Val Thr Ser Gln
        275                 280                 285
Val Asp His Lys Ala Val Arg Ser Glu Phe Glu Ala Asp Gln Asp Asn
    290                 295                 300
Pro Gly Val Trp Arg Leu Asp Met Cys Phe Arg Arg Glu Ser Glu Asp
305                 310                 315                 320
Asp Ile Ala Asn Gly Glu Ser Trp Leu Pro Ser Ala Leu Val Phe Val
                325                 330                 335
Leu Tyr Gln Ala Glu Tyr Asn Phe Trp Ser Asn Tyr His Asn Asp Asn
            340                 345                 350
Phe Val Val Pro Val Ala Pro Pro Ala Pro Ser Val Leu Glu Asp Val
        355                 360                 365
Tyr Ala Ser Tyr Leu His Thr Leu Gln Glu Gln Glu Lys Met Leu Gly
    370                 375                 380
Asp Arg Ala Gln Gly Glu Glu Pro Glu Thr Leu Pro Val Gly Thr Ile
385                 390                 395                 400
Leu Gly Leu Glu Arg Arg Ser Leu Asp Asp Gly Glu Thr Val Ile
                405                 410                 415
Cys Phe Ser Val Glu Glu Asp Gly Phe Ala Leu Arg Val His Ala Asp
            420                 425                 430
Leu Ser Pro Leu Val Ile His Trp Gly Ile Ala Arg His Arg Val Thr
        435                 440                 445
Glu Phe Leu Gln Pro Asp Glu Ser Leu Ala Val Glu Thr Lys Gly Arg
    450                 455                 460
Thr Tyr Arg Phe Glu Asn Lys Ala Met Arg Thr Glu Phe Val Pro Asp
465                 470                 475                 480
Glu His His Gln Gly Thr Tyr Tyr Ala Glu Ile His Leu Lys Lys Glu
                485                 490                 495
His Ala Pro Arg Ala Val Thr Phe Val Leu Phe Asn Pro Glu Leu Asn
```

```
                500             505             510
Arg Trp Tyr Arg Ala Glu Gly Gly Gly Asn Phe Val Leu Arg Met Asp
            515             520             525

Leu Glu Ser Phe Ser Gln Leu Pro Gly Ser Val Gly Lys His Glu Asp
            530             535             540

Val Ala Gln Lys Ile Ile Glu Val Glu Val Glu Tyr Gly Ser Trp Thr
545             550             555             560

Leu Met His Arg Tyr Asn Leu Ala Asn Asp Ile Leu Arg Asn Ser Met
                565             570             575

Ser Ala Leu Asp Ala Asp Leu Leu Gln Ile Val Phe Val Trp Leu Arg
            580             585             590

Tyr Ser Phe Leu Arg Gln Leu Asp Trp Gln Arg Ser Tyr Asn Thr Gln
            595             600             605

Pro Arg Leu Leu Ala His Ala Gln Glu Gln Leu Thr Thr Thr Leu Ala
            610             615             620

Gln Val Phe Val Ser Arg Pro Asp Leu Arg Leu Trp Val Arg Leu Cys
625             630             635             640

Leu Ser Met Leu Gly Arg Gly Gly Asn Gly Gln Arg Ile Arg Asp
                645             650             655

Asp Ile Leu Arg Ile Met His Lys His Ile Pro Glu Thr Pro Gly
            660             665             670

His Phe Met Glu Gln Trp His Gln Lys Leu His Asn Asn Thr Thr Pro
            675             680             685

Asp Asp Val Ala Ile Cys Glu Ser Tyr Leu Ala Phe Leu Arg Ser Asn
            690             695             700

Gly Asp Lys Asn Val Phe Tyr Glu Thr Leu Gln Lys His Gly Val Thr
705             710             715             720

Lys Glu Arg Leu Ala Ser Tyr Glu Arg Pro Ile Phe Ala Glu Val Gln
                725             730             735

Thr Tyr Pro Cys Asp Thr Asn Ser Leu Ile His Asp Phe Glu Glu Tyr
            740             745             750

Leu His Val Leu Lys Ser Val His Ser Gly Thr Asp Leu Ala Val Val
            755             760             765

Leu Asp Tyr Ala Arg Trp Thr Leu Asp Gln Glu Leu Ile Ser Lys Val
            770             775             780

Glu His Ile Gln Ser Val Arg Ala Glu Leu Met Ala Ser Pro Gln Gly
785             790             795             800

Ala Leu Glu Phe Ser Phe Leu Ile Ala Glu Ala Arg Lys Met Leu Gln
                805             810             815

Ser Thr Leu Glu His Val Glu Asp Pro Thr Arg Val Arg Asp Met Leu
            820             825             830

Phe Leu Asp Leu Ala Leu Asp Glu Leu Ala Arg Leu Ala Val Glu Ser
            835             840             845

Gln Gly Leu Ala Asp Tyr Val Ala Glu Thr Asp Val Gln Lys Ala Cys
            850             855             860

Asn Leu Leu Val Val Leu Ala Gln His Val Gly Trp Ser Met Leu Ser
865             870             875             880

Ser Ala Phe Leu Glu Thr Ser Tyr Asp Leu Ala Ala Leu Val Tyr Gly
                885             890             895

Ile Gln Ser Asp Val Gln Leu Gln Glu Pro Asp Phe Gly Leu Arg Leu
            900             905             910

Tyr Ala Thr Met Glu Arg Leu Met Asp Cys Val Gly His Asp Val Val
            915             920             925
```

```
Glu Arg Leu His His Asp Val Gln Pro Lys Ala Val Tyr Ile Gly Val
    930                 935                 940

Gly Cys Asn Ile Asp Gln Lys Val Val Thr Leu Phe Ser Glu Glu Leu
945                 950                 955                 960

Ile Arg Gly Gln Ala Ala Phe Ala Leu Ala Gln Val Leu Arg Pro Leu
                965                 970                 975

Met Arg Asn Ile Arg Lys Gln Ala Asn Leu Gly Asn Trp Gln Val Ile
            980                 985                 990

Ser Pro Gly Ser Cys Thr Gly Gln Gly Ala Val Phe Asp Glu Leu Leu
        995                 1000                1005

Ser Ile Gln Tyr Lys Thr Phe Ala Glu Pro Thr Val Ala Phe Val
    1010                1015                1020

Arg Arg Ile Ser Gly Glu Glu Ile Pro Thr Gly Met Val Gly
    1025                1030                1035

Leu Ile Thr Thr Asp Thr Leu Asp Ile Leu Ser His Cys Ala Val
    1040                1045                1050

Arg Ala Arg Asn Glu His Val Val Leu Ala Cys Cys Phe Ser Glu
    1055                1060                1065

Glu Leu Phe Asp Gln Leu Thr Glu Arg Phe Arg Gly Ala Trp Val
    1070                1075                1080

Ala Val Arg Ser Leu Thr Asp Gly Ser Leu Asp Phe Gln Pro Ile
    1085                1090                1095

Gln Glu Gly Ala Gly Arg Thr Thr Ala Ala Asp Thr Thr Asp Gly
    1100                1105                1110

Ala Ser Glu His Ala Gln Arg Arg Ala Val Ser Met Arg Ser Asp
    1115                1120                1125

Ile Glu Lys Lys Pro Val Lys Ser Val Leu Gly Ile Ala Gln Phe
    1130                1135                1140

Asn Thr Gln Arg Gly Gly Ser Lys Ser Asn Ser Leu Ala Lys Leu
    1145                1150                1155

Ile Arg Val Ile Pro Asp Trp Ile His Ile Pro Pro Cys Ala Leu
    1160                1165                1170

Leu Pro Phe Gly Val Cys Glu Gln Val Leu Ala Glu Ala Gln Asn
    1175                1180                1185

Ser Asp Val Gly Glu Arg Phe Gln Gln Leu Met Ala Glu Leu Asp
    1190                1195                1200

Gly Lys Gly Pro Thr Asp Asp Cys Ser Ala Leu Leu Ala Arg Leu
    1205                1210                1215

Arg His Cys Val Arg Gln Leu Ala Pro Ser Asp Thr Phe Met Lys
    1220                1225                1230

Glu Leu Gln Gln Val Leu Gln His Glu Gly Phe His Ser Ile Asp
    1235                1240                1245

Asn Leu Asp Met Arg Arg Ala Trp Glu Cys Ile Leu Asp Val Trp
    1250                1255                1260

Ala Ser Lys Phe Asn Asp Arg Ala Phe Leu Ala Leu Arg Lys Ala
    1265                1270                1275

Gly Ala Val Gly Lys Thr Ser Leu Ser Ser Leu Tyr Met Ala Val
    1280                1285                1290

Leu Val Gln Glu Val Val Pro Ala Asp Tyr Ala Phe Val Leu His
    1295                1300                1305

Thr Lys Asn Pro Phe Thr Gly Glu Pro Ser Glu Ile Tyr Gly Glu
    1310                1315                1320
```

| | | | | | | | | | | |
|---|---|---|---|---|---|---|---|---|---|---|
| Leu | Val | His | Gly | Leu | Gly | Glu | Val | Leu | Val | Gly | Asn | Tyr | Pro | Gly |
| | 1325 | | | | 1330 | | | | 1335 | |

| Arg | Ala | Leu | Gly | Phe | Thr | Tyr | Ser | Lys | Ser | Thr | Gly | Gln | Val | Arg |
|---|---|---|---|---|---|---|---|---|---|---|---|---|---|---|
| | 1340 | | | | 1345 | | | | 1350 | |

| Val | Cys | Asn | Tyr | Pro | Ser | Lys | Thr | Lys | Ala | Leu | Ile | Pro | Arg | Gly |
|---|---|---|---|---|---|---|---|---|---|---|---|---|---|---|
| | 1355 | | | | 1360 | | | | 1365 | |

| Gly | Leu | Ile | Phe | Arg | Ser | Asp | Ser | Asn | Gly | Glu | Asp | Leu | Glu | Asp |
|---|---|---|---|---|---|---|---|---|---|---|---|---|---|---|
| | 1370 | | | | 1375 | | | | 1380 | |

| Phe | Ala | Gly | Ala | Gly | Leu | Phe | Asp | Ser | Ile | Leu | Met | Gln | Pro | Ala |
|---|---|---|---|---|---|---|---|---|---|---|---|---|---|---|
| | 1385 | | | | 1390 | | | | 1395 | |

| Glu | Glu | Val | Val | Val | Arg | Tyr | Arg | Glu | Leu | Lys | Ile | Leu | Gln | Asp |
|---|---|---|---|---|---|---|---|---|---|---|---|---|---|---|
| | 1400 | | | | 1405 | | | | 1410 | |

| Lys | Ala | Tyr | Leu | Glu | Arg | Ile | Leu | Ser | Lys | Ile | Gly | Lys | Cys | Gly |
|---|---|---|---|---|---|---|---|---|---|---|---|---|---|---|
| | 1415 | | | | 1420 | | | | 1425 | |

| Ile | Glu | Ile | Glu | Ser | Asn | Cys | Gly | Asn | Lys | Pro | Gln | Asp | Ile | Glu |
|---|---|---|---|---|---|---|---|---|---|---|---|---|---|---|
| | 1430 | | | | 1435 | | | | 1440 | |

| Gly | Cys | Ile | Cys | Gly | Glu | Asp | Val | Tyr | Val | Gln | Ser | Arg | Asp |
|---|---|---|---|---|---|---|---|---|---|---|---|---|---|
| | 1445 | | | | 1450 | | | | 1455 |

Gln Val
    1460

<210> SEQ ID NO 5
<211> LENGTH: 4344
<212> TYPE: DNA
<213> ORGANISM: Artificial Sequence
<220> FEATURE:
<223> OTHER INFORMATION: Fragment of Cyanidioschyzon merolae GWD
      polypeptide

<400> SEQUENCE: 5

```
atggaatgga gccgtattct gcaaaatcgt ccgacgtatc tgcattgggg cgtggcccgc      60
gaccacccgg atgaatggac cctgccggaa gcaaaaacgt ttccgccggg caccattcgc     120
ttcgataaaa tcgctgtgcg tacgaatttt ccggcggaaa tccgcgtat cgcatcaac      180 gttccgtttt tcgaaagcgg taatgaactg cgtaccattc gtggcatcaa agctgtggtt     240
tatcgtgcga agatcacaa atactttaaa gacggccgtc gcgatatttt cgttccggtc     300
tgggacagcg ttcgcacctg ggtcattgat ggcgccggta tcgaagaaaa tgtggcagaa     360
ctgagtctga cggaatccgc atttcgcacc gctctgggtg ttagtcgttc cgactcatat     420
atgtcgctga gccgtgaaac ctctccgggc ccggatgctt ctggcagtgg tcgctctgcg     480
gttcgtcgta gcattagcct gagcagcgtg cgcaaactga aagttccgc aagtctggac      540 cgtctggtga agcaggtgc tccgcaggat cgctccctga agcagtgcg tcgcatccat      600 acggcggcca ccgttctgtt tgaagaactg ttcggcggtg tcgtcgcgg cggttcaggt     660 cacctggacg tcgtggttga agaaatggaa ccgcagtcgg aatatcatat tcacatggcc     720
acggatattt caggtctggc actgcattgg ggcgtgtcgc gtaaaaaacc gggtcaatgg     780
gttctgccgc gtcgcgactg gtggccggcc ggcgtgacca gccaggttga tcacaaagct     840
gtgcgttctg aatttgaagc ggaccaagat aatccgggcg tgtggcgcct ggatatgtgc     900
tttcgtcgcg aaagcgaaga tgacattgcg aatggcgaat catggctgcc gtcggctctg     960
gtgtttgttc tgtatcaggc ggaatacaac ttctggtcta actaccataa cgacaacttc    1020
gtcgtgccgc tggcaccgcc ggccccgagc gtcctggaag atgtgtatgc ttcttacctg    1080
cacaccctgc aagaacaaga aaaaatgctg ggtgatcgcg cacagggcga agaaccggaa    1140
```

```
acgctgccgg ttggcaccat tctgggtctg aacgtcgct cactggatga cgatggtgaa    1200
accgtgattt gcttttcggt cgaagaagac ggcttcgccc tgcgtgtcca tgcggatctg    1260
agtccgctgg tgattcattg gggtatcgcg cgtcaccgcg tgaccgaatt tctgcaaccg    1320
gatgaatccc tggctgttga aacgaaaggc cgtacctatc gcttcgaaaa taaagcgatg    1380
cgtacggaat tgtgccgga tgaacatcac cagggcacct attacgccga aattcatctg    1440
aaaaaagaac acgcaccgcg cgctgttacc tttgtcctgt tcaacccgga actgaatcgt    1500
tggtatcgtg cggaaggcgg tggcaacttc gtgctgcgta tggacctgga atcgtttagc    1560
cagctgccgg gctcagtggg taaacatgaa gatgttgcgc aaaaaatcat cgaagtcgaa    1620
gtggaatatg gctcgtggac cctgatgcac cgctacaacc tggccaatga tattctgcgt    1680
aattctatga gtgcgctgga cgcggatctg ctgcaaatcg ttttgtctg gctgcgctat    1740 agtttcctgc gtcagctgga ttggcaacgc tcctacaaca cccagccgcg tctgctggca    1800
catgcacagg aacaactgac cacgaccctg cgcaagtgt tcgttagccg tccggatctg    1860
cgcctgtggg tgcgtctgtg cctgtctatg ctgggtcgtg gtggcggtaa tggccagcgt    1920
attcgcgacg atattctgcg catcatgcat aaacatcaca tccccggaaac gccgggccac    1980 tttatggaac agtggcatca aaaactgcac aacaatacga ccccgacga tgtggccatt    2040 tgcgaaagtt atctggcatt cctgcgctcc aacggtgata aaaacgtgtt ttatgaaacg    2100
ctgcaaaaac atggcgtcac caaagaacgc ctggccagtt atgaacgtcc gattttcgca    2160
gaagtgcaaa cgtacccgtg tgacaccaac tccctgatcc acgatttcga agaatatctg    2220
catgttctga aaagcgtcca ctctggcacg gacctggccg ttgtcctgga ttacgcacgt    2280
tggaccctgg atcaggaact gatttcaaaa gtcgaacata tccaatcggt gcgtgcagaa    2340
ctgatggcca gtccgcaggg tgccctggaa ttttccttcc tgattgcaga agctcgcaaa    2400
atgctgcaaa gtacgctgga acacgttgaa gacccgaccc gtgtccgcga tatgctgttt    2460
ctggacctgg cgctggatga actggcacgt ctggctgtgg aatcccaggg cctggcagac    2520
tatgtggctg aaacggatgt tcagaaagcg tgcaacctgc tggttgtgct ggcgcaacat    2580
gttggttggt caatgctgtc atcggcgttc ctggaaacct cgtatgatct ggcagctctg    2640
gtgtacggta tccagtctga cgttcagctg caagaaccgg attttggcct gcgcctgtat    2700
gccacgatga acgtctgat ggactgcgtc ggccatgatg tcgtggaacg cctgcatcac    2760
gacgttcagc cgaaagcagt gtacattggc gttggttgta atatcgatca aaaagttgtc    2820
accctgttca gcgaagaact gattcgtggt caggcagcat ttgcactggc acaagtgctg    2880
cgcccgctga tgcgtaacat tcgcaaacag gccaacctgg gtaattggca agtgatcagt    2940
ccgggctcct gcaccggtca gggtgcagtt tttgatgaac tgctgtcaat ccaatataaa    3000
acgtttgctg aaccgaccgt ggcgttcgtt cgtcgcattt cgggcgaaga agaaatcccg    3060
acgggcatgg tgggtctgat tacgaccgac accctggata ttctgagcca ttgtgcggtt    3120
cgtgcccgca cgaacacgt ggttctggcc tgctgttttt ctgaagaact gttcgatcag    3180
ctgacggaac gtttccgcgg tgcatgggtc gctgtgcgta gcctgaccga cggctctctg    3240
gattttcagc cgattcaaga aggcgcgggt cgcacgaccg cagctgacac gaccgatggt    3300
gcaagcgaac atgcacagcg tcgcgcagtg tcaatgcgtt cggatattga gaaaaaaccg    3360
gtcaaatctg tgctgggtat cgcccagttt aacacccaac gtggcggttc caaatcaaat    3420
tcgctggcaa aactgattcg cgtgatcccg gattggattc atatcccgcc gtgcgcactg    3480
ctgccgttcg gtgtctgtga acaggtgctg gcagaagctc aaaatagcga cgttggcgaa    3540
```

```
cgctttcagc aactgatggc cgaactggat ggcaaaggtc cgacggacga ttgcagcgca    3600
ctgctggcac gtctgcgtca ttgtgtgcgt cagctggcgc cgtctgatac cttcatgaaa    3660
gaactgcaac aagttctgca acatgaaggc tttcacagta ttgacaacct ggatatgcgt    3720
cgcgcctggg aatgcatcct ggacgtgtgg gcatccaaat ttaatgatcg cgcattcctg    3780
gctctgcgta aagcgggcgc cgttggtaaa accagcctga gcagcctgta tatggcggtt    3840
ctggtccagg aagtcgtgcc ggcggattac gcctttgtgc tgcatacgaa aaacccgttc    3900
accggtgaac cgagcgaaat ttatggcgaa ctggttcacg gcctgggtga agtgctggtt    3960
ggcaactatc cgggtcgtgc actgggcttc acgtacagca atctaccggc caggtccgc    4020
gtgtgtaatt acccgagcaa aaccaaagcg ctgattccgc gcggcggtct gatctttcgt    4080
agtgactcca acggtgaaga cctggaagat tttgcaggcg ctggtctgtt cgattctatt    4140
ctgatgcagc cggcggaaga agttgtcgtg cgttatcgcg aactgaaaat cctgcaagat    4200
aaagcctacc tggaacgtat tctgagtaaa atcggcaaat gcggtattga aatcgaatcc    4260
aactgtggta ataaaccgca ggatattgaa ggctgtattt gtggcgaaga tgtttatgtc    4320
gtccagtcac gcgatcaggt ttga                                            4344
```

<210> SEQ ID NO 6
<211> LENGTH: 1447
<212> TYPE: PRT
<213> ORGANISM: Artificial Sequence
<220> FEATURE:
<223> OTHER INFORMATION: Fragment of Cyanidioschyzon merolae GWD
      polypeptide

<400> SEQUENCE: 6

```
Met Glu Trp Ser Arg Ile Leu Gln Asn Arg Pro Thr Tyr Leu His Trp
1               5                   10                  15

Gly Val Ala Arg Asp His Pro Asp Glu Trp Thr Leu Pro Glu Ala Lys
            20                  25                  30

Thr Phe Pro Pro Gly Thr Ile Arg Phe Asp Lys Ile Ala Val Arg Thr
        35                  40                  45

Glu Phe Pro Ala Glu His Pro Arg Ile Arg Ile Asn Val Pro Phe Phe
    50                  55                  60

Glu Ser Gly Asn Glu Leu Arg Thr Ile Arg Gly Ile Lys Ala Val Val
65                  70                  75                  80

Tyr Arg Ala Lys Asp His Lys Tyr Phe Lys Asp Gly Arg Arg Asp Ile
                85                  90                  95

Phe Val Pro Val Trp Asp Ser Val Arg Thr Trp Val Ile Asp Gly Ala
            100                 105                 110

Gly Ile Glu Glu Asn Val Ala Glu Leu Ser Leu Thr Glu Ser Ala Phe
        115                 120                 125

Arg Thr Ala Leu Gly Val Ser Arg Ser Asp Ser Tyr Met Ser Leu Ser
    130                 135                 140

Arg Glu Thr Ser Pro Gly Pro Asp Ala Ser Gly Ser Gly Arg Ser Ala
145                 150                 155                 160

Val Arg Arg Ser Ile Ser Leu Ser Ser Val Arg Lys Leu Lys Ser Ser
                165                 170                 175

Ala Ser Leu Asp Arg Leu Val Lys Ala Gly Ala Pro Gln Asp Arg Ser
            180                 185                 190

Leu Lys Ala Val Arg Arg Ile His Thr Ala Ala Thr Val Leu Phe Glu
        195                 200                 205
```

```
Glu Leu Phe Gly Gly Val Gly Arg Gly Gly Ser Gly His Leu Asp Val
    210                 215                 220

Val Val Glu Glu Met Glu Pro Gln Ser Glu Tyr His Ile His Met Ala
225                 230                 235                 240

Thr Asp Ile Ser Gly Leu Ala Leu His Trp Gly Val Ser Arg Lys Lys
                245                 250                 255

Pro Gly Gln Trp Val Leu Pro Arg Arg Asp Trp Trp Pro Ala Gly Val
            260                 265                 270

Thr Ser Gln Val Asp His Lys Ala Val Arg Ser Glu Phe Glu Ala Asp
        275                 280                 285

Gln Asp Asn Pro Gly Val Trp Arg Leu Asp Met Cys Phe Arg Arg Glu
    290                 295                 300

Ser Glu Asp Asp Ile Ala Asn Gly Glu Ser Trp Leu Pro Ser Ala Leu
305                 310                 315                 320

Val Phe Val Leu Tyr Gln Ala Glu Tyr Asn Phe Trp Ser Asn Tyr His
                325                 330                 335

Asn Asp Asn Phe Val Val Pro Val Ala Pro Ala Pro Ser Val Leu
            340                 345                 350

Glu Asp Val Tyr Ala Ser Tyr Leu His Thr Leu Gln Glu Gln Glu Lys
        355                 360                 365

Met Leu Gly Asp Arg Ala Gln Gly Glu Glu Pro Glu Thr Leu Pro Val
    370                 375                 380

Gly Thr Ile Leu Gly Leu Glu Arg Arg Ser Leu Asp Asp Asp Gly Glu
385                 390                 395                 400

Thr Val Ile Cys Phe Ser Val Glu Glu Asp Gly Phe Ala Leu Arg Val
                405                 410                 415

His Ala Asp Leu Ser Pro Leu Val Ile His Trp Gly Ile Ala Arg His
            420                 425                 430

Arg Val Thr Glu Phe Leu Gln Pro Asp Glu Ser Leu Ala Val Glu Thr
        435                 440                 445

Lys Gly Arg Thr Tyr Arg Phe Glu Asn Lys Ala Met Arg Thr Glu Phe
    450                 455                 460

Val Pro Asp Glu His His Gln Gly Thr Tyr Tyr Ala Glu Ile His Leu
465                 470                 475                 480

Lys Lys Glu His Ala Pro Arg Ala Val Thr Phe Val Leu Phe Asn Pro
                485                 490                 495

Glu Leu Asn Arg Trp Tyr Arg Ala Glu Gly Gly Asn Phe Val Leu
            500                 505                 510

Arg Met Asp Leu Glu Ser Phe Ser Gln Leu Pro Gly Ser Val Gly Lys
        515                 520                 525

His Glu Asp Val Ala Gln Lys Ile Ile Glu Val Glu Val Glu Tyr Gly
    530                 535                 540

Ser Trp Thr Leu Met His Arg Tyr Asn Leu Ala Asn Asp Ile Leu Arg
545                 550                 555                 560

Asn Ser Met Ser Ala Leu Asp Ala Asp Leu Leu Gln Ile Val Phe Val
                565                 570                 575

Trp Leu Arg Tyr Ser Phe Leu Arg Gln Leu Asp Trp Gln Arg Ser Tyr
            580                 585                 590

Asn Thr Gln Pro Arg Leu Leu Ala His Ala Gln Glu Leu Thr Thr
        595                 600                 605

Thr Leu Ala Gln Val Phe Val Ser Arg Pro Asp Leu Arg Leu Trp Val
    610                 615                 620

Arg Leu Cys Leu Ser Met Leu Gly Arg Gly Gly Gly Asn Gly Gln Arg
```

-continued

```
              625                 630                 635                 640
        Ile Arg Asp Asp Ile Leu Arg Ile Met His Lys His His Ile Pro Glu
                          645                 650                 655
        Thr Pro Gly His Phe Met Glu Gln Trp His Gln Lys Leu His Asn Asn
                          660                 665                 670
        Thr Thr Pro Asp Asp Val Ala Ile Cys Glu Ser Tyr Leu Ala Phe Leu
                          675                 680                 685
        Arg Ser Asn Gly Asp Lys Asn Val Phe Tyr Glu Thr Leu Gln Lys His
                690                 695                 700
        Gly Val Thr Lys Glu Arg Leu Ala Ser Tyr Glu Arg Pro Ile Phe Ala
        705                 710                 715                 720
        Glu Val Gln Thr Tyr Pro Cys Asp Thr Asn Ser Leu Ile His Asp Phe
                          725                 730                 735
        Glu Glu Tyr Leu His Val Leu Lys Ser Val His Ser Gly Thr Asp Leu
                          740                 745                 750
        Ala Val Val Leu Asp Tyr Ala Arg Trp Thr Leu Asp Gln Glu Leu Ile
                          755                 760                 765
        Ser Lys Val Glu His Ile Gln Ser Val Arg Ala Glu Leu Met Ala Ser
                770                 775                 780
        Pro Gln Gly Ala Leu Glu Phe Ser Phe Leu Ile Ala Glu Ala Arg Lys
        785                 790                 795                 800
        Met Leu Gln Ser Thr Leu Glu His Val Glu Asp Pro Thr Arg Val Arg
                          805                 810                 815
        Asp Met Leu Phe Leu Asp Leu Ala Leu Asp Glu Leu Ala Arg Leu Ala
                          820                 825                 830
        Val Glu Ser Gln Gly Leu Ala Asp Tyr Val Ala Glu Thr Asp Val Gln
                835                 840                 845
        Lys Ala Cys Asn Leu Leu Val Val Leu Ala Gln His Val Gly Trp Ser
        850                 855                 860
        Met Leu Ser Ser Ala Phe Leu Glu Thr Ser Tyr Asp Leu Ala Ala Leu
        865                 870                 875                 880
        Val Tyr Gly Ile Gln Ser Asp Val Gln Leu Gln Glu Pro Asp Phe Gly
                          885                 890                 895
        Leu Arg Leu Tyr Ala Thr Met Glu Arg Leu Met Asp Cys Val Gly His
                          900                 905                 910
        Asp Val Val Glu Arg Leu His His Asp Val Gln Pro Lys Ala Val Tyr
                          915                 920                 925
        Ile Gly Val Gly Cys Asn Ile Asp Gln Lys Val Val Thr Leu Phe Ser
                930                 935                 940
        Glu Glu Leu Ile Arg Gly Gln Ala Ala Phe Ala Leu Ala Gln Val Leu
        945                 950                 955                 960
        Arg Pro Leu Met Arg Asn Ile Arg Lys Gln Ala Asn Leu Gly Asn Trp
                          965                 970                 975
        Gln Val Ile Ser Pro Gly Ser Cys Thr Gly Gln Gly Ala Val Phe Asp
                          980                 985                 990
        Glu Leu Leu Ser Ile Gln Tyr Lys Thr Phe Ala Glu Pro Thr Val Ala
                          995                1000                1005
        Phe Val Arg Arg Ile Ser Gly Glu Glu Glu Ile Pro Thr Gly Met
                1010                1015                1020
        Val Gly Leu Ile Thr Thr Asp Thr Leu Asp Ile Leu Ser His Cys
                1025                1030                1035
        Ala Val Arg Ala Arg Asn Glu His Val Val Leu Ala Cys Cys Phe
                1040                1045                1050
```

-continued

Ser Glu Glu Leu Phe Asp Gln Leu Thr Glu Arg Phe Arg Gly Ala
1055                1060                1065

Trp Val Ala Val Arg Ser Leu Thr Asp Gly Ser Leu Asp Phe Gln
1070                1075                1080

Pro Ile Gln Glu Gly Ala Gly Arg Thr Thr Ala Ala Asp Thr Thr
1085                1090                1095

Asp Gly Ala Ser Glu His Ala Gln Arg Arg Ala Val Ser Met Arg
1100                1105                1110

Ser Asp Ile Glu Lys Lys Pro Val Lys Ser Val Leu Gly Ile Ala
1115                1120                1125

Gln Phe Asn Thr Gln Arg Gly Gly Ser Lys Ser Asn Ser Leu Ala
1130                1135                1140

Lys Leu Ile Arg Val Ile Pro Asp Trp Ile His Ile Pro Pro Cys
1145                1150                1155

Ala Leu Leu Pro Phe Gly Val Cys Glu Gln Val Leu Ala Glu Ala
1160                1165                1170

Gln Asn Ser Asp Val Gly Glu Arg Phe Gln Gln Leu Met Ala Glu
1175                1180                1185

Leu Asp Gly Lys Gly Pro Thr Asp Asp Cys Ser Ala Leu Leu Ala
1190                1195                1200

Arg Leu Arg His Cys Val Arg Gln Leu Ala Pro Ser Asp Thr Phe
1205                1210                1215

Met Lys Glu Leu Gln Gln Val Leu Gln His Glu Gly Phe His Ser
1220                1225                1230

Ile Asp Asn Leu Asp Met Arg Arg Ala Trp Glu Cys Ile Leu Asp
1235                1240                1245

Val Trp Ala Ser Lys Phe Asn Asp Arg Ala Phe Leu Ala Leu Arg
1250                1255                1260

Lys Ala Gly Ala Val Gly Lys Thr Ser Leu Ser Ser Leu Tyr Met
1265                1270                1275

Ala Val Leu Val Gln Glu Val Val Pro Ala Asp Tyr Ala Phe Val
1280                1285                1290

Leu His Thr Lys Asn Pro Phe Thr Gly Glu Pro Ser Glu Ile Tyr
1295                1300                1305

Gly Glu Leu Val His Gly Leu Gly Glu Val Leu Val Gly Asn Tyr
1310                1315                1320

Pro Gly Arg Ala Leu Gly Phe Thr Tyr Ser Lys Ser Thr Gly Gln
1325                1330                1335

Val Arg Val Cys Asn Tyr Pro Ser Lys Thr Lys Ala Leu Ile Pro
1340                1345                1350

Arg Gly Gly Leu Ile Phe Arg Ser Asp Ser Asn Gly Glu Asp Leu
1355                1360                1365

Glu Asp Phe Ala Gly Ala Gly Leu Phe Asp Ser Ile Leu Met Gln
1370                1375                1380

Pro Ala Glu Glu Val Val Val Arg Tyr Arg Glu Leu Lys Ile Leu
1385                1390                1395

Gln Asp Lys Ala Tyr Leu Glu Arg Ile Leu Ser Lys Ile Gly Lys
1400                1405                1410

Cys Gly Ile Glu Ile Glu Ser Asn Cys Gly Asn Lys Pro Gln Asp
1415                1420                1425

Ile Glu Gly Cys Ile Cys Gly Glu Asp Val Tyr Val Gln Ser
1430                1435                1440

Arg Asp Gln Val
    1445

<210> SEQ ID NO 7
<211> LENGTH: 4304
<212> TYPE: DNA
<213> ORGANISM: Artificial Sequence
<220> FEATURE:
<223> OTHER INFORMATION: Fragment of Cyanidioschyzon merolae GWD
      polypeptide

<400> SEQUENCE: 7

| | | | |
|---|---|---|---|
| atgattgggg cgtggcccgc gaccacccgg atgaatggac cctgccggaa gcaaaaacgt | | | 60 |
| ttccgccggg caccattcgc ttcgataaaa tcgctgtgcg tacggaattt ccggcggaac | | | 120 |
| atccgcgtat tcgcatcaac gttccgtttt cgaaagcgg taatgaactg cgtaccattc | | | 180 |
| gtggcatcaa agctgtggtt tatcgtgcga agatcacaa atactttaaa gacggccgtc | | | 240 |
| gcgatatttt cgttccggtc tgggacagcg ttcgcacctg ggtcattgat ggcgccggta | | | 300 |
| tcgaagaaaa tgtggcagaa ctgagtctga cggaatccgc atttcgcacc gctctgggtg | | | 360 |
| ttagtcgttc cgactcatat atgtcgctga ccgtgaaaac ctctccgggc ccggatgctt | | | 420 |
| ctggcagtgg tcgctctgcg gttcgtcgta gcattagcct gagcagcgtg cgcaaactga | | | 480 |
| aaagttccgc aagtctggac cgtctggtga agcaggtgc tccgcaggat cgctccctga | | | 540 |
| aagcagtgcg tcgcatccat acggcggcca ccgttctgtt tgaagaactg ttcggcggtg | | | 600 |
| tcggtcgcgg cggttcaggt cacctggacg tcgtggttga agaaatggaa ccgcagtcgg | | | 660 |
| aatatcatat tcacatggcc acggatattt caggtctggc actgcattgg ggcgtgtcgc | | | 720 |
| gtaaaaaacc gggtcaatgg gttctgccgc gtcgcgactg gtggccggcc ggcgtgacca | | | 780 |
| gccaggttga tcacaaagct gtgcgttctg aatttgaagc ggaccaagat aatccgggcg | | | 840 |
| tgtggcgcct ggatatgtgc tttcgtcgcg aaagcgaaga tgacattgcg aatggcgaat | | | 900 |
| catggctgcc gtcggctctg gtgtttgttc tgtatcaggc ggaatacaac ttctggtcta | | | 960 |
| actaccataa cgacaacttc gtcgtgccgg tggcaccgcc ggccccgagc gtcctggaag | | | 1020 |
| atgtgtatgc ttcttacctg cacaccctgc aagaacaaga aaaaatgctg ggtgatcgcg | | | 1080 |
| cacagggcga agaaccggaa acgctgccgg ttggcaccat tctgggtctg aacgtcgct | | | 1140 |
| cactggatga cgatggtgaa accgtgattt gcttttcggt cgaagaagac ggcttcgccc | | | 1200 |
| tgcgtgtcca tgcggatctg agtccgctgg tgattcattg gggtatcgcg cgtcaccgcg | | | 1260 |
| tgaccgaatt tctgcaaccg gatgaatccc tggctgttga aacgaaaggc cgtacctatc | | | 1320 |
| gcttcgaaaa taaagcgatg cgtacggaat ttgtgccgga tgaacatcac cagggcacct | | | 1380 |
| attacgccga aattcatctg aaaaaagaac acgaccgcg cgctgttacc tttgtcctgt | | | 1440 |
| tcaacccgga actgaatcgt tggtatcgtg cggaaggcgg tggcaacttc gtgctgcgta | | | 1500 |
| tggacctgga atcgtttagc cagctgccgg gctcagtggg taaacatgaa gatgttgcgc | | | 1560 |
| aaaaaatcat cgaagtcgaa gtggaatatg gctcgtggac cctgatgcac cgctacaacc | | | 1620 |
| tggccaatga tattctgcgt aattctatga gtgcgctgga cgcggatctg ctgcaaatcg | | | 1680 |
| tttttgtctg gctgcgctat agtttcctgc gtcagctgga ttggcaacgc tcctacaaca | | | 1740 |
| cccagccgcg tctgctggca catgcacagg aacaactgac cacgaccctg cgcaagtgt | | | 1800 |
| tcgttagccg tccggatctg cgcctgtggg tgcgtctgtg cctgtctatg ctgggtcgtg | | | 1860 |
| gtggcggtaa tggccagcgt attcgcgacg atattctgcg catcatgcat aaacatcaca | | | 1920 |
| tcccggaaac gccgggccac tttatggaac agtggcatca aaaactgcac aacaatacga | | | 1980 |

```
ccccggacga tgtggccatt tgcgaaagtt atctggcatt cctgcgctcc aacggtgata    2040
aaaacgtgtt ttatgaaacg ctgcaaaaac atggcgtcac caaagaacgc ctggccagtt    2100
atgaacgtcc gattttcgca gaagtgcaaa cgtacccgtg tgacaccaac tccctgatcc    2160
acgatttcga gaatatctg catgttctga aaagcgtcca ctctggcacg acctggccg     2220 ttgtcctgga ttacgcacgt tggaccctgg atcaggaact gatttcaaaa gtcgaacata    2280
tccaatcggt gcgtgcagaa ctgatggcca gtccgcaggg tgccctggaa ttttccttcc    2340
tgattgcaga agctcgcaaa atgctgcaaa gtacgctgga acacgttgaa gacccgaccc    2400
gtgtccgcga tatgctgttt ctggacctgg cgctggatga actggcacgt ctggctgtgg    2460
aatcccaggg cctggcagac tatgtggctg aaacggatgt tcagaaagcg tgcaacctgc    2520
tggttgtgct ggcgcaacat gttggttggt caatgctgtc atcggcgttc ctggaaacct    2580
cgtatgatct ggcagctctg gtgtacggta tccagtctga cgttcagctg caagaaccgg    2640
attttggcct gcgcctgtat gccacgatgg aacgtctgat ggactgcgtc ggccatgatg    2700
tcgtggaacg cctgcatcac gacgttcagc cgaaagcagt gtacattggc gttggttgta    2760
atatcgatca aaaagttgtc accctgttca gcgaagaact gattcgtggt caggcagcat    2820
ttgcactggc acaagtgctg cgcccgctga tgcgtaacat tcgcaaacag gccaacctgg    2880
gtaattggca agtgatcagt ccgggctcct gcaccggtca gggtgcagtt tttgatgaac    2940
tgctgtcaat ccaatataaa acgtttgctg aaccgaccgt ggcgttcgtt cgtcgcattt    3000
cgggcgaaga agaaatcccg acgggcatgg tgggtctgat tacgaccgac accctggata    3060
ttctgagcca ttgtgcggtt cgtgcccgca cgaacacgt ggttctggcc tgctgttttt     3120
ctgaagaact gttcgatcag ctgacggaac gtttccgcgg tgcatgggtc gctgtgcgta    3180
gcctgaccga cggctctctg gattttcagc cgattcaaga aggcgcgggt cgcacgaccg    3240
cagctgacac gaccgatggt gcaagcgaac atgcacagcg tcgcgcagtg tcaatgcgtt    3300
cggatattga gaaaaaaccg gtcaaatctg tgctgggtat cgcccagttt aacacccaac    3360
gtggcggttc caaatcaaat tcgctggcaa aactgattcg cgtgatcccg gattggattc    3420
atatcccgcc gtgcgcactg ctgccgttcg gtgtctgtga acaggtgctg gcagaagctc    3480
aaaatagcga cgttggcgaa cgcttcagc aactgatggc cgaactggat ggcaaaggtc     3540
cgacggacga ttgcagcgca ctgctggcac gtctgcgtca ttgtgtgcgt cagctggcgc    3600
cgtctgatac cttcatgaaa gaactgcaac aagttctgca acatgaaggc tttcacagta    3660
ttgacaacct ggatatgcgt cgcgcctggg aatgcatcct ggacgtgtgg gcatccaaat    3720
ttaatgatcg cgcattcctg gctctgcgta agcgggcgc cgttggtaaa accagcctga     3780
gcagcctgta tatggcggtt ctggtccagg aagtcgtgcc ggcggattac gcctttgtgc    3840
tgcatacgaa aaacccgttc accggtgaac cgagcgaaat ttatggcgaa ctggttcacg    3900
gcctgggtga agtgctggtt ggcaactatc cgggtcgtgc actgggcttc acgtacagca    3960
aatctaccgg ccaggtccgc gtgtgtaatt acccgagcaa aaccaaagcg ctgattccgc    4020
gcggcggtct gatctttcgt agtgactcca acggtgaaga cctggaagat tttgcaggcg    4080
ctggtctgtt cgattctatt ctgatgcagc cggcggaaga agttgtcgtg cgttatcgcg    4140
aactgaaaat cctgcaagat aaagcctacc tggaacgtat tctgagtaaa atcggcaaat    4200
gcggtattga aatcgaatcc aactgtggta ataaaccgca ggatattgaa ggctgtattt    4260
gtggcgaaga tgtttatgtc gtccagtcac gcgatcaggt ttga                    4304
```

```
<210> SEQ ID NO 8
<211> LENGTH: 1441
<212> TYPE: PRT
<213> ORGANISM: Artificial Sequence
<220> FEATURE:
<223> OTHER INFORMATION: Fragment of Cyanidioschyzon merolae GWD
      polypeptide

<400> SEQUENCE: 8

Met Gln Asn Arg Pro Thr Tyr Leu His Trp Gly Val Ala Arg Asp His
1               5                   10                  15

Pro Asp Glu Trp Thr Leu Pro Glu Ala Lys Thr Phe Pro Pro Gly Thr
            20                  25                  30

Ile Arg Phe Asp Lys Ile Ala Val Arg Thr Glu Phe Pro Ala Glu His
        35                  40                  45

Pro Arg Ile Arg Ile Asn Val Pro Phe Phe Glu Ser Gly Asn Glu Leu
    50                  55                  60

Arg Thr Ile Arg Gly Ile Lys Ala Val Val Tyr Arg Ala Lys Asp His
65                  70                  75                  80

Lys Tyr Phe Lys Asp Gly Arg Arg Asp Ile Phe Val Pro Val Trp Asp
                85                  90                  95

Ser Val Arg Thr Trp Val Ile Asp Gly Ala Gly Ile Glu Glu Asn Val
            100                 105                 110

Ala Glu Leu Ser Leu Thr Glu Ser Ala Phe Arg Thr Ala Leu Gly Val
        115                 120                 125

Ser Arg Ser Asp Ser Tyr Met Ser Leu Ser Arg Glu Thr Ser Pro Gly
    130                 135                 140

Pro Asp Ala Ser Gly Ser Gly Arg Ser Ala Val Arg Arg Ser Ile Ser
145                 150                 155                 160

Leu Ser Ser Val Arg Lys Leu Lys Ser Ser Ala Ser Leu Asp Arg Leu
                165                 170                 175

Val Lys Ala Gly Ala Pro Gln Asp Arg Ser Leu Lys Ala Val Arg Arg
            180                 185                 190

Ile His Thr Ala Ala Thr Val Leu Phe Glu Glu Leu Phe Gly Gly Val
        195                 200                 205

Gly Arg Gly Gly Ser Gly His Leu Asp Val Val Glu Glu Met Glu
    210                 215                 220

Pro Gln Ser Glu Tyr His Ile His Met Ala Thr Asp Ile Ser Gly Leu
225                 230                 235                 240

Ala Leu His Trp Gly Val Ser Arg Lys Lys Pro Gly Gln Trp Val Leu
                245                 250                 255

Pro Arg Arg Asp Trp Trp Pro Ala Gly Val Thr Ser Gln Val Asp His
            260                 265                 270

Lys Ala Val Arg Ser Glu Phe Glu Ala Asp Gln Asp Asn Pro Gly Val
        275                 280                 285

Trp Arg Leu Asp Met Cys Phe Arg Arg Glu Ser Glu Asp Asp Ile Ala
    290                 295                 300

Asn Gly Glu Ser Trp Leu Pro Ser Ala Leu Val Phe Val Leu Tyr Gln
305                 310                 315                 320

Ala Glu Tyr Asn Phe Trp Ser Asn Tyr His Asn Asp Asn Phe Val Val
                325                 330                 335

Pro Val Ala Pro Pro Ala Pro Ser Val Leu Glu Asp Val Tyr Ala Ser
            340                 345                 350

Tyr Leu His Thr Leu Gln Glu Gln Glu Lys Met Leu Gly Asp Arg Ala
        355                 360                 365
```

-continued

Gln Gly Glu Glu Pro Glu Thr Leu Pro Val Gly Thr Ile Leu Gly Leu
    370                 375                 380

Glu Arg Arg Ser Leu Asp Asp Gly Glu Thr Val Ile Cys Phe Ser
385                 390                 395                 400

Val Glu Glu Asp Gly Phe Ala Leu Arg Val His Ala Asp Leu Ser Pro
                    405                 410                 415

Leu Val Ile His Trp Gly Ile Ala Arg His Arg Val Thr Glu Phe Leu
                420                 425                 430

Gln Pro Asp Glu Ser Leu Ala Val Glu Thr Lys Gly Arg Thr Tyr Arg
            435                 440                 445

Phe Glu Asn Lys Ala Met Arg Thr Glu Phe Val Pro Asp Glu His His
    450                 455                 460

Gln Gly Thr Tyr Tyr Ala Glu Ile His Leu Lys Lys Glu His Ala Pro
465                 470                 475                 480

Arg Ala Val Thr Phe Val Leu Phe Asn Pro Glu Leu Asn Arg Trp Tyr
                    485                 490                 495

Arg Ala Glu Gly Gly Asn Phe Val Leu Arg Met Asp Leu Glu Ser
                500                 505                 510

Phe Ser Gln Leu Pro Gly Ser Val Gly Lys His Glu Asp Val Ala Gln
            515                 520                 525

Lys Ile Ile Glu Val Glu Val Glu Tyr Gly Ser Trp Thr Leu Met His
    530                 535                 540

Arg Tyr Asn Leu Ala Asn Asp Ile Leu Arg Asn Ser Met Ser Ala Leu
545                 550                 555                 560

Asp Ala Asp Leu Leu Gln Ile Val Phe Val Trp Leu Arg Tyr Ser Phe
                    565                 570                 575

Leu Arg Gln Leu Asp Trp Gln Arg Ser Tyr Asn Thr Gln Pro Arg Leu
                580                 585                 590

Leu Ala His Ala Gln Glu Gln Leu Thr Thr Thr Leu Ala Gln Val Phe
            595                 600                 605

Val Ser Arg Pro Asp Leu Arg Leu Trp Val Arg Leu Cys Leu Ser Met
    610                 615                 620

Leu Gly Arg Gly Gly Gly Asn Gly Gln Arg Ile Arg Asp Asp Ile Leu
625                 630                 635                 640

Arg Ile Met His Lys His His Ile Pro Glu Thr Pro Gly His Phe Met
                    645                 650                 655

Glu Gln Trp His Gln Lys Leu His Asn Asn Thr Thr Pro Asp Asp Val
                660                 665                 670

Ala Ile Cys Glu Ser Tyr Leu Ala Phe Leu Arg Ser Asn Gly Asp Lys
            675                 680                 685

Asn Val Phe Tyr Glu Thr Leu Gln Lys His Gly Val Thr Lys Glu Arg
    690                 695                 700

Leu Ala Ser Tyr Glu Arg Pro Ile Phe Ala Glu Val Gln Thr Tyr Pro
705                 710                 715                 720

Cys Asp Thr Asn Ser Leu Ile His Asp Phe Glu Glu Tyr Leu His Val
                    725                 730                 735

Leu Lys Ser Val His Ser Gly Thr Asp Leu Ala Val Val Leu Asp Tyr
                740                 745                 750

Ala Arg Trp Thr Leu Asp Gln Glu Leu Ile Ser Lys Val Glu His Ile
            755                 760                 765

Gln Ser Val Arg Ala Glu Leu Met Ala Ser Pro Gln Gly Ala Leu Glu
    770                 775                 780

```
Phe Ser Phe Leu Ile Ala Glu Ala Arg Lys Met Leu Gln Ser Thr Leu
785                 790                 795                 800

Glu His Val Glu Asp Pro Thr Arg Val Arg Asp Met Leu Phe Leu Asp
            805                 810                 815

Leu Ala Leu Asp Glu Leu Ala Arg Leu Ala Val Glu Ser Gln Gly Leu
            820                 825                 830

Ala Asp Tyr Val Ala Glu Thr Asp Val Gln Lys Ala Cys Asn Leu Leu
            835                 840                 845

Val Val Leu Ala Gln His Val Gly Trp Ser Met Leu Ser Ser Ala Phe
850                 855                 860

Leu Glu Thr Ser Tyr Asp Leu Ala Ala Leu Val Tyr Gly Ile Gln Ser
865                 870                 875                 880

Asp Val Gln Leu Gln Glu Pro Asp Phe Gly Leu Arg Leu Tyr Ala Thr
                885                 890                 895

Met Glu Arg Leu Met Asp Cys Val Gly His Asp Val Val Glu Arg Leu
            900                 905                 910

His His Asp Val Gln Pro Lys Ala Val Tyr Ile Gly Val Gly Cys Asn
            915                 920                 925

Ile Asp Gln Lys Val Val Thr Leu Phe Ser Glu Glu Leu Ile Arg Gly
930                 935                 940

Gln Ala Ala Phe Ala Leu Ala Gln Val Leu Arg Pro Leu Met Arg Asn
945                 950                 955                 960

Ile Arg Lys Gln Ala Asn Leu Gly Asn Trp Gln Val Ile Ser Pro Gly
                965                 970                 975

Ser Cys Thr Gly Gln Gly Ala Val Phe Asp Glu Leu Leu Ser Ile Gln
            980                 985                 990

Tyr Lys Thr Phe Ala Glu Pro Thr  Val Ala Phe Val Arg  Arg Ile Ser
        995                 1000                1005

Gly Glu  Glu Glu Ile Pro Thr  Gly Met Val Gly Leu  Ile Thr Thr
1010                1015                1020

Asp Thr  Leu Asp Ile Leu Ser  His Cys Ala Val Arg  Ala Arg Asn
    1025                1030                1035

Glu His  Val Val Leu Ala Cys  Cys Phe Ser Glu Glu  Leu Phe Asp
    1040                1045                1050

Gln Leu  Thr Glu Arg Phe Arg  Gly Ala Trp Val Ala  Val Arg Ser
    1055                1060                1065

Leu Thr  Asp Gly Ser Leu Asp  Phe Gln Pro Ile Gln  Glu Gly Ala
    1070                1075                1080

Gly Arg  Thr Thr Ala Ala Asp  Thr Thr Asp Gly Ala  Ser Glu His
    1085                1090                1095

Ala Gln  Arg Arg Ala Val Ser  Met Arg Ser Asp Ile  Glu Lys Lys
    1100                1105                1110

Pro Val  Lys Ser Val Leu Gly  Ile Ala Gln Phe Asn  Thr Gln Arg
    1115                1120                1125

Gly Gly  Ser Lys Ser Asn Ser  Leu Ala Lys Leu Ile  Arg Val Ile
    1130                1135                1140

Pro Asp  Trp Ile His Ile Pro  Pro Cys Ala Leu Leu  Pro Phe Gly
    1145                1150                1155

Val Cys  Glu Gln Val Leu Ala  Glu Ala Gln Asn Ser  Asp Val Gly
    1160                1165                1170

Glu Arg  Phe Gln Gln Leu Met  Ala Glu Leu Asp Gly  Lys Gly Pro
    1175                1180                1185

Thr Asp  Asp Cys Ser Ala Leu  Leu Ala Arg Leu Arg  His Cys Val
```

```
Arg Gln Leu Ala Pro Ser Asp Thr Phe Met Lys Glu Leu Gln Gln
    1205                1210                1215

Val Leu Gln His Glu Gly Phe His Ser Ile Asp Asn Leu Asp Met
    1220                1225                1230

Arg Arg Ala Trp Glu Cys Ile Leu Asp Val Trp Ala Ser Lys Phe
    1235                1240                1245

Asn Asp Arg Ala Phe Leu Ala Leu Arg Lys Ala Gly Ala Val Gly
    1250                1255                1260

Lys Thr Ser Leu Ser Ser Leu Tyr Met Ala Val Leu Val Gln Glu
    1265                1270                1275

Val Val Pro Ala Asp Tyr Ala Phe Val Leu His Thr Lys Asn Pro
    1280                1285                1290

Phe Thr Gly Glu Pro Ser Glu Ile Tyr Gly Glu Leu Val His Gly
    1295                1300                1305

Leu Gly Glu Val Leu Val Gly Asn Tyr Pro Gly Arg Ala Leu Gly
    1310                1315                1320

Phe Thr Tyr Ser Lys Ser Thr Gly Gln Val Arg Val Cys Asn Tyr
    1325                1330                1335

Pro Ser Lys Thr Lys Ala Leu Ile Pro Arg Gly Gly Leu Ile Phe
    1340                1345                1350

Arg Ser Asp Ser Asn Gly Glu Asp Leu Glu Asp Phe Ala Gly Ala
    1355                1360                1365

Gly Leu Phe Asp Ser Ile Leu Met Gln Pro Ala Glu Glu Val Val
    1370                1375                1380

Val Arg Tyr Arg Glu Leu Lys Ile Leu Gln Asp Lys Ala Tyr Leu
    1385                1390                1395

Glu Arg Ile Leu Ser Lys Ile Gly Lys Cys Gly Ile Glu Ile Glu
    1400                1405                1410

Ser Asn Cys Gly Asn Lys Pro Gln Asp Ile Glu Gly Cys Ile Cys
    1415                1420                1425

Gly Glu Asp Val Tyr Val Val Gln Ser Arg Asp Gln Val
    1430                1435                1440

<210> SEQ ID NO 9
<211> LENGTH: 4308
<212> TYPE: DNA
<213> ORGANISM: Artificial Sequence
<220> FEATURE:
<223> OTHER INFORMATION: Fragment of Cyanidioschyzon merolae GWD
      polypeptide

<400> SEQUENCE: 9
atgctgcatt ggggcgtggc ccgcgaccac ccggatgaat ggaccctgcc ggaagcaaaa      60
acgtttccgc cgggcaccat tcgcttcgat aaaatcgctg tgcgtacgga atttccggcg     120
gaacatccgc gtattcgcat caacgttccg tttttcgaaa gcgtaatga actgcgtacc     180 attcgtggca tcaaagctgt ggtttatcgt gcgaaagatc acaaatactt taagacggc     240 cgtcgcgata ttttcgttcc ggtctgggac agcgttcgca cctgggtcat tgatggcgcc     300
ggtatcgaag aaaatgtggc agaactgagt ctgacgaat ccgcatttcg caccgctctg     360
ggtgttagtc gttccgactc atatatgtcg ctgagccgtg aaacctctcc gggcccggat     420
gcttctggca gtggtcgctc tgcggttcgt cgtagcatta gcctgagcag cgtgcgcaaa     480
ctgaaaagtt ccgcaagtct ggaccgtctg gtgaaagcag gtgctccgca ggatcgctcc     540
```

-continued

```
ctgaaagcag tgcgtcgcat ccatacggcg gccaccgttc tgtttgaaga actgttcggc    600
ggtgtcggtc gcggcggttc aggtcacctg gacgtcgtgg ttgaagaaat ggaaccgcag    660
tcggaatatc atattcacat ggccacggat atttcaggtc tggcactgca ttggggcgtg    720
tcgcgtaaaa aaccgggtca atgggttctg ccgcgtcgcg actggtggcc ggccggcgtg    780
accagccagg ttgatcacaa agctgtgcgt tctgaatttg aagcggacca agataatccg    840
ggcgtgtggc gcctggatat gtgctttcgt cgcgaaagcg aagatgacat tgcgaatggc    900
gaatcatggc tgccgtcggc tctggtgttt gttctgtatc aggcggaata caacttctgg    960
tctaactacc ataacgacaa cttcgtcgtg ccggtggcac cgccggcccc gagcgtcctg   1020
gaagatgtgt atgcttctta cctgcacacc ctgcaagaac aagaaaaaat gctgggtgat   1080
cgcgcacagg gcgaagaacc ggaaacgctg ccggttggca ccattctggg tctgaacgt    1140 cgctcactgg atgacgatgg tgaaaccgtg atttgctttt cggtcgaaga agacggcttc   1200
gccctgcgtg tccatgcgga tctgagtccg ctggtgattc attggggtat cgcgcgtcac   1260
cgcgtgaccg aatttctgca accggatgaa tccctggctg ttgaaacgaa aggccgtacc   1320
tatcgcttcg aaaataaagc gatgcgtacg gaatttgtgc cggatgaaca tcaccagggc   1380
acctattacg ccgaaattca tctgaaaaaa gaacacgcac cgcgcgctgt tacctttgtc   1440
ctgttcaacc cggaactgaa tcgttggtat cgtgcggaag gcggtggcaa cttcgtgctg   1500
cgtatggacc tggaatcgtt tagccagctg ccgggctcag tgggtaaaca tgaagatgtt   1560
gcgcaaaaaa tcatcgaagt cgaagtggaa tatggctcgt ggaccctgat gcaccgctac   1620
aacctggcca atgatattct gcgtaattct atgagtgcgc tggacgcgga tctgctgcaa   1680
atcgtttttg tctggctgcg ctatagtttc ctgcgtcagc tggattggca acgtcctac    1740 aacacccagc cgcgtctgct ggcacatgca caggaacaac tgaccacgac cctggcgcaa   1800
gtgttcgtta gccgtccgga tctgcgcctg tgggtgcgtc tgtgcctgtc tatgctgggt   1860
cgtggtggcg gtaatggcca gcgtattcgc gacgatattc tgcgcatcat gcataaacat   1920
cacatcccgg aaacgccggg ccactttatg gaacagtggc atcaaaaact gcacaacaat   1980 acgacccccgg acgatgtggc catttgcgaa agttatctgg cattcctgcg ctccaacggt   2040
gataaaaacg tgttttatga aacgctgcaa aaacatggcg tcaccaaaga acgcctggcc   2100
agttatgaac gtccgatttt cgcagaagtg caaacgtacc cgtgtgacac caactccctg   2160
atccacgatt tcgaagaata tctgcatgtt ctgaaaagcg tccactctgg cacggacctg   2220
gccgttgtcc tggattacgc acgttggacc ctggatcagg aactgatttc aaaagtcgaa   2280
catatccaat cggtgcgtgc agaactgatg gccagtccgc agggtgccct ggaattttcc   2340
ttcctgattg cagaagctcg caaaatgctg caaagtacgc tggaacacgt tgaagacccg   2400
acccgtgtcc gcgatatgct gtttctggac ctggcgctgg atgaactggc acgtctggct   2460
gtggaatccc agggcctggc agactatgtg gctgaaacgg atgttcagaa agcgtgcaac   2520
ctgctggttg tgctggcgca acatgttggt tggtcaatgc tgtcatcggc gttcctggaa   2580
acctcgtatg atctggcagc tctggtgtac ggtatccagt ctgacgttca gctgcaagaa   2640
ccggattttg gcctgcgcct gtatgccacg atggaacgtc tgatggactg cgtcggccat   2700
gatgtcgtgg aacgcctgca tcacgacgtt cagccgaaag cagtgtacat tggcgttggt   2760
tgtaatatcg atcaaaaagt tgtcaccctg ttcagcgaag aactgattcg tggtcaggca   2820
gcatttgcac tggcacaagt gctgcgcccg ctgatgcgta acattcgcaa acaggccaac   2880
ctgggtaatt ggcaagtgat cagtccgggc tcctgcaccg gtcagggtgc agtttttgat   2940
```

```
gaactgctgt caatccaata taaaacgttt gctgaaccga ccgtggcgtt cgttcgtcgc    3000
atttcgggcg aagaagaaat cccgacgggc atggtgggtc tgattacgac cgacaccctg    3060
gatattctga gccattgtgc ggttcgtgcc cgcaacgaac acgtggttct ggcctgctgt    3120
ttttctgaag aactgttcga tcagctgacg gaacgtttcc gcggtgcatg ggtcgctgtg    3180
cgtagcctga ccgacggctc tctggatttt cagccgattc aagaaggcgc gggtcgcacg    3240
accgcagctg acacgaccga tggtgcaagc gaacatgcac agcgtcgcgc agtgtcaatg    3300
cgttcggata ttgagaaaaa accggtcaaa tctgtgctgg gtatcgccca gtttaacacc    3360
caacgtggcg gttccaaatc aaattcgctg caaaactga ttcgcgtgat cccggattgg     3420
attcatatcc cgccgtgcgc actgctgccg ttcggtgtct gtgaacaggt gctggcagaa    3480
gctcaaaata gcgacgttgg cgaacgcttt cagcaactga tggccgaact ggatggcaaa    3540
ggtccgacgg acgattgcag cgcactgctg gcacgtctgc gtcattgtgt gcgtcagctg    3600
gcgccgtctg ataccttcat gaagaactg caacaagttc tgcaacatga aggctttcac     3660
agtattgaca acctggatat gcgtcgcgcc tgggaatgca tcctggacgt gtgggcatcc    3720
aaatttaatg atcgcgcatt cctggctctg cgtaaagcgg gcgccgttgg taaaaccagc    3780
ctgagcagcc tgtatatggc ggttctggtc caggaagtcg tgccggcgga ttacgccttt    3840
gtgctgcata cgaaaaaccc gttcaccggt gaaccgagcg aaatttatgg cgaactggtt    3900
cacggcctgg gtgaagtgct ggttggcaac tatccgggtc gtgcactggg cttcacgtac    3960
agcaaatcta ccggccaggt ccgcgtgtgt aattacccga gcaaaaccaa agcgctgatt    4020
ccgcgcggcg gtctgatctt tcgtagtgac tccaacggtg aagacctgga agattttgca    4080
ggcgctggtc tgttcgattc tattctgatg cagccggcgg aagaagttgt cgtgcgttat    4140
cgcgaactga aaatcctgca agataaagcc tacctggaac gtattctgag taaaatcggc    4200
aaatgcggta ttgaaatcga atccaactgt ggtaataaac cgcaggatat tgaaggctgt    4260
atttgtggcg aagatgttta tgtcgtccag tcacgcgatc aggtttga                 4308
```

<210> SEQ ID NO 10
<211> LENGTH: 1435
<212> TYPE: PRT
<213> ORGANISM: Artificial Sequence
<220> FEATURE:
<223> OTHER INFORMATION: Fragment of Cyanidioschyzon merolae GWD
      polypeptide

<400> SEQUENCE: 10

```
Met Leu His Trp Gly Val Ala Arg Asp His Pro Asp Glu Trp Thr Leu
1               5                   10                  15

Pro Glu Ala Lys Thr Phe Pro Pro Gly Thr Ile Arg Phe Asp Lys Ile
            20                  25                  30

Ala Val Arg Thr Glu Phe Pro Ala Glu His Pro Arg Ile Arg Ile Asn
        35                  40                  45

Val Pro Phe Phe Glu Ser Gly Asn Glu Leu Arg Thr Ile Arg Gly Ile
    50                  55                  60

Lys Ala Val Val Tyr Arg Ala Lys Asp His Lys Tyr Phe Lys Asp Gly
65                  70                  75                  80

Arg Arg Asp Ile Phe Val Pro Val Trp Asp Ser Val Arg Thr Trp Val
                85                  90                  95

Ile Asp Gly Ala Gly Ile Glu Glu Asn Val Ala Glu Leu Ser Leu Thr
            100                 105                 110
```

-continued

```
Glu Ser Ala Phe Arg Thr Ala Leu Gly Val Ser Arg Ser Asp Ser Tyr
                115                 120                 125

Met Ser Leu Ser Arg Glu Thr Ser Pro Gly Pro Asp Ala Ser Gly Ser
130                 135                 140

Gly Arg Ser Ala Val Arg Arg Ser Ile Ser Leu Ser Ser Val Arg Lys
145                 150                 155                 160

Leu Lys Ser Ser Ala Ser Leu Asp Arg Leu Val Lys Ala Gly Ala Pro
                165                 170                 175

Gln Asp Arg Ser Leu Lys Ala Val Arg Arg Ile His Thr Ala Ala Thr
            180                 185                 190

Val Leu Phe Glu Glu Leu Phe Gly Gly Val Gly Arg Gly Ser Gly
        195                 200                 205

His Leu Asp Val Val Glu Glu Met Glu Pro Gln Ser Glu Tyr His
210                 215                 220

Ile His Met Ala Thr Asp Ile Ser Gly Leu Ala Leu His Trp Gly Val
225                 230                 235                 240

Ser Arg Lys Lys Pro Gly Gln Trp Val Leu Pro Arg Arg Asp Trp Trp
                245                 250                 255

Pro Ala Gly Val Thr Ser Gln Val Asp His Lys Ala Val Arg Ser Glu
            260                 265                 270

Phe Glu Ala Asp Gln Asp Asn Pro Gly Val Trp Arg Leu Asp Met Cys
        275                 280                 285

Phe Arg Arg Glu Ser Glu Asp Ile Ala Asn Gly Glu Ser Trp Leu
        290                 295                 300

Pro Ser Ala Leu Val Phe Val Leu Tyr Gln Ala Glu Tyr Asn Phe Trp
305                 310                 315                 320

Ser Asn Tyr His Asn Asp Asn Phe Val Val Pro Val Ala Pro Pro Ala
                325                 330                 335

Pro Ser Val Leu Glu Asp Val Tyr Ala Ser Tyr Leu His Thr Leu Gln
            340                 345                 350

Glu Gln Glu Lys Met Leu Gly Asp Arg Ala Gln Gly Glu Glu Pro Glu
        355                 360                 365

Thr Leu Pro Val Gly Thr Ile Leu Gly Leu Glu Arg Arg Ser Leu Asp
370                 375                 380

Asp Asp Gly Glu Thr Val Ile Cys Phe Ser Val Glu Glu Asp Gly Phe
385                 390                 395                 400

Ala Leu Arg Val His Ala Asp Leu Ser Pro Leu Val Ile His Trp Gly
                405                 410                 415

Ile Ala Arg His Arg Val Thr Glu Phe Leu Gln Pro Asp Glu Ser Leu
            420                 425                 430

Ala Val Glu Thr Lys Gly Arg Thr Tyr Arg Phe Glu Asn Lys Ala Met
        435                 440                 445

Arg Thr Glu Phe Val Pro Asp Glu His His Gln Gly Thr Tyr Tyr Ala
450                 455                 460

Glu Ile His Leu Lys Lys Glu His Ala Pro Arg Ala Val Thr Phe Val
465                 470                 475                 480

Leu Phe Asn Pro Glu Leu Asn Arg Trp Tyr Arg Ala Glu Gly Gly Gly
                485                 490                 495

Asn Phe Val Leu Arg Met Asp Leu Glu Ser Phe Ser Gln Leu Pro Gly
            500                 505                 510

Ser Val Gly Lys His Glu Asp Val Ala Gln Lys Ile Ile Glu Val Glu
        515                 520                 525

Val Glu Tyr Gly Ser Trp Thr Leu Met His Arg Tyr Asn Leu Ala Asn
```

```
                530               535               540
Asp Ile Leu Arg Asn Ser Met Ser Ala Leu Asp Ala Asp Leu Leu Gln
545                 550                 555                 560

Ile Val Phe Val Trp Leu Arg Tyr Ser Phe Leu Arg Gln Leu Asp Trp
                565                 570                 575

Gln Arg Ser Tyr Asn Thr Gln Pro Arg Leu Leu Ala His Ala Gln Glu
                580                 585                 590

Gln Leu Thr Thr Thr Leu Ala Gln Val Phe Val Ser Arg Pro Asp Leu
                595                 600                 605

Arg Leu Trp Val Arg Leu Cys Leu Ser Met Leu Gly Arg Gly Gly Gly
                610                 615                 620

Asn Gly Gln Arg Ile Arg Asp Asp Ile Leu Arg Ile Met His Lys His
625                 630                 635                 640

His Ile Pro Glu Thr Pro Gly His Phe Met Glu Gln Trp His Gln Lys
                645                 650                 655

Leu His Asn Asn Thr Thr Pro Asp Asp Val Ala Ile Cys Glu Ser Tyr
                660                 665                 670

Leu Ala Phe Leu Arg Ser Asn Gly Asp Lys Asn Val Phe Tyr Glu Thr
                675                 680                 685

Leu Gln Lys His Gly Val Thr Lys Glu Arg Leu Ala Ser Tyr Glu Arg
                690                 695                 700

Pro Ile Phe Ala Glu Val Gln Thr Tyr Pro Cys Asp Thr Asn Ser Leu
705                 710                 715                 720

Ile His Asp Phe Glu Glu Tyr Leu His Val Leu Lys Ser Val His Ser
                725                 730                 735

Gly Thr Asp Leu Ala Val Val Leu Asp Tyr Ala Arg Trp Thr Leu Asp
                740                 745                 750

Gln Glu Leu Ile Ser Lys Val Glu His Ile Gln Ser Val Arg Ala Glu
                755                 760                 765

Leu Met Ala Ser Pro Gln Gly Ala Leu Glu Phe Ser Phe Leu Ile Ala
                770                 775                 780

Glu Ala Arg Lys Met Leu Gln Ser Thr Leu Glu His Val Glu Asp Pro
785                 790                 795                 800

Thr Arg Val Arg Asp Met Leu Phe Leu Asp Leu Ala Leu Asp Glu Leu
                    805                 810                 815

Ala Arg Leu Ala Val Glu Ser Gln Gly Leu Ala Asp Tyr Val Ala Glu
                820                 825                 830

Thr Asp Val Gln Lys Ala Cys Asn Leu Leu Val Val Leu Ala Gln His
                835                 840                 845

Val Gly Trp Ser Met Leu Ser Ser Ala Phe Leu Glu Thr Ser Tyr Asp
850                 855                 860

Leu Ala Ala Leu Val Tyr Gly Ile Gln Ser Asp Val Gln Leu Gln Glu
865                 870                 875                 880

Pro Asp Phe Gly Leu Arg Leu Tyr Ala Thr Met Glu Arg Leu Met Asp
                885                 890                 895

Cys Val Gly His Asp Val Val Glu Arg Leu His His Asp Val Gln Pro
                900                 905                 910

Lys Ala Val Tyr Ile Gly Val Gly Cys Asn Ile Asp Gln Lys Val Val
                915                 920                 925

Thr Leu Phe Ser Glu Glu Leu Ile Arg Gly Gln Ala Ala Phe Ala Leu
                930                 935                 940

Ala Gln Val Leu Arg Pro Leu Met Arg Asn Ile Arg Lys Gln Ala Asn
945                 950                 955                 960
```

```
Leu Gly Asn Trp Gln Val Ile Ser Pro Gly Ser Cys Thr Gly Gln Gly
            965                 970                 975

Ala Val Phe Asp Glu Leu Leu Ser Ile Gln Tyr Lys Thr Phe Ala Glu
            980                 985                 990

Pro Thr Val Ala Phe Val Arg Arg  Ile Ser Gly Glu Glu  Glu Ile Pro
            995                 1000                1005

Thr Gly  Met Val Gly Leu Ile  Thr Thr Asp Thr Leu  Asp Ile Leu
         1010                1015                1020

Ser His  Cys Ala Val Arg Ala  Arg Asn Glu His Val  Val Leu Ala
         1025                1030                1035

Cys Cys  Phe Ser Glu Glu Leu  Phe Asp Gln Leu Thr  Glu Arg Phe
         1040                1045                1050

Arg Gly  Ala Trp Val Ala Val  Arg Ser Leu Thr Asp  Gly Ser Leu
         1055                1060                1065

Asp Phe  Gln Pro Ile Gln Glu  Gly Ala Gly Arg Thr  Thr Ala Ala
         1070                1075                1080

Asp Thr  Thr Asp Gly Ala Ser  Glu His Ala Gln Arg  Arg Ala Val
         1085                1090                1095

Ser Met  Arg Ser Asp Ile Glu  Lys Lys Pro Val Lys  Ser Val Leu
         1100                1105                1110

Gly Ile  Ala Gln Phe Asn Thr  Gln Arg Gly Gly Ser  Lys Ser Asn
         1115                1120                1125

Ser Leu  Ala Lys Leu Ile Arg  Val Ile Pro Asp Trp  Ile His Ile
         1130                1135                1140

Pro Pro  Cys Ala Leu Leu Pro  Phe Gly Val Cys Glu  Gln Val Leu
         1145                1150                1155

Ala Glu  Ala Gln Asn Ser Asp  Val Gly Glu Arg Phe  Gln Gln Leu
         1160                1165                1170

Met Ala  Glu Leu Asp Gly Lys  Gly Pro Thr Asp Cys  Ser Ala
         1175                1180                1185

Leu Leu  Ala Arg Leu Arg His  Cys Val Arg Gln Leu  Ala Pro Ser
         1190                1195                1200

Asp Thr  Phe Met Lys Glu Leu  Gln Gln Val Leu Gln  His Glu Gly
         1205                1210                1215

Phe His  Ser Ile Asp Asn Leu  Asp Met Arg Arg Ala  Trp Glu Cys
         1220                1225                1230

Ile Leu  Asp Val Trp Ala Ser  Lys Phe Asn Asp Arg  Ala Phe Leu
         1235                1240                1245

Ala Leu  Arg Lys Ala Gly Ala  Val Gly Lys Thr Ser  Leu Ser Ser
         1250                1255                1260

Leu Tyr  Met Ala Val Leu Val  Gln Glu Val Val Pro  Ala Asp Tyr
         1265                1270                1275

Ala Phe  Val Leu His Thr Lys  Asn Pro Phe Thr Gly  Glu Pro Ser
         1280                1285                1290

Glu Ile  Tyr Gly Glu Leu Val  His Gly Leu Gly Glu  Val Leu Val
         1295                1300                1305

Gly Asn  Tyr Pro Gly Arg Ala  Leu Gly Phe Thr Tyr  Ser Lys Ser
         1310                1315                1320

Thr Gly  Gln Val Arg Val Cys  Asn Tyr Pro Ser Lys  Thr Lys Ala
         1325                1330                1335

Leu Ile  Pro Arg Gly Gly Leu  Ile Phe Arg Ser Asp  Ser Asn Gly
         1340                1345                1350
```

| Glu | Asp | Leu | Glu | Asp | Phe | Ala | Gly | Ala | Gly | Leu | Phe | Asp | Ser | Ile |
|---|---|---|---|---|---|---|---|---|---|---|---|---|---|---|
| 1355 | | | | 1360 | | | | | 1365 | | | | | |

| Leu | Met | Gln | Pro | Ala | Glu | Val | Val | Val | Arg | Tyr | Arg | Glu | Leu |
|---|---|---|---|---|---|---|---|---|---|---|---|---|---|
| 1370 | | | | | 1375 | | | | 1380 | | | | |

| Lys | Ile | Leu | Gln | Asp | Lys | Ala | Tyr | Leu | Glu | Arg | Ile | Leu | Ser | Lys |
|---|---|---|---|---|---|---|---|---|---|---|---|---|---|---|
| 1385 | | | | | 1390 | | | | | 1395 | | | | |

| Ile | Gly | Lys | Cys | Gly | Ile | Glu | Ile | Glu | Ser | Asn | Cys | Gly | Asn | Lys |
|---|---|---|---|---|---|---|---|---|---|---|---|---|---|---|
| 1400 | | | | | 1405 | | | | 1410 | | | | | |

| Pro | Gln | Asp | Ile | Glu | Gly | Cys | Ile | Cys | Gly | Glu | Asp | Val | Tyr | Val |
|---|---|---|---|---|---|---|---|---|---|---|---|---|---|---|
| 1415 | | | | 1420 | | | | | 1425 | | | | | |

| Val | Gln | Ser | Arg | Asp | Gln | Val |
|---|---|---|---|---|---|---|
| 1430 | | | | | 1435 | |

<210> SEQ ID NO 11
<211> LENGTH: 3690
<212> TYPE: DNA
<213> ORGANISM: Artificial Sequence
<220> FEATURE:
<223> OTHER INFORMATION: Fragment of Cyanidioschyzon merolae GWD
   polypeptide

<400> SEQUENCE: 11

| | |
|---|---|
| atgggtcacc tggacgtcgt ggttgaagaa atggaaccgc agtcggaata tcatattcac | 60 |
| atggccacgg atatttcagg tctggcactg cattggggcg tgtcgcgtaa aaaaccgggt | 120 |
| caatgggttc tgccgcgtcg cgactggtgg ccggccggcg tgaccagcca ggttgatcac | 180 |
| aaagctgtgc gttctgaatt tgaagcgac caagataatc cgggcgtgtg cgcctggat | 240 |
| atgtgctttc gtcgcgaaag cgaagatgac attgcgaatg gcgaatcatg gctgccgtcg | 300 |
| gctctggtgt ttgttctgta tcaggcggaa tacaacttct ggtctaacta ccataacgac | 360 |
| aacttcgtcg tgccggtggc accgccggcc cgagcgtcc tggaagatgt gtatgcttct | 420 |
| tacctgcaca ccctgcaaga acaagaaaaa atgctgggtg atcgcgcaca gggcgaagaa | 480 |
| ccggaaacgc tgccggttgg caccattctg ggtctggaac gtcgctcact ggatgacgat | 540 |
| ggtgaaaccg tgatttgctt ttcggtcgaa gaagacggct tcgccctgcg tgtccatgcg | 600 |
| gatctgagtc cgctggtgat tcattggggt atcgcgcgtc accgcgtgac cgaatttctg | 660 |
| caaccggatg aatccctggc tgttgaaacg aaaggccgta cctatcgctt cgaaaataaa | 720 |
| gcgatgcgta cggaatttgt gccggatgaa catcaccagg gcacctatta cgccgaaatt | 780 |
| catctgaaaa agaacacgc accgcgcgct gttaccttg tcctgttcaa cccggaactg | 840 |
| aatcgttggt atcgtgcgga aggcggtggc aacttcgtgc tgcgtatgga cctgaatcg | 900 |
| tttagccagc tgccgggctc agtgggtaaa catgaagatg ttgcgcaaaa atcatcgaa | 960 |
| gtcgaagtgg aatatggctc gtggaccctg atgcaccgct acaacctggc caatgatatt | 1020 |
| ctgcgtaatt ctatgagtgc gctggacgcg gatctgctgc aaatcgttt tgtctggctg | 1080 |
| cgctatagtt tcctgcgtca gctggattgg caacgctcct acaacaccca gccgcgtctg | 1140 |
| ctggcacatg cacaggaaca actgaccacg accctggcgc aagtgttcgt tagccgtccg | 1200 |
| gatctgcgcc tgtgggtgcg tctgtgcctg tctatgctgg gtcgtggtgg cggtaatggc | 1260 |
| cagcgtattc gcgacgatat tctgcgcatc atgcataaac atcacatccc ggaaacgccg | 1320 |
| ggccactttta tggaacagtg gcatcaaaaa ctgcacaaca atacgacccc ggacgatgtg | 1380 |
| gccatttgcg aaagttatct ggcattcctg cgctccaacg tgataaaaa cgtgtttat | 1440 |
| gaaacgctgc aaaaacatgg cgtcaccaaa gaacgcctgg ccagttatga acgtccgatt | 1500 |

| | |
|---|---|
| ttcgcagaag tgcaaacgta cccgtgtgac accaactccc tgatccacga tttcgaagaa | 1560 |
| tatctgcatg ttctgaaaag cgtccactct ggcacggacc tggccgttgt cctggattac | 1620 |
| gcacgttgga ccctggatca ggaactgatt tcaaaagtcg aacatatcca atcggtgcgt | 1680 |
| gcagaactga tggccagtcc gcagggtgcc ctggaatttt ccttcctgat tgcagaagct | 1740 |
| cgcaaaatgc tgcaaagtac gctggaacac gttgaagacc cgacccgtgt ccgcgatatg | 1800 |
| ctgtttctgg acctggcgct ggatgaactg cacgtctgg ctgtggaatc ccagggcctg | 1860 |
| gcagactatg tggctgaaac ggatgttcag aaagcgtgca acctgctggt tgtgctggcg | 1920 |
| caacatgttg ttggtcaat gctgtcatcg gcgttcctgg aaacctcgta tgatctggca | 1980 |
| gctctggtgt acggtatcca gtctgacgtt cagctgcaag aaccggattt tggcctgcgc | 2040 |
| ctgtatgcca cgatggaacg tctgatggac tgcgtcggcc atgatgtcgt ggaacgcctg | 2100 |
| catcacgacg ttcagccgaa agcagtgtac attggcgttg ttgtaatat cgatcaaaaa | 2160 |
| gttgtcaccc tgttcagcga agaactgatt cgtggtcagg cagcatttgc actggcacaa | 2220 |
| gtgctgcgcc cgctgatgcg taacattcgc aaacaggcca acctgggtaa ttggcaagtg | 2280 |
| atcagtccgg gctcctgcac cggtcagggt gcagttttg atgaactgct gtcaatccaa | 2340 |
| tataaaacgt ttgctgaacc gaccgtggcg ttcgttcgtc gcatttcggg cgaagaagaa | 2400 |
| atcccgacgg gcatggtggg tctgattacg accgacaccc tggatattct gagccattgt | 2460 |
| gcggttcgtg cccgcaacga acacgtggtt ctggcctgct gttttctga agaactgttc | 2520 |
| gatcagctga cggaacgttt ccgcggtgca tgggtcgctg tgcgtagcct gaccgacggc | 2580 |
| tctctggatt ttcagccgat tcaagaaggc gcgggtcgca cgaccgcagc tgacacgacc | 2640 |
| gatggtgcaa gcgaacatgc acagcgtcgc gcagtgtcaa tgcgttcgga tattgagaaa | 2700 |
| aaaccggtca aatctgtgct gggtatcgcc cagtttaaca cccaacgtgg cggttccaaa | 2760 |
| tcaaattcgc tggcaaaact gattcgcgtg atcccggatt ggattcatat cccgccgtgc | 2820 |
| gcactgctgc cgttcggtgt ctgtgaacag gtgctggcag aagctcaaaa tagcgacgtt | 2880 |
| ggcgaacgct ttcagcaact gatggccgaa ctggatggca aaggtccgac ggacgattgc | 2940 |
| agcgcactgc tggcacgtct gcgtcattgt gtgcgtcagc tggcgccgtc tgataccttc | 3000 |
| atgaaagaac tgcaacaagt tctgcaacat gaaggctttc acagtattga caacctggat | 3060 |
| atgcgtcgcg cctgggaatg catcctggac gtgtgggcat ccaaatttaa tgatcgcgca | 3120 |
| ttcctggctc tgcgtaaagc gggcgccgtt ggtaaaacca gcctgagcag cctgtatatg | 3180 |
| gcggttctgg tccaggaagt cgtgccggcg gattacgcct ttgtgctgca tacgaaaaac | 3240 |
| ccgttcaccg gtgaaccgag cgaaatttat ggcgaactgg ttcacggcct gggtgaagtg | 3300 |
| ctggttggca actatccggg tcgtgcactg gcttcacgt acagcaaatc taccggccag | 3360 |
| gtccgcgtgt gtaattaccc gagcaaaacc aaagcgctga ttccgcgcgg cggtctgatc | 3420 |
| tttcgtagtg actccaacgg tgaagacctg gaagattttg caggcgctgg tctgttcgat | 3480 |
| tctattctga tgcagccggc ggaagaagtt gtcgtgcgtt atcgcgaact gaaaatcctg | 3540 |
| caagataaag cctacctgga acgtattctg agtaaaatcg gcaaatgcgg tattgaaatc | 3600 |
| gaatccaact gtggtaataa accgcaggat attgaaggct gtatttgtgg cgaagatgtt | 3660 |
| tatgtcgtcc agtcacgcga tcaggtttga | 3690 |

<210> SEQ ID NO 12
<211> LENGTH: 1229
<212> TYPE: PRT
<213> ORGANISM: Artificial Sequence
<220> FEATURE:
<223> OTHER INFORMATION: Fragment of Cyanidioschyzon merolae GWD
      polypeptide

<400> SEQUENCE: 12

Met Gly His Leu Asp Val Val Glu Glu Met Glu Pro Gln Ser Glu
1               5                   10                  15

Tyr His Ile His Met Ala Thr Asp Ile Ser Gly Leu Ala Leu His Trp
            20                  25                  30

Gly Val Ser Arg Lys Lys Pro Gly Gln Trp Val Leu Pro Arg Arg Asp
            35                  40                  45

Trp Trp Pro Ala Gly Val Thr Ser Gln Val Asp His Lys Ala Val Arg
50                  55                  60

Ser Glu Phe Glu Ala Asp Gln Asp Asn Pro Gly Val Trp Arg Leu Asp
65                  70                  75                  80

Met Cys Phe Arg Arg Glu Ser Glu Asp Asp Ile Ala Asn Gly Glu Ser
                85                  90                  95

Trp Leu Pro Ser Ala Leu Val Phe Val Leu Tyr Gln Ala Glu Tyr Asn
            100                 105                 110

Phe Trp Ser Asn Tyr His Asn Asp Asn Phe Val Val Pro Val Ala Pro
            115                 120                 125

Pro Ala Pro Ser Val Leu Glu Asp Val Tyr Ala Ser Tyr Leu His Thr
130                 135                 140

Leu Gln Glu Gln Glu Lys Met Leu Gly Asp Arg Ala Gln Gly Glu Glu
145                 150                 155                 160

Pro Glu Thr Leu Pro Val Gly Thr Ile Leu Gly Leu Glu Arg Arg Ser
                165                 170                 175

Leu Asp Asp Asp Gly Glu Thr Val Ile Cys Phe Ser Val Glu Glu Asp
            180                 185                 190

Gly Phe Ala Leu Arg Val His Ala Asp Leu Ser Pro Leu Val Ile His
            195                 200                 205

Trp Gly Ile Ala Arg His Arg Val Thr Glu Phe Leu Gln Pro Asp Glu
210                 215                 220

Ser Leu Ala Val Glu Thr Lys Gly Arg Thr Tyr Arg Phe Glu Asn Lys
225                 230                 235                 240

Ala Met Arg Thr Glu Phe Val Pro Asp Glu His His Gln Gly Thr Tyr
                245                 250                 255

Tyr Ala Glu Ile His Leu Lys Lys Glu His Ala Pro Arg Ala Val Thr
            260                 265                 270

Phe Val Leu Phe Asn Pro Glu Leu Asn Arg Trp Tyr Arg Ala Glu Gly
            275                 280                 285

Gly Gly Asn Phe Val Leu Arg Met Asp Leu Glu Ser Phe Ser Gln Leu
290                 295                 300

Pro Gly Ser Val Gly Lys His Glu Asp Val Ala Gln Lys Ile Ile Glu
305                 310                 315                 320

Val Glu Val Glu Tyr Gly Ser Trp Thr Leu Met His Tyr Asn Leu
                325                 330                 335

Ala Asn Asp Ile Leu Arg Asn Ser Met Ser Ala Leu Asp Ala Asp Leu
            340                 345                 350

Leu Gln Ile Val Phe Val Trp Leu Arg Tyr Ser Phe Leu Arg Gln Leu
            355                 360                 365

Asp Trp Gln Arg Ser Tyr Asn Thr Gln Pro Arg Leu Leu Ala His Ala
370                 375                 380

Gln Glu Gln Leu Thr Thr Thr Leu Ala Gln Val Phe Val Ser Arg Pro

-continued

```
            385                 390                 395                 400
        Asp Leu Arg Leu Trp Val Arg Leu Cys Leu Ser Met Leu Gly Arg Gly
                        405                 410                 415

Gly Gly Asn Gly Gln Arg Ile Arg Asp Asp Ile Leu Arg Ile Met His
                        420                 425                 430

Lys His His Ile Pro Glu Thr Pro Gly His Phe Met Glu Gln Trp His
                        435                 440                 445

Gln Lys Leu His Asn Asn Thr Thr Pro Asp Asp Val Ala Ile Cys Glu
            450                 455                 460

Ser Tyr Leu Ala Phe Leu Arg Ser Asn Gly Asp Lys Asn Val Phe Tyr
        465                 470                 475                 480

Glu Thr Leu Gln Lys His Gly Val Thr Lys Glu Arg Leu Ala Ser Tyr
                        485                 490                 495

Glu Arg Pro Ile Phe Ala Glu Val Gln Thr Tyr Pro Cys Asp Thr Asn
                        500                 505                 510

Ser Leu Ile His Asp Phe Glu Glu Tyr Leu His Val Leu Lys Ser Val
                        515                 520                 525

His Ser Gly Thr Asp Leu Ala Val Val Leu Asp Tyr Ala Arg Trp Thr
                        530                 535                 540

Leu Asp Gln Glu Leu Ile Ser Lys Val Glu His Ile Gln Ser Val Arg
        545                 550                 555                 560

Ala Glu Leu Met Ala Ser Pro Gln Gly Ala Leu Glu Phe Ser Phe Leu
                        565                 570                 575

Ile Ala Glu Ala Arg Lys Met Leu Gln Ser Thr Leu Glu His Val Glu
                        580                 585                 590

Asp Pro Thr Arg Val Arg Asp Met Leu Phe Leu Asp Leu Ala Leu Asp
                        595                 600                 605

Glu Leu Ala Arg Leu Ala Val Glu Ser Gln Gly Leu Ala Asp Tyr Val
                        610                 615                 620

Ala Glu Thr Asp Val Gln Lys Ala Cys Asn Leu Leu Val Val Leu Ala
        625                 630                 635                 640

Gln His Val Gly Trp Ser Met Leu Ser Ser Ala Phe Leu Glu Thr Ser
                        645                 650                 655

Tyr Asp Leu Ala Ala Leu Val Tyr Gly Ile Gln Ser Asp Val Gln Leu
                        660                 665                 670

Gln Glu Pro Asp Phe Gly Leu Arg Leu Tyr Ala Thr Met Glu Arg Leu
                        675                 680                 685

Met Asp Cys Val Gly His Asp Val Val Glu Arg Leu His His Asp Val
                        690                 695                 700

Gln Pro Lys Ala Val Tyr Ile Gly Val Gly Cys Asn Ile Asp Gln Lys
        705                 710                 715                 720

Val Val Thr Leu Phe Ser Glu Glu Leu Ile Arg Gly Gln Ala Ala Phe
                        725                 730                 735

Ala Leu Ala Gln Val Leu Arg Pro Leu Met Arg Asn Ile Arg Lys Gln
                        740                 745                 750

Ala Asn Leu Gly Asn Trp Gln Val Ile Ser Pro Gly Ser Cys Thr Gly
                        755                 760                 765

Gln Gly Ala Val Phe Asp Glu Leu Leu Ser Ile Gln Tyr Lys Thr Phe
                        770                 775                 780

Ala Glu Pro Thr Val Ala Phe Val Arg Arg Ile Ser Gly Glu Glu Glu
        785                 790                 795                 800

Ile Pro Thr Gly Met Val Gly Leu Ile Thr Thr Asp Thr Leu Asp Ile
                        805                 810                 815
```

-continued

```
Leu Ser His Cys Ala Val Arg Ala Arg Asn Glu His Val Val Leu Ala
            820                 825                 830

Cys Cys Phe Ser Glu Glu Leu Phe Asp Gln Leu Thr Glu Arg Phe Arg
            835                 840                 845

Gly Ala Trp Val Ala Val Arg Ser Leu Thr Asp Gly Ser Leu Asp Phe
            850                 855                 860

Gln Pro Ile Gln Glu Gly Ala Gly Arg Thr Thr Ala Ala Asp Thr Thr
865                 870                 875                 880

Asp Gly Ala Ser Glu His Ala Gln Arg Ala Val Ser Met Arg Ser
                885                 890                 895

Asp Ile Glu Lys Lys Pro Val Lys Ser Val Leu Gly Ile Ala Gln Phe
            900                 905                 910

Asn Thr Gln Arg Gly Gly Ser Lys Ser Asn Ser Leu Ala Lys Leu Ile
            915                 920                 925

Arg Val Ile Pro Asp Trp Ile His Ile Pro Pro Cys Ala Leu Leu Pro
            930                 935                 940

Phe Gly Val Cys Glu Gln Val Leu Ala Glu Ala Gln Asn Ser Asp Val
945                 950                 955                 960

Gly Glu Arg Phe Gln Gln Leu Met Ala Glu Leu Asp Gly Lys Gly Pro
            965                 970                 975

Thr Asp Asp Cys Ser Ala Leu Leu Ala Arg Leu Arg His Cys Val Arg
            980                 985                 990

Gln Leu Ala Pro Ser Asp Thr Phe Met Lys Glu Leu Gln Gln Val Leu
                995                 1000                1005

Gln His Glu Gly Phe His Ser Ile Asp Asn Leu Asp Met Arg Arg
            1010                1015                1020

Ala Trp Glu Cys Ile Leu Asp Val Trp Ala Ser Lys Phe Asn Asp
            1025                1030                1035

Arg Ala Phe Leu Ala Leu Arg Lys Ala Gly Ala Val Gly Lys Thr
            1040                1045                1050

Ser Leu Ser Ser Leu Tyr Met Ala Val Leu Val Gln Glu Val Val
            1055                1060                1065

Pro Ala Asp Tyr Ala Phe Val Leu His Thr Lys Asn Pro Phe Thr
            1070                1075                1080

Gly Glu Pro Ser Glu Ile Tyr Gly Glu Leu Val His Gly Leu Gly
            1085                1090                1095

Glu Val Leu Val Gly Asn Tyr Pro Gly Arg Ala Leu Gly Phe Thr
            1100                1105                1110

Tyr Ser Lys Ser Thr Gly Gln Val Arg Val Cys Asn Tyr Pro Ser
            1115                1120                1125

Lys Thr Lys Ala Leu Ile Pro Arg Gly Gly Leu Ile Phe Arg Ser
            1130                1135                1140

Asp Ser Asn Gly Glu Asp Leu Glu Asp Phe Ala Gly Ala Gly Leu
            1145                1150                1155

Phe Asp Ser Ile Leu Met Gln Pro Ala Glu Glu Val Val Val Arg
            1160                1165                1170

Tyr Arg Glu Leu Lys Ile Leu Gln Asp Lys Ala Tyr Leu Glu Arg
            1175                1180                1185

Ile Leu Ser Lys Ile Gly Lys Cys Gly Ile Glu Ile Glu Ser Asn
            1190                1195                1200

Cys Gly Asn Lys Pro Gln Asp Ile Glu Gly Cys Ile Cys Gly Glu
            1205                1210                1215
```

Asp Val Tyr Val Val Gln Ser Arg Asp Gln Val
    1220                1225

<210> SEQ ID NO 13
<211> LENGTH: 3192
<212> TYPE: DNA
<213> ORGANISM: Artificial Sequence
<220> FEATURE:
<223> OTHER INFORMATION: Fragment of Cyanidioschyzon merolae GWD
      polypeptide

<400> SEQUENCE: 13

| | |
|---|---|
| atgaccattc tgggtctgga acgtcgctca ctggatgacg atggtgaaac cgtgatttgc | 60 |
| ttttcggtcg aagaagacgg cttcgccctg cgtgtccatg cggatctgag tccgctggtg | 120 |
| attcattggg gtatcgcgcg tcaccgcgtg accgaattc tgcaaccgga tgaatccctg | 180 |
| gctgttgaaa cgaaaggccg tacctatcgc ttcgaaaata aagcgatgcg tacggaattt | 240 |
| gtgccggatg aacatcacca gggcacctat tacgccgaaa ttcatctgaa aaaagaacac | 300 |
| gcaccgcgcg ctgttacctt tgtcctgttc aacccgaac tgaatcgttg gtatcgtgcg | 360 |
| gaaggcggtg caacttcgt gctgcgtatg gacctggaat cgtttagcca gctgccgggc | 420 |
| tcagtgggta acatgaaga tgttgcgcaa aaaatcatcg aagtcgaagt ggaatatggc | 480 |
| tcgtggaccc tgatgcaccg ctacaacctg ccaatgata ttctgcgtaa ttctatgagt | 540 |
| gcgctggacg cggatctgct gcaaatcgtt tttgtctggc tgcgctatag tttcctgcgt | 600 |
| cagctggatt ggcaacgctc ctacaacacc cagccgcgtc tgctggcaca tgcacaggaa | 660 |
| caactgacca cgaccctggc gcaagtgttc gttagccgtc cggatctgcg cctgtgggtg | 720 |
| cgtctgtgcc tgtctatgct gggtcgtggt ggcggtaatg ccagcgtat tcgcgacgat | 780 |
| attctgcgca tcatgcataa acatcacatc ccggaaacgc cgggccactt tatggaacag | 840 |
| tggcatcaaa aactgcacaa caatacgacc ccggacgatg tggccatttg cgaaagttat | 900 |
| ctggcattcc tgcgctccaa cggtgataaa acgtgttttt atgaaacgct gcaaaaacat | 960 |
| ggcgtcacca agaacgcct ggccagttat gaacgtccga ttttcgcaga gtgcaaacg | 1020 |
| tacccgtgtg acaccaactc cctgatccac gatttcgaag aatatctgca tgttctgaaa | 1080 |
| agcgtccact ctggcacgga cctggccgtt gtcctggatt acgcacgttg gaccctggat | 1140 |
| caggaactga tttcaaaagt cgaacatatc caatcggtgc gtgcagaact gatggccagt | 1200 |
| ccgcagggtg ccctggaatt ttccttcctg attgcagaag ctcgcaaaat gctgcaaagt | 1260 |
| acgctggaac acgttgaaga cccgaccgt gtccgcgata tgctgttct ggacctggcg | 1320 |
| ctggatgaac tggcacgtct ggctgtggaa tcccagggcc tggcagacta tgtggctgaa | 1380 |
| acggatgttc agaaagcgtg caacctgctg gttgtgctgg cgcaacatgt tggttggtca | 1440 |
| atgctgtcat cggcgttcct ggaaacctcg tatgatctgg cagctctggt gtacggtatc | 1500 |
| cagtctgacg ttcagctgca agaaccggat tttggcctgc gcctgtatgc cacgatggaa | 1560 |
| cgtctgatgg actgcgtcgg ccatgatgtc gtggaacgcc tgcatcacga cgttcagccg | 1620 |
| aaagcagtgt acattggcgt tggttgtaat atcgatcaaa agttgtcac cctgttcagc | 1680 |
| gaagaactga ttcgtggtca ggcagcattt gcactggcac aagtgctgcg cccgctgatg | 1740 |
| cgtaacattc gcaaacaggc caacctgggt aattggcaag tgatcagtcc gggctcctgc | 1800 |
| accggtcagg gtgcagtttt tgatgaactg ctgtcaatcc aatataaaac gtttgctgaa | 1860 |
| ccgaccgtgg cgttcgttcg tcgcatttcg ggcgaagaag aaatcccgac gggcatggtg | 1920 |
| ggtctgatta cgaccgacac cctggatatt ctgagccatt gtgcggttcg tgcccgcaac | 1980 |

```
gaacacgtgg ttctggcctg ctgttttcct gaagaactgt tcgatcagct gacggaacgt    2040
ttccgcggtg catgggtcgc tgtgcgtagc ctgaccgacg gctctctgga ttttcagccg    2100
attcaagaag gcgcgggtcg cacgaccgca gctgacacga ccgatggtgc aagcgaacat    2160
gcacagcgtc gcgcagtgtc aatgcgttcg gatattgaga aaaaaccggt caaatctgtg    2220
ctgggtatcg cccagtttaa cacccaacgt ggcggttcca aatcaaattc gctggcaaaa    2280
ctgattcgcg tgatcccgga ttggattcat atcccgccgt gcgcactgct gccgttcggt    2340
gtctgtgaac aggtgctggc agaagctcaa aatagcgacg ttggcgaacg ctttcagcaa    2400
ctgatggccg aactggatgg caaaggtccg acggacgatt gcagcgcact gctggcacgt    2460
ctgcgtcatt gtgtgcgtca gctggcgccg tctgatacct tcatgaaaga actgcaacaa    2520
gttctgcaac atgaaggctt tcacagtatt gacaacctgg atatgcgtcg cgcctgggaa    2580
tgcatcctgg acgtgtgggc atccaaattt aatgatcgcg cattcctggc tctgcgtaaa    2640
gcgggcgccg ttggtaaaac cagcctgagc agcctgtata tggcggttct ggtccaggaa    2700
gtcgtgccgg cggattacgc ctttgtgctg catacgaaaa acccgttcac cggtgaaccg    2760
agcgaaattt atgcgaact ggttcacggc ctgggtgaag tgctggttgg caactatccg    2820
ggtcgtgcac tgggcttcac gtacagcaaa tctaccggcc aggtccgcgt gtgtaattac    2880
ccgagcaaaa ccaaagcgct gattccgcgc ggcggtctga tctttcgtag tgactccaac    2940
ggtgaagacc tggaagattt tgcaggcgct ggtctgttcg attctattct gatgcagccg    3000
gcggaagaag ttgtcgtgcg ttatcgcgaa ctgaaaatcc tgcaagataa agcctacctg    3060
gaacgtattc tgagtaaaat cggcaaatgc ggtattgaaa tcgaatccaa ctgtggtaat    3120
aaaccgcagg atattgaagg ctgtatttgt ggcgaagatg tttatgtcgt ccagtcacgc    3180
gatcaggttt ga                                                        3192
```

<210> SEQ ID NO 14
<211> LENGTH: 1063
<212> TYPE: PRT
<213> ORGANISM: Artificial Sequence
<220> FEATURE:
<223> OTHER INFORMATION: Fragment of Cyanidioschyzon merolae GWD
      polypeptide

<400> SEQUENCE: 14

Met Thr Ile Leu Gly Leu Glu Arg Arg Ser Leu Asp Asp Asp Gly Glu
1               5                   10                  15

Thr Val Ile Cys Phe Ser Val Glu Glu Asp Gly Phe Ala Leu Arg Val
            20                  25                  30

His Ala Asp Leu Ser Pro Leu Val Ile His Trp Gly Ile Ala Arg His
        35                  40                  45

Arg Val Thr Glu Phe Leu Gln Pro Asp Glu Ser Leu Ala Val Glu Thr
    50                  55                  60

Lys Gly Arg Thr Tyr Arg Phe Glu Asn Lys Ala Met Arg Thr Glu Phe
65                  70                  75                  80

Val Pro Asp Glu His His Gln Gly Thr Tyr Tyr Ala Glu Ile His Leu
                85                  90                  95

Lys Lys Glu His Ala Pro Arg Ala Val Thr Phe Val Leu Phe Asn Pro
            100                 105                 110

Glu Leu Asn Arg Trp Tyr Arg Ala Glu Gly Gly Gly Asn Phe Val Leu
        115                 120                 125

Arg Met Asp Leu Glu Ser Phe Ser Gln Leu Pro Gly Ser Val Gly Lys

```
                130                 135                 140
His Glu Asp Val Ala Gln Lys Ile Ile Glu Val Glu Val Tyr Gly
145                 150                 155                 160

Ser Trp Thr Leu Met His Arg Tyr Asn Leu Ala Asn Asp Ile Leu Arg
                165                 170                 175

Asn Ser Met Ser Ala Leu Asp Ala Asp Leu Leu Gln Ile Val Phe Val
                180                 185                 190

Trp Leu Arg Tyr Ser Phe Leu Arg Gln Leu Asp Trp Gln Arg Ser Tyr
            195                 200                 205

Asn Thr Gln Pro Arg Leu Leu Ala His Ala Gln Glu Gln Leu Thr Thr
        210                 215                 220

Thr Leu Ala Gln Val Phe Val Ser Arg Pro Asp Leu Arg Leu Trp Val
225                 230                 235                 240

Arg Leu Cys Leu Ser Met Leu Gly Arg Gly Gly Asn Gly Gln Arg
                245                 250                 255

Ile Arg Asp Asp Ile Leu Arg Ile Met His Lys His His Ile Pro Glu
            260                 265                 270

Thr Pro Gly His Phe Met Glu Gln Trp His Gln Lys Leu His Asn Asn
        275                 280                 285

Thr Thr Pro Asp Asp Val Ala Ile Cys Glu Ser Tyr Leu Ala Phe Leu
290                 295                 300

Arg Ser Asn Gly Asp Lys Asn Val Phe Tyr Glu Thr Leu Gln Lys His
305                 310                 315                 320

Gly Val Thr Lys Glu Arg Leu Ala Ser Tyr Glu Arg Pro Ile Phe Ala
                325                 330                 335

Glu Val Gln Thr Tyr Pro Cys Asp Thr Asn Ser Leu Ile His Asp Phe
            340                 345                 350

Glu Glu Tyr Leu His Val Leu Lys Ser Val His Ser Gly Thr Asp Leu
        355                 360                 365

Ala Val Val Leu Asp Tyr Ala Arg Trp Thr Leu Asp Gln Glu Leu Ile
    370                 375                 380

Ser Lys Val Glu His Ile Gln Ser Val Arg Ala Glu Leu Met Ala Ser
385                 390                 395                 400

Pro Gln Gly Ala Leu Glu Phe Ser Phe Leu Ile Ala Glu Ala Arg Lys
                405                 410                 415

Met Leu Gln Ser Thr Leu Glu His Val Glu Asp Pro Thr Arg Val Arg
            420                 425                 430

Asp Met Leu Phe Leu Asp Leu Ala Leu Asp Glu Leu Ala Arg Leu Ala
        435                 440                 445

Val Glu Ser Gln Gly Leu Ala Asp Tyr Val Ala Glu Thr Asp Val Gln
    450                 455                 460

Lys Ala Cys Asn Leu Leu Val Val Leu Ala Gln His Val Gly Trp Ser
465                 470                 475                 480

Met Leu Ser Ser Ala Phe Leu Glu Thr Ser Tyr Asp Leu Ala Ala Leu
                485                 490                 495

Val Tyr Gly Ile Gln Ser Asp Val Gln Leu Gln Glu Pro Asp Phe Gly
            500                 505                 510

Leu Arg Leu Tyr Ala Thr Met Glu Arg Leu Met Asp Cys Val Gly His
        515                 520                 525

Asp Val Val Glu Arg Leu His His Asp Val Gln Pro Lys Ala Val Tyr
    530                 535                 540

Ile Gly Val Gly Cys Asn Ile Asp Gln Lys Val Val Thr Leu Phe Ser
545                 550                 555                 560
```

Glu Glu Leu Ile Arg Gly Gln Ala Ala Phe Ala Leu Ala Gln Val Leu
            565                 570                 575

Arg Pro Leu Met Arg Asn Ile Arg Lys Gln Ala Asn Leu Gly Asn Trp
            580                 585                 590

Gln Val Ile Ser Pro Gly Ser Cys Thr Gly Gln Gly Ala Val Phe Asp
            595                 600                 605

Glu Leu Leu Ser Ile Gln Tyr Lys Thr Phe Ala Glu Pro Thr Val Ala
            610                 615                 620

Phe Val Arg Arg Ile Ser Gly Glu Glu Ile Pro Thr Gly Met Val
625                 630                 635                 640

Gly Leu Ile Thr Thr Asp Thr Leu Asp Ile Leu Ser His Cys Ala Val
            645                 650                 655

Arg Ala Arg Asn Glu His Val Val Leu Ala Cys Cys Phe Ser Glu Glu
            660                 665                 670

Leu Phe Asp Gln Leu Thr Glu Arg Phe Arg Gly Ala Trp Val Ala Val
            675                 680                 685

Arg Ser Leu Thr Asp Gly Ser Leu Asp Phe Gln Pro Ile Gln Glu Gly
            690                 695                 700

Ala Gly Arg Thr Thr Ala Ala Asp Thr Thr Asp Gly Ala Ser Glu His
705                 710                 715                 720

Ala Gln Arg Arg Ala Val Ser Met Arg Ser Asp Ile Glu Lys Lys Pro
            725                 730                 735

Val Lys Ser Val Leu Gly Ile Ala Gln Phe Asn Thr Gln Arg Gly Gly
            740                 745                 750

Ser Lys Ser Asn Ser Leu Ala Lys Leu Ile Arg Val Ile Pro Asp Trp
            755                 760                 765

Ile His Ile Pro Pro Cys Ala Leu Leu Pro Phe Gly Val Cys Glu Gln
            770                 775                 780

Val Leu Ala Glu Ala Gln Asn Ser Asp Val Gly Glu Arg Phe Gln Gln
785                 790                 795                 800

Leu Met Ala Glu Leu Asp Gly Lys Gly Pro Thr Asp Asp Cys Ser Ala
            805                 810                 815

Leu Leu Ala Arg Leu Arg His Cys Val Arg Gln Leu Ala Pro Ser Asp
            820                 825                 830

Thr Phe Met Lys Glu Leu Gln Gln Val Leu Gln His Glu Gly Phe His
            835                 840                 845

Ser Ile Asp Asn Leu Asp Met Arg Arg Ala Trp Glu Cys Ile Leu Asp
850                 855                 860

Val Trp Ala Ser Lys Phe Asn Asp Arg Ala Phe Leu Ala Leu Arg Lys
865                 870                 875                 880

Ala Gly Ala Val Gly Lys Thr Ser Leu Ser Ser Leu Tyr Met Ala Val
            885                 890                 895

Leu Val Gln Glu Val Val Pro Ala Asp Tyr Ala Phe Val Leu His Thr
            900                 905                 910

Lys Asn Pro Phe Thr Gly Glu Pro Ser Glu Ile Tyr Gly Glu Leu Val
            915                 920                 925

His Gly Leu Gly Glu Val Leu Val Gly Asn Tyr Pro Gly Arg Ala Leu
            930                 935                 940

Gly Phe Thr Tyr Ser Lys Ser Thr Gly Gln Val Arg Val Cys Asn Tyr
945                 950                 955                 960

Pro Ser Lys Thr Lys Ala Leu Ile Pro Arg Gly Gly Leu Ile Phe Arg
            965                 970                 975

```
Ser Asp Ser Asn Gly Glu Asp Leu Glu Asp Phe Ala Gly Ala Gly Leu
            980                 985                 990

Phe Asp Ser Ile Leu Met Gln Pro Ala Glu Glu Val Val Val Arg Tyr
        995                1000                1005

Arg Glu Leu Lys Ile Leu Gln Asp Lys Ala Tyr Leu Glu Arg Ile
    1010                1015                1020

Leu Ser Lys Ile Gly Lys Cys Gly Ile Glu Ile Glu Ser Asn Cys
    1025                1030                1035

Gly Asn Lys Pro Gln Asp Ile Glu Gly Cys Ile Cys Gly Glu Asp
    1040                1045                1050

Val Tyr Val Val Gln Ser Arg Asp Gln Val
    1055                1060

<210> SEQ ID NO 15
<211> LENGTH: 2248
<212> TYPE: DNA
<213> ORGANISM: Artificial Sequence
<220> FEATURE:
<223> OTHER INFORMATION: Fragment of Cyanidioschyzon merolae GWD
      polypeptide

<400> SEQUENCE: 15
```

| | | | | | |
|---|---|---|---|---|---|
| atggctgcaa | aaacatggcg | tcaccaaaga | acgcctggcc | agttatgaac | gtccgatttt | 60 |
| cgcagaagtg | caaacgtacc | cgtgtgacac | caactccctg | atccacgatt | tcgaagaata | 120 |
| tctgcatgtt | ctgaaaagcg | tccactctgg | cacggacctg | gccgttgtcc | tggattacgc | 180 |
| acgttggacc | ctggatcagg | aactgatttc | aaaagtcgaa | catatccaat | cggtgcgtgc | 240 |
| agaactgatg | gccagtccgc | agggtgccct | ggaattttcc | ttcctgattg | cagaagctcg | 300 |
| caaaatgctg | caaagtacgc | tggaacacgt | tgaagacccg | accgtgtccc | gcgatatgct | 360 |
| gtttctggac | ctggcgctgg | atgaactggc | acgtctggct | gtggaatccc | agggcctggc | 420 |
| agactatgtg | gctgaaacgg | atgttcagaa | agcgtgcaac | ctgctggttg | tgctggcgca | 480 |
| acatgttggt | tggtcaatgc | tgtcatcggc | gttcctggaa | acctcgtatg | atctggcagc | 540 |
| tctggtgtac | ggtatccagt | ctgacgttca | gctgcaagaa | ccggattttg | cctgcgcct | 600 |
| gtatgccacg | atgaacgtc | tgatggactg | cgtcggccat | gatgtcgtgg | aacgcctgca | 660 |
| tcacgacgtt | cagccgaaag | cagtgtacat | tggcgttggt | gtaatatcg | atcaaaaagt | 720 |
| tgtcacccctg | ttcagcgaag | aactgattcg | tggtcaggca | gcatttgcac | tggcacaagt | 780 |
| gctgcgcccg | ctgatgcgta | acattcgcaa | acaggccaac | ctgggtaatt | ggcaagtgat | 840 |
| cagtccgggc | tcctgcaccg | tcagggtgc | agtttttgat | gaactgctgt | caatccaata | 900 |
| taaaacgttt | gctgaaccga | ccgtggcgtt | cgttcgtcgc | atttcgggcg | aagaagaaat | 960 |
| cccgacgggc | atggtgggtc | tgattacgac | cgacacccctg | gatattctga | gccattgtgc | 1020 |
| ggttcgtgcc | cgcaacgaac | acgtggttct | ggcctgctgt | ttttctgaag | aactgttcga | 1080 |
| tcagctgacg | gaacgtttcc | gcggtgcatg | ggtcgctgtg | cgtagcctga | ccgacggctc | 1140 |
| tctggatttt | cagccgattc | aagaaggcgc | gggtcgcacg | accgcagctg | acacgaccga | 1200 |
| tggtgcaagc | gaacatgcac | agcgtcgcgc | agtgtcaatg | cgttcggata | ttgagaaaaa | 1260 |
| accggtcaaa | tctgtgctgg | gtatcgccca | gtttaacacc | caacgtggcg | ttccaaatc | 1320 |
| aaattcgctg | gcaaaactga | ttcgcgtgat | cccggattgg | attcatatcc | cgccgtgcgc | 1380 |
| actgctgccg | ttcggtgtct | gtgaacaggt | gctggcagaa | gctcaaaata | gcgacgttgg | 1440 |
| cgaacgcttt | cagcaactga | tggccgaact | ggatggcaaa | ggtccgacgg | acgattgcag | 1500 |

```
cgcactgctg gcacgtctgc gtcattgtgt gcgtcagctg gcgccgtctg ataccttcat    1560
gaaagaactg caacaagttc tgcaacatga aggctttcac agtattgaca acctggatat    1620
gcgtcgcgcc tgggaatgca tcctggacgt gtgggcatcc aaatttaatg atcgcgcatt    1680
cctggctctg cgtaaagcgg gcgccgttgg taaaaccagc ctgagcagcc tgtatatggc    1740
ggttctggtc caggaagtcg tgccggcgga ttacgccttt gtgctgcata cgaaaaaccc    1800
gttcaccggt gaaccgagcg aaatttatgg cgaactggtt cacggcctgg gtgaagtgct    1860
ggttggcaac tatccgggtc gtgcactggg cttcacgtac agcaaatcta ccggccaggt    1920
ccgcgtgtgt aattacccga gcaaaaccaa agcgctgatt ccgcgcggcg gtctgatctt    1980
tcgtagtgac tccaacggtg aagacctgga agattttgca ggcgctggtc tgttcgattc    2040
tattctgatg cagccggcgg aagaagttgt cgtgcgttat cgcgaactga aaatcctgca    2100
agataaagcc tacctggaac gtattctgag taaaatcggc aaatgcggta ttgaaatcga    2160
atccaactgt ggtaataaac cgcaggatat tgaaggctgt atttgtggcg aagatgttta    2220
tgtcgtccag tcacgcgatc aggtttga                                       2248
```

<210> SEQ ID NO 16
<211> LENGTH: 758
<212> TYPE: PRT
<213> ORGANISM: Artificial Sequence
<220> FEATURE:
<223> OTHER INFORMATION: Fragment of Cyanidioschyzon merolae GWD
      polypeptide

<400> SEQUENCE: 16

```
Met Asn Gly Asp Lys Asn Val Phe Tyr Glu Thr Leu Gln Lys His Gly
1               5                   10                  15

Val Thr Lys Glu Arg Leu Ala Ser Tyr Glu Arg Pro Ile Phe Ala Glu
            20                  25                  30

Val Gln Thr Tyr Pro Cys Asp Thr Asn Ser Leu Ile His Asp Phe Glu
        35                  40                  45

Glu Tyr Leu His Val Leu Lys Ser Val His Ser Gly Thr Asp Leu Ala
    50                  55                  60

Val Val Leu Asp Tyr Ala Arg Trp Thr Leu Asp Gln Glu Leu Ile Ser
65                  70                  75                  80

Lys Val Glu His Ile Gln Ser Val Arg Ala Glu Leu Met Ala Ser Pro
                85                  90                  95

Gln Gly Ala Leu Glu Phe Ser Phe Leu Ile Ala Glu Ala Arg Lys Met
            100                 105                 110

Leu Gln Ser Thr Leu Glu His Val Glu Asp Pro Thr Arg Val Arg Asp
        115                 120                 125

Met Leu Phe Leu Asp Leu Ala Leu Asp Glu Leu Ala Arg Leu Ala Val
    130                 135                 140

Glu Ser Gln Gly Leu Ala Asp Tyr Val Ala Glu Thr Asp Val Gln Lys
145                 150                 155                 160

Ala Cys Asn Leu Leu Val Leu Ala Gln His Val Gly Trp Ser Met
                165                 170                 175

Leu Ser Ser Ala Phe Leu Glu Thr Ser Tyr Asp Leu Ala Ala Leu Val
            180                 185                 190

Tyr Gly Ile Gln Ser Asp Val Gln Leu Gln Glu Pro Asp Phe Gly Leu
        195                 200                 205

Arg Leu Tyr Ala Thr Met Glu Arg Leu Met Asp Cys Val Gly His Asp
    210                 215                 220
```

-continued

Val Val Glu Arg Leu His His Asp Val Gln Pro Lys Ala Val Tyr Ile
225                 230                 235                 240

Gly Val Gly Cys Asn Ile Asp Gln Lys Val Val Thr Leu Phe Ser Glu
            245                 250                 255

Glu Leu Ile Arg Gly Gln Ala Ala Phe Ala Leu Ala Gln Val Leu Arg
        260                 265                 270

Pro Leu Met Arg Asn Ile Arg Lys Gln Ala Asn Leu Gly Asn Trp Gln
    275                 280                 285

Val Ile Ser Pro Gly Ser Cys Thr Gly Gln Gly Ala Val Phe Asp Glu
290                 295                 300

Leu Leu Ser Ile Gln Tyr Lys Thr Phe Ala Glu Pro Thr Val Ala Phe
305                 310                 315                 320

Val Arg Arg Ile Ser Gly Glu Glu Ile Pro Thr Gly Met Val Gly
            325                 330                 335

Leu Ile Thr Thr Asp Thr Leu Asp Ile Leu Ser His Cys Ala Val Arg
            340                 345                 350

Ala Arg Asn Glu His Val Val Leu Ala Cys Cys Phe Ser Glu Glu Leu
        355                 360                 365

Phe Asp Gln Leu Thr Glu Arg Phe Arg Gly Ala Trp Val Ala Val Arg
370                 375                 380

Ser Leu Thr Asp Gly Ser Leu Asp Phe Gln Pro Ile Gln Glu Gly Ala
385                 390                 395                 400

Gly Arg Thr Thr Ala Ala Asp Thr Thr Asp Gly Ala Ser Glu His Ala
            405                 410                 415

Gln Arg Arg Ala Val Ser Met Arg Ser Asp Ile Glu Lys Lys Pro Val
        420                 425                 430

Lys Ser Val Leu Gly Ile Ala Gln Phe Asn Thr Gln Arg Gly Gly Ser
    435                 440                 445

Lys Ser Asn Ser Leu Ala Lys Leu Ile Arg Val Ile Pro Asp Trp Ile
    450                 455                 460

His Ile Pro Pro Cys Ala Leu Leu Pro Phe Gly Val Cys Glu Gln Val
465                 470                 475                 480

Leu Ala Glu Ala Gln Asn Ser Asp Val Gly Glu Arg Phe Gln Gln Leu
            485                 490                 495

Met Ala Glu Leu Asp Gly Lys Gly Pro Thr Asp Asp Cys Ser Ala Leu
            500                 505                 510

Leu Ala Arg Leu Arg His Cys Val Arg Gln Leu Ala Pro Ser Asp Thr
        515                 520                 525

Phe Met Lys Glu Leu Gln Gln Val Leu Gln His Glu Gly Phe His Ser
530                 535                 540

Ile Asp Asn Leu Asp Met Arg Arg Ala Trp Glu Cys Ile Leu Asp Val
545                 550                 555                 560

Trp Ala Ser Lys Phe Asn Asp Arg Ala Phe Leu Ala Leu Arg Lys Ala
            565                 570                 575

Gly Ala Val Gly Lys Thr Ser Leu Ser Ser Leu Tyr Met Ala Val Leu
            580                 585                 590

Val Gln Glu Val Val Pro Ala Asp Tyr Ala Phe Val Leu His Thr Lys
        595                 600                 605

Asn Pro Phe Thr Gly Glu Pro Ser Glu Ile Tyr Gly Glu Leu Val His
    610                 615                 620

Gly Leu Gly Glu Val Leu Val Gly Asn Tyr Pro Gly Arg Ala Leu Gly
625                 630                 635                 640

Phe Thr Tyr Ser Lys Ser Thr Gly Gln Val Arg Val Cys Asn Tyr Pro

```
                  645                 650                 655
Ser Lys Thr Lys Ala Leu Ile Pro Arg Gly Gly Leu Ile Phe Arg Ser
            660                 665                 670

Asp Ser Asn Gly Glu Asp Leu Glu Asp Phe Ala Gly Ala Gly Leu Phe
            675                 680                 685

Asp Ser Ile Leu Met Gln Pro Ala Glu Glu Val Val Val Arg Tyr Arg
            690                 695                 700

Glu Leu Lys Ile Leu Gln Asp Lys Ala Tyr Leu Glu Arg Ile Leu Ser
705                 710                 715                 720

Lys Ile Gly Lys Cys Gly Ile Glu Ile Glu Ser Asn Cys Gly Asn Lys
                725                 730                 735

Pro Gln Asp Ile Glu Gly Cys Ile Cys Gly Glu Asp Val Tyr Val Val
            740                 745                 750

Gln Ser Arg Asp Gln Val
            755

<210> SEQ ID NO 17
<211> LENGTH: 2243
<212> TYPE: DNA
<213> ORGANISM: Artificial Sequence
<220> FEATURE:
<223> OTHER INFORMATION: Fragment of Cyanidioschyzon merolae GWD
      polypeptide

<400> SEQUENCE: 17
atgaaaaaca tggcgtcacc aaagaacgcc tggccagtta tgaacgtccg attttcgcag      60
aagtgcaaac gtaccccgtgt gacaccaact ccctgatcca cgatttcgaa gaatatctgc    120
atgttctgaa aagcgtccac tctggcacgg acctggccgt tgtcctggat tacgcacgtt    180
ggaccctgga tcaggaactg atttcaaaag tcgaacatat ccaatcggtg cgtgcagaac    240
tgatggccag tccgcagggt gccctggaat tttccttcct gattgcagaa gctcgcaaaa    300
tgctgcaaag tacgctggaa cacgttgaag acccgaccccg tgtccgcgat atgctgtttc    360
tggacctggc gctggatgaa ctggcacgtc tggctgtgga atcccagggc ctggcagact    420
atgtggctga aacggatgtt cagaaagcgt gcaacctgct ggttgtgctg cgcaacatg    480
ttggttggtc aatgctgtca tcggcgttcc tggaaaccctc gtatgatctg cagctctgg    540
tgtacggtat ccagtctgac gttcagctgc aagaaccgga ttttggcctg cgcctgtatg    600
ccacgatgga acgtctgatg gactgcgtcg gccatgatgt cgtggaacgc ctgcatcacg    660
acgttcagcc gaaagcagtg tacattggcg ttggttgtaa tatcgatcaa aaagttgtca    720
ccctgttcag cgaagaactg attcgtggtc aggcagcatt tgcactggca caagtgctgc    780
gcccgctgat gcgtaacatt cgcaaacagg ccaacctggg taattggcaa gtgatcagtc    840
cgggctcctg caccggtcag ggtgcagttt ttgatgaact gctgtcaatc caatataaaa    900
cgtttgctga accgaccgtg gcgttcgttc gtcgcatttc gggcgaagaa gaaatcccga    960
cgggcatggt gggtctgatt acgaccgaca ccctggatat tctgagccat gtgcggttc    1020
gtgcccgcaa cgaacacgtg gttctggcct gctgttttc tgaagaactg ttcgatcagc    1080
tgacggaacg tttccgcggt gcatgggtcg ctgtgcgtag cctgaccgac ggctctctgg    1140
attttcagcc gattcaagaa ggcgcgggtc gcacgaccgc agctgacacg accgatggtg    1200
caagcgaaca tgcacagcgt cgcgcagtgt caatgcgttc ggatattgag aaaaaaccgg    1260
tcaaatctgt gctgggtatc gcccagttta cacccaacg tggcggttcc aaatcaaatt    1320
cgctggcaaa actgattcgc gtgatcccgg attggattca tatcccgccg tgcgcactgc    1380
```

```
tgccgttcgg tgtctgtgaa caggtgctgg cagaagctca aaatagcgac gttggcgaac    1440
gctttcagca actgatggcc gaactggatg caaaggtcc  gacggacgat tgcagcgcac    1500
tgctggcacg tctgcgtcat tgtgtgcgtc agctggcgcc gtctgatacc ttcatgaaag    1560
aactgcaaca agttctgcaa catgaaggct tcacagtat  tgacaacctg gatatgcgtc    1620
gcgcctggga atgcatcctg gacgtgtggg catccaaatt taatgatcgc gcattcctgg    1680
ctctgcgtaa agcgggcgcc gttggtaaaa ccagcctgag cagcctgtat atggcggttc    1740
tggtccagga agtcgtgccg gcggattacg cctttgtgct gcatacgaaa aacccgttca    1800
ccggtgaacc gagcgaaatt tatggcgaac tggttcacgg cctgggtgaa gtgctggttg    1860
gcaactatcc gggtcgtgca ctgggcttca cgtacagcaa atctaccggc caggtccgcg    1920
tgtgtaatta cccgagcaaa accaaagcgc tgattccgcg cggcggtctg atctttcgta    1980
gtgactccaa cggtgaagac ctggaagatt ttgcaggcgc tggtctgttc gattctattc    2040
tgatgcagcc ggcggaagaa gttgtcgtgc gttatcgcga actgaaaatc ctgcaagata    2100
aagcctacct ggaacgtatt ctgagtaaaa tcggcaaatg cggtattgaa atcgaatcca    2160
actgtggtaa taaaccgcag gatattgaag gctgtatttg tggcgaagat gtttatgtcg    2220
tccagtcacg cgatcaggtt tga                                           2243
```

<210> SEQ ID NO 18
<211> LENGTH: 755
<212> TYPE: PRT
<213> ORGANISM: Artificial Sequence
<220> FEATURE:
<223> OTHER INFORMATION: Fragment of Cyanidioschyzon merolae GWD
      polypeptide

<400> SEQUENCE: 18

```
Met Lys Asn Val Phe Tyr Glu Thr Leu Gln Lys His Gly Val Thr Lys
1               5                   10                  15

Glu Arg Leu Ala Ser Tyr Glu Arg Pro Ile Phe Ala Glu Val Gln Thr
            20                  25                  30

Tyr Pro Cys Asp Thr Asn Ser Leu Ile His Asp Phe Glu Glu Tyr Leu
        35                  40                  45

His Val Leu Lys Ser Val His Ser Gly Thr Asp Leu Ala Val Val Leu
    50                  55                  60

Asp Tyr Ala Arg Trp Thr Leu Asp Gln Glu Leu Ile Ser Lys Val Glu
65                  70                  75                  80

His Ile Gln Ser Val Arg Ala Glu Leu Met Ala Ser Pro Gln Gly Ala
                85                  90                  95

Leu Glu Phe Ser Phe Leu Ile Ala Glu Ala Arg Lys Met Leu Gln Ser
            100                 105                 110

Thr Leu Glu His Val Glu Asp Pro Thr Arg Val Arg Asp Met Leu Phe
        115                 120                 125

Leu Asp Leu Ala Leu Asp Glu Leu Ala Arg Leu Ala Val Glu Ser Gln
    130                 135                 140

Gly Leu Ala Asp Tyr Val Ala Glu Thr Asp Val Gln Lys Ala Cys Asn
145                 150                 155                 160

Leu Leu Val Val Leu Ala Gln His Val Gly Trp Ser Met Leu Ser Ser
                165                 170                 175

Ala Phe Leu Glu Thr Ser Tyr Asp Leu Ala Ala Leu Val Tyr Gly Ile
            180                 185                 190

Gln Ser Asp Val Gln Leu Gln Glu Pro Asp Phe Gly Leu Arg Leu Tyr
```

```
            195                 200                 205
Ala Thr Met Glu Arg Leu Met Asp Cys Val Gly His Asp Val Val Glu
210                 215                 220

Arg Leu His His Asp Val Gln Pro Lys Ala Val Tyr Ile Gly Val Gly
225                 230                 235                 240

Cys Asn Ile Asp Gln Lys Val Val Thr Leu Phe Ser Glu Glu Leu Ile
                    245                 250                 255

Arg Gly Gln Ala Ala Phe Ala Leu Ala Gln Val Leu Arg Pro Leu Met
                260                 265                 270

Arg Asn Ile Arg Lys Gln Ala Asn Leu Gly Asn Trp Gln Val Ile Ser
            275                 280                 285

Pro Gly Ser Cys Thr Gly Gln Gly Ala Val Phe Asp Glu Leu Leu Ser
            290                 295                 300

Ile Gln Tyr Lys Thr Phe Ala Glu Pro Thr Val Ala Phe Val Arg Arg
305                 310                 315                 320

Ile Ser Gly Glu Glu Glu Ile Pro Thr Gly Met Val Gly Leu Ile Thr
                    325                 330                 335

Thr Asp Thr Leu Asp Ile Leu Ser His Cys Ala Val Arg Ala Arg Asn
                340                 345                 350

Glu His Val Val Leu Ala Cys Cys Phe Ser Glu Glu Leu Phe Asp Gln
            355                 360                 365

Leu Thr Glu Arg Phe Arg Gly Ala Trp Val Ala Val Arg Ser Leu Thr
370                 375                 380

Asp Gly Ser Leu Asp Phe Gln Pro Ile Gln Glu Gly Ala Gly Arg Thr
385                 390                 395                 400

Thr Ala Ala Asp Thr Thr Asp Gly Ala Ser Glu His Ala Gln Arg Arg
                    405                 410                 415

Ala Val Ser Met Arg Ser Asp Ile Glu Lys Lys Pro Val Lys Ser Val
                420                 425                 430

Leu Gly Ile Ala Gln Phe Asn Thr Gln Arg Gly Gly Ser Lys Ser Asn
            435                 440                 445

Ser Leu Ala Lys Leu Ile Arg Val Ile Pro Asp Trp Ile His Ile Pro
450                 455                 460

Pro Cys Ala Leu Leu Pro Phe Gly Val Cys Glu Gln Val Leu Ala Glu
465                 470                 475                 480

Ala Gln Asn Ser Asp Val Gly Glu Arg Phe Gln Gln Leu Met Ala Glu
                    485                 490                 495

Leu Asp Gly Lys Gly Pro Thr Asp Asp Cys Ser Ala Leu Leu Ala Arg
                500                 505                 510

Leu Arg His Cys Val Arg Gln Leu Ala Pro Ser Asp Thr Phe Met Lys
            515                 520                 525

Glu Leu Gln Gln Val Leu His Glu Gly Phe His Ser Ile Asp Asn
530                 535                 540

Leu Asp Met Arg Arg Ala Trp Glu Cys Ile Leu Asp Val Trp Ala Ser
545                 550                 555                 560

Lys Phe Asn Asp Arg Ala Phe Leu Ala Leu Arg Lys Ala Gly Ala Val
                    565                 570                 575

Gly Lys Thr Ser Leu Ser Ser Leu Tyr Met Ala Val Leu Val Gln Glu
                580                 585                 590

Val Val Pro Ala Asp Tyr Ala Phe Val Leu His Thr Lys Asn Pro Phe
            595                 600                 605

Thr Gly Glu Pro Ser Glu Ile Tyr Gly Glu Leu Val His Gly Leu Gly
610                 615                 620
```

Glu Val Leu Val Gly Asn Tyr Pro Gly Arg Ala Leu Gly Phe Thr Tyr
625                 630                 635                 640

Ser Lys Ser Thr Gly Gln Val Arg Val Cys Asn Tyr Pro Ser Lys Thr
            645                 650                 655

Lys Ala Leu Ile Pro Arg Gly Gly Leu Ile Phe Arg Ser Asp Ser Asn
                660                 665                 670

Gly Glu Asp Leu Glu Asp Phe Ala Gly Ala Gly Leu Phe Asp Ser Ile
        675                 680                 685

Leu Met Gln Pro Ala Glu Val Val Arg Tyr Arg Glu Leu Lys
    690                 695                 700

Ile Leu Gln Asp Lys Ala Tyr Leu Glu Arg Ile Leu Ser Lys Ile Gly
705                 710                 715                 720

Lys Cys Gly Ile Glu Ile Glu Ser Asn Cys Gly Asn Lys Pro Gln Asp
                725                 730                 735

Ile Glu Gly Cys Ile Cys Gly Glu Asp Val Tyr Val Val Gln Ser Arg
            740                 745                 750

Asp Gln Val
        755

<210> SEQ ID NO 19
<211> LENGTH: 3192
<212> TYPE: DNA
<213> ORGANISM: Artificial Sequence
<220> FEATURE:
<223> OTHER INFORMATION: Fragment of Cyanidioschyzon merolae GWD
      polypeptide

<400> SEQUENCE: 19
atgaccattc tgggtctgga acgtcgctca ctggatgacg atggtgaaac cgtgatttgc    60
ttttcggtcg aagaagacgg cttcgccctg cgtgtccatg cggatctgag tccgctggtg   120
attcattggg gtatcgcgcg tcaccgcgtg accgaatttc tgcaaccgga tgaatccctg   180
gctgttgaaa cgaaaggccg tacctatcgc ttcgaaaata agcgatgcg tacggaattt    240 gtgccggatg aacatcacca gggcacctat tacgccgaaa ttcatctgaa aaaagaacac   300
gcaccgcgcg ctgttacctt tgtcctgttc aacccggaac tgaatcgttg gtatcgtgcg   360
gaaggcggtg caacttcgt gctgcgtatg gacctggaat cgtttagcca gctgccgggc   420
tcagtgggta acatgaaga tgttgcgcaa aaaatcatcg aagtcgaagt ggaatatggc   480
tcgtggaccc tgatgcaccg ctacaacctg gccaatgata ttctgcgtaa ttctatgagt   540
gcgctggacg cggatctgct gcaaatcgtt tttgtctggc tgcgctatag tttcctgcgt   600
cagctggatt ggcaacgctc ctacaacacc cagccgcgtc tgctggcaca tgcacaggaa   660
caactgacca cgaccctggc gcaagtgttc gttagccgtc cggatctgcg cctgtgggtg   720
cgtctgtgcc tgtctatgct gggtcgtggt ggcggtaatg ccagcgtat cgcgacgat    780 attctgcgca tcatgcataa acatcacatc cggaaacgc cgggccactt tatgaaacag   840
tggcatcaaa aactgcacaa caatacgacc ccggacgatg tggccatttg cgaaagttat   900
ctggcattcc tgcgctccaa cggtgataaa acgtgttttt atgaaacgct gcaaaaacat   960
ggcgtcacca agaacgcct ggccagttat gaacgtccga ttttcgcaga agtgcaaacg   1020
tacccgtgtg acaccaactc cctgatccac gatttcgaag aatatctgca tgttctgaaa   1080
agcgtccact ctggcacgga cctggccgtt gtcctggatt acgacgttg gaccctggat   1140 caggaactga tttcaaagt cgaacatatc caatcggtgc gtgcagaact gatggccagt   1200

```
ccgcagggtg ccctggaatt ttccttcctg attgcagaag ctcgcaaaat gctgcaaagt    1260
acgctggaac acgttgaaga cccgacccgt gtccgcgata tgctgttcct ggacctggcg    1320
ctggatgaac tggcacgtct ggctgtggaa tcccagggcc tggcagacta tgtggctgaa    1380
acggatgttc agaaagcgtg caacctgctg gttgtgctgg cgcaacatgt tggttggtca    1440
atgctgtcat cggcgttcct ggaaacctcg tatgatctgg cagctctggt gtacggtatc    1500
cagtctgacg ttcagctgca agaaccggat tttggcctgc cctgtatgc cacgatggaa    1560 cgtctgatgg actgcgtcgg ccatgatgtc gtggaacgcc tgcatcacga cgttcagccg    1620
aaagcagtgt acattggcgt tggttgtaat atcgatcaaa aagttgtcac cctgttcagc    1680
gaagaactga ttcgtggtca ggcagcattt gcactggcac aagtgctgcg cccgctgatg    1740
cgtaacattc gcaaacaggc caacctgggt aattggcaag tgatcagtcc gggctcctgc    1800
accggtcagg gtgcagtttt tgatgaactg ctgtcaatcc aatataaaac gtttgctgaa    1860
ccgaccgtgg cgttcgttcg tcgcatttcg ggcgaagaag aaatcccgac gggcatggtg    1920
ggtctgatta cgaccgacac cctggatatt ctgagcgcgt gtgcggttcg tgcccgcaac    1980
gaacacgtgg ttctggcctg ctgttttttct gaagaactgt tcgatcagct gacggaacgt    2040
ttccgcggtg catgggtcgc tgtgcgtagc ctgaccgacg gctctctgga ttttcagccg    2100
attcaagaag gcgcgggtcg cacgaccgca gctgacacga ccgatggtgc aagcgaacat    2160
gcacagcgtc gcgcagtgtc aatgcgttcg gatattgaga aaaaaccggt caaatctgtg    2220
ctgggtatcg cccagtttaa cacccaacgt ggcggttcca atcaaattc gctggcaaaa    2280 ctgattcgcg tgatcccgga ttggattcat atcccgccgt gcgcactgct gccgttcggt    2340
gtctgtgaac aggtgctggc agaagctcaa aatagcgacg ttggcgaacg ctttcagcaa    2400
ctgatggccg aactggatgg caaaggtccg acggacgatt gcagcgcact gctggcacgt    2460
ctgcgtcatt gtgtgcgtca gctggcgccg tctgatacct tcatgaaaga actgcaacaa    2520
gttctgcaac atgaaggctt tcacagtatt gacaacctgg atatgcgtcg cgcctgggaa    2580
tgcatcctgg acgtgtgggc atccaaattt aatgatcgcg cattcctggc tctgcgtaaa    2640
gcgggcgccg ttggtaaaac cagcctgagc agcctgtata tggcggttct ggtccaggaa    2700
gtcgtgccgg cggattacgc cttttgtgctg catacgaaaa acccgttcac cggtgaaccg    2760
agcgaaattt atgcgaact ggttcacggc ctgggtgaag tgctggttgg caactatccg    2820
ggtcgtgcac tgggcttcac gtacagcaaa tctaccggcc aggtccgcgt gtgtaattac    2880
ccgagcaaaa ccaaagcgct gattccgcgc ggcggtctga tctttcgtag tgactccaac    2940
ggtgaagacc tggaagattt tgcaggcgct ggtctgttcg attctattct gatgcagccg    3000
gcggaagaag ttgtcgtgcg ttatcgcgaa ctgaaaatcc tgcaagataa agcctacctg    3060
gaacgtattc tgagtaaaat cggcaaatgc ggtattgaaa tcgaatccaa ctgtggtaat    3120
aaaccgcagg atattgaagg ctgtatttgt ggcgaagatg tttatgtcgt ccagtcacgc    3180
gatcaggttt ga                                                       3192
```

<210> SEQ ID NO 20
<211> LENGTH: 1063
<212> TYPE: PRT
<213> ORGANISM: Artificial Sequence
<220> FEATURE:
<223> OTHER INFORMATION: Fragment of Cyanidioschyzon merolae GWD
      polypeptide

<400> SEQUENCE: 20

```
Met Thr Ile Leu Gly Leu Glu Arg Arg Ser Leu Asp Asp Gly Glu
1               5                   10                  15

Thr Val Ile Cys Phe Ser Val Glu Glu Asp Gly Phe Ala Leu Arg Val
            20                  25                  30

His Ala Asp Leu Ser Pro Leu Val Ile His Trp Gly Ile Ala Arg His
                35                  40                  45

Arg Val Thr Glu Phe Leu Gln Pro Asp Glu Ser Leu Ala Val Glu Thr
    50                  55                  60

Lys Gly Arg Thr Tyr Arg Phe Glu Asn Lys Ala Met Arg Thr Glu Phe
65                  70                  75                  80

Val Pro Asp Glu His His Gln Gly Thr Tyr Tyr Ala Glu Ile His Leu
                85                  90                  95

Lys Lys Glu His Ala Pro Arg Ala Val Thr Phe Val Leu Phe Asn Pro
                100                 105                 110

Glu Leu Asn Arg Trp Tyr Arg Ala Glu Gly Gly Asn Phe Val Leu
            115                 120                 125

Arg Met Asp Leu Glu Ser Phe Ser Gln Leu Pro Gly Ser Val Gly Lys
    130                 135                 140

His Glu Asp Val Ala Gln Lys Ile Ile Glu Val Glu Val Glu Tyr Gly
145                 150                 155                 160

Ser Trp Thr Leu Met His Arg Tyr Asn Leu Ala Asn Asp Ile Leu Arg
                165                 170                 175

Asn Ser Met Ser Ala Leu Asp Ala Asp Leu Leu Gln Ile Val Phe Val
            180                 185                 190

Trp Leu Arg Tyr Ser Phe Leu Arg Gln Leu Asp Trp Gln Arg Ser Tyr
    195                 200                 205

Asn Thr Gln Pro Arg Leu Leu Ala His Ala Gln Glu Gln Leu Thr Thr
210                 215                 220

Thr Leu Ala Gln Val Phe Val Ser Arg Pro Asp Leu Arg Leu Trp Val
225                 230                 235                 240

Arg Leu Cys Leu Ser Met Leu Gly Arg Gly Gly Asn Gly Gln Arg
                245                 250                 255

Ile Arg Asp Asp Ile Leu Arg Ile Met His Lys His Ile Pro Glu
    260                 265                 270

Thr Pro Gly His Phe Met Glu Gln Trp His Gln Lys Leu His Asn Asn
    275                 280                 285

Thr Thr Pro Asp Asp Val Ala Ile Cys Glu Ser Tyr Leu Ala Phe Leu
    290                 295                 300

Arg Ser Asn Gly Asp Lys Asn Val Phe Tyr Glu Thr Leu Gln Lys His
305                 310                 315                 320

Gly Val Thr Lys Glu Arg Leu Ala Ser Tyr Glu Arg Pro Ile Phe Ala
                325                 330                 335

Glu Val Gln Thr Tyr Pro Cys Asp Thr Asn Ser Leu Ile His Asp Phe
                340                 345                 350

Glu Glu Tyr Leu His Val Leu Lys Ser Val His Ser Gly Thr Asp Leu
            355                 360                 365

Ala Val Val Leu Asp Tyr Ala Arg Trp Thr Leu Asp Gln Glu Leu Ile
    370                 375                 380

Ser Lys Val Glu His Ile Gln Ser Val Arg Ala Glu Leu Met Ala Ser
385                 390                 395                 400

Pro Gln Gly Ala Leu Glu Phe Ser Phe Leu Ile Ala Glu Ala Arg Lys
                405                 410                 415

Met Leu Gln Ser Thr Leu Glu His Val Glu Asp Pro Thr Arg Val Arg
```

```
            420             425             430
Asp Met Leu Phe Leu Asp Leu Ala Leu Asp Glu Leu Ala Arg Leu Ala
        435             440             445

Val Glu Ser Gln Gly Leu Ala Asp Tyr Val Ala Glu Thr Asp Val Gln
        450             455             460

Lys Ala Cys Asn Leu Leu Val Val Leu Ala Gln His Val Gly Trp Ser
465             470             475             480

Met Leu Ser Ser Ala Phe Leu Glu Thr Ser Tyr Asp Leu Ala Ala Leu
            485             490             495

Val Tyr Gly Ile Gln Ser Asp Val Gln Leu Gln Glu Pro Asp Phe Gly
            500             505             510

Leu Arg Leu Tyr Ala Thr Met Glu Arg Leu Met Asp Cys Val Gly His
        515             520             525

Asp Val Val Glu Arg Leu His His Asp Val Gln Pro Lys Ala Val Tyr
        530             535             540

Ile Gly Val Gly Cys Asn Ile Asp Gln Lys Val Val Thr Leu Phe Ser
545             550             555             560

Glu Glu Leu Ile Arg Gly Gln Ala Ala Phe Ala Leu Ala Gln Val Leu
            565             570             575

Arg Pro Leu Met Arg Asn Ile Arg Lys Gln Ala Asn Leu Gly Asn Trp
        580             585             590

Gln Val Ile Ser Pro Gly Ser Cys Thr Gly Gln Gly Ala Val Phe Asp
        595             600             605

Glu Leu Leu Ser Ile Gln Tyr Lys Thr Phe Ala Glu Pro Thr Val Ala
        610             615             620

Phe Val Arg Arg Ile Ser Gly Glu Glu Ile Pro Thr Gly Met Val
625             630             635             640

Gly Leu Ile Thr Thr Asp Thr Leu Asp Ile Leu Ser Ala Cys Ala Val
            645             650             655

Arg Ala Arg Asn Glu His Val Val Leu Ala Cys Cys Phe Ser Glu Glu
            660             665             670

Leu Phe Asp Gln Leu Thr Glu Arg Phe Arg Gly Ala Trp Val Ala Val
        675             680             685

Arg Ser Leu Thr Asp Gly Ser Leu Asp Phe Gln Pro Ile Gln Glu Gly
        690             695             700

Ala Gly Arg Thr Thr Ala Ala Asp Thr Thr Asp Gly Ala Ser Glu His
705             710             715             720

Ala Gln Arg Arg Ala Val Ser Met Arg Ser Asp Ile Glu Lys Lys Pro
            725             730             735

Val Lys Ser Val Leu Gly Ile Ala Gln Phe Asn Thr Gln Arg Gly Gly
            740             745             750

Ser Lys Ser Asn Ser Leu Ala Lys Leu Ile Arg Val Ile Pro Asp Trp
        755             760             765

Ile His Ile Pro Pro Cys Ala Leu Leu Pro Phe Gly Val Cys Glu Gln
        770             775             780

Val Leu Ala Glu Ala Gln Asn Ser Asp Val Gly Glu Arg Phe Gln Gln
785             790             795             800

Leu Met Ala Glu Leu Asp Gly Lys Gly Pro Thr Asp Asp Cys Ser Ala
            805             810             815

Leu Leu Ala Arg Leu Arg His Cys Val Arg Gln Leu Ala Pro Ser Asp
            820             825             830

Thr Phe Met Lys Glu Leu Gln Gln Val Leu Gln His Glu Gly Phe His
        835             840             845
```

```
Ser Ile Asp Asn Leu Asp Met Arg Arg Ala Trp Glu Cys Ile Leu Asp
    850                 855                 860

Val Trp Ala Ser Lys Phe Asn Asp Arg Ala Phe Leu Ala Leu Arg Lys
865                 870                 875                 880

Ala Gly Ala Val Gly Lys Thr Ser Leu Ser Ser Leu Tyr Met Ala Val
                885                 890                 895

Leu Val Gln Glu Val Val Pro Ala Asp Tyr Ala Phe Val Leu His Thr
            900                 905                 910

Lys Asn Pro Phe Thr Gly Glu Pro Ser Glu Ile Tyr Gly Glu Leu Val
        915                 920                 925

His Gly Leu Gly Glu Val Leu Val Gly Asn Tyr Pro Gly Arg Ala Leu
    930                 935                 940

Gly Phe Thr Tyr Ser Lys Ser Thr Gly Gln Val Arg Val Cys Asn Tyr
945                 950                 955                 960

Pro Ser Lys Thr Lys Ala Leu Ile Pro Arg Gly Gly Leu Ile Phe Arg
                965                 970                 975

Ser Asp Ser Asn Gly Glu Asp Leu Glu Asp Phe Ala Gly Ala Gly Leu
            980                 985                 990

Phe Asp Ser Ile Leu Met Gln Pro Ala Glu Glu Val Val  Val Arg Tyr
        995                1000                1005

Arg Glu  Leu Lys Ile Leu Gln  Asp Lys Ala Tyr Leu  Glu Arg Ile
    1010                1015                1020

Leu Ser Lys Ile Gly Lys Cys  Gly Ile Glu Ile Glu  Ser Asn Cys
    1025                1030                1035

Gly Asn Lys Pro Gln Asp Ile  Glu Gly Cys Ile Cys  Gly Glu Asp
    1040                1045                1050

Val Tyr Val Val Gln Ser Arg  Asp Gln Val
    1055                1060

<210> SEQ ID NO 21
<211> LENGTH: 4389
<212> TYPE: DNA
<213> ORGANISM: Solanum tuberosum

<400> SEQUENCE: 21
atgagtaatt ccttagggaa taacttgctg taccagggat tcctaacctc aacagtgttg      60
gaacataaaa gtagaatcag tcctccttgt gttggaggca attctttgtt tcaacaacaa     120
gtgatctcga aatcaccatt atcaactgag tttcgaggta acaggttaaa ggtgcagaaa     180
aagaaaatac ctatggaaaa gaagcgtgct ttttctagtt ctcctcatgc tgtacttacc     240
actgataccc ttctgagct agcagaaaag ttcagtctag aaaggaatat tgagctacag     300
gttgatgtta ggcctcccac ttcaggtgat gtgtcctttg tggattttca agctacaaat     360
ggtagtgata aactgttttt gcactggggg gcagtaaagt tcgggaaaga aacatggtct     420
cttcctaatg atcgtccaga tgggaccaaa gtgtacaaga caaagcact agaactcca     480 tttgttaaat ctggctctaa ctccatcctg agactggaga tacgggacac tgctatcgaa     540
gctattgagt ttctcatata cgatgaagcc tacgataaat ggataaagaa taatggtggc     600 aatttt cgtg tcaaattgtc aagaaaagag atacgaggcc cagatgtttc agttcctgag     660
gagcttgtac agatccaatc atatttgagg tgggagagga agggaaaaca gaattacacc     720
cctgagaaag agaaggagga atatgaggct gctcgaactg agctacagga ggaaatagct     780
cgtggtgctt ccatacagga cattcgagca aggctaacaa aaactaatga taaaagtcaa     840
```

-continued

```
agcaaagaag agcctcttca tgtaacaaag agtgaaatac ctgatgacct tgcccaagca    900
caagcttaca ttaggtggga gaaagcagga aagccgaact atcctccaga aaagcaaatt    960
gaagaactcg aagaagcaag agagaattg caacttgagc ttgagaaagg cattacccct   1020
gatgagttgc ggaaaaagat tacaaaaggg gagataaaaa ctaaggcgga aaagcacgtg   1080
aaaagaagct cttttgccgt tgaaagaatc aaagaaaga agagagactt tgggcagctt   1140
attaagtatc cttccagtcc tgcagtacaa gtacaaaagg tcttggaaga accaccagcc   1200
ttatctaaaa ttaagctgta tgccaaggag aaggaggagc agattgatga tccgatccta   1260
aataaaaaga tctttaaggt cgatgatggg gagctactgg tactggtagc aaagtcctct   1320
gggaagacaa aagtacatct agctacagat ctgaatcagc caattactct tcactgggca   1380
ttatccaaaa gtcgtggaga gtggatggta ccaccttcaa gcatattgcc tcctggatca   1440
attatttag acaaggctgc cgaaacacct ttttccgcca gttcttctga tggtctaact   1500
tctaaggtac aatctttgga tatagtaatt gaagatggca attttgtggg gatgccattt   1560
gttcttttgt ctggtgaaaa atggattaag aaccaagggt cggatttcta tgttgacttc   1620
agtgctgcat ccaaattagc actcaaggct gctggggatg gcagtggaac tgcaaagtct   1680
ttactggata aaatagcaga tatggaaagt gaggctcaga agtcatttat gcaccggttt   1740
aatattgctg ctgacttgat agaagatgcc actagtgctg gtgaacttgg ttttgctgga   1800
attcttgtat ggatgaggtt catggctaca aggcaactga tatggaacaa aaactataac   1860
gtaaaaccac gtgaaataag caaggctcag gacagactta cagacttgtt gcagaatgct   1920
ttcaccagtc accctcaata ccgtgaaatt ttgcggatga ttatgtcaac tgttggacgt   1980
ggaggtgaag gggatgtagg acagcgaatt agggatgaaa ttttggtcat ccagaggaaa   2040
aatgactgca agggtggtat gatggaagaa tggcatcaga aattgcataa taatactagt   2100
cctgatgatg ttgtgatctg tcaggcattg attgactaca tcaagagtga ttttgatctt   2160
ggtgtttatt ggaaaaccct gaatgagaac ggaataacaa agagcgtct tttgagttat   2220
gaccgtgcta tccattctga accgaatttt agaggagatc aaaagaatgg tcttttgcgt   2280
gatttaggtc actatatgag aacattgaag gctgttcatt caggtgcaga tcttgagtct   2340
gctattgcaa actgcatggg ctacaaaact gagggagaag ctttatggt tggagtccag   2400
ataaatcctg tatcaggctt gccatctggc tttcagggcc tcctccattt tgtcttggac   2460
catgtggaag ataaaaatgt ggaaactctt cttgagggat tgctagaggc tcgtgaggag   2520
cttaggcccct tgcttctcaa accaaacaac cgtctaaagg atctgctgtt tttggacata   2580
gcacttgatt ctacagttag aacagcagta gaaaggggat atgaagaatt gaacaacgct   2640
aatcctgaga aaatcatgta cttcatctcc ctcgttcttg aaaatctcgc actctctgtg   2700
gacgataatg aagatcttgt ttattgcttg aagggatgga tcaagctct ttcaatgtcc   2760
aatggtggag acaaccattg ggctttattt gcaaaagctg tacttgacag aacccgtctt   2820
gcacttgcaa gcaaggcaga gtggtaccat cacttattgc agccatctgc cgaatatcta   2880
ggatcaatcc ttggggtgga ccaatgggct ttgaacatat ttactgaaga aattatacgt   2940
gctggatcag cagcttcatt atcctctctt cttaatagac tcgatcccgt gcttcggaaa   3000
actgcaaatc taggaagttg gcagattatc agcccagttg aagccgttgg atatgttgtc   3060
gttgtggatg agttgctttc agttcagaat gaaatctacg agaagccac gatcttagta   3120
gcaaactctg ttaaaggaga ggaggaaatt cctgatggtg ctgttgccct gataacacca   3180
gacatgccag atgttctttc acatgtttct gttcgagcta gaaatgggaa ggtttgcttt   3240
```

```
gctacatgct tgatcccaa tatattggct gacctccaag caaaggaagg aaggattttg    3300
ctcttaaagc ctacaccttc agacataatc tatagtgagg tgaatgagat tgagctccaa    3360
agttcaagta acttggtaga agctgaaact tcagcaacac ttagattggt gaaaaagcaa    3420
tttggtggtt gttacgcaat atcagcagat gaattcacaa gtgaaatggt tggagctaaa    3480
tcacgtaata ttgcttatct gaaaggaaaa gtgccttcct cggtgggaat tcctacgtca    3540
gtagctcttc catttggagt ctttgagaaa gtactttcag acgacataaa tcagggagtg    3600
gcaaaagagt tgcaaattct gacgaaaaaa ctatctgaag gagacttcag cgctcttggt    3660
gaaattcgca aacgatttt agatctttca gcaccagctc aattggtcaa agagctgaag    3720
gaaaagatgc agggttctgg catgccttgg cctggtgatg aaggtccaaa gcggtgggaa    3780
caagcatgga tggccataaa aaaggtgtgg gcttcaaaat ggaatgagag agcatacttc    3840
agcacaagga aggtgaaact ggatcatgac tatctgtgta tggctgtcct tgttcaagaa    3900
ataataaatg ctgattatgc atttgtcatt cacgcaacca acccatcttc cggagacgac    3960
tcagaaatat atgccgaggt ggtcaggggc cttggggaaa cacttgttgg agcttatcca    4020
ggacgtgctt tgagttttat ctgcaagaaa aaggatctca actctactca agtgttaggt    4080
tacccaagca aaccgatcgg ccttttcata aaaagatcta tcatcttccg atctgattcc    4140
aatggggaag atttggaagg ttatgccggt gctggcctct acgacagtgt accaatggat    4200
gaggaggaaa aagttgtaat tgattactct tccgatccat tgataactga tggtaacttc    4260
cgccagacaa tcctgtccag cattgctcgt gctggacatg ctatcgagga gctatatggc    4320
tctcctcaag acatcgaggg tgtagtgagg gatggaaaga tttatgtcgt tcagacaaga    4380
cctcagatg                                                            4389
```

<210> SEQ ID NO 22
<211> LENGTH: 1463
<212> TYPE: PRT
<213> ORGANISM: Solanum tuberosum

<400> SEQUENCE: 22

```
Met Ser Asn Ser Leu Gly Asn Asn Leu Leu Tyr Gln Gly Phe Leu Thr
1               5                   10                  15

Ser Thr Val Leu Glu His Lys Ser Arg Ile Ser Pro Pro Cys Val Gly
            20                  25                  30

Gly Asn Ser Leu Phe Gln Gln Gln Val Ile Ser Lys Ser Pro Leu Ser
        35                  40                  45

Thr Glu Phe Arg Gly Asn Arg Leu Lys Val Gln Lys Lys Ile Pro
    50                  55                  60

Met Glu Lys Lys Arg Ala Phe Ser Ser Pro His Ala Val Leu Thr
65                  70                  75                  80

Thr Asp Thr Ser Ser Glu Leu Ala Glu Lys Phe Ser Leu Gly Gly Asn
            85                  90                  95

Ile Glu Leu Gln Val Asp Val Arg Pro Pro Thr Gly Asp Val Ser
            100                 105                 110

Phe Val Asp Phe Gln Val Thr Asn Gly Ser Asp Lys Leu Phe Leu His
        115                 120                 125

Trp Gly Ala Val Lys Phe Gly Lys Glu Thr Trp Ser Leu Pro Asn Asp
        130                 135                 140

Arg Pro Asp Gly Thr Lys Val Tyr Lys Asn Lys Ala Leu Arg Thr Pro
145                 150                 155                 160
```

```
Phe Val Lys Ser Gly Ser Asn Ser Ile Leu Arg Leu Glu Ile Arg Asp
            165                 170                 175
Thr Ala Ile Glu Ala Ile Glu Phe Leu Ile Tyr Asp Glu Ala His Asp
        180                 185                 190
Lys Trp Ile Lys Asn Asn Gly Gly Asn Phe Arg Val Lys Leu Ser Arg
        195                 200                 205
Lys Glu Ile Arg Gly Pro Asp Val Ser Val Pro Glu Glu Leu Val Gln
    210                 215                 220
Ile Gln Ser Tyr Leu Arg Trp Glu Arg Lys Gly Lys Gln Asn Tyr Pro
225                 230                 235                 240
Pro Glu Lys Glu Lys Glu Glu Tyr Glu Ala Ala Arg Thr Val Leu Gln
                245                 250                 255
Glu Glu Ile Ala Arg Gly Ala Ser Ile Gln Asp Ile Arg Ala Arg Leu
            260                 265                 270
Thr Lys Thr Asn Asp Lys Ser Gln Ser Lys Glu Glu Pro Leu His Val
        275                 280                 285
Thr Lys Ser Asp Ile Pro Asp Leu Ala Gln Ala Gln Ala Tyr Ile
        290                 295                 300
Arg Trp Glu Lys Ala Gly Lys Pro Asn Tyr Pro Pro Glu Lys Gln Ile
305                 310                 315                 320
Glu Glu Leu Glu Glu Ala Arg Arg Glu Leu Gln Leu Glu Leu Glu Lys
                325                 330                 335
Gly Ile Thr Leu Asp Glu Leu Arg Lys Thr Ile Thr Lys Gly Glu Ile
            340                 345                 350
Lys Thr Lys Val Glu Lys His Leu Lys Arg Ser Ser Phe Ala Val Glu
        355                 360                 365
Arg Ile Gln Arg Lys Lys Arg Asp Phe Gly His Leu Ile Asn Lys Tyr
    370                 375                 380
Thr Ser Ser Pro Ala Val Gln Val Gln Lys Val Leu Glu Glu Pro Pro
385                 390                 395                 400
Ala Leu Ser Lys Ile Lys Leu Tyr Ala Lys Glu Lys Glu Glu Gln Ile
                405                 410                 415
Asp Asp Pro Ile Leu Asn Lys Lys Ile Phe Lys Val Asp Asp Gly Glu
            420                 425                 430
Leu Leu Val Leu Val Ala Lys Ser Ser Gly Lys Thr Lys Val His Leu
        435                 440                 445
Ala Thr Asp Leu Asn Gln Pro Ile Thr Leu His Trp Ala Leu Ser Lys
        450                 455                 460
Ser Pro Gly Glu Trp Met Val Pro Pro Ser Ser Ile Leu Pro Pro Gly
465                 470                 475                 480
Ser Ile Ile Leu Asp Lys Ala Ala Glu Thr Pro Phe Ser Ala Ser Ser
                485                 490                 495
Ser Asp Gly Leu Thr Ser Lys Val Gln Ser Leu Asp Ile Val Ile Glu
            500                 505                 510
Asp Gly Asn Phe Val Gly Met Pro Phe Val Leu Leu Ser Gly Glu Lys
        515                 520                 525
Trp Ile Lys Asn Gln Gly Ser Asp Phe Tyr Val Gly Phe Ser Ala Ala
        530                 535                 540
Ser Lys Leu Ala Leu Lys Ala Ala Gly Asp Gly Ser Gly Thr Ala Lys
545                 550                 555                 560
Ser Leu Leu Asp Lys Ile Ala Asp Met Glu Ser Glu Ala Gln Lys Ser
                565                 570                 575
Phe Met His Arg Phe Asn Ile Ala Ala Asp Leu Ile Glu Asp Ala Thr
```

```
            580             585             590
Ser Ala Gly Glu Leu Gly Phe Ala Gly Ile Leu Val Trp Met Arg Phe
            595             600             605
Met Ala Thr Arg Gln Leu Ile Trp Asn Lys Asn Tyr Asn Val Lys Pro
            610             615             620
Arg Glu Ile Ser Lys Ala Gln Asp Arg Leu Thr Asp Leu Leu Gln Asn
625             630             635             640
Ala Phe Thr Ser His Pro Gln Tyr Arg Glu Ile Leu Arg Met Ile Met
                645             650             655
Ser Thr Val Gly Arg Gly Gly Glu Gly Asp Val Gly Gln Arg Ile Arg
            660             665             670
Asp Glu Ile Leu Val Ile Gln Arg Asn Asn Asp Cys Lys Gly Gly Met
            675             680             685
Met Gln Glu Trp His Gln Lys Leu His Asn Asn Thr Ser Pro Asp Asp
            690             695             700
Val Val Ile Cys Gln Ala Leu Ile Asp Tyr Lys Ser Asp Phe Asp Leu
705             710             715             720
Gly Val Tyr Trp Lys Thr Leu Asn Glu Asn Gly Ile Thr Lys Glu Arg
                725             730             735
Leu Leu Ser Tyr Asp Arg Ala Ile His Ser Glu Pro Asn Phe Arg Gly
            740             745             750
Asp Gln Lys Gly Gly Leu Leu Arg Asp Leu Gly His Tyr Met Arg Thr
            755             760             765
Leu Lys Ala Val His Ser Gly Ala Asp Leu Glu Ser Ala Ile Ala Asn
            770             775             780
Cys Met Gly Tyr Lys Thr Glu Gly Glu Gly Phe Met Val Gly Val Gln
785             790             795             800
Ile Asn Pro Val Ser Gly Leu Pro Ser Gly Phe Gln Asp Leu Leu His
                805             810             815
Phe Val Leu Asp His Val Glu Asp Lys Asn Val Glu Thr Leu Leu Glu
            820             825             830
Arg Leu Leu Glu Ala Arg Glu Glu Leu Arg Pro Leu Leu Lys Pro
            835             840             845
Asn Asn Arg Leu Lys Asp Leu Leu Phe Leu Asp Ile Ala Leu Asp Ser
            850             855             860
Thr Val Arg Thr Ala Val Glu Arg Gly Tyr Glu Glu Leu Asn Asn Ala
865             870             875             880
Asn Pro Glu Lys Ile Met Tyr Phe Ile Ser Leu Val Leu Glu Asn Leu
                885             890             895
Ala Leu Ser Val Asp Asp Asn Glu Asp Leu Val Tyr Cys Leu Lys Gly
            900             905             910
Trp Asn Gln Ala Leu Ser Met Ser Asn Gly Gly Asp Asn His Trp Ala
            915             920             925
Leu Phe Ala Lys Ala Val Leu Asp Arg Thr Arg Leu Ala Leu Ala Ser
            930             935             940
Lys Ala Glu Trp Tyr His His Leu Leu Gln Pro Ser Ala Glu Tyr Leu
945             950             955             960
Gly Ser Ile Leu Gly Val Asp Gln Trp Ala Leu Asn Ile Phe Thr Glu
                965             970             975
Glu Ile Ile Arg Ala Gly Ser Ala Ala Ser Leu Ser Ser Leu Leu Asn
            980             985             990
Arg Leu Asp Pro Val Leu Arg Lys  Thr Ala Asn Leu Gly  Ser Trp Gln
            995             1000             1005
```

Ile Ile Ser Pro Val Glu Ala Val Gly Tyr Val Val Val Asp
     1010                1015                1020

Glu Leu Leu Ser Val Gln Asn Glu Ile Tyr Glu Lys Pro Thr Ile
     1025                1030                1035

Leu Val Ala Lys Ser Val Lys Gly Glu Glu Ile Pro Asp Gly
     1040                1045                1050

Ala Val Ala Leu Ile Thr Pro Asp Met Pro Asp Val Leu Ser His
     1055                1060                1065

Val Ser Val Arg Ala Arg Asn Gly Lys Val Cys Phe Ala Thr Cys
     1070                1075                1080

Phe Asp Pro Asn Ile Leu Ala Asp Leu Gln Ala Lys Glu Gly Arg
     1085                1090                1095

Ile Leu Leu Leu Lys Pro Thr Pro Ser Asp Ile Ile Tyr Ser Glu
     1100                1105                1110

Val Asn Glu Ile Glu Leu Gln Ser Ser Ser Asn Leu Val Glu Ala
     1115                1120                1125

Glu Thr Ser Ala Thr Leu Arg Leu Val Lys Lys Gln Phe Gly Gly
     1130                1135                1140

Cys Tyr Ala Ile Ser Ala Asp Glu Phe Thr Ser Glu Met Val Gly
     1145                1150                1155

Ala Lys Ser Arg Asn Ile Ala Tyr Leu Lys Gly Lys Val Pro Ser
     1160                1165                1170

Ser Val Gly Ile Pro Thr Ser Val Ala Leu Pro Phe Gly Val Phe
     1175                1180                1185

Glu Lys Val Leu Ser Asp Asp Ile Asn Gln Gly Val Ala Lys Glu
     1190                1195                1200

Leu Gln Ile Leu Met Lys Lys Leu Ser Glu Gly Asp Phe Ser Ala
     1205                1210                1215

Leu Gly Glu Ile Arg Thr Thr Val Leu Asp Leu Ser Ala Pro Ala
     1220                1225                1230

Gln Leu Val Lys Glu Leu Lys Glu Lys Met Gln Gly Ser Gly Met
     1235                1240                1245

Pro Trp Pro Gly Asp Glu Gly Pro Lys Arg Trp Glu Gln Ala Trp
     1250                1255                1260

Met Ala Ile Lys Lys Val Trp Ala Ser Lys Trp Asn Glu Arg Ala
     1265                1270                1275

Tyr Phe Ser Thr Arg Lys Val Lys Leu Asp His Asp Tyr Leu Cys
     1280                1285                1290

Met Ala Val Leu Val Gln Glu Ile Ile Asn Ala Asp Tyr Ala Phe
     1295                1300                1305

Val Ile His Thr Thr Asn Pro Ser Ser Gly Asp Asp Ser Glu Ile
     1310                1315                1320

Tyr Ala Glu Val Val Arg Gly Leu Gly Glu Thr Leu Val Gly Ala
     1325                1330                1335

Tyr Pro Gly Arg Ala Leu Ser Phe Ile Cys Lys Lys Lys Asp Leu
     1340                1345                1350

Asn Ser Pro Gln Val Leu Gly Tyr Pro Ser Lys Pro Ile Gly Leu
     1355                1360                1365

Phe Ile Lys Arg Ser Ile Ile Phe Arg Ser Asp Ser Asn Gly Glu
     1370                1375                1380

Asp Leu Glu Gly Tyr Ala Gly Ala Gly Leu Tyr Asp Ser Val Pro
     1385                1390                1395

```
Met Asp Glu Glu Lys Val Val Ile Asp Tyr Ser  Ser Asp Pro
    1400          1405                1410

Leu Ile Thr Asp Gly Asn Phe Arg Gln Thr Ile Leu Ser Asn Ile
    1415              1420              1425

Ala Arg Ala Gly His Ala Ile Glu Glu Leu Tyr Gly Ser Pro Gln
    1430              1435              1440

Asp Ile Glu Gly Val Val Arg Asp Gly Lys Ile Tyr Val Val Gln
    1445              1450              1455

Thr Arg Pro Gln Met
    1460
```

<210> SEQ ID NO 23
<211> LENGTH: 4170
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 23

```
tctcctcatg ctgtacttac cactgatacc tcttctgagc tagcagaaaa gttcagtcta    60
gaaaggaata ttgagctaca ggttgatgtt aggcctccca cttcaggtga tgtgtccttt   120
gtggattttc aagctacaaa tggtagtgat aaactgtttt tgcactgggg ggcagtaaag   180
ttcgggaaag aaacatggtc tcttcctaat gatcgtccag atgggaccaa agtgtacaag   240
aacaaagcac ttagaactcc atttgttaaa tctggctcta actccatcct gagactggag   300
atacgggaca ctgctatcga agctattgag tttctcatat acgatgaagc ctacgataaa   360
tggataaaga ataatggtgg caattttcgt gtcaaattgt caagaaaaga gatacgaggc   420
ccagatgttt cagttcctga ggagcttgta cagatccaat catatttgag gtgggagagg   480
aagggaaaac agaattacac ccctgagaaa gagaaggagg aatatgaggc tgctcgaact   540
gagctacagg aggaaatagc tcgtggtgct tccatacagg acattcgagc aaggctaaca   600
aaaactaatg ataaaagtca agcaaagaa gagcctcttc atgtaacaaa gagtgaaata   660
cctgatgacc ttgcccaagc acaagcttac attaggtggg agaaagcagg aaagccgaac   720
tatcctccag aaaagcaaat tgaagaactc gaagaagcaa aagagaatt gcaacttgag   780
cttgagaaag gcattaccct tgatgagttg cggaaaaaga ttacaaaagg ggagataaaa   840
actaaggcgg aaaagcacgt gaaagaagc tcttttgccg ttgaaagaat ccaaagaaag   900
aagagagact ttgggcagct tattaagtat ccttccagtc ctgcagtaca agtacaaaag   960
gtcttggaag aaccaccagc cttatctaaa attaagctgt atgccaagga aggaggag    1020
cagattgatg atccgatcct aaataaaaag atctttaagg tcgatgatgg ggagctactg   1080
gtactggtag caaagtcctc tgggaagaca aaagtacatc tagctacaga tctgaatcag   1140
ccaattactc ttcactgggc attatccaaa agtcgtggag agtggatggt accaccttca   1200
agcatattgc ctcctggatc aattatttta gacaaggctg ccgaaacacc ttttccgcc   1260
agttcttctg atggtctaac ttctaaggta caatctttgg atatagtaat tgaagatggc   1320
aattttgtgg ggatgccatt tgttcttttg tctggtgaaa aatggattaa gaaccaaggg   1380
tcggatttct atgttgactt cagtgctgca tccaaattag cactcaaggc tgctgggat   1440
ggcagtggaa ctgcaaagtc tttactggat aaaatagcag atatggaaag tgaggctcag   1500
aagtcattta tgcaccggtt taatattgct gctgacttga tagaagatgc cactagtgct   1560
ggtgaacttg gttttgctgg aattcttgta tggatgaggt tcatggctac aaggcaactg   1620
```

```
atatggaaca aaaactataa cgtaaaacca cgtgaaataa gcaaggctca ggacagactt    1680
acagacttgt tgcagaatgc tttcaccagt caccctcaat accgtgaaat tttgcggatg    1740
attatgtcaa ctgttggacg tggaggtgaa ggggatgtag gacagcgaat tagggatgaa    1800
attttggtca tccagaggaa aaatgactgc aagggtggta tgatggaaga atggcatcag    1860
aaattgcata ataatactag tcctgatgat gttgtgatct gtcaggcatt gattgactac    1920
atcaagagtg attttgatct tggtgtttat tggaaaaccc tgaatgagaa cggaataaca    1980
aaagagcgtc ttttgagtta tgaccgtgct atccattctg aaccgaattt tagaggagat    2040
caaaagaatg gtcttttgcg tgatttaggt cactatatga aacattgaa ggctgttcat     2100 tcaggtgcag atcttgagtc tgctattgca aactgcatgg gctacaaaac tgagggagaa    2160
ggctttatgg ttggagtcca gataaatcct gtatcaggct tgccatctgg ctttcagggc    2220
ctcctccatt ttgtcttgga ccatgtggaa gataaaaatg tggaaactct tcttgaggga    2280
ttgctagagg ctcgtgagga gcttaggccc ttgcttctca aaccaaacaa ccgtctaaag    2340
gatctgctgt ttttggacat agcacttgat tctacagtta aacagcagt agaaagggga     2400 tatgaagaat tgaacaacgc taatcctgag aaaatcatgt acttcatctc cctcgttctt    2460
gaaaatctcg cactctctgt ggacgataat gaagatcttg tttattgctt gaagggatgg    2520
aatcaagctc tttcaatgtc caatggtgga gacaaccatt gggcttttat tgcaaaagct    2580
gtacttgaca gaacccgtct tgcacttgca agcaaggcag agtggtacca tcacttattg    2640
cagccatctg ccgaatatct aggatcaatc cttggggtgg accaatgggc tttgaacata    2700
tttactgaag aaattatacg tgctggatca gcagcttcat tatcctctct tcttaataga    2760
ctcgatcccg tgcttcggaa aactgcaaat ctaggaagtt ggcagattat cagcccagtt    2820
gaagccgttg gatatgttgt cgttgtggat gagttgcttt cagttcagaa tgaaatctac    2880
gagaagccca cgatcttagt agcaaactct gttaaggag aggaggaaat tcctgatggt     2940
gctgttgccc tgataacacc agacatgcca gatgttcttt cacatgtttc tgttcgagct    3000
agaaatggga aggtttgctt tgctacatgc tttgatccca atatattggc tgacctccaa    3060
gcaaaggaag gaaggatttt gctcttaaag cctacacctt cagacataat ctatagtgag    3120
gtgaatgaga ttgagctcca aagttcaagt aacttggtag aagctgaaac ttcagcaaca    3180
cttagattgg tgaaaaagca atttggtggt tgttacgcaa tatcagcaga tgaattcaca    3240
agtgaaatgg ttggagctaa atcacgtaat attgcttatc tgaaaggaaa agtgccttcc    3300
tcggtgggaa ttcctacgtc agtagctctt ccatttggag tctttgagaa gtactttca    3360 gacgacataa atcagggagt ggcaaaagag ttgcaaattc tgacgaaaaa actatctgaa    3420
ggagacttca gcgctcttgg tgaaattcgc acaacgattt tagatctttc agcaccagct    3480
caattggtca aagagctgaa ggaaaagatg cagggttctg gcatgccttg gcctggtgat    3540
gaaggtccaa gcggtggga acaagcatgg atggccataa aaaaggtgtg gcttcaaaa      3600 tggaatgaga gagcatactt cagcacaagg aaggtgaaac tggatcatga ctatctgtgt    3660
atggctgtcc ttgttcaaga aataataaat gctgattatg catttgtcat tcacgcaacc    3720
aacccatctt ccggagacga ctcagaaata tatgccgagg tggtcagggg ccttgggaa     3780 acacttgttg gagcttatcc aggacgtgct ttgagtttta tctgcaagaa aaaggatctc    3840
aactctactc aagtgttagg ttacccaagc aaaccgatcg gccttttcat aaaaagatct    3900
atcatcttcc gatctgattc caatgggaa gatttggaag gttatgccgg tgctggcctc     3960
tacgacagtg taccaatgga tgaggaggaa aaagttgtaa ttgattactc ttccgatcca    4020
```

-continued

```
ttgataactg atggtaactt ccgccagaca atcctgtcca gcattgctcg tgctggacat    4080
gctatcgagg agctatatgg ctctcctcaa gacatcgagg gtgtagtgag ggatggaaag    4140
atttatgtcg ttcagacaag acctcagatg                                    4170
```

<210> SEQ ID NO 24
<211> LENGTH: 1391
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 24

```
Ser Pro His Ala Val Leu Thr Thr Asp Thr Ser Ser Glu Leu Ala Glu
1               5                   10                  15

Lys Phe Ser Leu Gly Gly Asn Ile Glu Leu Gln Val Asp Val Arg Pro
            20                  25                  30

Pro Thr Ser Gly Asp Val Ser Phe Val Asp Phe Gln Val Thr Asn Gly
        35                  40                  45

Ser Asp Lys Leu Phe Leu His Trp Gly Ala Val Lys Phe Gly Lys Glu
    50                  55                  60

Thr Trp Ser Leu Pro Asn Asp Arg Pro Asp Gly Thr Lys Val Tyr Lys
65                  70                  75                  80

Asn Lys Ala Leu Arg Thr Pro Phe Val Lys Ser Gly Ser Asn Ser Ile
                85                  90                  95

Leu Arg Leu Glu Ile Arg Asp Thr Ala Ile Glu Ala Ile Glu Phe Leu
            100                 105                 110

Ile Tyr Asp Glu Ala His Asp Lys Trp Ile Lys Asn Asn Gly Gly Asn
        115                 120                 125

Phe Arg Val Lys Leu Ser Arg Lys Glu Ile Arg Gly Pro Asp Val Ser
    130                 135                 140

Val Pro Glu Glu Leu Val Gln Ile Gln Ser Tyr Leu Arg Trp Glu Arg
145                 150                 155                 160

Lys Gly Lys Gln Asn Tyr Pro Pro Glu Lys Glu Lys Glu Glu Tyr Glu
                165                 170                 175

Ala Ala Arg Thr Val Leu Gln Glu Glu Ile Ala Arg Gly Ala Ser Ile
            180                 185                 190

Gln Asp Ile Arg Ala Arg Leu Thr Lys Thr Asn Asp Lys Ser Gln Ser
        195                 200                 205

Lys Glu Glu Pro Leu His Val Thr Lys Ser Asp Ile Pro Asp Asp Leu
    210                 215                 220

Ala Gln Ala Gln Ala Tyr Ile Arg Trp Glu Lys Ala Gly Lys Pro Asn
225                 230                 235                 240

Tyr Pro Pro Glu Lys Gln Ile Glu Glu Leu Glu Ala Arg Arg Glu
                245                 250                 255

Leu Gln Leu Glu Leu Leu Lys Gly Ile Thr Leu Asp Glu Leu Arg Lys
            260                 265                 270

Thr Ile Thr Lys Gly Glu Ile Lys Thr Lys Val Glu Lys His Leu Lys
        275                 280                 285

Arg Ser Ser Phe Ala Val Glu Arg Ile Gln Arg Lys Arg Asp Phe
    290                 295                 300

Gly His Leu Ile Asn Lys Tyr Thr Ser Ser Pro Ala Val Gln Val Gln
305                 310                 315                 320

Lys Val Leu Glu Glu Pro Pro Ala Leu Ser Lys Ile Lys Leu Tyr Ala
                325                 330                 335
```

```
Lys Glu Lys Glu Glu Gln Ile Asp Asp Pro Ile Leu Asn Lys Lys Ile
            340                 345                 350

Phe Lys Val Asp Asp Gly Glu Leu Leu Val Leu Val Ala Lys Ser Ser
            355                 360                 365

Gly Lys Thr Lys Val His Leu Ala Thr Asp Leu Asn Gln Pro Ile Thr
            370                 375                 380

Leu His Trp Ala Leu Ser Lys Ser Pro Gly Glu Trp Met Val Pro Pro
385                 390                 395                 400

Ser Ser Ile Leu Pro Pro Gly Ser Ile Ile Leu Asp Lys Ala Ala Glu
                405                 410                 415

Thr Pro Phe Ser Ala Ser Ser Ser Asp Gly Leu Thr Ser Lys Val Gln
            420                 425                 430

Ser Leu Asp Ile Val Ile Glu Asp Gly Asn Phe Val Gly Met Pro Phe
            435                 440                 445

Val Leu Leu Ser Gly Glu Lys Trp Ile Lys Asn Gln Gly Ser Asp Phe
450                 455                 460

Tyr Val Gly Phe Ser Ala Ala Ser Lys Leu Ala Leu Lys Ala Ala Gly
465                 470                 475                 480

Asp Gly Ser Gly Thr Ala Lys Ser Leu Leu Asp Lys Ile Ala Asp Met
                485                 490                 495

Glu Ser Glu Ala Gln Lys Ser Phe Met His Arg Phe Asn Ile Ala Ala
            500                 505                 510

Asp Leu Ile Glu Asp Ala Thr Ser Ala Gly Glu Leu Gly Phe Ala Gly
            515                 520                 525

Ile Leu Val Trp Met Arg Phe Met Ala Thr Arg Gln Leu Ile Trp Asn
            530                 535                 540

Lys Asn Tyr Asn Val Lys Pro Arg Glu Ile Ser Lys Ala Gln Asp Arg
545                 550                 555                 560

Leu Thr Asp Leu Leu Gln Asn Ala Phe Thr Ser His Pro Gln Tyr Arg
                565                 570                 575

Glu Ile Leu Arg Met Ile Met Ser Thr Val Gly Arg Gly Gly Glu Gly
            580                 585                 590

Asp Val Gly Gln Arg Ile Arg Asp Glu Ile Leu Val Ile Gln Arg Asn
            595                 600                 605

Asn Asp Cys Lys Gly Gly Met Met Gln Glu Trp His Gln Lys Leu His
            610                 615                 620

Asn Asn Thr Ser Pro Asp Asp Val Val Ile Cys Gln Ala Leu Ile Asp
625                 630                 635                 640

Tyr Ile Lys Ser Asp Phe Asp Leu Gly Val Tyr Trp Lys Thr Leu Asn
                645                 650                 655

Glu Asn Gly Ile Thr Lys Glu Arg Leu Leu Ser Tyr Asp Arg Ala Ile
            660                 665                 670

His Ser Glu Pro Asn Phe Arg Gly Asp Gln Lys Gly Gly Leu Leu Arg
            675                 680                 685

Asp Leu Gly His Tyr Met Arg Thr Leu Lys Ala Val His Ser Gly Ala
            690                 695                 700

Asp Leu Glu Ser Ala Ile Ala Asn Cys Met Gly Tyr Lys Thr Glu Gly
705                 710                 715                 720

Glu Gly Phe Met Val Gly Val Gln Ile Asn Pro Val Ser Gly Leu Pro
                725                 730                 735

Ser Gly Phe Gln Asp Leu Leu His Phe Val Leu Asp His Val Glu Asp
            740                 745                 750
```

```
Lys Asn Val Glu Thr Leu Leu Glu Arg Leu Leu Ala Arg Glu Glu
        755                 760                 765

Leu Arg Pro Leu Leu Lys Pro Asn Asn Arg Leu Lys Asp Leu Leu
    770                 775                 780

Phe Leu Asp Ile Ala Leu Asp Ser Thr Val Arg Thr Ala Val Glu Arg
785                 790                 795                 800

Gly Tyr Glu Glu Leu Asn Asn Ala Asn Pro Glu Lys Ile Met Tyr Phe
                    805                 810                 815

Ile Ser Leu Val Leu Glu Asn Leu Ala Leu Ser Val Asp Asn Glu
                820                 825                 830

Asp Leu Val Tyr Cys Leu Lys Gly Trp Asn Gln Ala Leu Ser Met Ser
                    835                 840                 845

Asn Gly Gly Asp Asn His Trp Ala Leu Phe Ala Lys Ala Val Leu Asp
850                 855                 860

Arg Thr Arg Leu Ala Leu Ala Ser Lys Ala Glu Trp Tyr His His Leu
865                 870                 875                 880

Leu Gln Pro Ser Ala Glu Tyr Leu Gly Ser Ile Leu Gly Val Asp Gln
                    885                 890                 895

Trp Ala Leu Asn Ile Phe Thr Glu Glu Ile Ile Arg Ala Gly Ser Ala
                900                 905                 910

Ala Ser Leu Ser Ser Leu Leu Asn Arg Leu Asp Pro Val Leu Arg Lys
                915                 920                 925

Thr Ala Asn Leu Gly Ser Trp Gln Ile Ile Ser Pro Val Glu Ala Val
                930                 935                 940

Gly Tyr Val Val Val Asp Glu Leu Leu Ser Val Gln Asn Glu Ile
945                 950                 955                 960

Tyr Glu Lys Pro Thr Ile Leu Val Ala Lys Ser Val Lys Gly Glu Glu
                965                 970                 975

Glu Ile Pro Asp Gly Ala Val Ala Leu Ile Thr Pro Asp Met Pro Asp
                980                 985                 990

Val Leu Ser His Val Ser Val Arg  Ala Arg Asn Gly Lys  Val Cys Phe
                995                 1000                1005

Ala Thr  Cys Phe Asp Pro Asn  Ile Leu Ala Asp Leu  Gln Ala Lys
    1010                1015                1020

Glu Gly  Arg Ile Leu Leu Leu  Lys Pro Thr Pro Ser  Asp Ile Ile
    1025                1030                1035

Tyr Ser  Glu Val Asn Glu Ile  Glu Leu Gln Ser Ser  Ser Asn Leu
    1040                1045                1050

Val Glu  Ala Glu Thr Ser Ala  Thr Leu Arg Leu Val  Lys Lys Gln
    1055                1060                1065

Phe Gly  Gly Cys Tyr Ala Ile  Ser Ala Asp Glu Phe  Thr Ser Glu
    1070                1075                1080

Met Val  Gly Ala Lys Ser Arg  Asn Ile Ala Tyr Leu  Lys Gly Lys
    1085                1090                1095

Val Pro  Ser Ser Val Gly Ile  Pro Thr Ser Val Ala  Leu Pro Phe
    1100                1105                1110

Gly Val  Phe Glu Lys Val Leu  Ser Asp Asp Ile Asn  Gln Gly Val
    1115                1120                1125

Ala Lys  Glu Leu Gln Ile Leu  Met Lys Lys Leu Ser  Glu Gly Asp
    1130                1135                1140

Phe Ser  Ala Leu Gly Glu Ile  Arg Thr Thr Val Leu  Asp Leu Ser
    1145                1150                1155

Ala Pro  Ala Gln Leu Val Lys  Glu Leu Lys Glu Lys  Met Gln Gly
```

```
                    1160                1165                1170

Ser Gly Met Pro Trp Pro Gly Asp Glu Gly Pro Lys Arg Trp Glu
        1175                1180                1185

Gln Ala Trp Met Ala Ile Lys Lys Val Trp Ala Ser Lys Trp Asn
        1190                1195                1200

Glu Arg Ala Tyr Phe Ser Thr Arg Lys Val Lys Leu Asp His Asp
        1205                1210                1215

Tyr Leu Cys Met Ala Val Leu Val Gln Glu Ile Ile Asn Ala Asp
        1220                1225                1230

Tyr Ala Phe Val Ile His Thr Thr Asn Pro Ser Ser Gly Asp Asp
        1235                1240                1245

Ser Glu Ile Tyr Ala Glu Val Val Arg Gly Leu Gly Glu Thr Leu
        1250                1255                1260

Val Gly Ala Tyr Pro Gly Arg Ala Leu Ser Phe Ile Cys Lys Lys
        1265                1270                1275

Lys Asp Leu Asn Ser Pro Gln Val Leu Gly Tyr Pro Ser Lys Pro
        1280                1285                1290

Ile Gly Leu Phe Ile Lys Arg Ser Ile Ile Phe Arg Ser Asp Ser
        1295                1300                1305

Asn Gly Glu Asp Leu Glu Gly Tyr Ala Gly Ala Gly Leu Tyr Asp
        1310                1315                1320

Ser Val Pro Met Asp Glu Glu Lys Val Val Ile Asp Tyr Ser
        1325                1330                1335

Ser Asp Pro Leu Ile Thr Asp Gly Asn Phe Arg Gln Thr Ile Leu
        1340                1345                1350

Ser Asn Ile Ala Arg Ala Gly His Ala Ile Glu Glu Leu Tyr Gly
        1355                1360                1365

Ser Pro Gln Asp Ile Glu Gly Val Val Arg Asp Gly Lys Ile Tyr
        1370                1375                1380

Val Val Gln Thr Arg Pro Gln Met
        1385                1390

<210> SEQ ID NO 25
<211> LENGTH: 4065
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 25
ggtgatgtgt cctttgtgga ttttcaagct acaaatggta gtgataaact gttttttgcac    60 tgggggggcag taaagttcgg gaaagaaaca tggtctcttc ctaatgatcg tccagatggg   120
accaaagtgt acaagaacaa agcacttaga actccatttg ttaaatctgg ctctaactcc   180
atcctgagac tggagatacg ggacactgct atcgaagcta ttgagtttct catatacgat   240
gaagcctacg ataaatggat aaagaataat ggtggcaatt tcgtgtcaa attgtcaaga   300 aaagagatac gaggcccaga tgtttcagtt cctgaggagc ttgtacagat ccaatcatat   360
ttgaggtggg agaggaaggg aaaacagaat tacacccctg agaaagagaa ggaggaatat   420
gaggctgctc gaactgagct acaggaggaa atagctcgtg gtgcttccat acaggacatt   480
cgagcaaggc taacaaaaac taatgataaa agtcaaagca agaagagcc tcttcatgta   540 acaaagagtg aaatacctga tgaccttgcc caagcacaag cttacattag gtgggagaaa   600
gcaggaaagc cgaactatcc tccagaaaag caaattgaag aactcgaaga agcaagaaga   660
```

```
gaattgcaac ttgagcttga gaaaggcatt acccttgatg agttgcggaa aaagattaca    720
aaagggagag taaaaactaa ggcggaaaag cacgtgaaaa gaagctcttt tgccgttgaa    780
agaatccaaa gaaagaagag agactttggg cagcttatta agtatccttc cagtcctgca    840
gtacaagtac aaaaggtctt ggaagaacca ccagccttat ctaaaattaa gctgtatgcc    900
aaggagaagg aggagcagat tgatgatccg atcctaaata aaaagatctt taaggtcgat    960
gatggggagc tactggtact ggtagcaaag tcctctggga agacaaaagt acatctagct   1020
acagatctga atcagccaat tactcttcac tgggcattat ccaaaagtcg tggagagtgg   1080
atggtaccac cttcaagcat attgcctcct ggatcaatta ttttagacaa ggctgccgaa   1140
acaccttttt ccgccagttc ttctgatggt ctaacttcta aggtacaatc tttggatata   1200
gtaattgaag atgcaatttt gtggggatgc catttgttc ttttgtctgg tgaaaaatgg    1260
attaagaacc aagggtcgga tttctatgtt gacttcagtg ctgcatccaa attagcactc   1320
aaggctgctg gggatggcag tggaactgca agtctttac tggataaaat agcagatatg    1380
gaaagtgagg ctcagaagtc atttatgcac cggtttaata ttgctgctga cttgatagaa   1440
gatgccacta gtgctggtga acttggtttt gctggaattc ttgtatggat gaggttcatg   1500
gctacaaggc aactgatatg gaacaaaaac tataacgtaa aaccacgtga ataagcaag    1560
gctcaggaca gacttacaga cttgttgcag aatgctttca ccagtcaccc tcaataccgt   1620
gaaattttgc ggatgattat gtcaactgtt ggacgtggag gtgaagggga tgtaggacag   1680
cgaattaggg atgaaatttt ggtcatccag aggaaaaatg actgcaaggg tggtatgatg   1740
gaagaatggc atcagaaatt gcataataat actagtcctg atgatgttgt gatctgtcag   1800
gcattgattg actacatcaa gagtgatttt gatcttggtg tttattggaa accctgaat    1860
gagaacggaa taacaaaaga gcgtctttg agttatgacc gtgctatcca ttctgaaccg    1920
aattttagag gagatcaaaa gaatggtctt ttgcgtgatt taggtcacta tatgagaaca   1980
ttgaaggctg ttcattcagg tgcagatctt gagtctgcta ttgcaaactg catgggctac   2040
aaaactgagg gagaaggctt tatggttgga gtccagataa atcctgtatc aggcttgcca   2100
tctggctttc agggcctcct ccattttgtc ttggaccatg tggaagataa aaatgtggaa   2160
actcttcttg agggattgct agaggctcgt gaggagctta ggcccttgct tctcaaacca   2220
aacaaccgtc taaggatct gctgtttttg gacatagcac ttgattctac agttagaaca    2280
gcagtagaaa ggggatatga agaattgaac aacgctaatc ctgagaaaat catgtacttc   2340
atctccctcg ttcttgaaaa tctcgcactc tctgtggacg ataatgaaga tcttgtttat   2400
tgcttgaagg gatggaatca agctctttca atgtccaatg gtggagacaa ccattgggct   2460
ttatttgcaa aagctgtact tgacagaacc cgtcttgcac ttgcaagcaa ggcagagtgg   2520
taccatcact tattgcagcc atctgccgaa tatctaggat caatccttgg ggtggaccaa   2580
tgggctttga acatatttac tgaagaaatt atacgtgctg gatcagcagc ttcattatcc   2640
tctcttctta atagactcga tcccgtgctt cggaaaactg caaatctagg aagttggcag   2700
attatcagcc cagttgaagc cgttggatat gttgtcgttg tggatgagtt gctttcagtt   2760
cagaatgaaa tctacgagaa gcccacgatc ttagtagcaa actctgttaa aggagaggag   2820
gaaattcctg atggtgctgt tgccctgata acaccagaca tgccagatgt tctttcacat   2880
gtttctgttc gagctagaaa tgggaaggtt tgctttgcta catgctttga tcccaatata   2940
ttggctgacc tccaagcaaa ggaaggaagg atttttgctct taaagcctac acttcagac   3000
ataatctata gtgaggtgaa tgagattgag ctccaaagtt caagtaactt ggtagaagct   3060
```

```
gaaacttcag caacacttag attggtgaaa aagcaatttg gtggttgtta cgcaatatca   3120
gcagatgaat tcacaagtga atggttgga gctaaatcac gtaatattgc ttatctgaaa   3180
ggaaaagtgc cttcctcggt gggaattcct acgtcagtag ctcttccatt tggagtcttt   3240
gagaaagtac tttcagacga cataaatcag ggagtggcaa aagagttgca aattctgacg   3300
aaaaaactat ctgaaggaga cttcagcgct cttggtgaaa ttcgcacaac gattttagat   3360
ctttcagcac cagctcaatt ggtcaaagag ctgaaggaaa agatgcaggg ttctggcatg   3420
ccttggcctg tgatgaagg tccaaagcgg tgggaacaag catggatggc cataaaaaag   3480
gtgtgggctt caaatggaa tgagagagca tacttcagca aaggaaggt gaaactggat   3540 catgactatc tgtgtatggc tgtccttgtt caagaaataa taaatgctga ttatgcattt   3600
gtcattcacg caaccaaccc atcttccgga gacgactcag aaatatatgc cgaggtggtc   3660
aggggccttg ggaaacact tgttggagct tatccaggac gtgctttgag ttttatctgc   3720
aagaaaaagg atctcaactc tactcaagtg ttaggttacc caagcaaacc gatcggcctt   3780
ttcataaaaa gatctatcat cttccgatct gattccaatg gggaagattt ggaaggttat   3840
gccggtgctg gcctctacga cagtgtacca atggatgagg aggaaaaagt tgtaattgat   3900
tactcttccg atccattgat aactgatggt aacttccgcc agacaatcct gtccagcatt   3960
gctcgtgctg acatgctat cgaggagcta tatggctctc ctcaagacat cgagggtgta   4020
gtgagggatg gaaagattta tgtcgttcag acaagacctc agatg         4065
```

<210> SEQ ID NO 26
<211> LENGTH: 1356
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 26

```
Gly Asp Val Ser Phe Val Asp Phe Gln Val Thr Asn Gly Ser Asp Lys
1               5                   10                  15

Leu Phe Leu His Trp Gly Ala Val Lys Phe Gly Lys Glu Thr Trp Ser
            20                  25                  30

Leu Pro Asn Asp Arg Pro Asp Gly Thr Lys Val Tyr Lys Asn Lys Ala
        35                  40                  45

Leu Arg Thr Pro Phe Val Lys Ser Gly Ser Asn Ser Ile Leu Arg Leu
    50                  55                  60

Glu Ile Arg Asp Thr Ala Ile Glu Ala Ile Glu Phe Leu Ile Tyr Asp
65                  70                  75                  80

Glu Ala His Asp Lys Trp Ile Lys Asn Asn Gly Gly Asn Phe Arg Val
                85                  90                  95

Lys Leu Ser Arg Lys Glu Ile Arg Gly Pro Asp Val Ser Val Pro Glu
            100                 105                 110

Glu Leu Val Gln Ile Gln Ser Tyr Leu Arg Trp Glu Arg Lys Gly Lys
        115                 120                 125

Gln Asn Tyr Pro Pro Glu Lys Glu Lys Glu Glu Tyr Glu Ala Ala Arg
    130                 135                 140

Thr Val Leu Gln Glu Glu Ile Ala Arg Gly Ala Ser Ile Gln Asp Ile
145                 150                 155                 160

Arg Ala Arg Leu Thr Lys Thr Asn Asp Lys Ser Gln Ser Lys Glu Glu
                165                 170                 175

Pro Leu His Val Thr Lys Ser Asp Ile Pro Asp Asp Leu Ala Gln Ala
```

```
            180                 185                 190
Gln Ala Tyr Ile Arg Trp Glu Lys Ala Gly Lys Pro Asn Tyr Pro Pro
            195                 200                 205
Glu Lys Gln Ile Glu Glu Leu Glu Glu Ala Arg Arg Glu Leu Gln Leu
            210                 215                 220
Glu Leu Glu Lys Gly Ile Thr Leu Asp Glu Leu Arg Lys Thr Ile Thr
225                 230                 235                 240
Lys Gly Glu Ile Lys Thr Lys Val Glu Lys His Leu Lys Arg Ser Ser
                245                 250                 255
Phe Ala Val Glu Arg Ile Gln Arg Lys Lys Arg Asp Phe Gly His Leu
            260                 265                 270
Ile Asn Lys Tyr Thr Ser Ser Pro Ala Val Gln Val Gln Lys Val Leu
            275                 280                 285
Glu Glu Pro Pro Ala Leu Ser Lys Ile Lys Leu Tyr Ala Lys Glu Lys
            290                 295                 300
Glu Glu Gln Ile Asp Asp Pro Ile Leu Asn Lys Lys Ile Phe Lys Val
305                 310                 315                 320
Asp Asp Gly Glu Leu Leu Val Leu Val Ala Lys Ser Ser Gly Lys Thr
                325                 330                 335
Lys Val His Leu Ala Thr Asp Leu Asn Gln Pro Ile Thr Leu His Trp
                340                 345                 350
Ala Leu Ser Lys Ser Pro Gly Glu Trp Met Val Pro Ser Ser Ile
            355                 360                 365
Leu Pro Pro Gly Ser Ile Ile Leu Asp Lys Ala Ala Glu Thr Pro Phe
            370                 375                 380
Ser Ala Ser Ser Ser Asp Gly Leu Thr Ser Lys Val Gln Ser Leu Asp
385                 390                 395                 400
Ile Val Ile Glu Asp Gly Asn Phe Val Gly Met Pro Phe Val Leu Leu
                405                 410                 415
Ser Gly Glu Lys Trp Ile Lys Asn Gln Gly Ser Asp Phe Tyr Val Gly
            420                 425                 430
Phe Ser Ala Ala Ser Lys Leu Ala Leu Lys Ala Ala Gly Asp Gly Ser
            435                 440                 445
Gly Thr Ala Lys Ser Leu Leu Asp Lys Ile Ala Asp Met Glu Ser Glu
            450                 455                 460
Ala Gln Lys Ser Phe Met His Arg Phe Asn Ile Ala Ala Asp Leu Ile
465                 470                 475                 480
Glu Asp Ala Thr Ser Ala Gly Glu Leu Gly Phe Ala Gly Ile Leu Val
                485                 490                 495
Trp Met Arg Phe Met Ala Thr Arg Gln Leu Ile Trp Asn Lys Asn Tyr
            500                 505                 510
Asn Val Lys Pro Arg Glu Ile Ser Lys Ala Gln Asp Arg Leu Thr Asp
            515                 520                 525
Leu Leu Gln Asn Ala Phe Thr Ser His Pro Gln Tyr Arg Glu Ile Leu
            530                 535                 540
Arg Met Ile Met Ser Thr Val Gly Arg Gly Gly Glu Gly Asp Val Gly
545                 550                 555                 560
Gln Arg Ile Arg Asp Glu Ile Leu Val Ile Gln Arg Asn Asn Asp Cys
                565                 570                 575
Lys Gly Gly Met Met Gln Glu Trp His Gln Lys Leu His Asn Asn Thr
                580                 585                 590
Ser Pro Asp Asp Val Val Ile Cys Gln Ala Leu Ile Asp Tyr Ile Lys
                595                 600                 605
```

```
Ser Asp Phe Asp Leu Gly Val Tyr Trp Lys Thr Leu Asn Glu Asn Gly
610                 615                 620

Ile Thr Lys Glu Arg Leu Ser Tyr Asp Arg Ala Ile His Ser Glu
625                 630                 635                 640

Pro Asn Phe Arg Gly Asp Gln Lys Gly Leu Leu Arg Asp Leu Gly
            645                 650                 655

His Tyr Met Arg Thr Leu Lys Ala Val His Ser Gly Ala Asp Leu Glu
            660                 665                 670

Ser Ala Ile Ala Asn Cys Met Gly Tyr Lys Thr Glu Gly Glu Gly Phe
            675                 680                 685

Met Val Gly Val Gln Ile Asn Pro Val Ser Gly Leu Pro Ser Gly Phe
690                 695                 700

Gln Asp Leu Leu His Phe Val Leu Asp His Val Glu Asp Lys Asn Val
705                 710                 715                 720

Glu Thr Leu Leu Glu Arg Leu Leu Glu Ala Arg Glu Glu Leu Arg Pro
            725                 730                 735

Leu Leu Leu Lys Pro Asn Asn Arg Leu Lys Asp Leu Leu Phe Leu Asp
            740                 745                 750

Ile Ala Leu Asp Ser Thr Val Arg Thr Ala Val Glu Arg Gly Tyr Glu
            755                 760                 765

Glu Leu Asn Asn Ala Asn Pro Glu Lys Ile Met Tyr Phe Ile Ser Leu
770                 775                 780

Val Leu Glu Asn Leu Ala Leu Ser Val Asp Asp Asn Glu Asp Leu Val
785                 790                 795                 800

Tyr Cys Leu Lys Gly Trp Asn Gln Ala Leu Ser Met Ser Asn Gly Gly
            805                 810                 815

Asp Asn His Trp Ala Leu Phe Ala Lys Ala Val Leu Asp Arg Thr Arg
            820                 825                 830

Leu Ala Leu Ala Ser Lys Ala Glu Trp Tyr His His Leu Leu Gln Pro
            835                 840                 845

Ser Ala Glu Tyr Leu Gly Ser Ile Leu Gly Val Asp Gln Trp Ala Leu
850                 855                 860

Asn Ile Phe Thr Glu Glu Ile Ile Arg Ala Gly Ser Ala Ala Ser Leu
865                 870                 875                 880

Ser Ser Leu Leu Asn Arg Leu Asp Pro Val Leu Arg Lys Thr Ala Asn
            885                 890                 895

Leu Gly Ser Trp Gln Ile Ile Ser Pro Val Glu Ala Val Gly Tyr Val
            900                 905                 910

Val Val Val Asp Glu Leu Leu Ser Val Gln Asn Glu Ile Tyr Glu Lys
            915                 920                 925

Pro Thr Ile Leu Val Ala Lys Ser Val Lys Gly Glu Glu Glu Ile Pro
930                 935                 940

Asp Gly Ala Val Ala Leu Ile Thr Pro Asp Met Pro Asp Val Leu Ser
945                 950                 955                 960

His Val Ser Val Arg Ala Arg Asn Gly Lys Val Cys Phe Ala Thr Cys
            965                 970                 975

Phe Asp Pro Asn Ile Leu Ala Asp Leu Gln Ala Lys Glu Gly Arg Ile
            980                 985                 990

Leu Leu Leu Lys Pro Thr Pro Ser Asp Ile Ile Tyr Ser Glu Val Asn
            995                 1000                1005

Glu Ile Glu Leu Gln Ser Ser Ser Asn Leu Val Glu Ala Glu Thr
        1010                1015                1020
```

| | | | | | | | | | | |
|---|---|---|---|---|---|---|---|---|---|---|
| Ser | Ala | Thr | Leu | Arg | Leu | Val | Lys | Lys | Gln | Phe | Gly | Gly | Cys | Tyr |
| 1025 | | | | | 1030 | | | | | 1035 | | | | |
| Ala | Ile | Ser | Ala | Asp | Glu | Phe | Thr | Ser | Glu | Met | Val | Gly | Ala | Lys |
| 1040 | | | | | 1045 | | | | | 1050 | | | | |
| Ser | Arg | Asn | Ile | Ala | Tyr | Leu | Lys | Gly | Lys | Val | Pro | Ser | Ser | Val |
| 1055 | | | | | 1060 | | | | | 1065 | | | | |
| Gly | Ile | Pro | Thr | Ser | Val | Ala | Leu | Pro | Phe | Gly | Val | Phe | Glu | Lys |
| 1070 | | | | | 1075 | | | | | 1080 | | | | |
| Val | Leu | Ser | Asp | Asp | Ile | Asn | Gln | Gly | Val | Ala | Lys | Glu | Leu | Gln |
| 1085 | | | | | 1090 | | | | | 1095 | | | | |
| Ile | Leu | Met | Lys | Lys | Leu | Ser | Glu | Gly | Asp | Phe | Ser | Ala | Leu | Gly |
| 1100 | | | | | 1105 | | | | | 1110 | | | | |
| Glu | Ile | Arg | Thr | Thr | Val | Leu | Asp | Leu | Ser | Ala | Pro | Ala | Gln | Leu |
| 1115 | | | | | 1120 | | | | | 1125 | | | | |
| Val | Lys | Glu | Leu | Lys | Glu | Lys | Met | Gln | Gly | Ser | Gly | Met | Pro | Trp |
| 1130 | | | | | 1135 | | | | | 1140 | | | | |
| Pro | Gly | Asp | Glu | Gly | Pro | Lys | Arg | Trp | Glu | Gln | Ala | Trp | Met | Ala |
| 1145 | | | | | 1150 | | | | | 1155 | | | | |
| Ile | Lys | Lys | Val | Trp | Ala | Ser | Lys | Trp | Asn | Glu | Arg | Ala | Tyr | Phe |
| 1160 | | | | | 1165 | | | | | 1170 | | | | |
| Ser | Thr | Arg | Lys | Val | Lys | Leu | Asp | His | Asp | Tyr | Leu | Cys | Met | Ala |
| 1175 | | | | | 1180 | | | | | 1185 | | | | |
| Val | Leu | Val | Gln | Glu | Ile | Ile | Asn | Ala | Asp | Tyr | Ala | Phe | Val | Ile |
| 1190 | | | | | 1195 | | | | | 1200 | | | | |
| His | Thr | Thr | Asn | Pro | Ser | Ser | Gly | Asp | Asp | Ser | Glu | Ile | Tyr | Ala |
| 1205 | | | | | 1210 | | | | | 1215 | | | | |
| Glu | Val | Val | Arg | Gly | Leu | Gly | Glu | Thr | Leu | Val | Gly | Ala | Tyr | Pro |
| 1220 | | | | | 1225 | | | | | 1230 | | | | |
| Gly | Arg | Ala | Leu | Ser | Phe | Ile | Cys | Lys | Lys | Lys | Asp | Leu | Asn | Ser |
| 1235 | | | | | 1240 | | | | | 1245 | | | | |
| Pro | Gln | Val | Leu | Gly | Tyr | Pro | Ser | Lys | Pro | Ile | Gly | Leu | Phe | Ile |
| 1250 | | | | | 1255 | | | | | 1260 | | | | |
| Lys | Arg | Ser | Ile | Ile | Phe | Arg | Ser | Asp | Ser | Asn | Gly | Glu | Asp | Leu |
| 1265 | | | | | 1270 | | | | | 1275 | | | | |
| Glu | Gly | Tyr | Ala | Gly | Ala | Gly | Leu | Tyr | Asp | Ser | Val | Pro | Met | Asp |
| 1280 | | | | | 1285 | | | | | 1290 | | | | |
| Glu | Glu | Glu | Lys | Val | Val | Ile | Asp | Tyr | Ser | Ser | Asp | Pro | Leu | Ile |
| 1295 | | | | | 1300 | | | | | 1305 | | | | |
| Thr | Asp | Gly | Asn | Phe | Arg | Gln | Thr | Ile | Leu | Ser | Asn | Ile | Ala | Arg |
| 1310 | | | | | 1315 | | | | | 1320 | | | | |
| Ala | Gly | His | Ala | Ile | Glu | Glu | Leu | Tyr | Gly | Ser | Pro | Gln | Asp | Ile |
| 1325 | | | | | 1330 | | | | | 1335 | | | | |
| Glu | Gly | Val | Val | Arg | Asp | Gly | Lys | Ile | Tyr | Val | Val | Gln | Thr | Arg |
| 1340 | | | | | 1345 | | | | | 1350 | | | | |
| Pro | Gln | Met | | | | | | | | | | | | |
| 1355 | | | | | | | | | | | | | | |

<210> SEQ ID NO 27
<211> LENGTH: 3213
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 27

| | |
|---|---|
| aaggtcttgg aagaaccacc agccttatct aaaattaagc tgtatgccaa ggagaaggag | 60 |
| gagcagattg atgatccgat cctaaataaa aagatcttta aggtcgatga tggggagcta | 120 |
| ctggtactgg tagcaaagtc ctctgggaag acaaaagtac atctagctac agatctgaat | 180 |
| cagccaatta ctcttcactg gcattatcc aaaagtcgtg gagagtggat ggtaccacct | 240 |
| tcaagcatat tgcctcctgg atcaattatt ttagacaagg ctgccgaaac accttttcc | 300 |
| gccagttctt ctgatggtct aacttctaag gtacaatctt tggatatagt aattgaagat | 360 |
| ggcaattttg tggggatgcc atttgttctt ttgtctggtg aaaaatggat taagaaccaa | 420 |
| gggtcggatt tctatgttga cttcagtgct gcatccaaat tagcactcaa ggctgctggg | 480 |
| gatggcagtg aactgcaaa gtctttactg gataaaatag cagatatgga aagtgaggct | 540 |
| cagaagtcat ttatgcaccg gtttaatatt gctgctgact tgatagaaga tgccactagt | 600 |
| gctggtgaac ttggttttgc tggaattctt gtatggatga ggttcatggc tacaaggcaa | 660 |
| ctgatatgga acaaaaacta taacgtaaaa ccacgtgaaa taagcaaggc tcaggacaga | 720 |
| cttacagact tgttgcagaa tgctttcacc agtcaccctc aataccgtga aattttgcgg | 780 |
| atgattatgt caactgttgg acgtggaggt gaaggggatg taggacagcg aattagggat | 840 |
| gaaattttgg tcatccagag gaaaaatgac tgcaagggtg tatgatgga gaatggcat | 900 |
| cagaaattgc ataataatac tagtcctgat gatgttgtga tctgtcaggc attgattgac | 960 |
| tacatcaaga gtgattttga tcttggtgtt tattggaaaa ccctgaatga aacggaata | 1020 |
| acaaaagagc gtcttttgag ttatgaccgt gctatccatt ctgaaccgaa ttttagagga | 1080 |
| gatcaaaaga atggtctttt gcgtgattta ggtcactata tgagaacatt gaaggctgtt | 1140 |
| cattcaggtg cagatcttga gtctgctatt gcaaactgca tgggctacaa aactgaggga | 1200 |
| gaaggcttta tggttggagt ccagataaat cctgtatcag gcttgccatc tggctttcag | 1260 |
| ggcctcctcc atttgtctt ggaccatgtg aagataaaa atgtggaaac tcttcttgag | 1320 |
| ggattgctag aggctcgtga ggagcttagg cccttgcttc tcaaaccaaa caaccgtcta | 1380 |
| aaggatctgc tgttttgga catagcactt gattctacag ttagaacagc agtagaaagg | 1440 |
| ggatatgaag aattgaacaa cgctaatcct gagaaaatca tgtacttcat ctccctcgtt | 1500 |
| cttgaaaatc tcgcactctc tgtggacgat aatgaagatc ttgtttattg cttgaaggga | 1560 |
| tggaatcaag ctcttttcaat gtccaatggt ggagacaacc attgggcttt atttgcaaaa | 1620 |
| gctgtacttg acagaacccg tcttgcactt gcaagcaagg cagagtggta ccatcactta | 1680 |
| ttgcagccat ctgccgaata tctaggatca atccttgggg tggaccaatg ggctttgaac | 1740 |
| atatttactg aagaaattat acgtgctgga tcagcagctt cattatcctc tcttcttaat | 1800 |
| agactcgatc ccgtgcttcg gaaaactgca atctaggaa gttggcagat tatcagccca | 1860 |
| gttgaagccg ttggatatgt tgtcgttgtg gatgagttgc tttcagttca gaatgaaatc | 1920 |
| tacgagaagc ccacgatctt agtagcaaac tctgttaaag gagaggagga aattcctgat | 1980 |
| ggtgctgttg ccctgataac accagacatg ccagatgttc tttcacatgt ttctgttcga | 2040 |
| gctagaaatg ggaaggtttg ctttgctaca tgctttgatc ccaatatatt ggctgacctc | 2100 |
| caagcaaagg aaggaaggat tttgctctta aagcctacac cttcagacat aatctatagt | 2160 |
| gaggtgaatg agattgagct ccaaagttca gtaacttgg tagaagctga aacttcagca | 2220 |
| acacttagat tggtgaaaaa gcaatttggt ggttgttacg caatatcagc agatgaattc | 2280 |
| acaagtgaaa tggttggagc taaatcacgt aatattgctt atctgaaagg aaaagtgcct | 2340 |
| tcctcggtgg gaattcctac gtcagtagct cttccatttg gagtctttga gaaagtactt | 2400 |

```
tcagacgaca taaatcaggg agtggcaaaa gagttgcaaa ttctgacgaa aaaactatct   2460
gaaggagact tcagcgctct tggtgaaatt cgcacaacga ttttagatct ttcagcacca   2520
gctcaattgg tcaaagagct gaaggaaaag atgcagggtt ctggcatgcc ttggcctggt   2580
gatgaaggtc caaagcggtg ggaacaagca tggatggcca taaaaaaggt gtgggcttca   2640
aaatggaatg agagagcata cttcagcaca aggaaggtga aactggatca tgactatctg   2700
tgtatggctg tccttgttca agaaataata aatgctgatt atgcatttgt cattcacgca   2760
accaacccat cttccggaga cgactcagaa atatatgccg aggtggtcag ggccttggg    2820 gaaacacttg ttggagctta tccaggacgt gctttgagtt ttatctgcaa gaaaaaggat   2880
ctcaactcta ctcaagtgtt aggttaccca agcaaaccga tcggcctttt cataaaaaga   2940
tctatcatct tccgatctga ttccaatggg gaagatttgg aaggttatgc cggtgctggc   3000
ctctacgaca gtgtaccaat ggatgaggag gaaaaagttg taattgatta ctcttccgat   3060
ccattgataa ctgatggtaa cttccgccag acaatcctgt ccagcattgc tcgtgctgga   3120
catgctatcg aggagctata tggctctcct caagacatcg agggtgtagt gagggatgga   3180
aagatttatg tcgttcagac aagacctcag atg                                3213
```

```
<210> SEQ ID NO 28
<211> LENGTH: 1071
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 28

Lys Val Leu Glu Glu Pro Pro Ala Leu Ser Lys Ile Lys Leu Tyr Ala
1               5                   10                  15

Lys Glu Lys Glu Glu Gln Ile Asp Asp Pro Ile Leu Asn Lys Lys Ile
            20                  25                  30

Phe Lys Val Asp Asp Gly Glu Leu Leu Val Leu Val Ala Lys Ser Ser
        35                  40                  45

Gly Lys Thr Lys Val His Leu Ala Thr Asp Leu Asn Gln Pro Ile Thr
    50                  55                  60

Leu His Trp Ala Leu Ser Lys Ser Pro Gly Glu Trp Met Val Pro Pro
65                  70                  75                  80

Ser Ser Ile Leu Pro Pro Gly Ser Ile Ile Leu Asp Lys Ala Ala Glu
                85                  90                  95

Thr Pro Phe Ser Ala Ser Ser Ser Asp Gly Leu Thr Ser Lys Val Gln
            100                 105                 110

Ser Leu Asp Ile Val Ile Glu Asp Gly Asn Phe Val Gly Met Pro Phe
        115                 120                 125

Val Leu Leu Ser Gly Glu Lys Trp Ile Lys Asn Gln Gly Ser Asp Phe
    130                 135                 140

Tyr Val Gly Phe Ser Ala Ala Ser Lys Leu Ala Leu Lys Ala Ala Gly
145                 150                 155                 160

Asp Gly Ser Gly Thr Ala Lys Ser Leu Leu Asp Lys Ile Ala Asp Met
                165                 170                 175

Glu Ser Glu Ala Gln Lys Ser Phe Met His Arg Phe Asn Ile Ala Ala
            180                 185                 190

Asp Leu Ile Glu Asp Ala Thr Ser Ala Gly Glu Leu Gly Phe Ala Gly
        195                 200                 205

Ile Leu Val Trp Met Arg Phe Met Ala Thr Arg Gln Leu Ile Trp Asn
```

```
              210                 215                 220
Lys Asn Tyr Asn Val Lys Pro Arg Glu Ile Ser Lys Ala Gln Asp Arg
225                 230                 235                 240

Leu Thr Asp Leu Leu Gln Asn Ala Phe Thr Ser His Pro Gln Tyr Arg
                245                 250                 255

Glu Ile Leu Arg Met Ile Met Ser Thr Val Gly Arg Gly Gly Glu Gly
                260                 265                 270

Asp Val Gly Gln Arg Ile Arg Asp Glu Ile Leu Val Ile Gln Arg Asn
                275                 280                 285

Asn Asp Cys Lys Gly Gly Met Met Gln Glu Trp His Gln Lys Leu His
290                 295                 300

Asn Asn Thr Ser Pro Asp Asp Val Val Ile Cys Gln Ala Leu Ile Asp
305                 310                 315                 320

Tyr Ile Lys Ser Asp Phe Asp Leu Gly Val Tyr Trp Lys Thr Leu Asn
                325                 330                 335

Glu Asn Gly Ile Thr Lys Glu Arg Leu Leu Ser Tyr Asp Arg Ala Ile
                340                 345                 350

His Ser Glu Pro Asn Phe Arg Gly Asp Gln Lys Gly Gly Leu Leu Arg
                355                 360                 365

Asp Leu Gly His Tyr Met Arg Thr Leu Lys Ala Val His Ser Gly Ala
                370                 375                 380

Asp Leu Glu Ser Ala Ile Ala Asn Cys Met Gly Tyr Lys Thr Glu Gly
385                 390                 395                 400

Glu Gly Phe Met Val Gly Val Gln Ile Asn Pro Val Ser Gly Leu Pro
                405                 410                 415

Ser Gly Phe Gln Asp Leu Leu His Phe Val Leu Asp His Val Glu Asp
                420                 425                 430

Lys Asn Val Glu Thr Leu Leu Glu Arg Leu Leu Glu Ala Arg Glu Glu
                435                 440                 445

Leu Arg Pro Leu Leu Leu Lys Pro Asn Asn Arg Leu Lys Asp Leu Leu
450                 455                 460

Phe Leu Asp Ile Ala Leu Asp Ser Thr Val Arg Thr Ala Val Glu Arg
465                 470                 475                 480

Gly Tyr Glu Glu Leu Asn Asn Ala Asn Pro Glu Lys Ile Met Tyr Phe
                485                 490                 495

Ile Ser Leu Val Leu Glu Asn Leu Ala Leu Ser Val Asp Asp Asn Glu
                500                 505                 510

Asp Leu Val Tyr Cys Leu Lys Gly Trp Asn Gln Ala Leu Ser Met Ser
                515                 520                 525

Asn Gly Gly Asp Asn His Trp Ala Leu Phe Ala Lys Ala Val Leu Asp
530                 535                 540

Arg Thr Arg Leu Ala Leu Ala Ser Lys Ala Glu Trp Tyr His His Leu
545                 550                 555                 560

Leu Gln Pro Ser Ala Glu Tyr Leu Gly Ser Ile Leu Gly Val Asp Gln
                565                 570                 575

Trp Ala Leu Asn Ile Phe Thr Glu Glu Ile Arg Ala Gly Ser Ala
                580                 585                 590

Ala Ser Leu Ser Ser Leu Leu Asn Arg Leu Asp Pro Val Leu Arg Lys
                595                 600                 605

Thr Ala Asn Leu Gly Ser Trp Gln Ile Ile Ser Pro Val Glu Ala Val
                610                 615                 620

Gly Tyr Val Val Val Val Asp Glu Leu Leu Ser Val Gln Asn Glu Ile
625                 630                 635                 640
```

-continued

```
Tyr Glu Lys Pro Thr Ile Leu Val Ala Lys Ser Val Lys Gly Glu Glu
                645                 650                 655
Glu Ile Pro Asp Gly Ala Val Ala Leu Ile Thr Pro Asp Met Pro Asp
            660                 665                 670
Val Leu Ser His Val Ser Val Arg Ala Arg Asn Gly Lys Val Cys Phe
        675                 680                 685
Ala Thr Cys Phe Asp Pro Asn Ile Leu Ala Asp Leu Gln Ala Lys Glu
    690                 695                 700
Gly Arg Ile Leu Leu Leu Lys Pro Thr Pro Ser Asp Ile Ile Tyr Ser
705                 710                 715                 720
Glu Val Asn Glu Ile Glu Leu Gln Ser Ser Asn Leu Val Glu Ala
                725                 730                 735
Glu Thr Ser Ala Thr Leu Arg Leu Val Lys Lys Gln Phe Gly Gly Cys
            740                 745                 750
Tyr Ala Ile Ser Ala Asp Glu Phe Thr Ser Glu Met Val Gly Ala Lys
        755                 760                 765
Ser Arg Asn Ile Ala Tyr Leu Lys Gly Lys Val Pro Ser Ser Val Gly
    770                 775                 780
Ile Pro Thr Ser Val Ala Leu Pro Phe Gly Val Phe Glu Lys Val Leu
785                 790                 795                 800
Ser Asp Asp Ile Asn Gln Gly Val Ala Lys Glu Leu Gln Ile Leu Met
                805                 810                 815
Lys Lys Leu Ser Glu Gly Asp Phe Ser Ala Leu Gly Glu Ile Arg Thr
            820                 825                 830
Thr Val Leu Asp Leu Ser Ala Pro Ala Gln Leu Val Lys Glu Leu Lys
        835                 840                 845
Glu Lys Met Gln Gly Ser Gly Met Pro Trp Pro Gly Asp Glu Gly Pro
    850                 855                 860
Lys Arg Trp Glu Gln Ala Trp Met Ala Ile Lys Lys Val Trp Ala Ser
865                 870                 875                 880
Lys Trp Asn Glu Arg Ala Tyr Phe Ser Thr Arg Lys Val Lys Leu Asp
                885                 890                 895
His Asp Tyr Leu Cys Met Ala Val Leu Val Gln Glu Ile Ile Asn Ala
            900                 905                 910
Asp Tyr Ala Phe Val Ile His Thr Thr Asn Pro Ser Ser Gly Asp Asp
        915                 920                 925
Ser Glu Ile Tyr Ala Glu Val Val Arg Gly Leu Gly Glu Thr Leu Val
    930                 935                 940
Gly Ala Tyr Pro Gly Arg Ala Leu Ser Phe Ile Cys Lys Lys Lys Asp
945                 950                 955                 960
Leu Asn Ser Pro Gln Val Leu Gly Tyr Pro Ser Lys Pro Ile Gly Leu
                965                 970                 975
Phe Ile Lys Arg Ser Ile Ile Phe Arg Ser Asp Ser Asn Gly Glu Asp
            980                 985                 990
Leu Glu Gly Tyr Ala Gly Ala Gly Leu Tyr Asp Ser Val Pro Met Asp
        995                 1000                1005
Glu Glu Glu Lys Val Val Ile Asp Tyr Ser Ser Asp Pro Leu Ile
    1010                1015                1020
Thr Asp Gly Asn Phe Arg Gln Thr Ile Leu Ser Asn Ile Ala Arg
    1025                1030                1035
Ala Gly His Ala Ile Glu Glu Leu Tyr Gly Ser Pro Gln Asp Ile
    1040                1045                1050
```

```
Glu Gly Val Val Arg Asp Gly Lys Ile Tyr Val Val Gln Thr Arg
    1055                1060                1065

Pro Gln Met
    1070

<210> SEQ ID NO 29
<211> LENGTH: 3063
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 29
acaaaagtac atctagctac agatctgaat cagccaatta ctcttcactg gcattatcc      60 aaaagtcgtg gagagtggat ggtaccacct tcaagcatat tgcctcctgg atcaattatt    120
ttagacaagg ctgccgaaac acctttttcc gccagttctt ctgatggtct aacttctaag    180
gtacaatctt tggatatagt aattgaagat ggcaattttg tggggatgcc atttgttctt    240
ttgtctggtg aaaaatggat taagaaccaa gggtcggatt tctatgttga cttcagtgct    300
gcatccaaat tagcactcaa ggctgctggg gatggcagtg gaactgcaaa gtctttactg    360
gataaaatag cagatatgga aagtgaggct cagaagtcat ttatgcaccg gtttaatatt    420
gctgctgact tgatagaaga tgccactagt gctggtgaac ttggttttgc tggaattctt    480
gtatggatga ggttcatggc tacaaggcaa ctgatatgga caaaaacta taacgtaaaa     540 ccacgtgaaa taagcaaggc tcaggacaga cttacagact tgttgcagaa tgctttcacc    600
agtcaccctc aataccgtga aattttgcgg atgattatgt caactgttgg acgtggaggt    660
gaaggggatg taggacagcg aattagggat gaaattttgg tcatccagag gaaaaatgac    720
tgcaagggtg gtatgatgga agaatggcat cagaaattgc ataataatac tagtcctgat    780
gatgttgtga tctgtcaggc attgattgac tacatcaaga gtgattttga tcttggtgtt    840
tattggaaaa ccctgaatga aacggaata acaaaagagc gtcttttgag ttatgaccgt    900
gctatccatt ctgaaccgaa ttttagagga gatcaaaaga atggtctttt gcgtgattta    960
ggtcactata tgagaacatt gaaggctgtt cattcaggtg cagatcttga gtctgctatt   1020
gcaaactgca tgggctacaa aactgaggga aaggcttta tggttggagt ccagataaat    1080
cctgtatcag gcttgccatc tggctttcag ggcctcctcc attttgtctt ggaccatgtg   1140
gaagataaaa atgtggaaac tcttcttgag ggattgctag aggctcgtga ggagcttagg   1200
cccttgcttc tcaaaccaaa caaccgtcta aaggatctgc tgtttttgga catagcactt   1260
gattctacag ttagaacagc agtagaaagg ggatatgaag aattgaacaa cgctaatcct   1320
gagaaaatca tgtacttcat ctccctcgtt cttgaaaatc tcgcactctc tgtgacgat    1380 aatgaagatc ttgtttattg cttgaaggga tggaatcaag ctctttcaat gtccaatggt   1440
ggagacaacc attgggcttt atttgcaaaa gctgtacttg acagaacccg tcttgcactt   1500
gcaagcaagg cagagtggta ccatcactta ttgcagccat ctgccgaata tctaggatca   1560
atccttgggg tggaccaatg ggctttgaac atatttactg aagaaattat acgtgctgga   1620
tcagcagctt cattatcctc tcttcttaat agactcgatc ccgtgcttcg gaaaactgca   1680
aatctaggaa gttggcagat tatcagccca gttgaagccg ttggatatgt tgtcgttgtg   1740
gatgagttgc tttcagttca gaatgaaatc tacgagaagc ccacgatctt agtagcaaac   1800
tctgttaaag gagaggagga aattcctgat ggtgctgttg ccctgataac accagacatg   1860
ccagatgttc tttcacatgt ttctgttcga gctagaaatg ggaaggtttg ctttgctaca   1920
```

```
tgctttgatc ccaatatatt ggctgacctc caagcaaagg aaggaaggat tttgctctta    1980
aagcctacac cttcagacat aatctatagt gaggtgaatg agattgagct ccaaagttca    2040
agtaacttgg tagaagctga aacttcagca acacttagat tggtgaaaaa gcaatttggt    2100
ggttgttacg caatatcagc agatgaattc acaagtgaaa tggttggagc taaatcacgt    2160
aatattgctt atctgaaagg aaaagtgcct tcctcggtgg gaattcctac gtcagtagct    2220
cttccatttg gagtctttga gaagtactt tcagacgaca taaatcaggg agtggcaaaa    2280
gagttgcaaa ttctgacgaa aaaactatct gaaggagact cagcgctct tggtgaaatt    2340 cgcacaacga ttttagatct ttcagcacca gctcaattgg tcaaagagct gaaggaaaag    2400
atgcagggtt ctggcatgcc ttggcctggt gatgaaggtc caaagcggtg ggaacaagca    2460
tggatggcca taaaaaaggt gtgggcttca aaatggaatg agagagcata cttcagcaca    2520
aggaaggtga aactggatca tgactatctg tgtatggctg tccttgttca agaaataata    2580
aatgctgatt atgcatttgt cattcacgca accaacccat cttccggaga cgactcagaa    2640
atatatgccg aggtggtcag gggccttggg gaaacacttg ttggagctta ccaggacgt    2700 gctttgagtt ttatctgcaa gaaaaaggat ctcaactcta ctcaagtgtt aggttaccca    2760
agcaaaccga tcggcctttt cataaaaaga tctatcatct tccgatctga ttccaatggg    2820
gaagatttgg aaggttatgc cggtgctggc ctctacgaca gtgtaccaat ggatgaggag    2880
gaaaaagttg taattgatta ctcttccgat ccattgataa ctgatggtaa cttccgccag    2940
acaatcctgt ccagcattgc tcgtgctgga catgctatcg aggagctata tggctctcct    3000
caagacatcg agggtgtagt gagggatgga aagatttatg tcgttcagac aagacctcag    3060
atg                                                                3063
```

<210> SEQ ID NO 30
<211> LENGTH: 1021
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 30

```
Thr Lys Val His Leu Ala Thr Asp Leu Asn Gln Pro Ile Thr Leu His
1               5                   10                  15

Trp Ala Leu Ser Lys Ser Pro Gly Glu Trp Met Val Pro Ser Ser
                20                  25                  30

Ile Leu Pro Pro Gly Ser Ile Ile Leu Asp Lys Ala Ala Glu Thr Pro
            35                  40                  45

Phe Ser Ala Ser Ser Ser Asp Gly Leu Thr Ser Lys Val Gln Ser Leu
        50                  55                  60

Asp Ile Val Ile Glu Asp Gly Asn Phe Val Gly Met Pro Phe Val Leu
65                  70                  75                  80

Leu Ser Gly Glu Lys Trp Ile Lys Asn Gln Ser Asp Phe Tyr Val
                85                  90                  95

Gly Phe Ser Ala Ala Ser Lys Leu Ala Leu Lys Ala Ala Gly Asp Gly
            100                 105                 110

Ser Gly Thr Ala Lys Ser Leu Leu Asp Lys Ile Ala Asp Met Glu Ser
        115                 120                 125

Glu Ala Gln Lys Ser Phe Met His Arg Phe Asn Ile Ala Ala Asp Leu
    130                 135                 140

Ile Glu Asp Ala Thr Ser Ala Gly Glu Leu Gly Phe Ala Gly Ile Leu
```

```
            145                 150                 155                 160
Val Trp Met Arg Phe Met Ala Thr Arg Gln Leu Ile Trp Asn Lys Asn
                    165                 170                 175

Tyr Asn Val Lys Pro Arg Glu Ile Ser Lys Ala Gln Asp Arg Leu Thr
                    180                 185                 190

Asp Leu Leu Gln Asn Ala Phe Thr Ser His Pro Gln Tyr Arg Glu Ile
            195                 200                 205

Leu Arg Met Ile Met Ser Thr Val Gly Arg Gly Gly Glu Gly Asp Val
    210                 215                 220

Gly Gln Arg Ile Arg Asp Glu Ile Leu Val Ile Gln Arg Asn Asn Asp
225                 230                 235                 240

Cys Lys Gly Gly Met Met Gln Glu Trp His Gln Lys Leu His Asn Asn
                    245                 250                 255

Thr Ser Pro Asp Asp Val Val Ile Cys Gln Ala Leu Ile Asp Tyr Ile
                260                 265                 270

Lys Ser Asp Phe Asp Leu Gly Val Tyr Trp Lys Thr Leu Asn Glu Asn
            275                 280                 285

Gly Ile Thr Lys Glu Arg Leu Leu Ser Tyr Asp Arg Ala Ile His Ser
    290                 295                 300

Glu Pro Asn Phe Arg Gly Asp Gln Lys Gly Gly Leu Leu Arg Asp Leu
305                 310                 315                 320

Gly His Tyr Met Arg Thr Leu Lys Ala Val His Ser Gly Ala Asp Leu
                    325                 330                 335

Glu Ser Ala Ile Ala Asn Cys Met Gly Tyr Lys Thr Glu Gly Glu Gly
                340                 345                 350

Phe Met Val Gly Val Gln Ile Asn Pro Val Ser Gly Leu Pro Ser Gly
            355                 360                 365

Phe Gln Asp Leu Leu His Phe Val Leu Asp His Val Glu Asp Lys Asn
    370                 375                 380

Val Glu Thr Leu Leu Glu Arg Leu Leu Glu Ala Arg Glu Glu Leu Arg
385                 390                 395                 400

Pro Leu Leu Leu Lys Pro Asn Asn Arg Leu Lys Asp Leu Leu Phe Leu
                    405                 410                 415

Asp Ile Ala Leu Asp Ser Thr Val Arg Thr Ala Val Glu Arg Gly Tyr
                420                 425                 430

Glu Glu Leu Asn Ala Asn Pro Glu Lys Ile Met Tyr Phe Ile Ser
            435                 440                 445

Leu Val Leu Glu Asn Leu Ala Leu Ser Val Asp Asp Asn Glu Asp Leu
    450                 455                 460

Val Tyr Cys Leu Lys Gly Trp Asn Gln Ala Leu Ser Met Ser Asn Gly
465                 470                 475                 480

Gly Asp Asn His Trp Ala Leu Phe Ala Lys Ala Val Leu Asp Arg Thr
                    485                 490                 495

Arg Leu Ala Leu Ala Ser Lys Ala Glu Trp Tyr His His Leu Leu Gln
                500                 505                 510

Pro Ser Ala Glu Tyr Leu Gly Ser Ile Leu Gly Val Asp Gln Trp Ala
            515                 520                 525

Leu Asn Ile Phe Thr Glu Glu Ile Ile Arg Ala Gly Ser Ala Ala Ser
    530                 535                 540

Leu Ser Ser Leu Leu Asn Arg Leu Asp Pro Val Leu Arg Lys Thr Ala
545                 550                 555                 560

Asn Leu Gly Ser Trp Gln Ile Ile Ser Pro Val Glu Ala Val Gly Tyr
                    565                 570                 575
```

```
Val Val Val Val Asp Glu Leu Leu Ser Val Gln Asn Glu Ile Tyr Glu
            580                 585                 590

Lys Pro Thr Ile Leu Val Ala Lys Ser Val Lys Gly Glu Glu Ile
        595                 600                 605

Pro Asp Gly Ala Val Ala Leu Ile Thr Pro Asp Met Pro Asp Val Leu
    610                 615                 620

Ser His Val Ser Val Arg Ala Arg Asn Gly Lys Val Cys Phe Ala Thr
625                 630                 635                 640

Cys Phe Asp Pro Asn Ile Leu Ala Asp Leu Gln Ala Lys Glu Gly Arg
                645                 650                 655

Ile Leu Leu Leu Lys Pro Thr Pro Ser Asp Ile Ile Tyr Ser Glu Val
            660                 665                 670

Asn Glu Ile Glu Leu Gln Ser Ser Asn Leu Val Glu Ala Glu Thr
        675                 680                 685

Ser Ala Thr Leu Arg Leu Val Lys Lys Gln Phe Gly Gly Cys Tyr Ala
    690                 695                 700

Ile Ser Ala Asp Glu Phe Thr Ser Glu Met Val Gly Ala Lys Ser Arg
705                 710                 715                 720

Asn Ile Ala Tyr Leu Lys Gly Lys Val Pro Ser Ser Val Gly Ile Pro
                725                 730                 735

Thr Ser Val Ala Leu Pro Phe Gly Val Phe Glu Lys Val Leu Ser Asp
            740                 745                 750

Asp Ile Asn Gln Gly Val Ala Lys Glu Leu Gln Ile Leu Met Lys Lys
        755                 760                 765

Leu Ser Glu Gly Asp Phe Ser Ala Leu Gly Glu Ile Arg Thr Thr Val
770                 775                 780

Leu Asp Leu Ser Ala Pro Ala Gln Leu Val Lys Glu Leu Lys Glu Lys
785                 790                 795                 800

Met Gln Gly Ser Gly Met Pro Trp Pro Gly Asp Glu Gly Pro Lys Arg
                805                 810                 815

Trp Glu Gln Ala Trp Met Ala Ile Lys Lys Val Trp Ala Ser Lys Trp
            820                 825                 830

Asn Glu Arg Ala Tyr Phe Ser Thr Arg Lys Val Lys Leu Asp His Asp
        835                 840                 845

Tyr Leu Cys Met Ala Val Leu Val Gln Glu Ile Ile Asn Ala Asp Tyr
850                 855                 860

Ala Phe Val Ile His Thr Thr Asn Pro Ser Ser Gly Asp Asp Ser Glu
865                 870                 875                 880

Ile Tyr Ala Glu Val Val Arg Gly Leu Gly Glu Thr Leu Val Gly Ala
                885                 890                 895

Tyr Pro Gly Arg Ala Leu Ser Phe Ile Cys Lys Lys Lys Asp Leu Asn
            900                 905                 910

Ser Pro Gln Val Leu Gly Tyr Pro Ser Lys Pro Ile Gly Leu Phe Ile
        915                 920                 925

Lys Arg Ser Ile Ile Phe Arg Ser Asp Ser Asn Gly Glu Asp Leu Glu
930                 935                 940

Gly Tyr Ala Gly Ala Gly Leu Tyr Asp Ser Val Pro Met Asp Glu Glu
945                 950                 955                 960

Glu Lys Val Val Ile Asp Tyr Ser Ser Asp Pro Leu Ile Thr Asp Gly
                965                 970                 975

Asn Phe Arg Gln Thr Ile Leu Ser Asn Ile Ala Arg Ala Gly His Ala
            980                 985                 990
```

| Ile | Glu | Glu | Leu | Tyr | Gly | Ser | Pro | Gln | Asp | Ile | Glu | Gly | Val | Val | Arg |
|---|---|---|---|---|---|---|---|---|---|---|---|---|---|---|---|
| | | | | 995 | | | | 1000 | | | | 1005 | | | |

| Asp | Gly | Lys | Ile | Tyr | Val | Val | Gln | Thr | Arg | Pro | Gln | Met |
|---|---|---|---|---|---|---|---|---|---|---|---|---|
| | 1010 | | | | 1015 | | | | 1020 | | | |

<210> SEQ ID NO 31
<211> LENGTH: 2553
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 31

```
ctgatatgga acaaaaacta taacgtaaaa ccacgtgaaa taagcaaggc tcaggacaga      60
cttacagact tgttgcagaa tgctttcacc agtcaccctc aataccgtga aattttgcgg     120
atgattatgt caactgttgg acgtggaggt gaaggggatg taggacagcg aattagggat     180
gaaattttgg tcatccagag gaaaaatgac tgcaagggtg gtatgatgga agaatggcat     240
cagaaattgc ataataatac tagtcctgat gatgttgtga tctgtcaggc attgattgac     300
tacatcaaga gtgattttga tcttggtgtt tattggaaaa ccctgaatga aacggaata      360
acaaaagagc gtcttttgag ttatgaccgt gctatccatt ctgaaccgaa ttttagagga     420
gatcaaaaga atggtctttt gcgtgattta ggtcactata tgagaacatt gaaggctgtt     480
cattcaggtg cagatcttga gtctgctatt gcaaactgca tgggctacaa aactgaggga     540
gaaggcttta tggttggagt ccagataaat cctgtatcag gcttgccatc tggctttcag     600
ggcctcctcc attttgtctt ggaccatgtg aagataaaa atgtggaaac tcttcttgag     660
ggattgctag aggctcgtga ggagcttagg cccttgcttc tcaaaccaaa caaccgtcta     720
aaggatctgc tgttttgga catagcactt gattctacag ttagaacagc agtagaaagg     780
ggatatgaag aattgaacaa cgctaatcct gagaaaatca tgtacttcat ctccctcgtt     840
cttgaaaatc tcgcactctc tgtggacgat aatgaagatc ttgtttattg cttgaaggga     900
tggaatcaag ctcttttcaat gtccaatggt ggagacaacc attgggcttt atttgcaaaa     960
gctgtacttg acagaacccg tcttgcactt gcaagcaagg cagagtggta ccatcactta    1020
ttgcagccat ctgccgaata tctaggatca atccttgggg tggaccaatg ggctttgaac    1080
atatttactg aagaaattat acgtgctgga tcagcagctt cattatcctc tcttcttaat    1140
agactcgatc ccgtgcttcg gaaaactgca aatctaggaa gttggcagat tatcagccca    1200
gttgaagccg ttggatatgt tgtcgttgtg gatgagttgc tttcagttca gaatgaaatc    1260
tacgagaagc ccacgatctt agtagcaaac tctgttaaag gagaggagga aattcctgat    1320
ggtgctgttg ccctgataac accagacatg ccagatgttc tttcacatgt ttctgttcga    1380
gctagaaatg ggaaggtttg ctttgctaca tgctttgatc ccaatatatt ggctgacctc    1440
caagcaaagg aaggaaggat tttgctctta aagcctacac cttcagacat aatctatagt    1500
gaggtgaatg agattgagct ccaaagttca gtaacttgg tagaagctga aacttcagca    1560
acacttagat tggtgaaaaa gcaatttggt ggttgttacg caatatcagc agatgaattc    1620
acaagtgaaa tggttggagc taaatcacgt aatattgctt atctgaaagg aaaagtgcct    1680
tcctcggtgg gaattcctac gtcagtagct cttccatttg gagtctttga gaaagtactt    1740
tcagacgaca taaatcaggg agtggcaaaa gagttgcaaa ttctgacgaa aaaactatct    1800
gaaggagact cagcgctct tggtgaaatt cgcacaacga tttagatct tcagcacca    1860
gctcaattgg tcaaagagct gaaggaaag atgcagggtt ctggcatgcc ttggcctggt    1920
```

-continued

```
gatgaaggtc caaagcggtg ggaacaagca tggatggcca taaaaaaggt gtgggcttca    1980
aaatggaatg agagagcata cttcagcaca aggaaggtga aactggatca tgactatctg    2040
tgtatggctg tccttgttca agaaataata aatgctgatt atgcatttgt cattcacgca    2100
accaacccat cttccggaga cgactcagaa atatatgccg aggtggtcag gggccttggg    2160
gaaacacttg ttggagctta tccaggacgt gctttgagtt ttatctgcaa gaaaaaggat    2220
ctcaactcta ctcaagtgtt aggttaccca agcaaaccga tcggccttt cataaaaaga    2280 tctatcatct tccgatctga ttccaatggg aagatttgg aaggttatgc cggtgctggc    2340
ctctacgaca gtgtaccaat ggatgaggag gaaaaagttg taattgatta ctcttccgat    2400
ccattgataa ctgatggtaa cttccgccag acaatcctgt ccagcattgc tcgtgctgga    2460
catgctatcg aggagctata tggctctcct caagacatcg agggtgtagt gagggatgga    2520
aagatttatg tcgttcagac aagacctcag atg                                2553
```

<210> SEQ ID NO 32
<211> LENGTH: 851
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 32

```
Leu Ile Trp Asn Lys Asn Tyr Asn Val Lys Pro Arg Glu Ile Ser Lys
1               5                   10                  15

Ala Gln Asp Arg Leu Thr Asp Leu Leu Gln Asn Ala Phe Thr Ser His
            20                  25                  30

Pro Gln Tyr Arg Glu Ile Leu Arg Met Ile Met Ser Thr Val Gly Arg
        35                  40                  45

Gly Gly Glu Gly Asp Val Gly Gln Arg Ile Arg Asp Glu Ile Leu Val
    50                  55                  60

Ile Gln Arg Asn Asn Asp Cys Lys Gly Gly Met Met Gln Glu Trp His
65                  70                  75                  80

Gln Lys Leu His Asn Asn Thr Ser Pro Asp Asp Val Val Ile Cys Gln
                85                  90                  95

Ala Leu Ile Asp Tyr Ile Lys Ser Asp Phe Asp Leu Gly Val Tyr Trp
            100                 105                 110

Lys Thr Leu Asn Glu Asn Gly Ile Thr Lys Glu Arg Leu Leu Ser Tyr
        115                 120                 125

Asp Arg Ala Ile His Ser Glu Pro Asn Phe Arg Gly Asp Gln Lys Gly
    130                 135                 140

Gly Leu Leu Arg Asp Leu Gly His Tyr Met Arg Thr Leu Lys Ala Val
145                 150                 155                 160

His Ser Gly Ala Asp Leu Glu Ser Ala Ile Ala Asn Cys Met Gly Tyr
                165                 170                 175

Lys Thr Glu Gly Glu Gly Phe Met Val Gly Val Gln Ile Asn Pro Val
            180                 185                 190

Ser Gly Leu Pro Ser Gly Phe Gln Asp Leu Leu His Phe Val Leu Asp
        195                 200                 205

His Val Glu Asp Lys Asn Val Glu Thr Leu Leu Glu Arg Leu Leu Glu
    210                 215                 220

Ala Arg Glu Glu Leu Arg Pro Leu Leu Leu Lys Pro Asn Asn Arg Leu
225                 230                 235                 240

Lys Asp Leu Leu Phe Leu Asp Ile Ala Leu Asp Ser Thr Val Arg Thr
```

```
                245                 250                 255
Ala Val Glu Arg Gly Tyr Glu Glu Leu Asn Asn Ala Asn Pro Glu Lys
            260                 265                 270

Ile Met Tyr Phe Ile Ser Leu Val Leu Glu Asn Leu Ala Leu Ser Val
    275                 280                 285

Asp Asp Asn Glu Asp Leu Val Tyr Cys Leu Lys Gly Trp Asn Gln Ala
    290                 295                 300

Leu Ser Met Ser Asn Gly Gly Asp Asn His Trp Ala Leu Phe Ala Lys
305                 310                 315                 320

Ala Val Leu Asp Arg Thr Arg Leu Ala Leu Ala Ser Lys Ala Glu Trp
                325                 330                 335

Tyr His His Leu Leu Gln Pro Ser Ala Glu Tyr Leu Gly Ser Ile Leu
            340                 345                 350

Gly Val Asp Gln Trp Ala Leu Asn Ile Phe Thr Glu Glu Ile Ile Arg
        355                 360                 365

Ala Gly Ser Ala Ala Ser Leu Ser Ser Leu Leu Asn Arg Leu Asp Pro
    370                 375                 380

Val Leu Arg Lys Thr Ala Asn Leu Gly Ser Trp Gln Ile Ile Ser Pro
385                 390                 395                 400

Val Glu Ala Val Gly Tyr Val Val Val Asp Glu Leu Leu Ser Val
                405                 410                 415

Gln Asn Glu Ile Tyr Glu Lys Pro Thr Ile Leu Val Ala Lys Ser Val
            420                 425                 430

Lys Gly Glu Glu Glu Ile Pro Asp Gly Ala Val Ala Leu Ile Thr Pro
        435                 440                 445

Asp Met Pro Asp Val Leu Ser His Val Ser Val Arg Ala Arg Asn Gly
    450                 455                 460

Lys Val Cys Phe Ala Thr Cys Phe Asp Pro Asn Ile Leu Ala Asp Leu
465                 470                 475                 480

Gln Ala Lys Glu Gly Arg Ile Leu Leu Leu Lys Pro Thr Pro Ser Asp
                485                 490                 495

Ile Ile Tyr Ser Glu Val Asn Glu Ile Glu Leu Gln Ser Ser Ser Asn
            500                 505                 510

Leu Val Glu Ala Glu Thr Ser Ala Thr Leu Arg Leu Val Lys Lys Gln
        515                 520                 525

Phe Gly Gly Cys Tyr Ala Ile Ser Ala Asp Glu Phe Thr Ser Glu Met
    530                 535                 540

Val Gly Ala Lys Ser Arg Asn Ile Ala Tyr Leu Lys Gly Lys Val Pro
545                 550                 555                 560

Ser Ser Val Gly Ile Pro Thr Ser Val Ala Leu Pro Phe Gly Val Phe
                565                 570                 575

Glu Lys Val Leu Ser Asp Asp Ile Asn Gln Gly Val Ala Lys Glu Leu
            580                 585                 590

Gln Ile Leu Met Lys Lys Leu Ser Glu Gly Asp Phe Ser Ala Leu Gly
        595                 600                 605

Glu Ile Arg Thr Thr Val Leu Asp Leu Ser Ala Pro Ala Gln Leu Val
    610                 615                 620

Lys Glu Leu Lys Glu Lys Met Gln Gly Ser Gly Met Pro Trp Pro Gly
625                 630                 635                 640

Asp Glu Gly Pro Lys Arg Trp Glu Gln Ala Trp Met Ala Ile Lys Lys
                645                 650                 655

Val Trp Ala Ser Lys Trp Asn Glu Arg Ala Tyr Phe Ser Thr Arg Lys
            660                 665                 670
```

```
Val Lys Leu Asp His Asp Tyr Leu Cys Met Ala Val Leu Val Gln Glu
        675                 680                 685

Ile Ile Asn Ala Asp Tyr Ala Phe Val Ile His Thr Thr Asn Pro Ser
    690                 695                 700

Ser Gly Asp Asp Ser Glu Ile Tyr Ala Glu Val Val Arg Gly Leu Gly
705                 710                 715                 720

Glu Thr Leu Val Gly Ala Tyr Pro Gly Arg Ala Leu Ser Phe Ile Cys
                725                 730                 735

Lys Lys Asp Leu Asn Ser Pro Gln Val Leu Gly Tyr Pro Ser Lys
            740                 745                 750

Pro Ile Gly Leu Phe Ile Lys Arg Ser Ile Ile Phe Arg Ser Asp Ser
                755                 760                 765

Asn Gly Glu Asp Leu Glu Gly Tyr Ala Gly Ala Gly Leu Tyr Asp Ser
    770                 775                 780

Val Pro Met Asp Glu Glu Lys Val Val Ile Asp Tyr Ser Ser Asp
785                 790                 795                 800

Pro Leu Ile Thr Asp Gly Asn Phe Arg Gln Thr Ile Leu Ser Asn Ile
                805                 810                 815

Ala Arg Ala Gly His Ala Ile Glu Glu Leu Tyr Gly Ser Pro Gln Asp
                820                 825                 830

Ile Glu Gly Val Val Arg Asp Gly Lys Ile Tyr Val Val Gln Thr Arg
            835                 840                 845

Pro Gln Met
        850

<210> SEQ ID NO 33
<211> LENGTH: 2004
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 33
atggttggag tccagataaa tcctgtatca ggcttgccat ctggctttca gggcctcctc       60
cattttgtct tggaccatgt ggaagataaa aatgtggaaa ctcttcttga gggattgcta      120
gaggctcgtg aggagcttag gcccttgctt ctcaaaccaa caaccgtctc aaaggatctg      180
ctgtttttgg acatagcact tgattctaca gttagaacag cagtagaaag gggatatgaa      240
gaattgaaca cgctaatcct gagaaaatca tgtacttcat ctccctcgtt tcttgaaaat      300
ctcgcactct ctgtggacga taatgaagat cttgttattg cttgaagggg atggaatcaa      360
gctctttcaa tgtccaatgg tggagacaac cattgggctt tatttgcaaa gctgtactt       420 gacagaaccc gtcttgcact tgcaagcaag gcagagtggt accatcactt attgcagcca      480
tctgccgaat atctaggatc aatccttggg gtggaccaat gggctttgaa catatttact      540
gaagaaatta tacgtgctgg atcagcagct tcattatcct ctcttcttaa tagactcgat      600
cccgtgcttc ggaaaactgc aaatctagga agttggcaga ttatcagccc agttgaagcc      660
gttggatatg ttgtcgttgt ggatgagttg ctttcagttc agaatgaaat ctacgagaag      720
cccacgatct tagtagcaaa ctctgttaaa ggagaggagg aaattcctga tggtgctgtt      780
gccctgataa caccagacat gccagatgtt ctttcacatg tttctgttcg agctagaaat      840
gggaaggttt gctttgctac atgctttgat cccaatatat tggctgacct ccaagcaaag      900
gaaggaagga ttttgctctt aaagcctaca ccttcagaca taatctatag tgaggtgaat      960
```

-continued

```
gagattgagc tccaaagttc aagtaacttg gtagaagctg aaacttcagc aacacttaga   1020
ttggtgaaaa agcaatttgg tggttgttac gcaatatcag cagatgaatt cacaagtgaa   1080
atggttggag ctaaatcacg taatattgct tatctgaaag gaaaagtgcc ttcctcggtg   1140
ggaattccta cgtcagtagc tcttccattt ggagtctttg agaaagtact ttcagacgac   1200
ataaatcagg gagtggcaaa agagttgcaa attctgacga aaaactatc tgaaggagac    1260 ttcagcgctc ttggtgaaat cgcacaacg attttagatc tttcagcacc agctcaattg    1320
gtcaaagagc tgaaggaaaa gatgcagggt tctggcatgc cttggcctgg tgatgaaggt   1380
ccaaagcggt gggaacaagc atggatggcc ataaaaaagg tgtgggcttc aaaatggaat   1440
gagagagcat acttcagcac aaggaaggtg aaactggatc atgactatct gtgtatggct   1500
gtccttgttc aagaaataat aaatgctgat tatgcatttg tcattcacgc aaccaaccca   1560
tcttccggag acgactcaga aatatatgcc gaggtggtca ggggccttgg ggaaacactt   1620
gttgagcttt atccaggacg tgctttgagt tttatctgca agaaaaagga tctcaactct   1680
actcaagtgt taggttaccc aagcaaaccg atcggccttt tcataaaaag atctatcatc   1740
ttccgatctg attccaatgg ggaagatttg gaaggttatg ccggtgctgg cctctacgac   1800
agtgtaccaa tggatgagga ggaaaaagtt gtaattgatt actcttccga tccattgata   1860
actgatggta acttccgcca gacaatcctg tccagcattg ctcgtgctgg acatgctatc   1920
gaggagctat atggctctcc tcaagacatc gagggtgtag tgagggatgg aaagatttat   1980
gtcgttcaga caagacctca gatg                                          2004
```

<210> SEQ ID NO 34
<211> LENGTH: 668
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 34

```
Met Val Gly Val Gln Ile Asn Pro Val Ser Gly Leu Pro Ser Gly Phe
1               5                   10                  15

Gln Asp Leu Leu His Phe Val Leu Asp His Val Glu Asp Lys Asn Val
            20                  25                  30

Glu Thr Leu Leu Glu Arg Leu Leu Glu Ala Arg Glu Glu Leu Arg Pro
        35                  40                  45

Leu Leu Leu Lys Pro Asn Asn Arg Leu Lys Asp Leu Leu Phe Leu Asp
    50                  55                  60

Ile Ala Leu Asp Ser Thr Val Arg Thr Ala Val Glu Arg Gly Tyr Glu
65                  70                  75                  80

Glu Leu Asn Asn Ala Asn Pro Glu Lys Ile Met Tyr Phe Ile Ser Leu
                85                  90                  95

Val Leu Glu Asn Leu Ala Leu Ser Val Asp Asp Asn Glu Asp Leu Val
            100                 105                 110

Tyr Cys Leu Lys Gly Trp Asn Gln Ala Leu Ser Met Ser Asn Gly Gly
        115                 120                 125

Asp Asn His Trp Ala Leu Phe Ala Lys Ala Val Leu Asp Arg Thr Arg
    130                 135                 140

Leu Ala Leu Ala Ser Lys Ala Glu Trp Tyr His His Leu Leu Gln Pro
145                 150                 155                 160

Ser Ala Glu Tyr Leu Gly Ser Ile Leu Gly Val Asp Gln Trp Ala Leu
                165                 170                 175
```

```
Asn Ile Phe Thr Glu Glu Ile Ile Arg Ala Gly Ser Ala Ala Ser Leu
            180                 185                 190

Ser Ser Leu Leu Asn Arg Leu Asp Pro Val Leu Arg Lys Thr Ala Asn
        195                 200                 205

Leu Gly Ser Trp Gln Ile Ile Ser Pro Val Glu Ala Val Gly Tyr Val
    210                 215                 220

Val Val Val Asp Glu Leu Leu Ser Val Gln Asn Glu Ile Tyr Glu Lys
225                 230                 235                 240

Pro Thr Ile Leu Val Ala Lys Ser Val Lys Gly Glu Glu Ile Pro
                245                 250                 255

Asp Gly Ala Val Ala Leu Ile Thr Pro Asp Met Pro Asp Val Leu Ser
            260                 265                 270

His Val Ser Val Arg Ala Arg Asn Gly Lys Val Cys Phe Ala Thr Cys
        275                 280                 285

Phe Asp Pro Asn Ile Leu Ala Asp Leu Gln Ala Lys Glu Gly Arg Ile
    290                 295                 300

Leu Leu Leu Lys Pro Thr Pro Ser Asp Ile Ile Tyr Ser Glu Val Asn
305                 310                 315                 320

Glu Ile Glu Leu Gln Ser Ser Ser Asn Leu Val Glu Ala Glu Thr Ser
                325                 330                 335

Ala Thr Leu Arg Leu Val Lys Lys Gln Phe Gly Gly Cys Tyr Ala Ile
            340                 345                 350

Ser Ala Asp Glu Phe Thr Ser Glu Met Val Gly Ala Lys Ser Arg Asn
        355                 360                 365

Ile Ala Tyr Leu Lys Gly Lys Val Pro Ser Ser Val Gly Ile Pro Thr
    370                 375                 380

Ser Val Ala Leu Pro Phe Gly Val Phe Glu Lys Val Leu Ser Asp Asp
385                 390                 395                 400

Ile Asn Gln Gly Val Ala Lys Glu Leu Gln Ile Leu Met Lys Lys Leu
                405                 410                 415

Ser Glu Gly Asp Phe Ser Ala Leu Gly Glu Ile Arg Thr Thr Val Leu
            420                 425                 430

Asp Leu Ser Ala Pro Ala Gln Leu Val Lys Glu Leu Lys Glu Lys Met
        435                 440                 445

Gln Gly Ser Gly Met Pro Trp Pro Gly Asp Glu Gly Pro Lys Arg Trp
    450                 455                 460

Glu Gln Ala Trp Met Ala Ile Lys Lys Val Trp Ala Ser Lys Trp Asn
465                 470                 475                 480

Glu Arg Ala Tyr Phe Ser Thr Arg Lys Val Lys Leu Asp His Asp Tyr
                485                 490                 495

Leu Cys Met Ala Val Leu Val Gln Glu Ile Ile Asn Ala Asp Tyr Ala
            500                 505                 510

Phe Val Ile His Thr Thr Asn Pro Ser Ser Gly Asp Ser Glu Ile
        515                 520                 525

Tyr Ala Glu Val Val Arg Gly Leu Gly Glu Thr Leu Val Gly Ala Tyr
    530                 535                 540

Pro Gly Arg Ala Leu Ser Phe Ile Cys Lys Lys Lys Asp Leu Asn Ser
545                 550                 555                 560

Pro Gln Val Leu Gly Tyr Pro Ser Lys Pro Ile Gly Leu Phe Ile Lys
                565                 570                 575

Arg Ser Ile Ile Phe Arg Ser Asp Ser Asn Gly Glu Asp Leu Glu Gly
            580                 585                 590

Tyr Ala Gly Ala Gly Leu Tyr Asp Ser Val Pro Met Asp Glu Glu Glu
```

```
                    595                 600                 605
Lys Val Val Ile Asp Tyr Ser Ser Asp Pro Leu Ile Thr Asp Gly Asn
            610                 615                 620

Phe Arg Gln Thr Ile Leu Ser Asn Ile Ala Arg Ala Gly His Ala Ile
625                 630                 635                 640

Glu Glu Leu Tyr Gly Ser Pro Gln Asp Ile Glu Gly Val Val Arg Asp
                645                 650                 655

Gly Lys Ile Tyr Val Val Gln Thr Arg Pro Gln Met
            660                 665

<210> SEQ ID NO 35
<211> LENGTH: 1032
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 35
caaagttcaa gtaacttggt agaagctgaa acttcagcaa cacttagatt ggtgaaaaag      60
caatttggtg gttgttacgc aatatcagca gatgaattca caagtgaaat ggttggagct     120
aaatcacgta atattgctta tctgaaagga aaagtgcctt cctcggtggg aattcctacg     180
tcagtagctc ttccatttgg agtctttgag aaagtacttt cagacgacat aaatcaggga     240
gtggcaaaag agttgcaaat tctgacgaaa aaactatctg aaggagactt cagcgctctt     300
ggtgaaattc gcacaacgat tttagatctt tcagcaccag ctcaattggt caaagagctg     360
aaggaaaaga tgcagggttc tggcatgcct tggcctggtg atgaaggtcc aaagcggtgg     420
gaacaagcat ggatggccat aaaaaaggtg tgggcttcaa atggaatgag agagcatac     480 ttcagcacaa ggaaggtgaa actggatcat gactatctgt gtatggctgt ccttgttcaa     540
gaaataataa atgctgatta tgcatttgtc attcacgcaa ccaacccatc ttccggagac     600
gactcagaaa tatatgccga ggtggtcagg ggccttgggg aaacacttgt tggagcttat     660
ccaggacgtg ctttgagttt tatctgcaag aaaaaggatc tcaactctac tcaagtgtta     720
ggttacccaa gcaaaccgat cggccttttc ataaaaagat ctatcatctt ccgatctgat     780
tccaatgggg aagatttgga aggttatgcc ggtgctggcc tctacgacag tgtaccaatg     840
gatgaggagg aaaaagttgt aattgattac tcttccgatc cattgataac tgatggtaac     900
ttccgccaga caatcctgtc cagcattgct cgtgctggac atgctatcga ggagctatat     960
ggctctcctc aagacatcga gggtgtagtg agggatggaa agatttatgt cgttcagaca    1020
agacctcaga tg                                                        1032

<210> SEQ ID NO 36
<211> LENGTH: 344
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 36

Gln Ser Ser Ser Asn Leu Val Glu Ala Glu Thr Ser Ala Thr Leu Arg
1               5                   10                  15

Leu Val Lys Lys Gln Phe Gly Gly Cys Tyr Ala Ile Ser Ala Asp Glu
            20                  25                  30

Phe Thr Ser Glu Met Val Gly Ala Lys Ser Arg Asn Ile Ala Tyr Leu
        35                  40                  45
```

Lys Gly Lys Val Pro Ser Ser Val Gly Ile Pro Thr Ser Val Ala Leu
 50                  55                  60

Pro Phe Gly Val Phe Glu Lys Val Leu Ser Asp Asp Ile Asn Gln Gly
 65                  70                  75                  80

Val Ala Lys Glu Leu Gln Ile Leu Met Lys Lys Leu Ser Glu Gly Asp
                 85                  90                  95

Phe Ser Ala Leu Gly Glu Ile Arg Thr Thr Val Leu Asp Leu Ser Ala
            100                 105                 110

Pro Ala Gln Leu Val Lys Glu Leu Lys Glu Lys Met Gln Gly Ser Gly
        115                 120                 125

Met Pro Trp Pro Gly Asp Glu Gly Pro Lys Arg Trp Glu Gln Ala Trp
130                 135                 140

Met Ala Ile Lys Lys Val Trp Ala Ser Lys Trp Asn Glu Arg Ala Tyr
145                 150                 155                 160

Phe Ser Thr Arg Lys Val Lys Leu Asp His Asp Tyr Leu Cys Met Ala
                165                 170                 175

Val Leu Val Gln Glu Ile Ile Asn Ala Asp Tyr Ala Phe Val Ile His
            180                 185                 190

Thr Thr Asn Pro Ser Ser Gly Asp Asp Ser Glu Ile Tyr Ala Glu Val
        195                 200                 205

Val Arg Gly Leu Gly Glu Thr Leu Val Gly Ala Tyr Pro Gly Arg Ala
210                 215                 220

Leu Ser Phe Ile Cys Lys Lys Asp Leu Asn Ser Pro Gln Val Leu
225                 230                 235                 240

Gly Tyr Pro Ser Lys Pro Ile Gly Leu Phe Ile Lys Arg Ser Ile Ile
                245                 250                 255

Phe Arg Ser Asp Ser Asn Gly Glu Asp Leu Glu Gly Tyr Ala Gly Ala
            260                 265                 270

Gly Leu Tyr Asp Ser Val Pro Met Asp Glu Glu Lys Val Val Ile
        275                 280                 285

Asp Tyr Ser Ser Asp Pro Leu Ile Thr Asp Gly Asn Phe Arg Gln Thr
290                 295                 300

Ile Leu Ser Asn Ile Ala Arg Ala Gly His Ala Ile Glu Glu Leu Tyr
305                 310                 315                 320

Gly Ser Pro Gln Asp Ile Glu Gly Val Val Arg Asp Gly Lys Ile Tyr
                325                 330                 335

Val Val Gln Thr Arg Pro Gln Met
            340

<210> SEQ ID NO 37
<211> LENGTH: 978
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 37

```
atggttggag tccagataaa tcctgtatca ggcttgccat ctggctttca gggcctcctc      60
cattttgtct tggaccatgt ggaagataaa aatgtggaaa ctcttcttga gggattgcta     120
gaggctcgtg aggagcttag gcccttgctt ctcaaaccaa acaaccgtct aaaggatctg     180
ctgtttttgg acatagcact tgattctaca gttagaacag cagtagaaag gggatatgaa     240
gaattgaaca acgctaatcc tgagaaaatc atgtacttca tctccctcgt tcttgaaaat     300
ctcgcactct ctgtggacga taatgaagat cttgtttatt gcttgaaggg atggaatcaa     360
```

```
gctctttcaa tgtccaatgg tggagacaac cattgggctt tatttgcaaa agctgtactt    420
gacagaaccc gtcttgcact tgcaagcaag gcagagtggt accatcactt attgcagcca    480
tctgccgaat atctaggatc aatccttggg gtggaccaat gggctttgaa catatttact    540
gaagaaatta tacgtgctgg atcagcagct tcattatcct ctcttcttaa tagactcgat    600
cccgtgcttc ggaaaactgc aaatctagga agttggcaga ttatcagccc agttgaagcc    660
gttggatatg ttgtcgttgt ggatgagttg ctttcagttc agaatgaaat ctacgagaag    720
cccacgatct tagtagcaaa ctctgttaaa ggagaggagg aaattcctga tggtgctgtt    780
gccctgataa caccagacat gccagatgtt ctttcacatg tttctgttcg agctagaaat    840
gggaaggttt gctttgctac atgctttgat cccaatatat tggctgacct ccaagcaaag    900
gaaggaagga ttttgctctt aaagcctaca ccttcagaca taatctatag tgaggtgaat    960
gagattgagc tccaaagt                                                 978
```

<210> SEQ ID NO 38
<211> LENGTH: 326
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 38

```
Met Val Gly Val Gln Ile Asn Pro Val Ser Gly Leu Pro Ser Gly Phe
1               5                   10                  15

Gln Asp Leu Leu His Phe Val Leu Asp His Val Glu Asp Lys Asn Val
            20                  25                  30

Glu Thr Leu Leu Glu Arg Leu Leu Glu Ala Arg Glu Leu Arg Pro
        35                  40                  45

Leu Leu Leu Lys Pro Asn Asn Arg Leu Lys Asp Leu Leu Phe Leu Asp
50                  55                  60

Ile Ala Leu Asp Ser Thr Val Arg Thr Ala Val Glu Arg Gly Tyr Glu
65                  70                  75                  80

Glu Leu Asn Asn Ala Asn Pro Glu Lys Ile Met Tyr Phe Ile Ser Leu
            85                  90                  95

Val Leu Glu Asn Leu Ala Leu Ser Val Asp Asp Asn Glu Asp Leu Val
            100                 105                 110

Tyr Cys Leu Lys Gly Trp Asn Gln Ala Leu Ser Met Ser Asn Gly Gly
            115                 120                 125

Asp Asn His Trp Ala Leu Phe Ala Lys Ala Val Leu Asp Arg Thr Arg
        130                 135                 140

Leu Ala Leu Ala Ser Lys Ala Glu Trp Tyr His His Leu Leu Gln Pro
145                 150                 155                 160

Ser Ala Glu Tyr Leu Gly Ser Ile Leu Gly Val Asp Gln Trp Ala Leu
                165                 170                 175

Asn Ile Phe Thr Glu Glu Ile Ile Arg Ala Gly Ser Ala Ala Ser Leu
            180                 185                 190

Ser Ser Leu Leu Asn Arg Leu Asp Pro Val Leu Arg Lys Thr Ala Asn
        195                 200                 205

Leu Gly Ser Trp Gln Ile Ile Ser Pro Val Glu Ala Val Gly Tyr Val
        210                 215                 220

Val Val Val Asp Glu Leu Leu Ser Val Gln Asn Glu Ile Tyr Glu Lys
225                 230                 235                 240

Pro Thr Ile Leu Val Ala Lys Ser Val Lys Gly Glu Glu Glu Ile Pro
                245                 250                 255
```

Asp Gly Ala Val Ala Leu Ile Thr Pro Asp Met Pro Asp Val Leu Ser
            260                 265                 270

His Val Ser Val Arg Ala Arg Asn Gly Lys Val Cys Phe Ala Thr Cys
        275                 280                 285

Phe Asp Pro Asn Ile Leu Ala Asp Leu Gln Ala Lys Glu Gly Arg Ile
    290                 295                 300

Leu Leu Leu Lys Pro Thr Pro Ser Asp Ile Ile Tyr Ser Glu Val Asn
305                 310                 315                 320

Glu Ile Glu Leu Gln Ser
            325

<210> SEQ ID NO 39
<211> LENGTH: 1002
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 39
ggtgatgtgt cctttgtgga ttttcaagct acaaatggta gtgataaact gttttttgcac      60
tgggggggcag taaagttcgg gaaagaaaca tggtctcttc ctaatgatcg tccagatggg    120
accaaagtgt acaagaacaa agcacttaga actccatttg ttaaatctgg ctctaactcc    180
atcctgagac tggagatacg ggacactgct atcgaagcta ttgagtttct catatacgat    240
gaagcctacg ataaatggat aaagaataat ggtggcaatt tcgtgtcaa attgtcaaga    300
aaagagatac gaggcccaga tgtttcagtt cctgaggagc ttgtacagat ccaatcatat    360
ttgaggtggg agaggaaggg aaaacagaat tacaccccctg agaaagagaa ggaggaatat    420
gaggctgctc gaactgagct acaggaggaa atagctcgtg gtgcttccat acaggacatt    480
cgagcaaggc taacaaaaac taatgataaa agtcaaagca agaagagcc tcttcatgta    540
acaaagagtg aaatacctga tgaccttgcc caagcacaag cttacattag gtgggagaaa    600
gcaggaaagc cgaactatcc tccagaaaag caaattgaag aactcgaaga agcaagaaga    660
gaattgcaac ttgagcttga aaaggcatt ccccttgatg agttgcggaa aaagattaca    720
aaaggggaga taaaaactaa ggcggaaaag cacgtgaaaa gaagctcttt tgccgttgaa    780
agaatccaaa gaaagaagag agactttggg cagcttatta agtatccttc cagtcctgca    840
gtacaagtac aaaaggtctt ggaagaacca ccagccttat ctaaaattaa gctgtatgcc    900
aaggagaagg aggagcagat tgatgatccg atcctaaata aaaagatctt taaggtcgat    960
gatggggagc tactggtact ggtagcaaag tcctctggga ag                        1002

<210> SEQ ID NO 40
<211> LENGTH: 335
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 40

Gly Asp Val Ser Phe Val Asp Phe Gln Val Thr Asn Gly Ser Asp Lys
1               5                   10                  15

Leu Phe Leu His Trp Gly Ala Val Lys Phe Gly Lys Glu Thr Trp Ser
            20                  25                  30

Leu Pro Asn Asp Arg Pro Asp Gly Thr Lys Val Tyr Lys Asn Lys Ala
        35                  40                  45

```
Leu Arg Thr Pro Phe Val Lys Ser Gly Ser Asn Ser Ile Leu Arg Leu
 50                  55                  60

Glu Ile Arg Asp Thr Ala Ile Glu Ala Ile Glu Phe Leu Ile Tyr Asp
 65                  70                  75                  80

Glu Ala His Asp Lys Trp Ile Lys Asn Asn Gly Gly Asn Phe Arg Val
                 85                  90                  95

Lys Leu Ser Arg Lys Glu Ile Arg Gly Pro Asp Val Ser Val Pro Glu
                100                 105                 110

Glu Leu Val Gln Ile Gln Ser Tyr Leu Arg Trp Glu Lys Gly Lys
            115                 120                 125

Gln Asn Tyr Pro Pro Glu Lys Glu Lys Glu Tyr Glu Ala Ala Arg
130                 135                 140

Thr Val Leu Gln Glu Glu Ile Ala Arg Gly Ala Ser Ile Gln Asp Ile
145                 150                 155                 160

Arg Ala Arg Leu Thr Lys Thr Asn Asp Lys Ser Gln Ser Lys Glu Glu
                165                 170                 175

Pro Leu His Val Thr Lys Ser Asp Ile Pro Asp Leu Ala Gln Ala
                180                 185                 190

Gln Ala Tyr Ile Arg Trp Glu Lys Ala Gly Lys Pro Asn Tyr Pro Pro
            195                 200                 205

Glu Lys Gln Ile Glu Glu Leu Glu Ala Arg Arg Glu Leu Gln Leu
210                 215                 220

Glu Leu Glu Lys Gly Ile Thr Leu Asp Glu Leu Arg Lys Thr Ile Thr
225                 230                 235                 240

Lys Gly Glu Ile Lys Thr Lys Val Glu Lys His Leu Lys Arg Ser Ser
                245                 250                 255

Phe Ala Val Glu Arg Ile Gln Arg Lys Lys Arg Asp Phe Gly His Leu
                260                 265                 270

Ile Asn Lys Tyr Thr Ser Ser Pro Ala Val Gln Val Gln Lys Val Leu
                275                 280                 285

Glu Glu Pro Pro Ala Leu Ser Lys Ile Lys Leu Tyr Ala Lys Glu Lys
                290                 295                 300

Glu Glu Gln Ile Asp Asp Pro Ile Leu Asn Lys Lys Ile Phe Lys Val
305                 310                 315                 320

Asp Asp Gly Glu Leu Leu Val Leu Val Ala Lys Ser Ser Gly Lys
                325                 330                 335
```

<210> SEQ ID NO 41
<211> LENGTH: 1059
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 41

```
acaaaagtac atctagctac agatctgaat cagccaatta ctcttcactg ggcattatcc      60
aaaagtcgtg gagagtggat ggtaccacct tcaagcatat tgcctcctgg atcaattatt    120
ttagacaagg ctgccgaaac accttttttcc gccagttctt ctgatggtct aacttctaag   180
gtacaatctt tggatatagt aattgaagat ggcaattttg tggggatgcc atttgttctt    240
ttgtctggtg aaaaatggat taagaaccaa gggtcggatt tctatgttga cttcagtgct    300
gcatccaaat tagcactcaa ggctgctggg gatggcagtg gaactgcaaa gtctttactg    360
gataaaatag cagatatgga aagtgaggct cagaagtcat ttatgcaccg gtttaatatt    420
gctgctgact tgatagaaga tgccactagt gctggtgaac ttggttttgc tggaattctt    480
```

```
gtatggatga ggttcatggc tacaaggcaa ctgatatgga acaaaaacta taacgtaaaa    540
ccacgtgaaa taagcaaggc tcaggacaga cttacagact tgttgcagaa tgctttcacc    600
agtcaccctc aataccgtga aattttgcgg atgattatgt caactgttgg acgtggaggt    660
gaagggdatg taggacagcg aattaggdat gaaattttgg tcatccagag gaaaaatgac    720
tgcaagggtg gtatgatgga agaatggcat cagaaattgc ataataatac tagtcctgat    780
gatgttgtga tctgtcaggc attgattgac tacatcaaga gtgatttdga tcttggtgtt    840
tattggaaaa ccctgaatga gaacggaata acaaagagc gtcttttgag ttatgaccgt    900
gctatccatt ctgaaccgaa ttttagagga gatcaaaaga atggtctttt gcgtgattta    960
ggtcactata tgagaacatt gaaggctgtt cattcaggtg cagatcttga gtctgctatt   1020
gcaaactgca tgggctacaa aactgaggga gaaggcttt                          1059
```

<210> SEQ ID NO 42
<211> LENGTH: 353
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 42

```
Thr Lys Val His Leu Ala Thr Asp Leu Asn Gln Pro Ile Thr Leu His
1               5                   10                  15

Trp Ala Leu Ser Lys Ser Pro Gly Glu Trp Met Val Pro Ser Ser
            20                  25                  30

Ile Leu Pro Pro Gly Ser Ile Ile Leu Asp Lys Ala Ala Glu Thr Pro
        35                  40                  45

Phe Ser Ala Ser Ser Asp Gly Leu Thr Ser Lys Val Gln Ser Leu
    50                  55                  60

Asp Ile Val Ile Glu Asp Gly Asn Phe Val Gly Met Pro Phe Val Leu
65                  70                  75                  80

Leu Ser Gly Glu Lys Trp Ile Lys Asn Gln Gly Ser Asp Phe Tyr Val
                85                  90                  95

Gly Phe Ser Ala Ala Ser Lys Leu Ala Leu Lys Ala Ala Gly Asp Gly
            100                 105                 110

Ser Gly Thr Ala Lys Ser Leu Leu Asp Lys Ile Ala Asp Met Glu Ser
        115                 120                 125

Glu Ala Gln Lys Ser Phe Met His Arg Phe Asn Ile Ala Ala Asp Leu
    130                 135                 140

Ile Glu Asp Ala Thr Ser Ala Gly Glu Leu Gly Phe Ala Gly Ile Leu
145                 150                 155                 160

Val Trp Met Arg Phe Met Ala Thr Arg Gln Leu Ile Trp Asn Lys Asn
                165                 170                 175

Tyr Asn Val Lys Pro Arg Glu Ile Ser Lys Ala Gln Asp Arg Leu Thr
            180                 185                 190

Asp Leu Leu Gln Asn Ala Phe Thr Ser His Pro Gln Tyr Arg Glu Ile
        195                 200                 205

Leu Arg Met Ile Met Ser Thr Val Gly Arg Gly Gly Glu Gly Asp Val
    210                 215                 220

Gly Gln Arg Ile Arg Asp Glu Ile Leu Val Ile Gln Arg Asn Asn Asp
225                 230                 235                 240

Cys Lys Gly Gly Met Met Gln Glu Trp His Gln Lys Leu His Asn Asn
                245                 250                 255
```

```
Thr Ser Pro Asp Asp Val Val Ile Cys Gln Ala Leu Ile Asp Tyr Ile
            260                 265                 270

Lys Ser Asp Phe Asp Leu Gly Val Tyr Trp Lys Thr Leu Asn Glu Asn
        275                 280                 285

Gly Ile Thr Lys Glu Arg Leu Leu Ser Tyr Asp Arg Ala Ile His Ser
    290                 295                 300

Glu Pro Asn Phe Arg Gly Asp Gln Lys Gly Gly Leu Leu Arg Asp Leu
305                 310                 315                 320

Gly His Tyr Met Arg Thr Leu Lys Ala Val His Ser Gly Ala Asp Leu
                325                 330                 335

Glu Ser Ala Ile Ala Asn Cys Met Gly Tyr Lys Thr Glu Gly Glu Gly
            340                 345                 350

Phe
```

<210> SEQ ID NO 43
<211> LENGTH: 3033
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 43

```
ggtgatgtgt cctttgtgga ttttcaagct acaaatggta gtgataaact gttttgcac      60
tgggggcag taaagttcgg aaagaaaca tggtctcttc ctaatgatcg tccagatggg     120
accaaagtgt acaagaacaa agcacttaga actccatttg ttaaatctgg ctctaactcc     180
atcctgagac tggagatacg ggacactgct atcgaagcta ttgagtttct catatacgat     240
gaagcctacg ataaatggat aaagaataat ggtggcaatt tcgtgtcaa attgtcaaga      300
aaagagatac gaggcccaga tgtttcagtt cctgaggagc ttgtacagat ccaatcatat     360
ttgaggtggg agaggaaggg aaaacagaat tacacccctg agaaagagaa ggaggaatat     420
gaggctgctc gaactgagct acaggaggaa atagctcgtg gtgcttccat acaggacatt     480
cgagcaaggc taacaaaaac taatgataaa agtcaaagca agaagagcc tcttcatgta     540
acaaagagtg aaatacctga tgaccttgcc aagcacaag cttacattag gtgggagaaa      600
gcaggaaagc cgaactatcc tccagaaaag caaattgaag aactcgaaga agcaagaaga      660
gaattgcaac ttgagcttga aaaggcatt accccttgatg agttgcggaa aaagattaca      720
aagggggaga taaaaactaa ggcggaaaag cacgtgaaaa gaagctcttt tgccgttgaa      780
agaatccaaa gaaagaagag agactttggg cagcttatta gtatccttc cagtcctgca      840
gtacaagtac aaaaggtctt ggaagaacca ccagccttat ctaaaattaa gctgtatgcc      900
aaggagaagg aggagcagat tgatgatccg atcctaaata aaaagatctt taaggtcgat     960
gatggggagc tactggtact ggtagcaaag tcctctggga agacaaaagt acatctagct    1020
acagatctga atcagccaat tactcttcac tgggcattat ccaaaagtcg tggagagtgg    1080
atggtaccac cttcaagcat attgcctcct ggatcaatta ttttagacaa ggctgccgaa    1140
acaccttttt ccgccagttc ttctgatggt ctaacttcta aggtacaatc tttggatata    1200
gtaattgaag atggcaattt tgtgggatg ccatttgttc ttttgtctgg tgaaaaatgg     1260
attaagaacc aagggtcgga tttctatgtt gacttcagtg ctgcatccaa attagcactc    1320
aaggctgctg gggatggcag tggaactgca aagtctttac tggataaaat agcagatatg    1380
gaaagtgagc tcagaagtc atttatgcac cggtttaata ttgctgctga cttgataaa      1440
gatgccacta gtgctggtga acttggtttt gctggaattc ttgtatggat gaggttcatg    1500
```

```
gctacaaggc aactgatatg gaacaaaaac tataacgtaa aaccacgtga aataagcaag   1560
gctcaggaca gacttacaga cttgttgcag aatgctttca ccagtcaccc tcaataccgt   1620
gaaattttgc ggatgattat gtcaactgtt ggacgtggag gtgaagggga tgtaggacag   1680
cgaattaggg atgaaatttt ggtcatccag aggaaaaatg actgcaaggg tggtatgatg   1740
gaagaatggc atcagaaatt gcataataat actagtcctg atgatgttgt gatctgtcag   1800
gcattgattg actacatcaa gagtgatttt gatcttggtg tttattggaa accctgaat   1860 gagaacggaa taacaaaaga gcgtcttttg agttatgacc gtgctatcca ttctgaaccg   1920
aattttagag gagatcaaaa gaatggtctt ttgcgtgatt taggtcacta tatgagaaca   1980
ttgaaggctg ttcattcagg tgcagatctt gagtctgcta ttgcaaactg catgggctac   2040
aaaactgagg gagaaggctt tatggttgga gtccagataa atcctgtatc aggcttgcca   2100
tctggctttc agggcctcct ccatttgtc ttggaccatg tggaagataa aaatgtggaa   2160
actcttcttg agggattgct agaggctcgt gaggagctta ggcccttgct tctcaaacca   2220
aacaaccgtc taaaggatct gctgtttttg gacatagcac ttgattctac agttagaaca   2280
gcagtagaaa ggggatatga agaattgaac aacgctaatc ctgagaaaat catgtacttc   2340
atctccctcg ttcttgaaaa tctcgcactc tctgtggacg ataatgaaga tcttgtttat   2400
tgcttgaagg gatggaatca agctctttca atgtccaatg gtgggagacaa ccattgggct   2460 ttatttgcaa aagctgtact tgacagaacc cgtcttgcac ttgcaagcaa ggcagagtgg   2520
taccatcact tattgcagcc atctgccgaa tatctaggat caatccttgg ggtggaccaa   2580
tgggctttga acatatttac tgaagaaatt atacgtgctg gatcagcagc ttcattatcc   2640
tctcttctta atagactcga tcccgtgctt cggaaaactg caaatctagg aagttggcag   2700
attatcagcc cagttgaagc cgttggatat gttgtcgttg tggatgagtt gctttcagtt   2760
cagaatgaaa tctacgagaa gcccacgatc ttagtagcaa actctgttaa aggagaggag   2820
gaaattcctg atggtgctgt tgccctgata acaccagaca tgccagatgt tctttcacat   2880
gtttctgttc gagctagaaa tgggaaggtt tgctttgcta catgctttga tcccaatata   2940
ttggctgacc tccaagcaaa ggaaggaagg attttgctct aaagcctac accttcagac   3000 ataatctata gtgaggtgaa tgagattgag ctc                                3033
```

<210> SEQ ID NO 44
<211> LENGTH: 1011
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 44

Gly Asp Val Ser Phe Val Asp Phe Gln Val Thr Asn Gly Ser Asp Lys
1               5                   10                  15

Leu Phe Leu His Trp Gly Ala Val Lys Phe Gly Lys Glu Thr Trp Ser
            20                  25                  30

Leu Pro Asn Asp Arg Pro Asp Gly Thr Lys Val Tyr Lys Asn Lys Ala
        35                  40                  45

Leu Arg Thr Pro Phe Val Lys Ser Gly Ser Asn Ser Ile Leu Arg Leu
    50                  55                  60

Glu Ile Arg Asp Thr Ala Ile Glu Ala Ile Glu Phe Leu Ile Tyr Asp
65                  70                  75                  80

Glu Ala His Asp Lys Trp Ile Lys Asn Asn Gly Gly Asn Phe Arg Val

```
                85                  90                  95
Lys Leu Ser Arg Lys Glu Ile Arg Gly Pro Asp Val Ser Val Pro Glu
            100                 105                 110

Glu Leu Val Gln Ile Gln Ser Tyr Leu Arg Trp Glu Arg Lys Gly Lys
            115                 120                 125

Gln Asn Tyr Pro Pro Glu Lys Glu Lys Glu Glu Tyr Glu Ala Ala Arg
            130                 135                 140

Thr Val Leu Gln Glu Glu Ile Ala Arg Gly Ala Ser Ile Gln Asp Ile
145                 150                 155                 160

Arg Ala Arg Leu Thr Lys Thr Asn Asp Lys Ser Gln Ser Lys Glu Glu
                165                 170                 175

Pro Leu His Val Thr Lys Ser Asp Ile Pro Asp Asp Leu Ala Gln Ala
            180                 185                 190

Gln Ala Tyr Ile Arg Trp Glu Lys Ala Gly Lys Pro Asn Tyr Pro Pro
            195                 200                 205

Glu Lys Gln Ile Glu Glu Leu Glu Glu Ala Arg Arg Glu Leu Gln Leu
            210                 215                 220

Glu Leu Glu Lys Gly Ile Thr Leu Asp Glu Leu Arg Thr Ile Thr Lys
225                 230                 235                 240

Gly Glu Ile Lys Thr Lys Val Glu Lys His Leu Lys Arg Ser Ser Phe
                245                 250                 255

Ala Val Glu Arg Ile Gln Arg Lys Lys Arg Asp Phe Gly His Leu Ile
            260                 265                 270

Asn Lys Tyr Thr Ser Ser Pro Ala Val Gln Val Gln Lys Val Leu Glu
            275                 280                 285

Glu Pro Pro Ala Leu Ser Lys Ile Lys Leu Tyr Ala Lys Glu Lys Glu
            290                 295                 300

Glu Gln Ile Asp Asp Pro Ile Leu Asn Lys Lys Ile Phe Lys Val Asp
305                 310                 315                 320

Asp Gly Glu Leu Leu Val Leu Val Ala Lys Ser Ser Gly Lys Thr Lys
                325                 330                 335

Val His Leu Ala Thr Asp Leu Asn Gln Pro Ile Thr Leu His Trp Ala
            340                 345                 350

Leu Ser Lys Ser Pro Gly Glu Trp Met Val Pro Pro Ser Ser Ile Leu
            355                 360                 365

Pro Pro Gly Ser Ile Ile Leu Asp Lys Ala Ala Glu Thr Pro Phe Ser
            370                 375                 380

Ala Ser Ser Ser Asp Gly Leu Thr Ser Lys Val Gln Ser Leu Asp Ile
385                 390                 395                 400

Val Ile Glu Asp Gly Asn Phe Val Gly Met Pro Phe Val Leu Leu Ser
                405                 410                 415

Gly Glu Lys Trp Ile Lys Asn Gln Gly Ser Asp Phe Tyr Val Gly Phe
            420                 425                 430

Ser Ala Ala Ser Lys Leu Ala Leu Lys Ala Ala Gly Asp Gly Ser Gly
            435                 440                 445

Thr Ala Lys Ser Leu Leu Asp Lys Ile Ala Asp Met Glu Ser Glu Ala
            450                 455                 460

Gln Lys Ser Phe Met His Arg Phe Asn Ile Ala Ala Asp Leu Ile Glu
465                 470                 475                 480

Asp Ala Thr Ser Ala Gly Glu Leu Gly Phe Ala Gly Ile Leu Val Trp
                485                 490                 495

Met Arg Phe Met Ala Thr Arg Gln Leu Ile Trp Asn Lys Asn Tyr Asn
            500                 505                 510
```

```
Val Lys Pro Arg Glu Ile Ser Lys Ala Gln Asp Arg Leu Thr Asp Leu
        515                 520                 525

Leu Gln Asn Ala Phe Thr Ser His Pro Gln Tyr Arg Glu Ile Leu Arg
        530                 535                 540

Met Ile Met Ser Thr Val Gly Arg Gly Glu Gly Asp Val Gly Gln
545                 550                 555                 560

Arg Ile Arg Asp Glu Ile Leu Val Ile Gln Arg Asn Asn Asp Cys Lys
                565                 570                 575

Gly Gly Met Met Gln Glu Trp His Gln Lys Leu His Asn Asn Thr Ser
                580                 585                 590

Pro Asp Asp Val Val Ile Cys Gln Ala Leu Ile Asp Tyr Ile Lys Ser
        595                 600                 605

Asp Phe Asp Leu Gly Val Tyr Trp Lys Thr Leu Asn Glu Asn Gly Ile
        610                 615                 620

Thr Lys Glu Arg Leu Leu Ser Tyr Asp Arg Ala Ile His Ser Glu Pro
625                 630                 635                 640

Asn Phe Arg Gly Asp Gln Lys Gly Gly Leu Leu Arg Asp Leu Gly His
                645                 650                 655

Tyr Met Arg Thr Leu Lys Ala Val His Ser Gly Ala Asp Leu Glu Ser
                660                 665                 670

Ala Ile Ala Asn Cys Met Gly Tyr Lys Thr Glu Gly Glu Gly Phe Met
        675                 680                 685

Val Gly Val Gln Ile Asn Pro Val Ser Gly Leu Pro Ser Gly Phe Gln
        690                 695                 700

Asp Leu Leu His Phe Val Leu Asp His Val Glu Asp Lys Asn Val Glu
705                 710                 715                 720

Thr Leu Leu Glu Arg Leu Leu Glu Ala Arg Glu Glu Leu Arg Pro Leu
                725                 730                 735

Leu Leu Lys Pro Asn Asn Arg Leu Lys Asp Leu Leu Phe Leu Asp Ile
                740                 745                 750

Ala Leu Asp Ser Thr Val Arg Thr Ala Val Glu Arg Gly Tyr Glu Glu
        755                 760                 765

Leu Asn Asn Ala Asn Pro Glu Lys Ile Met Tyr Phe Ile Ser Leu Val
        770                 775                 780

Leu Glu Asn Leu Ala Leu Ser Val Asp Asp Asn Glu Asp Leu Val Tyr
785                 790                 795                 800

Cys Leu Lys Gly Trp Asn Gln Ala Leu Ser Met Ser Asn Gly Gly Asp
                805                 810                 815

Asn His Trp Ala Leu Phe Ala Lys Ala Val Leu Asp Arg Thr Arg Leu
                820                 825                 830

Ala Leu Ala Ser Lys Ala Glu Trp Tyr His His Leu Leu Gln Pro Ser
        835                 840                 845

Ala Glu Tyr Leu Gly Ser Ile Leu Gly Val Asp Gln Trp Ala Leu Asn
        850                 855                 860

Ile Phe Thr Glu Glu Ile Ile Arg Ala Gly Ser Ala Ala Ser Leu Ser
865                 870                 875                 880

Ser Leu Leu Asn Arg Leu Asp Pro Val Leu Arg Lys Thr Ala Asn Leu
                885                 890                 895

Gly Ser Trp Gln Ile Ile Ser Pro Val Glu Ala Val Gly Tyr Val Val
                900                 905                 910

Val Val Asp Glu Leu Leu Ser Val Gln Asn Glu Ile Tyr Glu Lys Pro
        915                 920                 925
```

```
Thr Ile Leu Val Ala Lys Ser Val Lys Gly Glu Glu Ile Pro Asp
        930             935             940

Gly Ala Val Ala Leu Ile Thr Pro Asp Met Pro Asp Val Leu Ser His
945             950             955             960

Val Ser Val Arg Ala Arg Asn Gly Lys Val Cys Phe Ala Thr Cys Phe
                965             970             975

Asp Pro Asn Ile Leu Ala Asp Leu Gln Ala Lys Glu Gly Arg Ile Leu
            980             985             990

Leu Leu Lys Pro Thr Pro Ser Asp  Ile Ile Tyr Ser Glu  Val Asn Glu
        995             1000             1005

Ile Glu  Leu
    1010

<210> SEQ ID NO 45
<211> LENGTH: 2031
<212> TYPE: DNA
<213> ORGANISM: Artificial Sequence
<220> FEATURE:
<223> OTHER INFORMATION: Variant of Solanum tuberosum GWD polypeptide

<400> SEQUENCE: 45
acaaaagtac atctagctac agatctgaat cagccaatta ctcttcactg gcattatcc        60 aaaagtcgtg gagagtggat ggtaccacct tcaagcatat tgcctcctgg atcaattatt     120
ttagacaagg ctgccgaaac accttttttcc gccagttctt ctgatggtct aacttctaag    180
gtacaatctt tggatatagt aattgaagat ggcaattttg tggggatgcc atttgttctt     240
ttgtctggtg aaaaatggat taagaaccaa gggtcggatt tctatgttga cttcagtgct    300
gcatccaaat tagcactcaa ggctgctggg gatggcagtg gaactgcaaa gtctttactg    360
gataaaatag cagatatgga aagtgaggct cagaagtcat ttatgcaccg gtttaatatt    420
gctgctgact tgatagaaga tgccactagt gctggtgaac ttggttttgc tggaattctt    480
gtatggatga ggttcatggc tacaaggcaa ctgatatgga acaaaaacta taacgtaaaa    540
ccacgtgaaa taagcaaggc tcaggacaga cttacagact tgttgcagaa tgctttcacc    600
agtcaccctc aataccgtga aattttgcgg atgattatgt caactgttgg acgtggaggt    660
gaaggggatg taggacagcg aattagggat gaaattttgg tcatccagag gaaaaatgac    720
tgcaagggtg gtatgatgga agaatggcat cagaaattgc ataataatac tagtcctgat    780
gatgttgtga tctgtcaggc attgattgac tacatcaaga gtgattttga tcttggtgtt    840
tattggaaaa ccctgaatga aacggaata acaaaagagc gtcttttgag ttatgaccgt    900
gctatccatt ctgaaccgaa ttttagagga gatcaaaaga atggtctttt gcgtgattta    960
ggtcactata tgagaacatt gaaggctgtt cattcaggtg cagatcttga gtctgctatt    1020
gcaaactgca tgggctacaa aactgaggga gaaggcttta tggttggagt ccagataaat    1080
cctgtatcag gcttgccatc tggctttcag ggcctcctcc atttttgtctt ggaccatgtg    1140 gaagataaaa atgtggaaac tcttcttgag ggattgctag aggctcgtga ggagcttagg    1200
cccttgcttc tcaaaccaaa caaccgtcta aaggatctgc tgtttttgga catagcactt    1260
gattctacag ttagaacagc agtagaaagg ggatatgaag aattgaacaa cgctaatcct    1320
gagaaaatca tgtacttcat ctccctcgtt cttgaaaatc tcgcactctc tgtggacgat    1380
aatgaagatc ttgtttattg cttgaaggga tggaatcaag ctctttcaat gtccaatggt    1440
ggagacaacc attgggcttt attgcaaaaa gctgtacttg acagaacccg tcttgcactt    1500
gcaagcaagg cagagtggta ccatcactta ttgcagccat ctgccgaata tctaggatca    1560
```

```
atccttgggg tggaccaatg ggctttgaac atatttactg aagaaattat acgtgctgga   1620
tcagcagctt cattatcctc tcttcttaat agactcgatc ccgtgcttcg gaaaactgca   1680
aatctaggaa gttggcagat tatcagccca gttgaagccg ttggatatgt tgtcgttgtg   1740
gatgagttgc tttcagttca gaatgaaatc tacgagaagc ccacgatctt agtagcaaac   1800
tctgttaaag gagaggagga aattcctgat ggtgctgttg ccctgataac accagacatg   1860
ccagatgttc tttcacatgt ttctgttcga gctagaaatg ggaaggtttg ctttgctaca   1920
tgctttgatc ccaatatatt ggctgacctc caagcaaagg aaggaaggat tttgctctta   1980
aagcctacac cttcagacat aatctatagt gaggtgaatg agattgagct c            2031
```

<210> SEQ ID NO 46
<211> LENGTH: 677
<212> TYPE: PRT
<213> ORGANISM: Artificial Sequence
<220> FEATURE:
<223> OTHER INFORMATION: Variant of Solanum tuberosum GWD polypeptide

<400> SEQUENCE: 46

```
Thr Lys Val His Leu Ala Thr Asp Leu Asn Gln Pro Ile Thr Leu His
1               5                   10                  15

Trp Ala Leu Ser Lys Ser Pro Gly Glu Trp Met Val Pro Pro Ser Ser
            20                  25                  30

Ile Leu Pro Pro Gly Ser Ile Ile Leu Asp Lys Ala Ala Glu Thr Pro
        35                  40                  45

Phe Ser Ala Ser Ser Ser Asp Gly Leu Thr Ser Lys Val Gln Ser Leu
    50                  55                  60

Asp Ile Val Ile Glu Asp Gly Asn Phe Val Gly Met Pro Phe Val Leu
65                  70                  75                  80

Leu Ser Gly Glu Lys Trp Ile Lys Asn Gln Gly Ser Asp Phe Tyr Val
                85                  90                  95

Gly Phe Ser Ala Ala Ser Lys Leu Ala Leu Lys Ala Ala Gly Asp Gly
            100                 105                 110

Ser Gly Thr Ala Lys Ser Leu Leu Asp Lys Ile Ala Asp Met Glu Ser
        115                 120                 125

Glu Ala Gln Lys Ser Phe Met His Arg Phe Asn Ile Ala Ala Asp Leu
    130                 135                 140

Ile Glu Asp Ala Thr Ser Ala Gly Glu Leu Gly Phe Ala Gly Ile Leu
145                 150                 155                 160

Val Trp Met Arg Phe Met Ala Thr Arg Gln Leu Ile Trp Asn Lys Asn
                165                 170                 175

Tyr Asn Val Lys Pro Arg Glu Ile Ser Lys Ala Gln Asp Arg Leu Thr
            180                 185                 190

Asp Leu Leu Gln Asn Ala Phe Thr Ser His Pro Gln Tyr Arg Glu Ile
        195                 200                 205

Leu Arg Met Ile Met Ser Thr Val Gly Arg Gly Glu Gly Asp Val
    210                 215                 220

Gly Gln Arg Ile Arg Asp Glu Ile Leu Val Ile Gln Arg Asn Asn Asp
225                 230                 235                 240

Cys Lys Gly Gly Met Met Gln Glu Trp His Gln Lys Leu His Asn Asn
                245                 250                 255

Thr Ser Pro Asp Asp Val Val Ile Cys Gln Ala Leu Ile Asp Tyr Ile
            260                 265                 270

Lys Ser Asp Phe Asp Leu Gly Val Tyr Trp Lys Thr Leu Asn Glu Asn
```

```
            275                 280                 285
Gly Ile Thr Lys Glu Arg Leu Leu Ser Tyr Asp Arg Ala Ile His Ser
    290                 295                 300
Glu Pro Asn Phe Arg Gly Asp Gln Lys Gly Gly Leu Leu Arg Asp Leu
305                 310                 315                 320
Gly His Tyr Met Arg Thr Leu Lys Ala Val His Ser Gly Ala Asp Leu
                325                 330                 335
Glu Ser Ala Ile Ala Asn Cys Met Gly Tyr Lys Thr Glu Gly Glu Gly
            340                 345                 350
Phe Met Val Gly Val Gln Ile Asn Pro Val Ser Gly Leu Pro Ser Gly
        355                 360                 365
Phe Gln Asp Leu Leu His Phe Val Leu Asp His Val Glu Asp Lys Asn
    370                 375                 380
Val Glu Thr Leu Leu Glu Arg Leu Leu Glu Ala Arg Glu Glu Leu Arg
385                 390                 395                 400
Pro Leu Leu Lys Pro Asn Asn Arg Leu Lys Asp Leu Leu Phe Leu
                405                 410                 415
Asp Ile Ala Leu Asp Ser Thr Val Arg Thr Ala Val Glu Arg Gly Tyr
            420                 425                 430
Glu Glu Leu Asn Asn Ala Asn Pro Glu Lys Ile Met Tyr Phe Ile Ser
        435                 440                 445
Leu Val Leu Glu Asn Leu Ala Leu Ser Val Asp Asn Glu Asp Leu
    450                 455                 460
Val Tyr Cys Leu Lys Gly Trp Asn Gln Ala Leu Ser Met Ser Asn Gly
465                 470                 475                 480
Gly Asp Asn His Trp Ala Leu Phe Ala Lys Ala Val Leu Asp Arg Thr
                485                 490                 495
Arg Leu Ala Leu Ala Ser Lys Ala Glu Trp Tyr His His Leu Leu Gln
            500                 505                 510
Pro Ser Ala Glu Tyr Leu Gly Ser Ile Leu Gly Val Asp Gln Trp Ala
        515                 520                 525
Leu Asn Ile Phe Thr Glu Glu Ile Ile Arg Ala Gly Ser Ala Ala Ser
    530                 535                 540
Leu Ser Ser Leu Leu Asn Arg Leu Asp Pro Val Leu Arg Lys Thr Ala
545                 550                 555                 560
Asn Leu Gly Ser Trp Gln Ile Ile Ser Pro Val Glu Ala Val Gly Tyr
                565                 570                 575
Val Val Val Val Asp Glu Leu Leu Ser Val Gln Asn Glu Ile Tyr Glu
            580                 585                 590
Lys Pro Thr Ile Leu Val Ala Lys Ser Val Lys Gly Glu Glu Glu Ile
        595                 600                 605
Pro Asp Gly Ala Val Ala Leu Ile Thr Pro Asp Met Pro Asp Val Leu
    610                 615                 620
Ser His Val Ser Val Arg Ala Arg Asn Gly Lys Val Cys Phe Ala Thr
625                 630                 635                 640
Cys Phe Asp Pro Asn Ile Leu Ala Asp Leu Gln Ala Lys Glu Gly Arg
                645                 650                 655
Ile Leu Leu Leu Lys Pro Thr Pro Ser Asp Ile Tyr Ser Glu Val
            660                 665                 670
Asn Glu Ile Glu Leu
        675

<210> SEQ ID NO 47
```

<211> LENGTH: 2565
<212> TYPE: DNA
<213> ORGANISM: Artificial Sequence
<220> FEATURE:
<223> OTHER INFORMATION: Chimeric Protein

<400> SEQUENCE: 47

| | | | | | |
|---|---|---|---|---|---|
| atgggacatc | accatcatca | tcacatggag | cagaagctga | tctcagagga | ggacctgact | 60 |
| agtgctagct | gcaccccggc | ggcgaccgtg | gcggttacct | taaccaccct | ggcgagcacc | 120 |
| agctacggtg | aaagcatcaa | gattgtgggt | agcatcagcc | aactgggtag | ctggagcgcg | 180 |
| agcagcggcg | ttgcgctgag | cgcgagccaa | taccaccacca | gcaacccgct | gtggaccgcg | 240 |
| accgtgagcc | tgccggcggg | taccaaattc | gagtataagt | ttgtgaaagt | tagcagcgaa | 300 |
| ggtagcgcgg | tgacctggga | aagcgacccg | aaccgtagct | ataccgttcc | gcagagctgc | 360 |
| gcggagagcg | tggcggttga | aagcagctgg | aagggagaat | caagcaatgt | tttggagttg | 420 |
| attaaaacca | tgcattctct | agcttcttta | agagaaacaa | ttataaagga | acttaatagc | 480 |
| ggcttgcgaa | atgatgctcc | tgatactgcc | attgcaatgc | ccagaagtg | gcgcctttgt | 540 |
| gagatcggcc | tcgaggacta | cttctttgtt | ctactaagca | gattcctcaa | tgctcttgaa | 600 |
| actatgggag | gagctgatca | actggcaaaa | gatgtgggat | caagaaacgt | tgcctcatgg | 660 |
| aatgatccac | tagatgcttt | ggtgttgggt | gttcaccaag | taggtctatc | tggttggaag | 720 |
| caagaagaat | gtttagccat | tggaaatgaa | ctccttgctt | ggcgagaaag | ggacctactt | 780 |
| gaaaagaag | gggaagagga | tggaaaaaca | atttgggcca | tgaggctgaa | agcaactctt | 840 |
| gatcgagcac | gcagattaac | agcagaatat | tctgatttgc | ttcttcaaat | atttcctcct | 900 |
| aatgtggaga | ttttaggaaa | agctctaggt | attccagaga | atagtgtcaa | gacctataca | 960 |
| gaagcagaga | ttcgtgctgg | aattattttc | cagatctcaa | agctctgcac | tgttcttcta | 1020 |
| aaagctgtaa | gaaattcact | tggttctgag | gctgggatg | tcgttgtacc | tggatcgacg | 1080 |
| tctgggacat | tagttcaggt | tgagagcatt | gttccgggat | cattgccagc | aacttctggt | 1140 |
| ggtcctatta | ttctcttggt | caataaagct | gatggcgatg | aagaggtaag | tgctgctaat | 1200 |
| gggaacatag | ctggagtcat | gcttctgcag | gagctgcctc | acttgtctca | ccttggcgtt | 1260 |
| agagcgcggc | aggagaaaat | tgtctttgtg | acatgtgatg | atgatgacaa | ggttgctgat | 1320 |
| atacgacgac | ttgtgggaaa | atttgtgagg | ttggaagcat | ctccaagtca | tgtgaatctg | 1380 |
| atactttcaa | ctgagggtag | gagtcgcact | tccaaatcca | gtgcgaccaa | aaaaacggat | 1440 |
| aagaacagct | atctcaagaa | aaaaacagat | aagaagagct | atctatcga | tgatgaagaa | 1500 |
| tcaaagcctg | gttcctcatc | ttccaatagc | ctcctttact | cttccaagga | tatccctagt | 1560 |
| ggaggaatca | tagcacttgc | tgatgcagat | gtaccaactt | ctggttcaaa | atctgctgca | 1620 |
| tgtggtcttc | ttgcatcttt | agcagaagcc | tctagtaaag | tgcacagcga | acacggagtt | 1680 |
| ccggcatcat | ttaaggttcc | aactggagtt | gtcataacct | ttggatcgat | ggaattagct | 1740 |
| ttaaagcaaa | ataattcgga | agaaaagttt | gcgtctttgc | tagaaaaact | agaaaccgcc | 1800 |
| agacctgagg | gtggtgagct | agacgacata | tgtgaccaga | tccatgaagt | gatgaaaacg | 1860 |
| ttgcaagtgc | ctaaagaaac | aatcaacagc | ataagcaaag | cgtttctcaa | agatgctcgt | 1920 |
| ctcattgttc | gttcaagtgc | taacgtcgag | gacttagccg | gaatgtcagc | tgcaggactc | 1980 |
| tatgaatcaa | tccctaacgt | gagtccctct | gatcctttgg | tgttttcaga | ttcggtttgc | 2040 |
| caagtttggg | cttctctcta | cacaagaaga | gctgttctaa | gccgtagagc | tgctggtgtc | 2100 |
| tctcaaagag | aagcttcaat | ggctgttctc | gttcaagaaa | tgctttcgcc | ggacttatca | 2160 |

```
ttcgttctgc acacagtgag tccagctgat ccggacagta accttgtgga agccgagatc    2220
gctcctggtt taggtgagac tttagcttca ggaacaagag gaacaccatg gagactcgct    2280
tcgggtaagc tcgacgggat tgtacaaacc ttagctttcg caaacttcag cgaagagctt    2340
cttgtgtcag gaacaggtcc tgctgatgga aaatacgttc ggttgaccgt ggactatagc    2400
aaaaaacgtt taactgttga ctcggtgttt agacagcagc tcggtcagag actcggttcg    2460
gttggtttct tcttggaaag aaactttggc tgtgctcaag acgttgaagg ttgtttggtt    2520
ggtgaagatg tttacattgt tcagtcaagg ccacaacctc tgtaa                   2565
```

<210> SEQ ID NO 48
<211> LENGTH: 854
<212> TYPE: PRT
<213> ORGANISM: Artificial Sequence
<220> FEATURE:
<223> OTHER INFORMATION: Chimeric Protein

<400> SEQUENCE: 48

```
Met Gly His His His His His His Met Glu Gln Lys Leu Ile Ser Glu
1               5                   10                  15

Glu Asp Leu Thr Ser Ala Ser Cys Thr Pro Ala Ala Thr Val Ala Val
            20                  25                  30

Thr Phe Asn His Leu Ala Ser Thr Ser Tyr Gly Glu Ser Ile Lys Ile
        35                  40                  45

Val Gly Ser Ile Ser Gln Leu Gly Ser Trp Ser Ala Ser Ser Gly Val
    50                  55                  60

Ala Leu Ser Ala Ser Gln Tyr Thr Thr Ser Asn Pro Leu Trp Thr Ala
65                  70                  75                  80

Thr Val Ser Leu Pro Ala Gly Thr Lys Phe Glu Tyr Lys Phe Val Lys
                85                  90                  95

Val Ser Ser Glu Gly Ser Ala Val Thr Trp Glu Ser Asp Pro Asn Arg
            100                 105                 110

Ser Tyr Thr Val Pro Gln Ser Cys Ala Glu Ser Val Ala Val Glu Ser
        115                 120                 125

Ser Trp Lys Gly Glu Ser Ser Asn Val Leu Glu Leu Ile Lys Thr Met
    130                 135                 140

His Ser Leu Ala Ser Leu Arg Glu Thr Ile Ile Lys Glu Leu Asn Ser
145                 150                 155                 160

Gly Leu Arg Asn Asp Ala Pro Asp Thr Ala Ile Ala Met Arg Gln Lys
                165                 170                 175

Trp Arg Leu Cys Glu Ile Gly Leu Glu Asp Tyr Phe Phe Val Leu Leu
            180                 185                 190

Ser Arg Phe Leu Asn Ala Leu Glu Thr Met Gly Gly Ala Asp Gln Leu
        195                 200                 205

Ala Lys Asp Val Gly Ser Arg Asn Val Ala Ser Trp Asn Asp Pro Leu
    210                 215                 220

Asp Ala Leu Val Leu Gly Val His Gln Val Gly Leu Ser Gly Trp Lys
225                 230                 235                 240

Gln Glu Glu Cys Leu Ala Ile Gly Asn Glu Leu Leu Ala Trp Arg Glu
                245                 250                 255

Arg Asp Leu Leu Glu Lys Glu Gly Glu Asp Gly Lys Thr Ile Trp
            260                 265                 270

Ala Met Arg Leu Lys Ala Thr Leu Asp Arg Ala Arg Arg Leu Thr Ala
        275                 280                 285
```

-continued

| | | | | | | | | | | | | | |
|---|---|---|---|---|---|---|---|---|---|---|---|---|---|
|Glu|Tyr|Ser|Asp|Leu|Leu|Gln|Ile|Phe|Pro|Pro|Asn|Val|Glu|Ile|
| |290| | | |295| | | |300| | | | | |

Leu Gly Lys Ala Leu Gly Ile Pro Glu Asn Ser Val Lys Thr Tyr Thr
305                 310                 315                 320

Glu Ala Glu Ile Arg Ala Gly Ile Ile Phe Gln Ile Ser Lys Leu Cys
            325                 330                 335

Thr Val Leu Leu Lys Ala Val Arg Asn Ser Leu Gly Ser Glu Gly Trp
        340                 345                 350

Asp Val Val Pro Gly Ser Thr Ser Gly Thr Leu Val Gln Val Glu
            355                 360                 365

Ser Ile Val Pro Gly Ser Leu Pro Ala Thr Ser Gly Gly Pro Ile Ile
370                 375                 380

Leu Leu Val Asn Lys Ala Asp Gly Asp Glu Glu Val Ser Ala Ala Asn
385                 390                 395                 400

Gly Asn Ile Ala Gly Val Met Leu Leu Gln Glu Leu Pro His Leu Ser
                405                 410                 415

His Leu Gly Val Arg Ala Arg Gln Glu Lys Ile Val Phe Val Thr Cys
            420                 425                 430

Asp Asp Asp Lys Val Ala Asp Ile Arg Arg Leu Val Gly Lys Phe
    435                 440                 445

Val Arg Leu Glu Ala Ser Pro Ser His Val Asn Leu Ile Leu Ser Thr
450                 455                 460

Glu Gly Arg Ser Arg Thr Ser Lys Ser Ser Ala Thr Lys Lys Thr Asp
465                 470                 475                 480

Lys Asn Ser Leu Ser Lys Lys Thr Asp Lys Lys Ser Leu Ser Ile
                485                 490                 495

Asp Asp Glu Glu Ser Lys Pro Gly Ser Ser Ser Asn Ser Leu Leu
            500                 505                 510

Tyr Ser Ser Lys Asp Ile Pro Ser Gly Gly Ile Ile Ala Leu Ala Asp
            515                 520                 525

Ala Asp Val Pro Thr Ser Gly Ser Lys Ser Ala Ala Cys Gly Leu Leu
    530                 535                 540

Ala Ser Leu Ala Glu Ala Ser Ser Lys Val His Ser Glu His Gly Val
545                 550                 555                 560

Pro Ala Ser Phe Lys Val Pro Thr Gly Val Val Ile Pro Phe Gly Ser
                565                 570                 575

Met Glu Leu Ala Leu Lys Gln Asn Asn Ser Glu Glu Lys Phe Ala Ser
            580                 585                 590

Leu Leu Glu Lys Leu Glu Thr Ala Arg Pro Glu Gly Gly Glu Leu Asp
        595                 600                 605

Asp Ile Cys Asp Gln Ile His Glu Val Met Lys Thr Leu Gln Val Pro
    610                 615                 620

Lys Glu Thr Ile Asn Ser Ile Ser Lys Ala Phe Leu Lys Asp Ala Arg
625                 630                 635                 640

Leu Ile Val Arg Ser Ser Ala Asn Val Glu Asp Leu Ala Gly Met Ser
                645                 650                 655

Ala Ala Gly Leu Tyr Glu Ser Ile Pro Asn Val Ser Pro Ser Asp Pro
            660                 665                 670

Leu Val Phe Ser Asp Ser Val Cys Gln Val Trp Ala Ser Leu Tyr Thr
        675                 680                 685

Arg Arg Ala Val Leu Ser Arg Arg Ala Ala Gly Val Ser Gln Arg Glu
    690                 695                 700

Ala Ser Met Ala Val Leu Val Gln Glu Met Leu Ser Pro Asp Leu Ser

```
                            705                 710                 715                 720
              Phe Val Leu His Thr Val Ser Pro Ala Asp Pro Asp Ser Asn Leu Val
                              725                 730                 735

Glu Ala Glu Ile Ala Pro Gly Leu Gly Glu Thr Leu Ala Ser Gly Thr
                              740                 745                 750

Arg Gly Thr Pro Trp Arg Leu Ala Ser Gly Lys Leu Asp Gly Ile Val
                              755                 760                 765

Gln Thr Leu Ala Phe Ala Asn Phe Ser Glu Glu Leu Leu Val Ser Gly
                              770                 775                 780

Thr Gly Pro Ala Asp Gly Lys Tyr Val Arg Leu Thr Val Asp Tyr Ser
              785                 790                 795                 800

Lys Lys Arg Leu Thr Val Asp Ser Val Phe Arg Gln Gln Leu Gly Gln
                              805                 810                 815

Arg Leu Gly Ser Val Gly Phe Phe Leu Glu Arg Asn Phe Gly Cys Ala
                              820                 825                 830

Gln Asp Val Glu Gly Cys Leu Val Gly Glu Asp Val Tyr Ile Val Gln
                              835                 840                 845

Ser Arg Pro Gln Pro Leu
                  850

<210> SEQ ID NO 49
<211> LENGTH: 2397
<212> TYPE: DNA
<213> ORGANISM: Artificial Sequence
<220> FEATURE:
<223> OTHER INFORMATION: Chimeric Protein

<400> SEQUENCE: 49
atgggacatc accatcatca tcacatggag cagaagctga tctcagagga ggacctgact    60
agtgctagct gcaccccggc ggcgaccgtg gcggttacct ttaaccacct ggcgagcacc   120
agctacggtg aaagcatcaa gattgtgggt agcatcagcc aactgggtag ctggagcgcg   180
agcagcggcg ttgcgctgag cgcgagccaa tacaccacca gcaacccgct gtggaccgcg   240
accgtgagcc tgccggcggg taccaaattc gagtataagt ttgtgaaagt tagcagcgaa   300
ggtagcgcgg tgacctggga aagcgacccg aaccgtagct ataccgttcc gcagagctgc   360
gcggagagcg tggcggttga aagcagctgg aaggtgggcg ttcaaattaa cccggttagc   420
ggtctgccga gcgtttccca ggacctgctg cactttgtgc tggaccacgt tgaggataaa   480
aacgttgaga ccctgctgga acgtctgctg gaggcgcgtg aggaactgcg tccgctgctg   540
ctgaagccga caaccgtctg aaagatctg ctgttcctgg acatcgcgct ggatagcacc   600
gtgcgtaccg cggttgaacg tggttacgag gaactgaaca cgcgaaccc ggagaagatc   660 atgtatttta ttagcctggt tctggaaaac ctggcgctga gcgtggacga taacgaggac   720
ctggtttatt gcctgaaagg ctggaaccag gcgctgagca tgagcaacgg tggcgacaac   780
cactgggcgc tgttcgcgaa ggcggtgctg gatcgtaccc gtctggcgct ggcgagcaaa   840
gcggaatggt atcaccacct gctgcaaccg agcgcggagt atctgggtag catcctgggc   900
gtggaccagt gggcgctgaa catttttacc gaggaaatca ttcgtgcggg tagcgcggcg   960
agcctgagca gcctgctgaa ccgtctggac cggttctgc gtaagaccgc gaacctgggt  1020
agctggcaaa tcattagccc ggtggaagcg gttggctacg tggttgtggt tgacgagctg  1080
ctgagcgtgc agaacgagat ctatgaaaaa ccgaccattc tggtggcgaa aagcgttaag  1140
ggcgaggaag agatccccgga cggtgcggtg gcgctgatta ccccggacat gccggatgtt  1200
```

```
ctgagccacg tgagcgttcg tgcgcgtaac ggcaaggttt gcttcgcgac ctgctttgac    1260
ccgaacatcc tggcggatct gcaggcgaag gaaggccgta ttctgctgct gaaaccgacc    1320
ccgagcgata tcatttacag cgaggtgaac gagatcgaac tgcagagcag cagcaacctg    1380
gtggaggcgg aaaccagcgc gaccctgcgt ctggttaaga aacagttcgg tggctgctac    1440
gcgattagcg cggacgaatt taccagcgag atggttggtg cgaagagccg taacatcgcg    1500
tatctgaaag caaggtgcc gagcagcgtt ggcattccga ccagcgtggc gctgccgttc    1560
ggtgtgtttg aaaaggttct gagcgacgat atcaaccagg gcgttgcgaa agagctgcaa    1620
attctgatga agaaactgag cgaggtgac ttcagcgcgc tgggcgagat ccgtaccacc    1680
gtgctggatc tgagcgcgcc ggcgcaactg gttaagagc tgaaagaaaa gatgcagggt    1740
agcggtatgc cgtggccggg tgacgaaggt ccgaagcgtt gggagcaagc gtggatggcg    1800
atcaagaaag tgtgggcgag caaatggaac gaacgtgcgt acttcagcac ccgtaaagtt    1860
aagctggacc acgattatct gtgcatggcg gtgctggttc aggagatcat taacgcggat    1920
tacgcgtttg ttatccacac caccaacccg agcagcggtg acgatagcga aatttacgcg    1980
gaggtggttc gtggtctggg cgagaccctg gtgggtgcgt atccgggtcg tgcgctgagc    2040
ttcatctgca agaaaaagga cctgaacagc ccgcaggttc tgggttatcc gagcaagccg    2100
atcggcctgt tcattaaacg tagcatcatt tttcgtagcg acagcaacgg cgaggatctg    2160
gaaggctacg cgggtgcggg tctgtatgac agcgtgccga tggatgaaga ggaaaaagtg    2220
gttatcgact acagcagcga tccgctgatt accgacggta actttcgtca aaccatcctg    2280
agcaacattg cgcgtgcggg tcacgcgatc gaggaactgt atggcagccc gcaggatatt    2340
gagggcgtgg ttcgtgatgg taaaatctat gtggttcaga cccgtccgca aatgtaa      2397
```

<210> SEQ ID NO 50
<211> LENGTH: 798
<212> TYPE: PRT
<213> ORGANISM: Artificial Sequence
<220> FEATURE:
<223> OTHER INFORMATION: Chimeric Protein

<400> SEQUENCE: 50

```
Met Gly His His His His His His Met Glu Gln Lys Leu Ile Ser Glu
1               5                   10                  15

Glu Asp Leu Thr Ser Ala Ser Cys Thr Pro Ala Ala Thr Val Ala Val
            20                  25                  30

Thr Phe Asn His Leu Ala Ser Thr Ser Tyr Gly Glu Ser Ile Lys Ile
        35                  40                  45

Val Gly Ser Ile Ser Gln Leu Gly Ser Trp Ser Ala Ser Ser Gly Val
    50                  55                  60

Ala Leu Ser Ala Ser Gln Tyr Thr Thr Ser Asn Pro Leu Trp Thr Ala
65                  70                  75                  80

Thr Val Ser Leu Pro Ala Gly Thr Lys Phe Glu Tyr Lys Phe Val Lys
                85                  90                  95

Val Ser Ser Glu Gly Ser Ala Val Thr Trp Glu Ser Asp Pro Asn Arg
            100                 105                 110

Ser Tyr Thr Val Pro Gln Ser Cys Ala Glu Ser Val Ala Val Glu Ser
        115                 120                 125

Ser Trp Lys Val Gly Val Gln Ile Asn Pro Val Ser Gly Leu Pro Ser
    130                 135                 140

Gly Phe Gln Asp Leu Leu His Phe Val Leu Asp His Val Glu Asp Lys
145                 150                 155                 160
```

```
Asn Val Glu Thr Leu Leu Glu Arg Leu Leu Glu Ala Arg Glu Glu Leu
            165                 170                 175

Arg Pro Leu Leu Leu Lys Pro Asn Asn Arg Leu Lys Asp Leu Leu Phe
            180                 185                 190

Leu Asp Ile Ala Leu Asp Ser Thr Val Arg Thr Ala Val Glu Arg Gly
            195                 200                 205

Tyr Glu Glu Leu Asn Asn Ala Asn Pro Glu Lys Ile Met Tyr Phe Ile
            210                 215                 220

Ser Leu Val Leu Glu Asn Leu Ala Leu Ser Val Asp Asp Asn Glu Asp
225                 230                 235                 240

Leu Val Tyr Cys Leu Lys Gly Trp Asn Gln Ala Leu Ser Met Ser Asn
            245                 250                 255

Gly Gly Asp Asn His Trp Ala Leu Phe Ala Lys Ala Val Leu Asp Arg
            260                 265                 270

Thr Arg Leu Ala Leu Ala Ser Lys Ala Glu Trp Tyr His His Leu Leu
            275                 280                 285

Gln Pro Ser Ala Glu Tyr Leu Gly Ser Ile Leu Gly Val Asp Gln Trp
            290                 295                 300

Ala Leu Asn Ile Phe Thr Glu Glu Ile Ile Arg Ala Gly Ser Ala Ala
305                 310                 315                 320

Ser Leu Ser Ser Leu Leu Asn Arg Leu Asp Pro Val Leu Arg Lys Thr
            325                 330                 335

Ala Asn Leu Gly Ser Trp Gln Ile Ile Ser Pro Val Glu Ala Val Gly
            340                 345                 350

Tyr Val Val Val Asp Glu Leu Leu Ser Val Gln Asn Glu Ile Tyr
            355                 360                 365

Glu Lys Pro Thr Ile Leu Val Ala Lys Ser Val Lys Gly Glu Glu
            370                 375                 380

Ile Pro Asp Gly Ala Val Ala Leu Ile Thr Pro Asp Met Pro Asp Val
385                 390                 395                 400

Leu Ser His Val Ser Val Arg Ala Arg Asn Gly Lys Val Cys Phe Ala
            405                 410                 415

Thr Cys Phe Asp Pro Asn Ile Leu Ala Asp Leu Gln Ala Lys Glu Gly
            420                 425                 430

Arg Ile Leu Leu Leu Lys Pro Thr Pro Ser Asp Ile Ile Tyr Ser Glu
            435                 440                 445

Val Asn Glu Ile Glu Leu Gln Ser Ser Ser Asn Leu Val Glu Ala Glu
450                 455                 460

Thr Ser Ala Thr Leu Arg Leu Val Lys Lys Gln Phe Gly Gly Cys Tyr
465                 470                 475                 480

Ala Ile Ser Ala Asp Glu Phe Thr Ser Glu Met Val Gly Ala Lys Ser
            485                 490                 495

Arg Asn Ile Ala Tyr Leu Lys Gly Lys Val Pro Ser Ser Val Gly Ile
            500                 505                 510

Pro Thr Ser Val Ala Leu Pro Phe Gly Val Phe Glu Lys Val Leu Ser
            515                 520                 525

Asp Asp Ile Asn Gln Gly Val Ala Lys Glu Leu Gln Ile Leu Met Lys
            530                 535                 540

Lys Leu Ser Glu Gly Asp Phe Ser Ala Leu Gly Glu Ile Arg Thr Thr
545                 550                 555                 560

Val Leu Asp Leu Ser Ala Pro Ala Gln Leu Val Lys Glu Leu Lys Glu
            565                 570                 575
```

```
Lys Met Gln Gly Ser Gly Met Pro Trp Pro Gly Asp Glu Gly Pro Lys
            580                 585                 590
Arg Trp Glu Gln Ala Trp Met Ala Ile Lys Lys Val Trp Ala Ser Lys
        595                 600                 605
Trp Asn Glu Arg Ala Tyr Phe Ser Thr Arg Lys Val Lys Leu Asp His
    610                 615                 620
Asp Tyr Leu Cys Met Ala Val Leu Val Gln Glu Ile Ile Asn Ala Asp
625                 630                 635                 640
Tyr Ala Phe Val Ile His Thr Thr Asn Pro Ser Ser Gly Asp Asp Ser
                645                 650                 655
Glu Ile Tyr Ala Glu Val Val Arg Gly Leu Gly Glu Thr Leu Val Gly
            660                 665                 670
Ala Tyr Pro Gly Arg Ala Leu Ser Phe Ile Cys Lys Lys Lys Asp Leu
        675                 680                 685
Asn Ser Pro Gln Val Leu Gly Tyr Pro Ser Lys Pro Ile Gly Leu Phe
    690                 695                 700
Ile Lys Arg Ser Ile Ile Phe Arg Ser Asp Ser Asn Gly Glu Asp Leu
705                 710                 715                 720
Glu Gly Tyr Ala Gly Ala Gly Leu Tyr Asp Ser Val Pro Met Asp Glu
                725                 730                 735
Glu Glu Lys Val Val Ile Asp Tyr Ser Ser Asp Pro Leu Ile Thr Asp
            740                 745                 750
Gly Asn Phe Arg Gln Thr Ile Leu Ser Asn Ile Ala Arg Ala Gly His
        755                 760                 765
Ala Ile Glu Glu Leu Tyr Gly Ser Pro Gln Asp Ile Glu Gly Val Val
    770                 775                 780
Arg Asp Gly Lys Ile Tyr Val Val Gln Thr Arg Pro Gln Met
785                 790                 795

<210> SEQ ID NO 51
<211> LENGTH: 2832
<212> TYPE: DNA
<213> ORGANISM: Artificial Sequence
<220> FEATURE:
<223> OTHER INFORMATION: Chimeric Protein

<400> SEQUENCE: 51
atgggacatc accatcatca tcacatggag cagaagctga tctcagagga ggacctgact      60
agtgctagca gcgcgagcgc ggaaaccgtg gcgccggaag gttaccgtaa gctgctggac     120
gttcagatct ttaaagatag cccggtggtt ggttggagcg gtagcggtat gggcgagctg     180
gaaaccattg gtgacaccct gccggtggat accaccgtta cctataacgg cctgccgacc     240
ctgcgtctga cgtgcagac accgttcaa agcggttggt ggatcagcct gctgaccctg     300
cgtggttgga cacccacga cctgagccag tacgtggaga cggctatct ggaattcgat     360
atcaagggta agagggtgg cgaagacttc gttattggct tcgtgataa ggtgtacgag     420
cgtgtttatg gtctggaaat cgacgtgacc accgttatta gcaactacgt gaccgttacc     480
accgattggc aacacgtgaa gatcccgctg cgtgacctga tgaaaattaa caacggtttc     540
gatccgagca gcgtgacctg cctggttttt agcaagcgtt atgcggaccc gttcaccgtg     600
tggtttagcg acatcaaaat taccagcgag ataacgaaa agagcgcgcc ggcgattaaa     660
ggagaatcaa gcaatgtttt ggagttgatt aaaaccatgc attctctagc ttctttaaga     720
gaaacaatta taaggaact taatagcggc ttgcgaaatg atgctcctga tactgccatt     780
gcaatgcgcc agaagtggcg cctttgtgag atcggcctcg aggactactt ctttgttcta     840
```

```
ctaagcagat tcctcaatgc tcttgaaact atgggaggag ctgatcaact ggcaaaagat      900
gtgggatcaa gaaacgttgc ctcatggaat gatccactag atgctttggt gttgggtgtt      960
caccaagtag gtctatctgg ttggaagcaa gaagaatgtt tagccattgg aaatgaactc     1020
cttgcttggc gagaaaggga cctacttgaa aagaaggggg aagaggatgg aaaaacaatt     1080
tgggccatga ggctgaaagc aactcttgat cgagcacgca gattaacagc agaatattct     1140
gatttgcttc ttcaaatatt tcctcctaat gtggagattt taggaaaagc tctaggtatt     1200
ccagagaata gtgtcaagac ctatacagaa gcagagattc gtgctggaat tattttccag     1260
atctcaaagc tctgcactgt tcttctaaaa gctgtaagaa attcacttgg ttctgagggc     1320
tgggatgtcg ttgtacctgg atcgacgtct gggacattag ttcaggttga gagcattgtt     1380
ccgggatcat tgccagcaac ttctggtggt cctattattc tcttggtcaa taaagctgat     1440
ggcgatgaag aggtaagtgc tgctaatggg aacatagctg gagtcatgct tctgcaggag     1500
ctgcctcact tgtctcacct tggcgttaga gcgcggcagg agaaaattgt ctttgtgaca     1560
tgtgatgatg atgacaaggt tgctgatata cgacgacttg tgggaaaatt tgtgaggttg     1620
gaagcatctc caagtcatgt gaatctgata ctttcaactg agggtaggag tcgcacttcc     1680
aaatccagtg cgaccaaaaa aacggataag aacagcttat ctaagaaaaa aacagataag     1740
aagagcttat ctatcgatga tgaagaatca aagcctggtt cctcatcttc caatagcctc     1800
ctttactctt ccaaggatat ccctagtgga ggaatcatag cacttgctga tgcagatgta     1860
ccaacttctg gttcaaaatc tgctgcatgt ggtcttcttg catctttagc agaagcctct     1920
agtaaagtgc acagcgaaca cggagttccg gcatcattta aggttccaac tggagttgtc     1980 atacctttg gatcgatgga attagcttta aagcaaaata attcggaaga aaagtttgcg     2040
tctttgctag aaaaactaga aaccgccaga cctgagggtg gtgagctaga cgacatatgt     2100
gaccagatcc atgaagtgat gaaaacgttg caagtgccta agaaacaat caacagcata     2160 agcaaagcgt ttctcaaaga tgctcgtctc attgttcgtt caagtgctaa cgtcgaggac     2220
ttagccggaa tgtcagctgc aggactctat gaatcaatcc ctaacgtgag tccctctgat     2280
cctttggtgt tttcagattc ggtttgccaa gtttgggctt ctctctacac aagaagagct     2340
gttctaagcc gtagagctgc tggtgtctct caaagagaag cttcaatggc tgttctcgtt     2400
caagaaatgc tttcgccgga cttatcattc gttctgcaca cagtgagtcc agctgatccg     2460
gacagtaacc ttgtggaagc cgagatcgct cctggtttag gtgagacttt agcttcagga     2520
acaagaggaa caccatggag actcgcttcg ggtaagctcg acgggattgt acaaacctta     2580
gctttcgcaa acttcagcga agagcttctt gtgtcaggaa caggtcctgc tgatggaaaa     2640
tacgttcggt tgaccgtgga ctatagcaaa aaacgtttaa ctgttgactc ggtgtttaga     2700
cagcagctcg gtcagagact cggttcggtt ggtttcttct tggaaagaaa ctttggctgt     2760
gctcaagacg ttgaaggttg tttggttggt gaagatgttt acattgttca gtcaaggcca     2820
caacctctgt aa                                                         2832
```

<210> SEQ ID NO 52
<211> LENGTH: 943
<212> TYPE: PRT
<213> ORGANISM: Artificial Sequence
<220> FEATURE:
<223> OTHER INFORMATION: Chimeric Protein

<400> SEQUENCE: 52

```
Met Gly His His His His His Met Glu Gln Lys Leu Ile Ser Glu
1               5                   10                  15

Glu Asp Leu Thr Ser Ala Ser Ser Ala Glu Thr Val Ala Pro
            20                  25                  30

Glu Gly Tyr Arg Lys Leu Leu Asp Val Gln Ile Phe Lys Asp Ser Pro
                35                  40                  45

Val Val Gly Trp Ser Gly Ser Gly Met Gly Glu Leu Glu Thr Ile Gly
    50                  55                  60

Asp Thr Leu Pro Val Asp Thr Thr Val Thr Tyr Asn Gly Leu Pro Thr
65                  70                  75                  80

Leu Arg Leu Asn Val Gln Thr Thr Val Gln Ser Gly Trp Trp Ile Ser
                85                  90                  95

Leu Leu Thr Leu Arg Gly Trp Asn Thr His Asp Leu Ser Gln Tyr Val
                100                 105                 110

Glu Asn Gly Tyr Leu Glu Phe Asp Ile Lys Gly Lys Glu Gly Gly Glu
                115                 120                 125

Asp Phe Val Ile Gly Phe Arg Asp Lys Val Tyr Glu Arg Val Tyr Gly
                130                 135                 140

Leu Glu Ile Asp Val Thr Thr Val Ile Ser Asn Tyr Val Thr Val Thr
145                 150                 155                 160

Thr Asp Trp Gln His Val Lys Ile Pro Leu Arg Asp Leu Met Lys Ile
                165                 170                 175

Asn Asn Gly Phe Asp Pro Ser Ser Val Thr Cys Leu Val Phe Ser Lys
                180                 185                 190

Arg Tyr Ala Asp Pro Phe Thr Val Trp Phe Ser Asp Ile Lys Ile Thr
                195                 200                 205

Ser Glu Asp Asn Glu Lys Ser Ala Pro Ala Ile Lys Gly Glu Ser Ser
210                 215                 220

Asn Val Leu Glu Leu Ile Lys Thr Met His Ser Leu Ala Ser Leu Arg
225                 230                 235                 240

Glu Thr Ile Ile Lys Glu Leu Asn Ser Gly Leu Arg Asn Asp Ala Pro
                245                 250                 255

Asp Thr Ala Ile Ala Met Arg Gln Lys Trp Arg Leu Cys Glu Ile Gly
                260                 265                 270

Leu Glu Asp Tyr Phe Phe Val Leu Leu Ser Arg Phe Leu Asn Ala Leu
                275                 280                 285

Glu Thr Met Gly Gly Ala Asp Gln Leu Ala Lys Asp Val Gly Ser Arg
                290                 295                 300

Asn Val Ala Ser Trp Asn Asp Pro Leu Asp Ala Leu Val Leu Gly Val
305                 310                 315                 320

His Gln Val Gly Leu Ser Gly Trp Lys Gln Glu Glu Cys Leu Ala Ile
                325                 330                 335

Gly Asn Glu Leu Leu Ala Trp Arg Glu Arg Asp Leu Leu Glu Lys Glu
                340                 345                 350

Gly Glu Glu Asp Gly Lys Thr Ile Trp Ala Met Arg Leu Lys Ala Thr
                355                 360                 365

Leu Asp Arg Ala Arg Arg Leu Thr Ala Glu Tyr Ser Asp Leu Leu Leu
                370                 375                 380

Gln Ile Phe Pro Pro Asn Val Glu Ile Leu Gly Lys Ala Leu Gly Ile
385                 390                 395                 400

Pro Glu Asn Ser Val Lys Thr Tyr Thr Glu Ala Glu Ile Arg Ala Gly
                405                 410                 415

Ile Ile Phe Gln Ile Ser Lys Leu Cys Thr Val Leu Leu Lys Ala Val
```

```
                420             425             430
Arg Asn Ser Leu Gly Ser Glu Gly Trp Asp Val Val Pro Gly Ser
                435             440             445
Thr Ser Gly Thr Leu Val Gln Val Glu Ser Ile Val Pro Gly Ser Leu
            450             455             460
Pro Ala Thr Ser Gly Pro Ile Ile Leu Leu Val Asn Lys Ala Asp
465             470             475             480
Gly Asp Glu Glu Val Ser Ala Ala Asn Gly Asn Ile Ala Gly Val Met
                485             490             495
Leu Leu Gln Glu Leu Pro His Leu Ser His Leu Gly Val Arg Ala Arg
                500             505             510
Gln Glu Lys Ile Val Phe Val Thr Cys Asp Asp Asp Lys Val Ala
                515             520             525
Asp Ile Arg Arg Leu Val Gly Lys Phe Val Arg Leu Glu Ala Ser Pro
            530             535             540
Ser His Val Asn Leu Ile Leu Ser Thr Glu Gly Arg Ser Arg Thr Ser
545             550             555             560
Lys Ser Ser Ala Thr Lys Lys Thr Asp Lys Asn Ser Leu Ser Lys Lys
                565             570             575
Lys Thr Asp Lys Lys Ser Leu Ser Ile Asp Asp Glu Ser Lys Pro
                580             585             590
Gly Ser Ser Ser Asn Ser Leu Leu Tyr Ser Ser Lys Asp Ile Pro
                595             600             605
Ser Gly Gly Ile Ile Ala Leu Ala Asp Ala Asp Val Pro Thr Ser Gly
            610             615             620
Ser Lys Ser Ala Ala Cys Gly Leu Leu Ala Ser Leu Ala Glu Ala Ser
625             630             635             640
Ser Lys Val His Ser Glu His Gly Val Pro Ala Ser Phe Lys Val Pro
                645             650             655
Thr Gly Val Val Ile Pro Phe Gly Ser Met Glu Leu Ala Leu Lys Gln
                660             665             670
Asn Asn Ser Glu Glu Lys Phe Ala Ser Leu Leu Glu Lys Leu Glu Thr
                675             680             685
Ala Arg Pro Glu Gly Gly Glu Leu Asp Asp Ile Cys Asp Gln Ile His
                690             695             700
Glu Val Met Lys Thr Leu Gln Val Pro Lys Glu Thr Ile Asn Ser Ile
705             710             715             720
Ser Lys Ala Phe Leu Lys Asp Ala Arg Leu Ile Val Arg Ser Ser Ala
                725             730             735
Asn Val Glu Asp Leu Ala Gly Met Ser Ala Ala Gly Leu Tyr Glu Ser
                740             745             750
Ile Pro Asn Val Ser Pro Ser Asp Pro Leu Val Phe Ser Asp Ser Val
                755             760             765
Cys Gln Val Trp Ala Ser Leu Tyr Thr Arg Arg Ala Val Leu Ser Arg
                770             775             780
Arg Ala Ala Gly Val Ser Gln Arg Glu Ala Ser Met Ala Val Leu Val
785             790             795             800
Gln Glu Met Leu Ser Pro Asp Leu Ser Phe Val Leu His Thr Val Ser
                805             810             815
Pro Ala Asp Pro Asp Ser Asn Leu Val Glu Ala Glu Ile Ala Pro Gly
                820             825             830
Leu Gly Glu Thr Leu Ala Ser Gly Thr Arg Gly Thr Pro Trp Arg Leu
                835             840             845
```

```
Ala Ser Gly Lys Leu Asp Gly Ile Val Gln Thr Leu Ala Phe Ala Asn
        850                 855                 860

Phe Ser Glu Glu Leu Leu Val Ser Gly Thr Gly Pro Ala Asp Gly Lys
865                 870                 875                 880

Tyr Val Arg Leu Thr Val Asp Tyr Ser Lys Lys Arg Leu Thr Val Asp
                885                 890                 895

Ser Val Phe Arg Gln Gln Leu Gly Gln Arg Leu Gly Ser Val Gly Phe
            900                 905                 910

Phe Leu Glu Arg Asn Phe Gly Cys Ala Gln Asp Val Glu Gly Cys Leu
        915                 920                 925

Val Gly Glu Asp Val Tyr Ile Val Gln Ser Arg Pro Gln Pro Leu
    930                 935                 940
```

<210> SEQ ID NO 53
<211> LENGTH: 2664
<212> TYPE: DNA
<213> ORGANISM: Artificial Sequence
<220> FEATURE:
<223> OTHER INFORMATION: Chimeric Protein

<400> SEQUENCE: 53

```
atgggacatc accatcatca tcacatggag cagaagctga tctcagagga ggacctgact    60
agtgctagca gcgcgagcgc ggaaaccgtg gcgccggaag gttaccgtaa gctgctggac   120
gttcagatct ttaaagatag cccggtggtt ggttggagcg gtagcggtat gggcgagctg   180
gaaaccattg gtgacaccct gccggtggat accaccgtta cctataacgg cctgccgacc   240
ctgcgtctga acgtgcagac caccgttcaa gcggttggt  ggatcagcct gctgaccctg   300
cgtggttgga cacccacga  cctgagccag tacgtggaga  acggctatct  ggaattcgat   360
atcaagggta agagggtgg  cgaagacttc gttattggct tcgtgataaa ggtgtacgag   420
cgtgtttatg gtctggaaat cgacgtgacc accgttatta gcaactacgt gaccgttacc   480
accgattggc aacacgtgaa gatcccgctg cgtgacctga tgaaaattaa caacggtttc   540
gatccgagca gcgtgacctg cctggttttt agcaagcgtt atgcggaccc gttcaccgtg   600
tggtttagcg acatcaaaat taccagcgag gataacgaaa gagcgcgcc  ggcgattaaa   660
gtgggcgttc aaattaaccc ggttagcggt ctgccgagcg gtttccagga cctgctgcac   720
tttgtgctgg accacgttga ggataaaaac gttgagaccc tgctggaacg tctgctggag   780
gcgcgtgagg aactgcgtcc gctgctgctg aagccgaaca accgtctgaa agatctgctg   840
ttcctggaca tcgcgctgga tagcaccgtg cgtaccgcgg ttgaacgtgg ttacgaggaa   900
ctgaacaacg cgaacccgga gaagatcatg tattttatta gcctggttct ggaaaacctg   960
gcgctgagcg tggacgataa cgaggacctg gtttattgcc tgaaaggctg gaaccaggcg  1020
ctgagcatga gcaacggtgg cgacaaccac tgggcgctgt cgcgaaggc  ggtgctggat  1080
cgtaccgtc  tggcgctggc gagcaaagcg gaatggtatc accacctgct gcaaccgagc  1140
gcggagtatc tgggtagcat cctgggcgtg gaccagtggg cgctgaacat  ttttaccgag  1200
gaaatcattc gtgcgggtag cgcggcgagc ctgagcagcc tgctgaaccg tctggacccg  1260
gttctgcgta agaccgcgaa cctgggtagc tggcaaatca ttagcccggt ggaagcggtt  1320
ggctacgtgg ttgtggttga cgagctgctg agcgtgcaga acgagatcta tgaaaaaccg  1380
accattctgg tggcgaaaag cgttaagggc gaggaagaga tcccggacgg tgcggtggcg  1440
ctgattaccc cggacatgcc ggatgttctg agccacgtga gcgttcgtgc gcgtaacggc  1500
```

```
aaggtttgct tcgcgacctg ctttgacccg aacatcctgg cggatctgca ggcgaaggaa    1560
ggccgtattc tgctgctgaa accgaccccg agcgatatca tttacagcga ggtgaacgag    1620
atcgaactgc agagcagcag caacctggtg gaggcggaaa ccagcgcgac cctgcgtctg    1680
gttaagaaac agttcggtgg ctgctacgcg attagcgcgg acgaatttac cagcgagatg    1740
gttggtgcga agagccgtaa catcgcgtat ctgaaaggca aggtgccgag cagcgttggc    1800
attccgacca gcgtggcgct gccgttcggt gtgtttgaaa aggttctgag cgacgatatc    1860
aaccagggcg ttgcgaaaga gctgcaaatt ctgatgaaga aactgagcga gggtgacttc    1920
agcgcgctgg gcgagatccg taccaccgtg ctggatctga gcgcgccggc gcaactggtt    1980
aaagagctga agaaaagat gcagggtagc ggtatgccgt ggccgggtga cgaaggtccg    2040
aagcgttggg agcaagcgtg gatggcgatc aagaaagtgt gggcgagcaa atggaacgaa    2100
cgtgcgtact tcagcacccg taaagttaag ctggaccacg attatctgtg catggcggtg    2160
ctggttcagg agatcattaa cgcggattac gcgtttgtta tccacaccac caacccgagc    2220
agcggtgacg atagcgaaat ttacgcggag gtggttcgtg gtctgggcga gaccctggtg    2280
ggtgcgtatc cgggtcgtgc gctgagcttc atctgcaaga aaaggaccct gaacagcccg    2340
caggttctgg gttatccgag caagccgatc ggcctgttca ttaaacgtag catcattttt    2400
cgtagcgaca gcaacggcga ggatctggaa ggctacgcgg gtgcgggtct gtatgacagc    2460
gtgccgatgg atgaagagga aaagtggtt atcgactaca gcagcgatcc gctgattacc    2520
gacggtaact ttcgtcaaac catcctgagc aacattgcgc gtgcgggtca cgcgatcgag    2580
gaactgtatg cagcccgca ggatattgag ggcgtggttc gtgatggtaa aatctatgtg    2640
gttcagaccc gtccgcaaat gtaa                                          2664
```

<210> SEQ ID NO 54
<211> LENGTH: 887
<212> TYPE: PRT
<213> ORGANISM: Artificial Sequence
<220> FEATURE:
<223> OTHER INFORMATION: Chimeric Protein

<400> SEQUENCE: 54

Met Gly His His His His His His Met Glu Gln Lys Leu Ile Ser Glu
1               5                   10                  15

Glu Asp Leu Thr Ser Ala Ser Ser Ala Ser Glu Thr Val Ala Pro
            20                  25                  30

Glu Gly Tyr Arg Lys Leu Leu Asp Val Gln Ile Phe Lys Asp Ser Pro
        35                  40                  45

Val Val Gly Trp Ser Gly Ser Gly Met Gly Glu Leu Glu Thr Ile Gly
    50                  55                  60

Asp Thr Leu Pro Val Asp Thr Val Thr Tyr Asn Gly Leu Pro Thr
65                  70                  75                  80

Leu Arg Leu Asn Val Gln Thr Thr Val Gln Ser Gly Trp Trp Ile Ser
                85                  90                  95

Leu Leu Thr Leu Arg Gly Trp Asn Thr His Asp Leu Ser Gln Tyr Val
            100                 105                 110

Glu Asn Gly Tyr Leu Glu Phe Asp Ile Lys Gly Lys Glu Gly Gly Glu
        115                 120                 125

Asp Phe Val Ile Gly Phe Arg Asp Lys Val Tyr Glu Arg Val Tyr Gly
    130                 135                 140

Leu Glu Ile Asp Val Thr Thr Val Ile Ser Asn Tyr Val Thr Val Thr
145                 150                 155                 160

```
Thr Asp Trp Gln His Val Lys Ile Pro Leu Arg Asp Leu Met Lys Ile
            165                 170                 175

Asn Asn Gly Phe Asp Pro Ser Ser Val Thr Cys Leu Val Phe Ser Lys
            180                 185                 190

Arg Tyr Ala Asp Pro Phe Thr Val Trp Phe Ser Asp Ile Lys Ile Thr
            195                 200                 205

Ser Glu Asp Asn Glu Lys Ser Ala Pro Ala Ile Lys Val Gly Val Gln
            210                 215                 220

Ile Asn Pro Val Ser Gly Leu Pro Ser Gly Phe Gln Asp Leu Leu His
225                 230                 235                 240

Phe Val Leu Asp His Val Glu Asp Lys Asn Val Glu Thr Leu Leu Glu
                245                 250                 255

Arg Leu Leu Glu Ala Arg Glu Glu Leu Arg Pro Leu Leu Lys Pro
            260                 265                 270

Asn Asn Arg Leu Lys Asp Leu Leu Phe Leu Asp Ile Ala Leu Asp Ser
            275                 280                 285

Thr Val Arg Thr Ala Val Glu Arg Gly Tyr Glu Glu Leu Asn Asn Ala
            290                 295                 300

Asn Pro Glu Lys Ile Met Tyr Phe Ile Ser Leu Val Leu Glu Asn Leu
305                 310                 315                 320

Ala Leu Ser Val Asp Asp Asn Glu Asp Leu Val Tyr Cys Leu Lys Gly
                325                 330                 335

Trp Asn Gln Ala Leu Ser Met Ser Asn Gly Gly Asp Asn His Trp Ala
            340                 345                 350

Leu Phe Ala Lys Ala Val Leu Asp Arg Thr Arg Leu Ala Leu Ala Ser
            355                 360                 365

Lys Ala Glu Trp Tyr His His Leu Leu Gln Pro Ser Ala Glu Tyr Leu
            370                 375                 380

Gly Ser Ile Leu Gly Val Asp Gln Trp Ala Leu Asn Ile Phe Thr Glu
385                 390                 395                 400

Glu Ile Ile Arg Ala Gly Ser Ala Ala Ser Leu Ser Ser Leu Leu Asn
                405                 410                 415

Arg Leu Asp Pro Val Leu Arg Lys Thr Ala Asn Leu Gly Ser Trp Gln
            420                 425                 430

Ile Ile Ser Pro Val Glu Ala Val Gly Tyr Val Val Val Asp Glu
            435                 440                 445

Leu Leu Ser Val Gln Asn Glu Ile Tyr Glu Lys Pro Thr Ile Leu Val
450                 455                 460

Ala Lys Ser Val Lys Gly Glu Glu Ile Pro Asp Gly Ala Val Ala
465                 470                 475                 480

Leu Ile Thr Pro Asp Met Pro Asp Val Leu Ser His Val Ser Val Arg
            485                 490                 495

Ala Arg Asn Gly Lys Val Cys Phe Ala Thr Cys Phe Asp Pro Asn Ile
            500                 505                 510

Leu Ala Asp Leu Gln Ala Lys Glu Gly Arg Ile Leu Leu Leu Lys Pro
            515                 520                 525

Thr Pro Ser Asp Ile Ile Tyr Ser Glu Val Asn Glu Ile Glu Leu Gln
            530                 535                 540

Ser Ser Ser Asn Leu Val Glu Ala Glu Thr Ser Ala Thr Leu Arg Leu
545                 550                 555                 560

Val Lys Lys Gln Phe Gly Gly Cys Tyr Ala Ile Ser Ala Asp Glu Phe
                565                 570                 575
```

```
Thr Ser Glu Met Val Gly Ala Lys Ser Arg Asn Ile Ala Tyr Leu Lys
            580                 585                 590

Gly Lys Val Pro Ser Ser Val Gly Ile Pro Thr Ser Val Ala Leu Pro
        595                 600                 605

Phe Gly Val Phe Glu Lys Val Leu Ser Asp Asp Ile Asn Gln Gly Val
        610                 615                 620

Ala Lys Glu Leu Gln Ile Leu Met Lys Lys Leu Ser Glu Gly Asp Phe
625                 630                 635                 640

Ser Ala Leu Gly Glu Ile Arg Thr Thr Val Leu Asp Leu Ser Ala Pro
                645                 650                 655

Ala Gln Leu Val Lys Glu Leu Lys Glu Lys Met Gln Gly Ser Gly Met
            660                 665                 670

Pro Trp Pro Gly Asp Glu Gly Pro Lys Arg Trp Glu Gln Ala Trp Met
        675                 680                 685

Ala Ile Lys Lys Val Trp Ala Ser Lys Trp Asn Glu Arg Ala Tyr Phe
        690                 695                 700

Ser Thr Arg Lys Val Lys Leu Asp His Asp Tyr Leu Cys Met Ala Val
705                 710                 715                 720

Leu Val Gln Glu Ile Ile Asn Ala Asp Tyr Ala Phe Val Ile His Thr
                725                 730                 735

Thr Asn Pro Ser Ser Gly Asp Ser Glu Ile Tyr Ala Glu Val Val
            740                 745                 750

Arg Gly Leu Gly Glu Thr Leu Val Gly Ala Tyr Pro Gly Arg Ala Leu
                755                 760                 765

Ser Phe Ile Cys Lys Lys Asp Leu Asn Ser Pro Gln Val Leu Gly
        770                 775                 780

Tyr Pro Ser Lys Pro Ile Gly Leu Phe Ile Lys Arg Ser Ile Ile Phe
785                 790                 795                 800

Arg Ser Asp Ser Asn Gly Asp Leu Glu Gly Tyr Ala Gly Ala Gly
            805                 810                 815

Leu Tyr Asp Ser Val Pro Met Asp Glu Glu Lys Val Val Ile Asp
        820                 825                 830

Tyr Ser Ser Asp Pro Leu Ile Thr Asp Gly Asn Phe Arg Gln Thr Ile
        835                 840                 845

Leu Ser Asn Ile Ala Arg Ala Gly His Ala Ile Glu Glu Leu Tyr Gly
850                 855                 860

Ser Pro Gln Asp Ile Glu Gly Val Val Arg Asp Gly Lys Ile Tyr Val
865                 870                 875                 880

Val Gln Thr Arg Pro Gln Met
                885
```

<210> SEQ ID NO 55
<211> LENGTH: 2694
<212> TYPE: DNA
<213> ORGANISM: Artificial Sequence
<220> FEATURE:
<223> OTHER INFORMATION: Chimeric Protein

<400> SEQUENCE: 55

```
atgggacatc accatcatca tcacatggag cagaagctga tctcagagga ggacctgact    60
agtgctagca agttcaactt tgaagatggc accctgggtg gctttaccac cagcggtacc   120
aacgcgaccg gcgtggttgt gaacaccacc gagaaggcgt tcaaaggtga cgtggcctg    180 aagtggaccg tgaccagcga gggtgaaggt accgcggagc tgaaactgga cgtgggcacc   240
atcgttgtgc cgggtaccac catgaccttt cgtatttgga ttccgagcgg tgcgccgatt   300
```

```
gcggcgattc agccgtacat tatgccgcac accccggatt ggagcgaagt tctgtggaac    360
agcacctgga agggttatac catggtgaaa accgacgatt ggaacgagat caccctgacc    420
ctgccggaag acgttgatcc gacctggccg cagcaaatgg gtatccaggt gcaaaccatt    480
gacgagggcg aattcaccat ctacgttgac gcgattgatt ggggagaatc aagcaatgtt    540
ttggagttga ttaaaaccat gcattctcta gcttctttaa gagaaacaat tataaaggaa    600
cttaatagcg gcttgcgaaa tgatgctcct gatactgcca ttgcaatgcg ccagaagtgg    660
cgcctttgtg agatcggcct cgaggactac ttctttgttc tactaagcag attcctcaat    720
gctcttgaaa ctatgggagg agctgatcaa ctggcaaaag atgtgggatc aagaaacgtt    780
gcctcatgga atgatccact agatgctttg gtgttgggtg ttcaccaagt aggtctatct    840
ggttggaagc aagaagaatg tttagccatt ggaaatgaac tccttgcttg gcagaaaagg    900
gacctacttg aaaagaagg ggaagaggat ggaaaaacaa tttgggccat gaggctgaaa    960
gcaactcttg atcgagcacg cagattaaca gcagaatatt ctgatttgct tcttcaaata   1020
tttcctccta atgtggagat tttaggaaaa gctctaggta ttccagagaa tagtgtcaag   1080
acctatacag aagcagagat tcgtgctgga attattttcc agatctcaaa gctctgcact   1140
gttcttctaa agctgtaag aaattcactt ggttctgagg gctgggatgt cgttgtacct   1200
ggatcgacgt ctgggacatt agttcaggtt gagagcattg ttccgggatc attgccagca   1260
acttctggtg gtcctattat tctcttggtc aataaagctg atggcgatga gaggtaagt   1320
gctgctaatg ggaacatagc tggagtcatg cttctgcagg agctgcctca cttgtctcac   1380
cttggcgtta gagcgcggca ggagaaaatt gtctttgtga catgtgatga tgatgacaag   1440
gttgctgata tacgacgact tgtgggaaaa tttgtgaggt tggaagcatc tccaagtcat   1500
gtgaatctga tactttcaac tgagggtagg agtcgcactt ccaaatccag tgcgaccaaa   1560
aaaacggata gaacagcttt atctaagaaa aaaacagata agaagagctt atctatcgat   1620
gatgaagaat caaagcctgg ttcctcatct tccaatagcc tcctttactc ttccaaggat   1680
atccctagtg gaggaatcat agcacttgct gatgcagatg taccaacttc tggttcaaaa   1740
tctgctgcat gtggtcttct tgcatcttta gcagaagcct ctagtaaagt gcacagcgaa   1800
cacggagttc cggcatcatt taaggttcca actggagttg tcataccttt tggatcgatg   1860
gaattagctt taaagcaaaa taattcggaa gaaaagtttg cgtctttgct agaaaaacta   1920
gaaaccgcca gacctgaggg tggtgagcta gacgacatat gtgaccagat ccatgaagtg   1980
atgaaaacgt tgcaagtgcc taagaaaaca atcaacagca taagcaaagc gtttctcaaa   2040
gatgctcgtc tcattgttcg ttcaagtgct aacgtcgagg acttagccgg aatgtcagct   2100
gcaggactct atgaatcaat ccctaacgtg agtccctctg atcctttggt gttttcagat   2160
tcggtttgcc aagtttgggc ttctctctac acaagaagag ctgttctaag ccgtagagct   2220
gctggtgtct ctcaaagaga agcttcaatg gctgttctcg ttcaagaaat gctttcgccg   2280
gacttatcat tcgttctgca cacagtgagt ccagctgatc cggacagtaa ccttgtggaa   2340
gccgagatcg ctcctggttt aggtgagact ttagcttcag gaacaagagg aacaccatgg   2400
agactcgctt cgggtaagct cgacgggatt gtacaaacct tagctttcgc aaacttcagc   2460
gaagagcttc ttgtgtcagg aacaggtcct gctgatggaa aatacgttcg gttgaccgtg   2520
gactatagca aaaaacgttt aactgttgac tcggtgttta gacagcagct cggtcagaga   2580
ctcggttcgg ttggtttctt cttggaaaga aactttggct gtgctcaaga cgttgaaggt   2640
```

-continued tgtttggttg gtgaagatgt ttacattgtt cagtcaaggc cacaacctct gtaa 2694

<210> SEQ ID NO 56
<211> LENGTH: 897
<212> TYPE: PRT
<213> ORGANISM: Artificial Sequence
<220> FEATURE:
<223> OTHER INFORMATION: Chimeric Protein

<400> SEQUENCE: 56

Met Gly His His His His His His Met Glu Gln Lys Leu Ile Ser Glu
1               5                   10                  15

Glu Asp Leu Thr Ser Ala Ser Lys Phe Asn Phe Glu Asp Gly Thr Leu
            20                  25                  30

Gly Gly Phe Thr Thr Ser Gly Thr Asn Ala Thr Gly Val Val Val Asn
        35                  40                  45

Thr Thr Glu Lys Ala Phe Lys Gly Glu Arg Gly Leu Lys Trp Thr Val
    50                  55                  60

Thr Ser Glu Gly Glu Gly Thr Ala Glu Leu Lys Leu Asp Gly Gly Thr
65                  70                  75                  80

Ile Val Val Pro Gly Thr Thr Met Thr Phe Arg Ile Trp Ile Pro Ser
                85                  90                  95

Gly Ala Pro Ile Ala Ala Ile Gln Pro Tyr Ile Met Pro His Thr Pro
            100                 105                 110

Asp Trp Ser Glu Val Leu Trp Asn Ser Thr Trp Lys Gly Tyr Thr Met
        115                 120                 125

Val Lys Thr Asp Asp Trp Asn Glu Ile Thr Leu Thr Leu Pro Glu Asp
    130                 135                 140

Val Asp Pro Thr Trp Pro Gln Gln Met Gly Ile Gln Val Gln Thr Ile
145                 150                 155                 160

Asp Glu Gly Glu Phe Thr Ile Tyr Val Asp Ala Ile Asp Trp Gly Glu
                165                 170                 175

Ser Ser Asn Val Leu Glu Leu Ile Lys Thr Met His Ser Leu Ala Ser
            180                 185                 190

Leu Arg Glu Thr Ile Ile Lys Glu Leu Asn Ser Gly Leu Arg Asn Asp
        195                 200                 205

Ala Pro Asp Thr Ala Ile Ala Met Arg Gln Lys Trp Arg Leu Cys Glu
    210                 215                 220

Ile Gly Leu Glu Asp Tyr Phe Phe Val Leu Leu Ser Arg Phe Leu Asn
225                 230                 235                 240

Ala Leu Glu Thr Met Gly Gly Ala Asp Gln Leu Ala Lys Asp Val Gly
                245                 250                 255

Ser Arg Asn Val Ala Ser Trp Asn Asp Pro Leu Asp Ala Leu Val Leu
            260                 265                 270

Gly Val His Gln Val Gly Leu Ser Gly Trp Lys Gln Glu Glu Cys Leu
        275                 280                 285

Ala Ile Gly Asn Glu Leu Leu Ala Trp Arg Glu Arg Asp Leu Leu Glu
    290                 295                 300

Lys Glu Gly Glu Glu Asp Gly Lys Thr Ile Trp Ala Met Arg Leu Lys
305                 310                 315                 320

Ala Thr Leu Asp Arg Ala Arg Arg Leu Thr Ala Glu Tyr Ser Asp Leu
                325                 330                 335

Leu Leu Gln Ile Phe Pro Pro Asn Val Glu Ile Leu Gly Lys Ala Leu
            340                 345                 350

Gly Ile Pro Glu Asn Ser Val Lys Thr Tyr Thr Glu Ala Glu Ile Arg

```
                355                 360                 365
Ala Gly Ile Ile Phe Gln Ile Ser Lys Leu Cys Thr Val Leu Leu Lys
370                 375                 380

Ala Val Arg Asn Ser Leu Gly Ser Glu Gly Trp Asp Val Val Pro
385                 390                 395                 400

Gly Ser Thr Ser Gly Thr Leu Val Gln Val Glu Ser Ile Val Pro Gly
                405                 410                 415

Ser Leu Pro Ala Thr Ser Gly Gly Pro Ile Ile Leu Leu Val Asn Lys
                420                 425                 430

Ala Asp Gly Asp Glu Glu Val Ser Ala Ala Asn Gly Asn Ile Ala Gly
                435                 440                 445

Val Met Leu Leu Gln Glu Leu Pro His Leu Ser His Leu Gly Val Arg
                450                 455                 460

Ala Arg Gln Glu Lys Ile Val Phe Val Thr Cys Asp Asp Asp Lys
465                 470                 475                 480

Val Ala Asp Ile Arg Arg Leu Val Gly Lys Phe Val Arg Leu Glu Ala
                485                 490                 495

Ser Pro Ser His Val Asn Leu Ile Leu Ser Thr Glu Gly Arg Ser Arg
                500                 505                 510

Thr Ser Lys Ser Ser Ala Thr Lys Thr Asp Lys Asn Ser Leu Ser
                515                 520                 525

Lys Lys Lys Thr Asp Lys Lys Ser Leu Ser Ile Asp Asp Glu Ser
530                 535                 540

Lys Pro Gly Ser Ser Ser Asn Ser Leu Leu Tyr Ser Ser Lys Asp
545                 550                 555                 560

Ile Pro Ser Gly Gly Ile Ile Ala Leu Ala Asp Ala Asp Val Pro Thr
                565                 570                 575

Ser Gly Ser Lys Ser Ala Ala Cys Gly Leu Leu Ala Ser Leu Ala Glu
                580                 585                 590

Ala Ser Ser Lys Val His Ser Glu His Gly Val Pro Ala Ser Phe Lys
                595                 600                 605

Val Pro Thr Gly Val Val Ile Pro Phe Gly Ser Met Glu Leu Ala Leu
610                 615                 620

Lys Gln Asn Asn Ser Glu Glu Lys Phe Ala Ser Leu Leu Glu Lys Leu
625                 630                 635                 640

Glu Thr Ala Arg Pro Glu Gly Gly Glu Leu Asp Asp Ile Cys Asp Gln
                645                 650                 655

Ile His Glu Val Met Lys Thr Leu Gln Val Pro Lys Glu Thr Ile Asn
                660                 665                 670

Ser Ile Ser Lys Ala Phe Leu Lys Asp Ala Arg Leu Ile Val Arg Ser
                675                 680                 685

Ser Ala Asn Val Glu Asp Leu Ala Gly Met Ser Ala Ala Gly Leu Tyr
                690                 695                 700

Glu Ser Ile Pro Asn Val Ser Pro Ser Asp Pro Leu Val Phe Ser Asp
705                 710                 715                 720

Ser Val Cys Gln Val Trp Ala Ser Leu Tyr Thr Arg Arg Ala Val Leu
                725                 730                 735

Ser Arg Arg Ala Ala Gly Val Ser Gln Arg Glu Ala Ser Met Ala Val
                740                 745                 750

Leu Val Gln Glu Met Leu Ser Pro Asp Leu Ser Phe Val Leu His Thr
                755                 760                 765

Val Ser Pro Ala Asp Pro Asp Ser Asn Leu Val Glu Ala Glu Ile Ala
770                 775                 780
```

```
Pro Gly Leu Gly Glu Thr Leu Ala Ser Gly Thr Arg Gly Thr Pro Trp
785                 790                 795                 800

Arg Leu Ala Ser Gly Lys Leu Asp Gly Ile Val Gln Thr Leu Ala Phe
            805                 810                 815

Ala Asn Phe Ser Glu Glu Leu Leu Val Ser Gly Thr Gly Pro Ala Asp
            820                 825                 830

Gly Lys Tyr Val Arg Leu Thr Val Asp Tyr Ser Lys Lys Arg Leu Thr
            835                 840                 845

Val Asp Ser Val Phe Arg Gln Gln Leu Gly Gln Arg Leu Gly Ser Val
        850                 855                 860

Gly Phe Phe Leu Glu Arg Asn Phe Gly Cys Ala Gln Asp Val Glu Gly
865                 870                 875                 880

Cys Leu Val Gly Glu Asp Val Tyr Ile Val Gln Ser Arg Pro Gln Pro
            885                 890                 895

Leu

<210> SEQ ID NO 57
<211> LENGTH: 2526
<212> TYPE: DNA
<213> ORGANISM: Artificial Sequence
<220> FEATURE:
<223> OTHER INFORMATION: Chimeric Protein

<400> SEQUENCE: 57
atgggacatc accatcatca tcacatggag cagaagctga tctcagagga ggacctgact      60
agtgctagca agttcaactt tgaagatggc accctgggtg gctttaccac cagcggtacc     120
aacgcgaccg gcgtggttgt gaacaccacc gagaaggcgt tcaaggtga acgtggcctg      180 aagtggaccg tgaccagcga gggtgaaggt accgcggagc tgaaactgga cggtggcacc     240
atcgttgtgc gggtaccac catgaccttt cgtatttgga ttccgagcgg tgcgccgatt      300
gcggcgattc agccgtacat tatgccgcac accccggatt ggagcgaagt tctgtggaac     360
agcacctgga agggttatac catggtgaaa accgacgatt ggaacgagat caccctgacc     420
ctgccggaag acgttgatcc gacctggccg cagcaaatgg gtatccaggt gcaaaccatt     480
gacgagggcg aattcaccat ctacgttgac gcgattgatt gggtgggcgt tcaaattaac     540
ccggttagcg tctgccgag cggtttccag gacctgctgc actttgtgct ggaccacgtt     600
gaggataaaa acgttgagac cctgctggaa cgtctgctgg aggcgcgtga ggaactgcgt     660
ccgctgctgc tgaagccgaa caaccgtctg aaagatctgc tgttcctgga catcgcgctg     720
gatagcaccg tgcgtaccgc ggttgaacgt ggttacgagg aactgaacaa cgcgaacccg     780
gagaagatca tgtattttat tagcctggtt ctggaaaaacc tggcgctgag cgtggacgat     840
aacgaggacc tggtttattg cctgaaaggc tggaaccagg cgctgagcat gagcaacggt     900
ggcgacaacc actgggcgct gttcgcgaag gcggtgctgg atcgtacccg tctggcgctg     960
gcgagcaaag cggaatggta tcaccacctg ctgcaaccga gcgcggagta tctgggtagc    1020
atcctgggcg tggaccagtg ggcgctgaac atttttaccg aggaaatcat tcgtgcgggt    1080
agcgcggcga gcctgagcag cctgctgaac cgtctggacc cggttctgcg taagaccgcg    1140
aacctgggta gctggcaaat cattagcccg gtggaagcgg ttggctacgt ggttgtggtt    1200
gacgagctgc tgagcgtgca gaacgagatc tatgaaaaac cgaccattct ggtggcgaaa    1260
agcgttaagg gcgaggaaga gatccccgac ggtgcggtgg cgctgattac cccggacatg    1320
ccggatgttc tgagccacgt gagcgttcgt gcgcgtaacg gcaaggtttg cttcgcgacc    1380
```

```
tgctttgacc cgaacatcct ggcggatctg caggcgaagg aaggccgtat tctgctgctg    1440
aaaccgaccc cgagcgatat catttacagc gaggtgaacg agatcgaact gcagagcagc    1500
agcaacctgg tggaggcgga aaccagcgcg accctgcgtc tggttaagaa acagttcggt    1560
ggctgctacg cgattagcgc ggacgaattt accagcgaga tggttggtgc gaagagccgt    1620
aacatcgcgt atctgaaagg caaggtgccg agcagcgttg cattccgac cagcgtggcg     1680 ctgccgttcg gtgtgtttga aaaggttctg agcgacgata tcaaccaggg cgttgcgaaa    1740
gagctgcaaa ttctgatgaa gaaactgagc gagggtgact cagcgcgct gggcgagatc     1800 cgtaccaccg tgctggatct gagcgcgccg gcgcaactgg ttaaagagct gaaagaaaag    1860 atgcaggta gcggtatgcc gtggccgggt gacgaaggtc cgaagcgttg ggagcaagcg     1920
tggatggcga tcaagaaagt gtgggcgagc aaatggaacg aacgtgcgta cttcagcacc    1980
cgtaaagtta agctggacca cgattatctg tgcatggcgg tgctggttca ggagatcatt    2040
aacgcggatt acgcgtttgt tatccacacc accaacccga gcagcggtga cgatagcgaa    2100
atttacgcgg aggtggttcg tggtctgggc gagaccctgg tgggtgcgta tccgggtcgt    2160
gcgctgagct tcatctgcaa gaaaaaggac ctgaacagcc gcaggttct gggttatccg     2220 agcaagccga tcggcctgtt cattaaacgt agcatcattt ttcgtagcga cagcaacggc    2280
gaggatctgg aaggctacgc gggtgcgggt ctgtatgaca cgtgccgat ggatgaagag     2340 gaaaaagtgg ttatcgacta cagcagcgat ccgctgatta ccgacggtaa ctttcgtcaa    2400
accatcctga gcaacattgc gcgtgcgggt cacgcgatcg aggaactgta tgcagcccg    2460 caggatattg agggcgtggt tcgtgatggt aaaatctatg tggttcagac ccgtccgcaa    2520
atgtaa                                                              2526

<210> SEQ ID NO 58
<211> LENGTH: 841
<212> TYPE: PRT
<213> ORGANISM: Artificial Sequence
<220> FEATURE:
<223> OTHER INFORMATION: Chimeric Protein

<400> SEQUENCE: 58

Met Gly His His His His His His Met Glu Gln Lys Leu Ile Ser Glu
1               5                   10                  15

Glu Asp Leu Thr Ser Ala Ser Lys Phe Asn Phe Glu Asp Gly Thr Leu
            20                  25                  30

Gly Gly Phe Thr Thr Ser Gly Thr Asn Ala Thr Gly Val Val Val Asn
        35                  40                  45

Thr Thr Glu Lys Ala Phe Lys Gly Glu Arg Gly Leu Lys Trp Thr Val
    50                  55                  60

Thr Ser Glu Gly Glu Gly Thr Ala Glu Leu Lys Leu Asp Gly Gly Thr
65                  70                  75                  80

Ile Val Val Pro Gly Thr Thr Met Thr Phe Arg Ile Trp Ile Pro Ser
                85                  90                  95

Gly Ala Pro Ile Ala Ala Ile Gln Pro Tyr Ile Met Pro His Thr Pro
            100                 105                 110

Asp Trp Ser Glu Val Leu Trp Asn Ser Thr Trp Lys Gly Tyr Thr Met
        115                 120                 125

Val Lys Thr Asp Asp Trp Asn Glu Ile Thr Leu Thr Leu Pro Glu Asp
    130                 135                 140

Val Asp Pro Thr Trp Pro Gln Gln Met Gly Ile Gln Val Gln Thr Ile
```

```
                145                 150                 155                 160
Asp Glu Gly Glu Phe Thr Ile Tyr Val Asp Ala Ile Asp Trp Val Gly
                    165                 170                 175

Val Gln Ile Asn Pro Val Ser Gly Leu Pro Ser Gly Phe Gln Asp Leu
                180                 185                 190

Leu His Phe Val Leu Asp His Val Glu Asp Lys Asn Val Glu Thr Leu
            195                 200                 205

Leu Glu Arg Leu Leu Glu Ala Arg Glu Glu Leu Arg Pro Leu Leu Leu
        210                 215                 220

Lys Pro Asn Asn Arg Leu Lys Asp Leu Leu Phe Leu Asp Ile Ala Leu
225                 230                 235                 240

Asp Ser Thr Val Arg Thr Ala Val Glu Arg Gly Tyr Glu Glu Leu Asn
                245                 250                 255

Asn Ala Asn Pro Glu Lys Ile Met Tyr Phe Ile Ser Leu Val Leu Glu
                260                 265                 270

Asn Leu Ala Leu Ser Val Asp Asp Asn Glu Asp Leu Val Tyr Cys Leu
            275                 280                 285

Lys Gly Trp Asn Gln Ala Leu Ser Met Ser Asn Gly Gly Asp Asn His
        290                 295                 300

Trp Ala Leu Phe Ala Lys Ala Val Leu Asp Arg Thr Arg Leu Ala Leu
305                 310                 315                 320

Ala Ser Lys Ala Glu Trp Tyr His His Leu Leu Gln Pro Ser Ala Glu
                325                 330                 335

Tyr Leu Gly Ser Ile Leu Gly Val Asp Gln Trp Ala Leu Asn Ile Phe
                340                 345                 350

Thr Glu Glu Ile Ile Arg Ala Gly Ser Ala Ala Ser Leu Ser Ser Leu
            355                 360                 365

Leu Asn Arg Leu Asp Pro Val Leu Arg Lys Thr Ala Asn Leu Gly Ser
        370                 375                 380

Trp Gln Ile Ile Ser Pro Val Glu Ala Gly Tyr Val Val Val
385                 390                 395                 400

Asp Glu Leu Leu Ser Val Gln Asn Glu Ile Tyr Glu Lys Pro Thr Ile
                405                 410                 415

Leu Val Ala Lys Ser Val Lys Gly Glu Glu Ile Pro Asp Gly Ala
                420                 425                 430

Val Ala Leu Ile Thr Pro Asp Met Pro Asp Val Leu Ser His Val Ser
            435                 440                 445

Val Arg Ala Arg Asn Gly Lys Val Cys Phe Ala Thr Cys Phe Asp Pro
        450                 455                 460

Asn Ile Leu Ala Asp Leu Gln Ala Lys Glu Gly Arg Ile Leu Leu Leu
465                 470                 475                 480

Lys Pro Thr Pro Ser Asp Ile Ile Tyr Ser Glu Val Asn Glu Ile Glu
                485                 490                 495

Leu Gln Ser Ser Ser Asn Leu Val Glu Ala Glu Thr Ser Ala Thr Leu
                500                 505                 510

Arg Leu Val Lys Lys Gln Phe Gly Gly Cys Tyr Ala Ile Ser Ala Asp
            515                 520                 525

Glu Phe Thr Ser Glu Met Val Gly Ala Lys Ser Arg Asn Ile Ala Tyr
        530                 535                 540

Leu Lys Gly Lys Val Pro Ser Ser Val Gly Ile Pro Thr Ser Val Ala
545                 550                 555                 560

Leu Pro Phe Gly Val Phe Glu Lys Val Leu Ser Asp Asp Ile Asn Gln
                565                 570                 575
```

-continued

```
Gly Val Ala Lys Glu Leu Gln Ile Leu Met Lys Lys Leu Ser Glu Gly
            580                 585                 590

Asp Phe Ser Ala Leu Gly Glu Ile Arg Thr Thr Val Leu Asp Leu Ser
            595                 600                 605

Ala Pro Ala Gln Leu Val Lys Glu Leu Lys Glu Lys Met Gln Gly Ser
            610                 615                 620

Gly Met Pro Trp Pro Gly Asp Glu Gly Pro Lys Arg Trp Glu Gln Ala
625                 630                 635                 640

Trp Met Ala Ile Lys Lys Val Trp Ala Ser Lys Trp Asn Glu Arg Ala
            645                 650                 655

Tyr Phe Ser Thr Arg Lys Val Lys Leu Asp His Asp Tyr Leu Cys Met
            660                 665                 670

Ala Val Leu Val Gln Glu Ile Ile Asn Ala Asp Tyr Ala Phe Val Ile
            675                 680                 685

His Thr Thr Asn Pro Ser Ser Gly Asp Asp Ser Glu Ile Tyr Ala Glu
            690                 695                 700

Val Val Arg Gly Leu Gly Glu Thr Leu Val Gly Ala Tyr Pro Gly Arg
705                 710                 715                 720

Ala Leu Ser Phe Ile Cys Lys Lys Lys Asp Leu Asn Ser Pro Gln Val
            725                 730                 735

Leu Gly Tyr Pro Ser Lys Pro Ile Gly Leu Phe Ile Lys Arg Ser Ile
            740                 745                 750

Ile Phe Arg Ser Asp Ser Asn Gly Glu Asp Leu Glu Gly Tyr Ala Gly
            755                 760                 765

Ala Gly Leu Tyr Asp Ser Val Pro Met Asp Glu Glu Glu Lys Val Val
            770                 775                 780

Ile Asp Tyr Ser Ser Asp Pro Leu Ile Thr Asp Gly Asn Phe Arg Gln
785                 790                 795                 800

Thr Ile Leu Ser Asn Ile Ala Arg Ala Gly His Ala Ile Glu Glu Leu
            805                 810                 815

Tyr Gly Ser Pro Gln Asp Ile Glu Gly Val Val Arg Asp Gly Lys Ile
            820                 825                 830

Tyr Val Val Gln Thr Arg Pro Gln Met
            835                 840
```

GLUCAN KINASES AND METHODS FOR PROCESSING STARCH USING THE SAME

RELATED APPLICATIONS

This application claims priority to U.S. Provisional Application Ser. No. 62/478,404, filed Mar. 29, 2017, which is incorporated herein by this reference.

SEQUENCE LISTING

The instant application contains a Sequence Listing which has been submitted in ASCII format via EFS-Web and is hereby incorporated by reference in its entirety. The ASCII copy of the Sequence Listing, which was created on Mar. 29, 2018, is named 13177N-1968US_ST25.txt and is 354 kilobytes in size.

TECHNICAL FIELD

The presently-disclosed subject matter relates to proteins such as kinases and methods of using the same to process starch. In particular, embodiments of the presently-disclosed subject matter relate to glucan dikinases as well as methods for processing starch utilizing a glucan dikinase and, optionally, a phosphatase and/or an amylase.

BACKGROUND

Starch is an important compound for many different purposes, including for food sources, beverages, the manufacture of plastics, energy sources such as biofuels, industrial feedstocks, and so forth. For instance, starch from the seeds of cereal crops and the tubers of potatoes and cassava accounts for 50-80% of daily caloric intake. In the United States, over 20% of corn starch is converted into ethanol for use as a renewable biofuel, and starch also plays a central role in the production of molecular hydrogen by some micro algae and in algal oil production. Microalgal oil production is increased by supplying starch to the microalgae so that they grow mixotrophically rather than autotrophically. Starch is also a cheap and renewable industrial feedstock for producing paper, textiles, adhesives, plastics, and pharmaceuticals.

Starch is comprised of amylose and amylopectin, which are both glucose polymers. Amylose, the minor component, is a linear molecule comprised of glucose moieties linked together by α-1,4-glycosidic bonds with very few branches. Amylopectin, the major component, is comprised of glucose linked together by α-1,4-glycosidic bonds with α-1,6-glycosidic branches occurring every 12-25 glucose moieties. The branches in amylopectin are arranged in clusters at regular intervals, resulting in a tree-like pattern. Within the clusters, adjacent glucose chains form double helices and the clusters organize into crystalline lamellae. The crystalline lamellae make amylopectin, and thus starch, water-insoluble. This insolubility renders the surface of starch inaccessible to most enzymes, including the amylases that can break it down for processing. The structures of amylopectin (1) and amylase (2) are shown below.

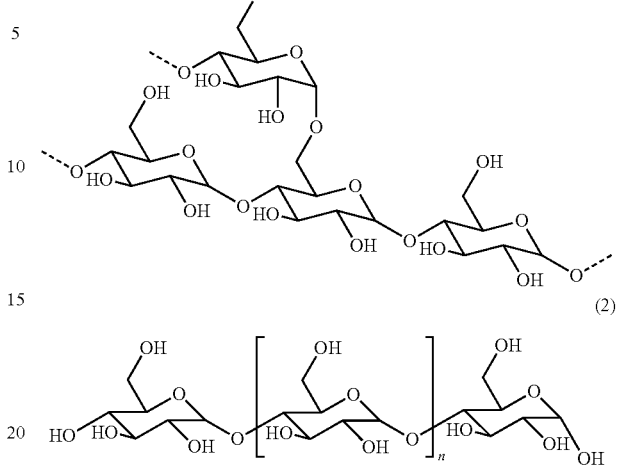

Therefore, to utilize starch for subsequent processing, starch-based feedstocks are generated by a three-phase approach that utilizes physical, chemical, and enzymatic modification (FIG. 1). The physical modification produces high energy costs due to both milling the material and cyclically modulating the temperature between 50° C. to over 100° C. to liquefy starch. In addition to physical modification, large amounts of acids and bases are utilized to increase enzymatic accessibility. Large quantities of these chemicals are costly to purchase and companies also incur the cost of disposing the hazardous waste. Finally, these processes require relatively large amounts of recombinant α-amylase, which cleave α-1,4-glycosidic linkages, to convert the complex sugar into fermentable glucose.

Over the last 25 years others have attempted to optimize α-amylase catalytic efficiency, thermostability, and pH tolerance to increase starch processing techniques. These efforts utilize a three-tiered approach of exploiting α-amylases' biological diversity, structure/function analysis, and directed evolution. Despite advances in increased catalytic efficiency as well as heat and pH tolerance, the amylases are still unable to degrade starch without mechanical and chemical assistance. Thus, generating starch-feedstocks using known techniques still results in high costs and environmental concerns related to feedstock chemical treatments.

Hence, there remains a need for compositions and methods for processing starch that are relatively less expensive, more efficient, and present fewer environmental concerns than known compositions and methods.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the presently disclosed subject matter includes a non-native glucan kinase polypeptide comprising an isolated polypeptide including a sequence selected from the group consisting of SEQ ID NO: 2, SEQ ID NO:22, fragments thereof, variants thereof, and combinations thereof. In one embodiment, the sequence is a fragment and/or variant selected from the group consisting of SEQ ID NO: 4, 6, 8, 10, 12, 14, 16, 18, 20, 24, 26, 28, 30, 32, 34, 36, 38, 40, 42, 44, 46, fragments thereof, variants thereof, and combinations thereof. In another embodiment, the fragment of the polypeptide includes about 1 to about 816 amino acid residues deleted from the N-terminus. In a further embodiment, the fragment of the polypeptide further includes one or more amino acid mutations.

In some embodiments, the polypeptide is a thermophile. In some embodiments, the polypeptide is stable at least at a 3.0 pH to about 8.0 pH. In some embodiments, the polypeptide is stable at least at a temperature of about 10° C. to about 75° C. In one embodiment, the polypeptide is stable at least at a temperature of about 37° C. to about 75° C. In some embodiments, the polypeptide includes constituents that share at least 75% homology with a wild type polypeptide.

In some embodiments, the polypeptide includes a non-native Cm-GWD polypeptide having the sequence of SEQ ID NO: 2, a fragment thereof, a variant thereof, or a combination thereof. In some embodiments, the polypeptide includes a non-native St-GWD polypeptide having the sequence of SEQ ID NO: 22, a fragment thereof, a variant thereof, or a combination thereof.

Also provided herein, in some embodiments is an isolated polynucleotide, comprising a nucleotide sequence selected from the group consisting of SEQ ID NO: 1, SEQ ID NO: 21, a fragment thereof, a variant thereof, and a combination thereof. In one embodiment, the sequence is a fragment and/or variant selected from the group consisting of SEQ ID NO: 3, 5, 7, 9, 11, 13, 15, 17, 19, 23, 35, 37, 29, 31, 33, 35, 37, 39, 41, 43, 45, a fragment thereof, a variant thereof, and a combination thereof. In another embodiment, the fragment of the isolated polynucleotide further includes one or more mutations.

Further provided herein, in some embodiments, is a method for processing starch, comprising providing a glucan dikinase; exposing a starch to the glucan dikinase; and collecting the starch that has been exposed to the glucan dikinase. In one embodiment, the glucan dikinase includes a sequence selected from the group consisting of SEQ ID NO: 2, 4, 6, 8, 10, 12, 14, 16, 18, 20, 24, 26, 28, 30, 32, 34, 36, 38, 40, 42, 44, 46, a fragment thereof, a variant thereof, and combinations thereof. In some embodiments, the method further comprises, before the collecting step, exposing the starch to a dikinase, an amylase, or both.

In one embodiment, the step of providing the glucan dikinase includes providing an organism expressing the glucan dikinase. In another embodiment, the step of exposing the starch to the glucan dikinase occurs in the organism. In a further embodiment, the organism is a plant.

BRIEF DESCRIPTION OF THE SEQUENCE LISTING

The following is a brief description of the Sequence Listing that is attached hereto and is hereby incorporated by reference in its entirety.

SEQ ID NO: 1 is a nucleic acid sequence encoding a full length *Cyanidioschyzon merolae* glucan, water dikinase (Cm-GWD) polypeptide of SEQ ID NO: 2;

SEQ ID NO: 2 is an amino acid sequence encoding a full length *Cyanidioschyzon merolae* GWD polypeptide;

SEQ ID NO: 3 is a nucleic acid sequence encoding a *Cyanidioschyzon merolae* 114C GWD polypeptide fragment of SEQ ID NO: 4;

SEQ ID NO: 4 is an amino acid sequence encoding a *Cyanidioschyzon merolae* 114C GWD polypeptide fragment;

SEQ ID NO: 5 is a nucleic acid sequence encoding a *Cyanidioschyzon merolae* 127C GWD polypeptide fragment of SEQ ID NO: 6;

SEQ ID NO: 6 is an amino acid sequence encoding a *Cyanidioschyzon merolae* 127C GWD polypeptide fragment;

SEQ ID NO: 7 is a nucleic acid sequence encoding a *Cyanidioschyzon merolae* 133C GWD polypeptide fragment of SEQ ID NO: 8;

SEQ ID NO: 8 is an amino acid sequence encoding a *Cyanidioschyzon merolae* 133C GWD polypeptide fragment;

SEQ ID NO: 9 is a nucleic acid sequence encoding a *Cyanidioschyzon merolae* 139C GWD polypeptide fragment of SEQ ID NO: 10;

SEQ ID NO: 10 is an amino acid sequence encoding a *Cyanidioschyzon merolae* 139C GWD polypeptide fragment;

SEQ ID NO: 11 is a nucleic acid sequence encoding a *Cyanidioschyzon merolae* 345C GWD polypeptide fragment of SEQ ID NO: 12;

SEQ ID NO: 12 is an amino acid sequence encoding a *Cyanidioschyzon merolae* 345C GWD polypeptide fragment;

SEQ ID NO: 13 is a nucleic acid sequence encoding a *Cyanidioschyzon merolae* 511C GWD polypeptide fragment of SEQ ID NO: 14;

SEQ ID NO: 14 is an amino acid sequence encoding a *Cyanidioschyzon merolae* 511C GWD polypeptide fragment;

SEQ ID NO: 15 is a nucleic acid sequence encoding a *Cyanidioschyzon merolae* 816C GWD polypeptide fragment of SEQ ID NO: 16;

SEQ ID NO: 16 is an amino acid sequence encoding a *Cyanidioschyzon merolae* 816C GWD polypeptide fragment;

SEQ ID NO: 17 is a nucleic acid sequence encoding a *Cyanidioschyzon merolae* 819C GWD polypeptide fragment of SEQ ID NO: 18;

SEQ ID NO: 18 is an amino acid sequence encoding a *Cyanidioschyzon merolae* 819C GWD polypeptide fragment;

SEQ ID NO: 19 is a nucleic acid sequence encoding a *Cyanidioschyzon merolae* H1162A 511C GWD polypeptide variant of SEQ ID NO: 8; and SEQ ID NO: 20 is an amino acid sequence encoding a *Cyanidioschyzon merolae* H1162A 511C GWD polypeptide variant.

SEQ ID NO: 21 is a nucleic acid sequence encoding a full length *Solanum tuberosum* glucan, water dikinase (St-GWD) polypeptide of SEQ ID NO:22.

SEQ ID NO: 22 is an amino acid sequence encoding a full length *Solanum tuberosum* GWD polypeptide.

SEQ ID NO: 23 is a nucleic acid sequence encoding a *Solanum tuberosum* (-cTP) GWD polypeptide variant.

SEQ ID NO: 24 is an amino acid sequence encoding a *Solanum tuberosum* (-cTP) GWD polypeptide variant.

SEQ ID NO: 25 is a nucleic acid sequence encoding a *Solanum tuberosum* GDV109 GWD polypeptide variant.

SEQ ID NO: 26 is an amino acid sequence encoding a *Solanum tuberosum* GDV109 GWD polypeptide variant.

SEQ ID NO: 27 is a nucleic acid sequence encoding a *Solanum tuberosum* KVL394 GWD polypeptide variant.

SEQ ID NO: 28 is an amino acid sequence encoding a *Solanum tuberosum* KVL394 GWD polypeptide variant.

SEQ ID NO: 29 is a nucleic acid sequence encoding a *Solanum tuberosum* TKV444 GWD polypeptide variant.

SEQ ID NO: 30 is an amino acid sequence encoding a *Solanum tuberosum* TKV444 GWD polypeptide variant.

SEQ ID NO: 31 is a nucleic acid sequence encoding a *Solanum tuberosum* LIW614 GWD polypeptide variant.

SEQ ID NO: 32 is an amino acid sequence encoding a *Solanum tuberosum* LIW614 GWD polypeptide variant.

SEQ ID NO: 33 is a nucleic acid sequence encoding a *Solanum tuberosum* MVG797 GWD polypeptide variant.

SEQ ID NO: 34 is an amino acid sequence encoding a *Solanum tuberosum* MVG797 GWD polypeptide variant.

SEQ ID NO: 35 is a nucleic acid sequence encoding a *Solanum tuberosum* QSS1121 GWD polypeptide variant.

SEQ ID NO: 36 is an amino acid sequence encoding a *Solanum tuberosum* QSS1121 GWD polypeptide variant.

SEQ ID NO: 37 is a nucleic acid sequence encoding a *Solanum tuberosum* MVG797 to LQS1120 GWD polypeptide variant.

SEQ ID NO: 38 is an amino acid sequence encoding a *Solanum tuberosum* MVG797 to LQS1120 GWD polypeptide variant.

SEQ ID NO: 39 is a nucleic acid sequence encoding a *Solanum tuberosum* GDV109-SGK443 GWD polypeptide variant.

SEQ ID NO: 40 is an amino acid sequence encoding a *Solanum tuberosum* GDV109-SGK443 GWD polypeptide variant.

SEQ ID NO: 41 is a nucleic acid sequence encoding a *Solanum tuberosum* TKV 444-EGF 796 GWD polypeptide variant.

SEQ ID NO: 42 is an amino acid sequence encoding a *Solanum tuberosum* TKV 444-EGF 796 GWD polypeptide variant.

SEQ ID NO: 43 is a nucleic acid sequence encoding a *Solanum tuberosum* GDV109-IEL1120 GWD polypeptide variant.

SEQ ID NO: 44 is an amino acid sequence encoding a *Solanum tuberosum* GDV109-IEL1120 GWD polypeptide variant.

SEQ ID NO: 45 is a nucleic acid sequence encoding a *Solanum tuberosum* TKV444-IEL 1120 GWD polypeptide variant.

SEQ ID NO: 46 is an amino acid sequence encoding a *Solanum tuberosum* TKV444-IEL 1120 GWD polypeptide variant.

SEQ ID NO: 47 is a nucleic acid sequence encoding a HisMYC-NcCBM20-AtPWDDKD chimeric protein.

SEQ ID NO: 48 is an amino acid sequence encoding a HisMYC-NcCBM20-AtPWDDKD chimeric protein.

SEQ ID NO: 49 is a nucleic acid sequence encoding a HisMYC-NcCBM20-StGWDDKD chimeric protein.

SEQ ID NO: 50 is an amino acid sequence encoding a HisMYC-NcCBM20-StGWDDKD chimeric protein.

SEQ ID NO: 51 is a nucleic acid sequence encoding a HisMYC-CtCBM30-AtPWDDKD chimeric protein.

SEQ ID NO: 52 is an amino acid sequence encoding a HisMYC-CtCBM30-AtPWDDKD chimeric protein.

SEQ ID NO: 53 is a nucleic acid sequence encoding a HisMYC-CtCBM30-StGWDDKD chimeric protein.

SEQ ID NO: 54 is an amino acid sequence encoding a HisMYC-CtCBM30-StGWDDKD chimeric protein.

SEQ ID NO: 55 is a nucleic acid sequence encoding a HisMYC-CtCBM44-AtPWDDKD chimeric protein.

SEQ ID NO: 56 is an amino acid sequence encoding a HisMYC-CtCBM44-AtPWDDKD chimeric protein.

SEQ ID NO: 57 is a nucleic acid sequence encoding a HisMYC-CtCBM44-StGWDDKD chimeric protein.

SEQ ID NO: 58 is an amino acid sequence encoding a HisMYC-CtCBM44-StGWDDKD chimeric protein.

DETAILED DESCRIPTION OF EXEMPLARY EMBODIMENTS

Figure 1:
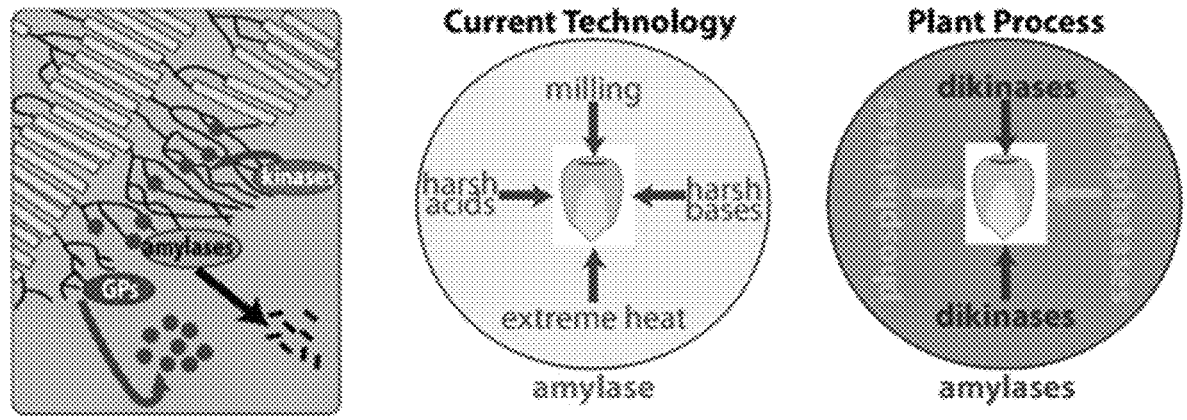
FIG. 1 includes a schematic showing a conventional method for processing starch compared to a plant-based starch processing method.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The present invention relates to novel, unique enzymes (i.e., polypeptides) for processing starch. Processing starch can include physically modifying the structure of a starch, and in certain instances includes degrading the starch. The polypeptides disclosed herein can also alter the biophysical properties of starch and/or total biomass starch production. For example, some embodiments of the present polypeptides can increase total biomass starch production and/or degrade starch in vitro, in planta, or both.

As used herein, the term "starch" is given its ordinary meaning in the art. In this regard, starches are heterogeneous, and their physicochemical properties, composition with respect to amylose versus amylopectin, amount of phosphorylation, and molecular structure all can vary greatly depending on the source of the starch. These properties can also affect starch gelatinization and viscosity, and thus impact starch processing. Exemplary starch sources include, but are not limited to, *Arabidopsis*, potato, corn, cassava, rice, wheat, and the like.

As used herein, the terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

In some embodiments, the presently-disclosed polypeptides include kinases. The term "kinase" is used herein to refer to any polypeptide of the kinase family, including dikinases and/or thermophilic polypeptides. In some embodiments, the kinases include glucan dikinases and/or thermophilic kinases. For example, in one embodiment, the kinases include thermophilic dikinases. In another embodiment, the polypeptide is a kinase polypeptide, or a fragment and/or variant thereof. Exemplary kinases can include about 85%, about 90%, or about 95% similarity with other kinases at the amino acid level.

In starch metabolism, glucan dikinases phosphorylate the outer glucose residues of starch, thereby rendering the granule surface accessible. In some instances, the phosphorylation and solubilization of the outer surface of starch permits the degradation of surface glucans by amylases. Additionally, glucan phosphates may remove phosphate groups during starch metabolism to permit processive glucan degradation. In this regard, plants contain two dikinases that phosphorylate starch glucan, water dikinase (GWD) and phosphoglucan, water dikinase (PWD). GWD and PWD are conserved from land plants to single-cell green algae, and the glucan dikinases contain a chloroplast targeting peptide (cTP), >1 carbohydrate binding module (CBM), and a pyruvate phosphate dikinase (PPDK) domain. In plant starch metabolism, GWD phosphorylates the oxygen at the C6 position of glucose and this triggers C3 phosphorylation by PWD. These events disrupt glucose chain helices, allow β-amylases (BAMs) and isoamylases (ISA) access to starch, and release maltose, glucose, and oligosaccharides. The glucan phosphatase activity of Starch EXcess4 (SEX4) and Like Sex Four2 (LSF2) then remove residual phosphate, allowing progressive starch degradation. LSF2 dephosphorylates the C3 position and SEX4 prefers the C6 position.

In some embodiments, the polypeptide includes a protozoan kinases, or a fragment and/or variant thereof. The kinases can be based on kinases obtained from protozoa including, but not limited to, Tetrahymena thermophile, *Eimeria tenella, Toxoplasma gondii, Paramecium tetraurelia, Neospora caninum*, and *Cyanidioschyzon merolae*. Exemplary protozoan kinase orthologs may include about 20% or more, about 25% or more, about 30% or more, or about 35% or more similarity with other kinases at the amino acid level.

In some embodiments, the polypeptide is a thermophile. The term "thermophile" herein refers to characteristic of operating normally (i.e., is stable) at least at temperatures above about 40° C. For example, a "thermophilic polypeptide," "thermophile," or and the like refer to a polypeptide that can function at least at temperatures above about 40° C., and a "thermophilic organism" is an organism that can function at least at temperatures above about 40° C. In some embodiments, the thermophile can operate at temperatures between about 37° C. and about 85° C., between about 40° C. and about 85° C., between about 37° C. to about 75° C., between about 40° C. to about 75° C., or any combination, sub-combination, range, or sub-range thereof. Some thermophiles can also be stable at relatively lower temperatures. For instance, some exemplary Cm-GWD polypeptides are stable at temperatures of about 10° C. to about 75° C. Additionally or alternatively, in some embodiments, the polypeptide is stable at non-neutral pH. In one embodiment, the polypeptide is stable at about 3.0 pH to about 8.0 pH. In specific embodiments, the polypeptide is stable at about 3.0 pH, about 4.0 pH, about 5.0 pH, about 6.0 pH, about 7.0 pH, or about 8.0 pH.

For example, certain species, such as single-cell algae *Cyanidioschyzon merolae* (*C. merolae*), include thermophilic polypeptides (thermophile) that can process and degrade native starch under harsh temperatures and extreme pH conditions. *C. merolae* lives in acidic environments at temperatures of about 50 to about 75° C., living in and around thermal vents. The present inventors have found that *C. merolae* includes GWD (hereinafter "Cm-GWD") polypeptides that can enhance starch degradation by amylases and allow amylases to release more glucose. A full length native wild-type protein sequence for Cm-GWD is included herein (SEQ ID NO: 2). Embodiments of the presently-disclosed polypeptides include isolated and/or non-naturally occurring fragments and/or variants of wild-type Cm-GWD. Similarly, *S. tuberosum* includes GWD (hereinafter "St-GWD") polypeptides that can enhance starch degradation by amylases and allow amylases to release more glucose. A full length native wild-type protein sequence for St-GWD is included herein (SEQ ID NO: 22). Embodiments of the presently-disclosed polypeptides include isolated and/or non-naturally occurring fragments and/or variants of wild-type St-GWD.

In some embodiments the polypeptide is a fragment of the polypeptide including the sequence of SEQ ID NO: 2 or SEQ ID NO: 22. The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus, carboxy-terminus of the reference polypeptide, or alternatively both. A fragment can also be a "functional fragment," in which case the fragment retains some or all of the activity of the reference polypeptide as described herein.

In some embodiments the polypeptide includes the sequence of SEQ ID NO: 2 or SEQ ID NO: 22 and may include about 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, or 1570 amino acid residues either alone or fused to functional domains from other carbohydrate-binding domains. In specific embodiments the polypeptide fragments include about 1 to about 819 amino acid residues deleted. In some embodiments the amino acid residues are deleted from the N-terminus of the polypeptide, the C-terminus of the polypeptide, a point between the N-terminus and the C-terminus of the polypeptide, or a combination thereof. In some embodiments of polypeptide fragments amino acid residues are deleted from the N-terminus immediately following the start methionine (M) amino acid.

As described herein, the presently disclosed subject matter also include variants of the presently-disclosed polypeptides. The term "variant" refers to an amino acid sequence that is different from the reference polypeptide by one or more amino acids, e.g., one or more amino acid substitutions. For example, a glucan dikinase polypeptide variant differs from wild-type glucan dikinase by one or more amino acid substitutions, i.e., mutations. In this regard, polypeptide variants comprising combinations of two or more mutations can respectively be referred to as double mutants, triple mutants, and so forth. It will be recognized that certain mutations can result in a notable change in function of a polypeptide, while other mutations will result in little to no notable change in function of the polypeptide.

In some embodiment the present polypeptides include constituents that share at least 75% homology with a wild type polypeptide. In some embodiments the polypeptides share at least 85% homology with the wild type polypeptide. In some embodiments the polypeptides share at least 90% homology with the wild type polypeptide. In some embodiments the polypeptides share at least 95% homology with the wild type polypeptide. The full length wild type polypeptide can include the non-native Cm-GWD polypeptide having the sequence of SEQ ID NO: 2. The full length wild type polypeptide can include the non-native St-GWD polypeptide have the sequence of SEQ ID NO: 22.

"Percent identity," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). BLAST nucleotide searches are performed with the NBLAST program, score+100, wordlength=12, to obtain nucleotide sequences homologous to a nucleic acid molecule of the invention. BLAST protein searches are performed with the)(BLAST program, score=50, word length=3, to obtain amino acid sequences homologous to a reference polypeptide (e.g., SEQ ID NO: X). To obtain gapped alignments for comparison purposes, Gapped BLAST is utilized as described in Altschul, et al. (Nucleic Acids Res. 25: 3389-3402, 1997). When utilizing BLAST and Gapped BLAST programs, the default parameters of the respective programs (e.g., XBLAST and NBLAST) are used. See http://www.ncbi.nlm.nik.gov, and reference is made to the most recent version of the programs that are available as of Jul. 19, 2012.

In one embodiment, the polypeptide comprises the sequence of SEQ ID NO: 4. In another embodiment, the polypeptide comprises a fragment, a variant, or both a fragment and variant of SEQ ID NO: 4. In one embodiment, the polypeptide comprises the sequence of SEQ ID NO: 6. In another embodiment, the polypeptide comprises a fragment, a variant, or both a fragment and variant of SEQ ID NO: 6. In one embodiment, the polypeptide comprises the sequence of SEQ ID NO: 8. In another embodiment, the polypeptide comprises a fragment, a variant, or both a fragment and variant of SEQ ID NO: 8. In one embodiment, the polypeptide comprises the sequence of SEQ ID NO: 10. In another embodiment, the polypeptide comprises a fragment, a variant, or both a fragment and variant of SEQ ID NO: 10. In one embodiment, the polypeptide comprises the sequence of SEQ ID NO: 12. In another embodiment, the polypeptide comprises a fragment, a variant, or both a fragment and variant of SEQ ID NO: 12. In one embodiment, the polypeptide comprises the sequence of SEQ ID NO: 14. In another embodiment, the polypeptide comprises a fragment, a variant, or both a fragment and variant of SEQ ID NO: 14. In one embodiment, the polypeptide comprises the sequence of SEQ ID NO: 16. In another embodiment, the polypeptide comprises a fragment, a variant, or both a fragment and variant of SEQ ID NO: 16. In one embodiment, the polypeptide comprises the sequence of SEQ ID NO: 18. In another embodiment, the polypeptide comprises a fragment, a variant, or both a fragment and variant of SEQ ID NO: 18. In one embodiment, the polypeptide comprises the sequence of SEQ ID NO: 20. In another embodiment, the polypeptide comprises a fragment, a variant, or both a fragment and variant of SEQ ID NO: 20.

In one embodiment, the polypeptide comprises the sequence of SEQ ID NO: 24. In another embodiment, the polypeptide comprises a fragment, a variant, or both a fragment and variant of SEQ ID NO: 24. In one embodiment, the polypeptide comprises the sequence of SEQ ID NO: 26. In another embodiment, the polypeptide comprises a fragment, a variant, or both a fragment and variant of SEQ ID NO: 26. In one embodiment, the polypeptide comprises the sequence of SEQ ID NO: 28. In another embodiment, the polypeptide comprises a fragment, a variant, or both a fragment and variant of SEQ ID NO: 28. In one embodiment, the polypeptide comprises the sequence of SEQ ID NO: 30. In another embodiment, the polypeptide comprises a fragment, a variant, or both a fragment and variant of SEQ ID NO: 30. In one embodiment, the polypeptide comprises the sequence of SEQ ID NO: 32. In another embodiment, the polypeptide comprises a fragment, a variant, or both a fragment and variant of SEQ ID NO: 32. In one embodiment, the polypeptide comprises the sequence of SEQ ID NO: 34. In another embodiment, the polypeptide comprises a fragment, a variant, or both a fragment and variant of SEQ ID NO: 34. In one embodiment, the polypeptide comprises the sequence of SEQ ID NO: 36. In another embodiment, the polypeptide comprises a fragment, a variant, or both a fragment and variant of SEQ ID NO: 36. In one embodiment, the polypeptide comprises the sequence of SEQ ID NO: 38. In another embodiment, the polypeptide comprises a fragment, a variant, or both a fragment and variant of SEQ ID NO: 38. In one embodiment, the polypeptide comprises the sequence of SEQ ID NO: 40. In another embodiment, the polypeptide comprises a fragment, a variant, or both a fragment and variant of SEQ ID NO: 40. In one embodiment, the polypeptide comprises the sequence of SEQ ID NO: 42. In another embodiment, the polypeptide comprises a fragment, a variant, or both a fragment and variant of SEQ ID NO: 42. In one embodiment, the polypeptide comprises the sequence of SEQ ID NO: 44. In another embodiment, the polypeptide comprises a fragment, a variant, or both a fragment and variant of SEQ ID NO: 44. In one embodiment, the polypeptide comprises the sequence of SEQ ID NO: 46. In another embodiment, the polypeptide comprises a fragment, a variant, or both a fragment and variant of SEQ ID NO: 46.

The presently-disclosed subject matter also includes isolated polynucleotides that encode any of the presently-disclosed polypeptides. The terms "nucleotide," "polynucleotide," "nucleic acid," and "nucleic acid sequence" refer to deoxyribonucleotides or ribonucleotides and polymers thereof in either single or double stranded form. Unless specifically limited, the term encompasses nucleic acids containing known analogues of natural nucleotides that have similar binding properties as the reference nucleic acid and are metabolized in a manner similar to naturally occurring nucleotides. The terms also include compounds only comprising the coding regions, or exons, of a particular DNA sequence. The terms are therefore inclusive of cDNA molecules.

The term "isolated", when used in the context of an isolated polynucleotide or an isolated polypeptide, is a polynucleotide or polypeptide that, by the hand of man, exists apart from its native environment and is therefore not a product of nature. An isolated polynucleotide or polypeptide can exist in a purified form or can exist in a non-native environment such as, for example, in a transgenic host cell. Unless otherwise indicated, all polypeptides and polynucleotides described herein include isolated forms thereof even where not explicitly recited. Thus, unless stated otherwise, all the polypeptide and polynucleotide described herein can be modified by the term isolated.

In some embodiments, the polynucleotides encode a thermophilic dikinase and/or a Cm-GWD polypeptide. In one embodiment, the polynucleotide includes the sequence of SEQ ID NO: 1, and the polynucleotide encodes the polypeptide including the sequence of SEQ ID NO: 2. In another embodiment, the polynucleotide encodes a fragment and/or a variant of the polypeptide including the sequence of SEQ ID NO: 2 (e.g., SEQ ID NO: 3, 5, 7, 9, 11, 13, 15, 17, or 19). For example, in one embodiment, the polynucleotide includes the nucleotide sequence of SEQ ID NO: 3. In one embodiment, the polynucleotide includes the nucleotide sequence of SEQ ID NO: 5. In one embodiment, the polynucleotide includes the nucleotide sequence of SEQ ID NO: 7. In one embodiment, the polynucleotide includes the nucleotide sequence of SEQ ID NO: 9. In one embodiment, the polynucleotide includes the nucleotide sequence of SEQ ID NO: 11. In one embodiment, the polynucleotide includes the nucleotide sequence of SEQ ID NO: 13. In one embodiment, the polynucleotide includes the nucleotide sequence of SEQ ID NO: 15. In one embodiment, the polynucleotide includes the nucleotide sequence of SEQ ID NO: 17. In one embodiment, the polynucleotide includes the nucleotide sequence of SEQ ID NO: 19.

In some embodiments, the polynucleotides encode a thermophilic dikinase and/or a St-GWD polypeptide. In one embodiment, the polynucleotide includes the sequence of SEQ ID NO: 21, and the polynucleotide encodes the polypeptide including the sequence of SEQ ID NO: 22. In another embodiment, the polynucleotide encodes a fragment and/or a variant of the polypeptide including the sequence of SEQ ID NO: 22 (e.g., SEQ ID NO: 23, 25, 27, 29, 31, 33, 35, 37, 39, 41, 43, or 45). For example, in one embodiment, the polynucleotide includes the nucleotide sequence of SEQ ID NO: 23. In one embodiment, the polynucleotide includes the nucleotide sequence of SEQ ID NO: 25. In one embodiment, the polynucleotide includes the nucleotide sequence of SEQ ID NO: 27. In one embodiment, the polynucleotide includes the nucleotide sequence of SEQ ID NO: 29. In one embodiment, the polynucleotide includes the nucleotide sequence of SEQ ID NO: 31. In one embodiment, the polynucleotide includes the nucleotide sequence of SEQ ID NO: 33. In one embodiment, the polynucleotide includes the nucleotide sequence of SEQ ID NO: 35. In one embodiment, the polynucleotide includes the nucleotide sequence of SEQ ID NO: 37. In one embodiment, the polynucleotide includes the nucleotide sequence of SEQ ID NO: 39. In one embodiment, the polynucleotide includes the nucleotide sequence of SEQ ID NO: 41. In one embodiment, the polynucleotide includes the nucleotide sequence of SEQ ID NO: 43. In one embodiment, the polynucleotide includes the nucleotide sequence of SEQ ID NO: 45.

As before, the term "polynucleotide fragment" or the like can refer to a polynucleotide in which nucleic acids are deleted as compared to the reference polynucleotide itself, but where the remaining nucleic acid sequence is usually identical to the corresponding positions in the reference polynucleotide. Such deletions can occur at any location of the sequence. In some embodiments, the polynucleotide includes a fragment of the isolated polynucleotide having the sequence of SEQ ID NO: 1 or SEQ ID NO: 21.

The term "variant" in reference to a polynucleotide can refer to a polynucleotide that is different from the reference polynucleotide by one or more nucleic acids. In this regard, some polynucleotide variants have been codon optimized relative to a reference polynucleotide, and the polynucleotide variant can produce polypeptide more effectively in certain organisms relative to the reference polynucleotide.

Unless otherwise indicated, a particular nucleic acid sequence also implicitly encompasses conservatively modified versions thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed base and/or deoxyinosine residues (Batzer et al. (1991) Nucleic Acid Res 19:5081; Ohtsuka et al. (1985) J Biol Chem 260:2605 2608; Rossolini et al. (1994) Mol Cell Probes 8:91 98). Thus, the term polynucleotide includes both deoxyribonucleic acid (DNA) and ribonucleic acid, and therefore the term polynucleotide specifically includes complementary DNA as used herein.

The presently-disclosed subject matter further includes a composition comprising starch, wherein the starch is from a plant expressing one of the polypeptides described herein. In some embodiments, the polypeptide includes a kinase polypeptide. In some embodiments, the polypeptides includes a thermophilic kinase and/or Cm-GWD polypeptide. As discussed herein, organisms expressing the present polypeptides can produce starch with altered biophysical properties, which can be beneficial for manufacturing processes in various industries, including food, beverage, confectionary, plastic, paper, building, energy, textile, agriculture, and pharmaceutical industries.

The presently-disclosed subject matter further includes methods for processing starch, wherein processing can include degrading starch to smaller polysaccharides and/or monosaccharides. In some embodiments, the methods for processing starch comprise providing a starch, exposing the starch to a kinase, and collecting the starch that has been exposed to the kinase. In some embodiments, the present polypeptides can be used in a method for processing starch that does not require harsh acids and harsh bases. Thus, the present methods can be more cost-effective and have a smaller environmental impact relative to known methods.

The term "providing" as used herein to refer to delivering, obtaining, procuring, or the like a substance. For instance, a polypeptide, a starch, or both may be provided by any suitable method. In some embodiments, the polypeptide is provided in an isolated form that can be exposed directly to a starch. In other embodiments, an organism expresses the polypeptide, and the polypeptide is thereby provided by the organism. Likewise, starch may be provided by itself or may be provided within a plant.

In some embodiments, the exposing step occurs within a plant. That is, a plant can express a thermophilic kinase, and the thermophilic kinase can be exposed to starch within the plant. On the other hand, in industrial applications a thermophilic kinase can be provided in an isolated form, and can be exposed to a starch by mixing the two components in a container.

The term "collecting" is used herein to refer to any process or method where starch is used, obtained, cultivated, ingested, or the like. For example, in some embodiments, starch is collected by harvesting a plant that comprises starch and processing the plant in order to obtain starch or other sugars derived therefrom. In some embodiments, collecting refers to ingesting a plant that comprises a thermophilic kinase. In other embodiments, collecting refers to collecting starch that has been processed in a container with a thermophilic kinase.

The presently-described starch processing methods do not suffer from the inability of amylases to access starch's water insoluble surface. Amylases degrade starch to maltose and glucose, but despite industry's 25 years of optimizing amylase to work under extreme conditions, amylase cannot degrade its own starch. In order to solubilize starch and to make it accessible to amylase, milling, extreme heat and acids and bases are required. One recent improved method for processing starch is described in U.S. Pat. No. 9,410,133, which is incorporated herein by reference, and which describes non-thermophilic glucan phosphatase variants for starch dephosphorylation.

However, in order to overcome problems in the art, the present inventors discovered that use of the present polypeptides permit the starch to be processed without the milling and chemical treatments that are typically required. Thus, in some instances the present polypeptides make a starch accessible to amylases for processing. Additionally or alternatively, the present methods may utilize polypeptides that include a thermophilic kinase. In specific embodiments, the thermophilic kinase includes the sequence of SEQ ID NO: 2, or a fragment and/or variant thereof, or the sequence of SEQ ID NO: 22, or a fragment and/or variant thereof.

Some methods further comprise exposing the starch to a phosphatase, an amylase, or both before the collecting step. Some embodied methods comprise a three-step exposing step wherein the starch is sequentially exposed to, not necessarily in the following order, a kinase, a phosphatase, and an amylase, any one of which may be thermophilic and used in combination with the kinases. In some embodied methods, glucan dikinases phosphorylate the outer starch surface and solubilize the outer surface allowing amylases to bind and degrade starch, and glucan phosphatases release phosphate and reset the cycle so that amylase-directed degradation can continue past the phosphate. In contrast to existing methods, the methods disclosed herein facilitate processing of starches without harsh acids and bases. Additionally, the present polypeptides can increase amylase-directed degradation of starch. Accordingly, the present methods that use one or more different polypeptides are superior to prior know methods for processing starch.

The presently-disclosed subject matter also includes methods for making an isolated polypeptide. In some embodiments the method comprises providing a cell that includes at least one of the presently-described polynucleotides, culturing the cell under conditions that permit the cell to produce a polypeptide encoded by the polynucleotide, and collecting the polypeptide. The cell can naturally include the polynucleotide or the polynucleotide can be introduced to the cell by known methods. For instance, a vector can be utilized to introduce an embodiment of the present polynucleotides to the cell.

The cell is not particularly limited except that it must be capable of producing the polypeptide encoded by the polynucleotide. In some embodiments the polynucleotides can be sequence optimized for the production of a polypeptide in a particular cell, such as *E. coli* cells. The polypeptide produced by the cell can be collected by known means, thereby providing the isolated polypeptide.

The presently-disclosed subject matter is further illustrated by the following specific but non-limiting examples.

Some examples are prophetic. Some of the following examples may include compilations of data that are representative of data gathered at various times during the course of development and experimentation related to the presently-disclosed subject matter.

EXAMPLES

Example 1

This Example describes the discovery and characterization of certain glucan dikinases. More specifically, it was determined that glucan dikinases are conserved in photosynthetic organisms across kingdoms, and a particular glucan dikinase was found in red algae.

Glucan, water dikinase (GWD) and phosphoglucan, water dikinase (PWD) orthologs from higher plants are about 70% identical at the amino acid level. Using bioinformatic analysis, the genome of photosynthetic organisms across kingdoms for proteins homologous to *Arabidopsis* GWD (At-GWD) and At-PWD was scanned. A putative glucan dikinase from *Cyanidioschyzon merolae* that is about 25% identical to At-GWD was identified. The *C. merolae* GWD (Cm-GWD) shares a similar predicted architecture with plant dikinases possessing predicted N-terminal CBM domains and a C-terminal catalytic dikinase domain. The *C. merolae* putative dikinase is more similar to GWD than PWD (25% identity versus 15%) and it shares a CBM45 with GWD from higher plants while PWD contains a CBM20, leading us to putatively name the protein Cm-GWD. To test if Cm-GWD is a functional glucan dikinase, Cm-GWD was expressed with an N-terminal 6x-His tag from pET28 in *E. Coli*. The protein was soluble and was purified using Immoblized Metal Affinity Chromatography (IMAC) followed by Size Exclusion Chromotography (SEC).

Figure 2:
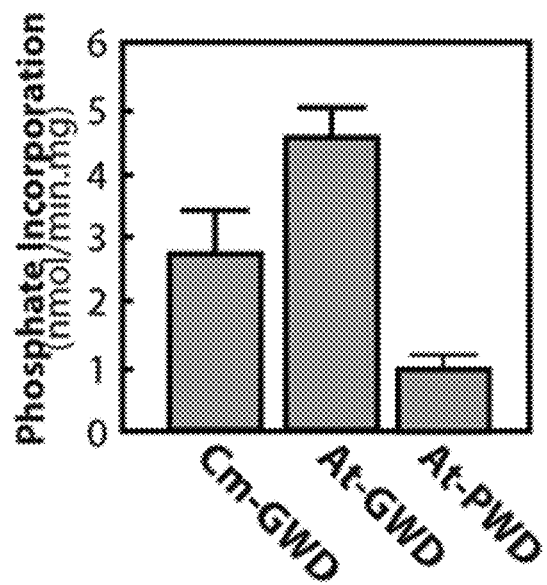
FIG. 2 includes a plot showing the ability of Cm-GWD, At-GWD, and At-PWD to add radiolabelled phosphate to starch.

The ability for the Cm-GWD to phosphorylate starch was analyzed. It was found that it possesses robust specific activity (FIG. 2). At-GWD and At-PWD were utilized for comparison, and it was found that the activity of Cm-GWD is between that of At-GWD and At-PWD. These data confirm that the protein identified, Cm-GWD, is an active glucan dikinase, demonstrating the conservation of the protein family across kingdoms.

Example 2

This Example characterizes how glucan dikinases utilize an integrated binding mode to specifically phosphorylate different positions. It has been shown that At-GWD phosphorylates the C6 and At-PWD phosphorylates the C3 position of glucose. Given the different specificity of plant dikinases, it appeared that there was little understanding of what dictates differences in C6 versus C3 specificity, the contribution of different dikinase domains is not fully understood, and it is unknown whether this specificity is conserved. This Example therefore focuses on determining the enzymatic activity and site preferences of the glucan dikinases across kingdoms, and further probes regions and/or amino acids to determine which dictate these preferences.

Figure 3:
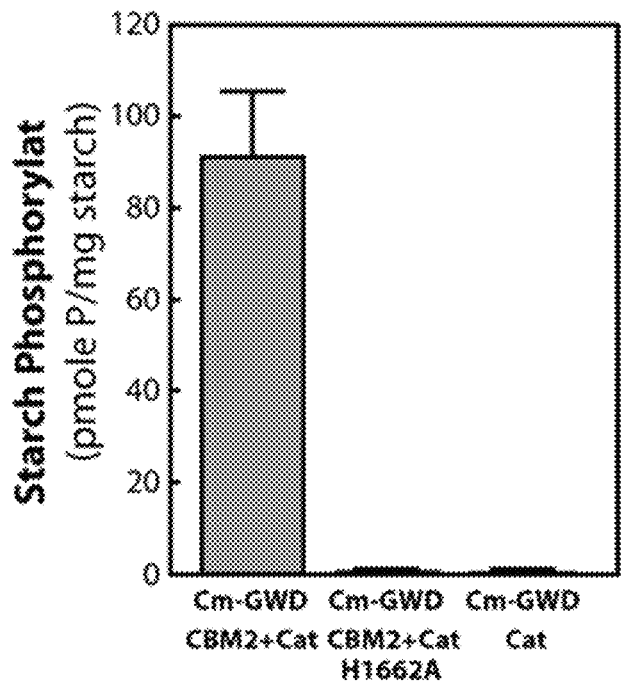
FIG. 3 includes a plot showing the activity of Cm-GWD with CBM2 and catalytic domain measured and compared to that with an active site mutant (H1162A) and the catalytic domain alone.

As an initial step, a truncated Cm-GWD construct (residues 511-1572) was produced, which encodes the second predicted CBM and catalytic dikinase domain, to determine its specific activity. The activity of this protein was measured, and it was found that it is an active glucan dikinase (FIG. 3). The observed activity critically depends on His1162, since Cm-GWD H1162A lacked activity. Cm-GWD H1162 is analogous to the catalytic domain histidine identified in plant GWD as critical for enzyme activity. A construct encoding the catalytic domain alone had no measurable activity. This result demonstrates that the CBM and catalytic domains cooperate together to produce an active specific glucan dikinase.

Figure 8:
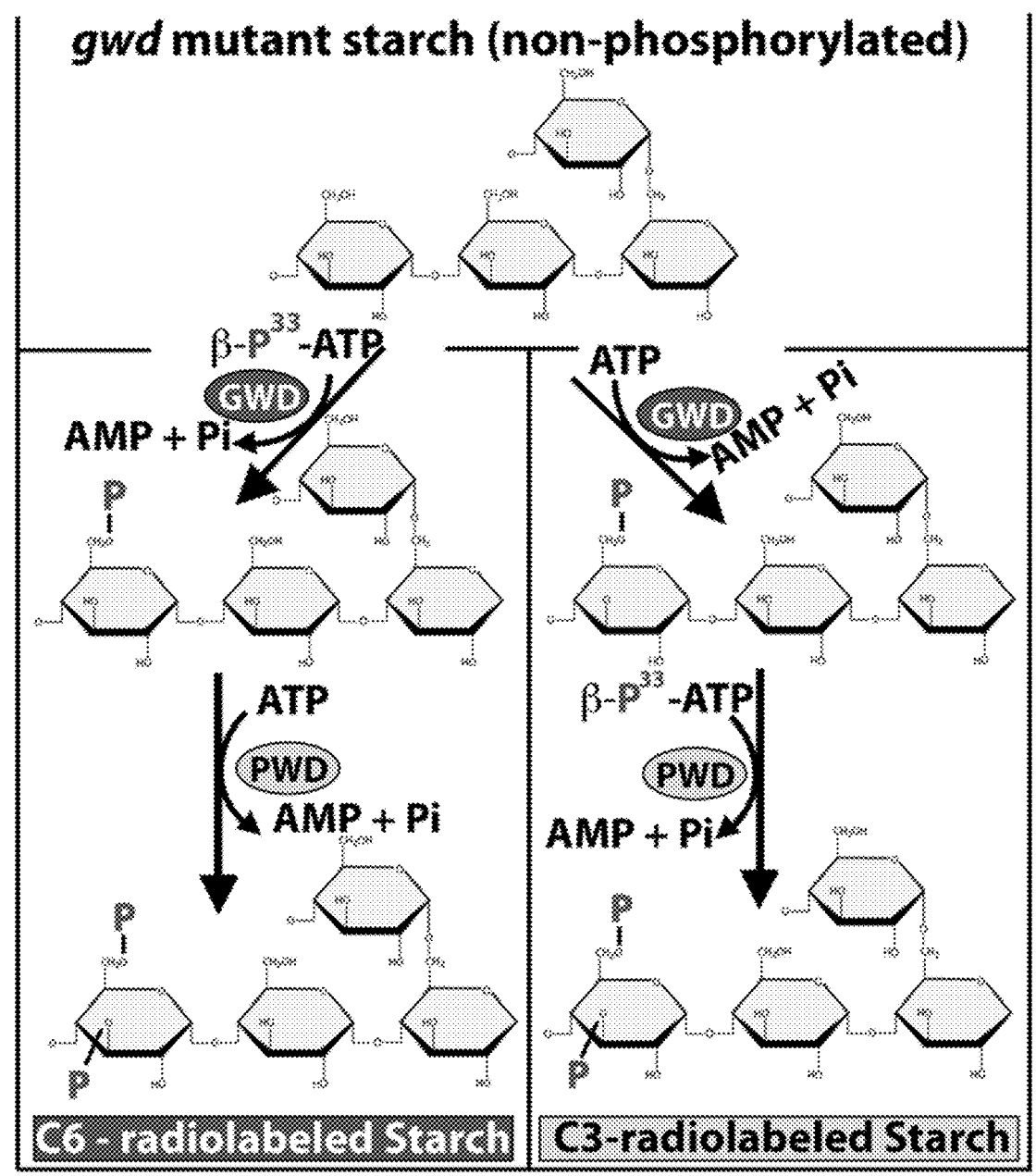
FIG. 8 includes the framework for the C6 versus C3 assay. To label the C6-position, non-phosphorylated starch is incubated in the presence of GWD and $^{33}$P-β-ATP, the protein and label are washed away, and the starch is incubated in the presence of ATP and PWD. The C3 position is labeled in a similar manner, except $^{33}$P-β-ATP is used with PWD. These products are then used as substrates in dephosphorylation assays.

A starch-phosphorylation assay is routinely used in the lab to measure the specific activity of protein constructs. This assay has 3 benefits: it utilizes an endogenous substrate, measures the amount of phosphate added to glucose (dikinase activity), and allows comparison of addition to the C3- and C6-positions (site-specific activity) (FIG. 8). Phosphate-free starch was isolated from plants lacking the dikinase GWD, and the sample dialyzed to remove free phosphate. To measure dikinase activity, this phosphate-free starch was used as the substrate. The starch was incubated with the dikinase in question along with $^{33}$P-β-ATP, the $^{33}$P-β-ATP and dikinase was washed out, and radio-label incorporation into the starch was measured.

In particular, this position-specific activity assay was utilized to probe the ability of dikinases from different organisms and truncations to specifically phosphorylate different positions in starch. Intriguingly, the red algae *C. merolae* possesses only one glucan dikinase while all plant genomes contain both GWD and PWD, suggesting that it may be able to phosphorylate both C3 and C6-positions.

The glucan dikinases are predicted to have one or more N-terminal CBM domains and a C-terminal catalytic dikinase domain. To determine the specific role that the CBM and catalytic domains play in directing binding substrate and controlling site-specific enzymatic activity, constructs were produced and purified spanning the glucan dikinase catalytic domain with varying N-terminal extensions and test the ability to bind to starch and specific activity.

Example 3

In this Example procedures are described that elucidate the structural basis underlying the function of glucan dikinases. The previous lack of structural information on glucan dikinase enzyme families was due, in part, to difficulty in purifying and manipulating the enzyme in vitro, and as a large multi-domain protein they have proven difficult to crystallize. Without being bound by theory or mechanism, Glucan dikinases may have a complex multi-domain architecture.

Figure 4A:
FIGS. 4A-B include images of glucan dikinase domains. (A) shows a schematic of carbohydrate binding modules (CBMs) with a dikinase domain. (B) shows a schematic of glucan dikinase domains, where At=*Arabidopsis*, Cm=*C. merolae*, St=*S. tuberosum*, cTP=chloroplast targeting peptide, CBM=carbohydrate binding module, PPDK=pyruvate phosphate dikinase domain.
Figure 4B:
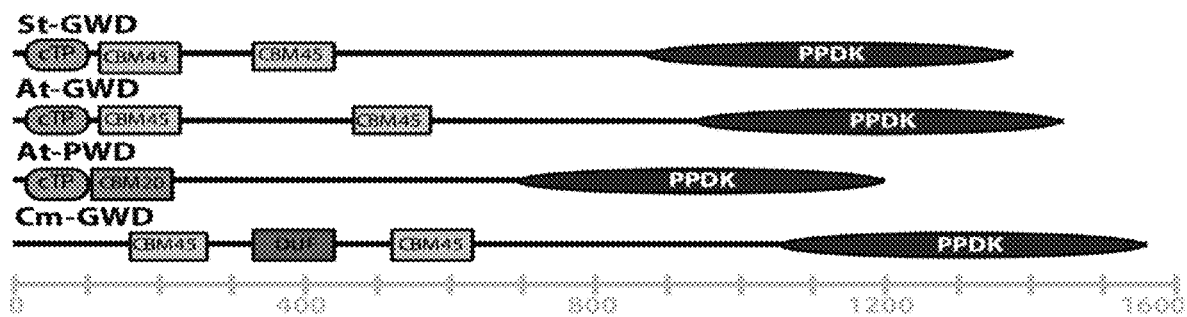
Figure 5A:
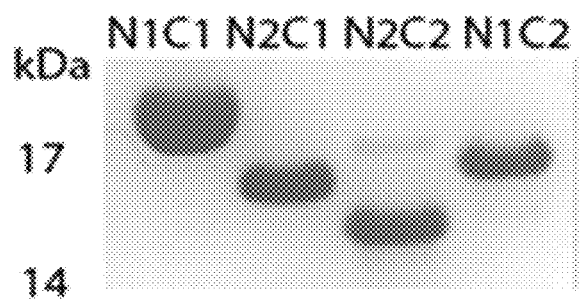
FIGS. 5A-C show graphs and images illustrating expression and thermal shift of various domains of the Cm-GWD. (A) is an image showing the expression of the Cm-GWD DUF domain constructs with varying N- and C-termini. (B) is an image showing the expression of individual N-terminal domains of Cm-GWD. (C) is a plot showing a DSF-thermal shift assay demonstrating that the DUF is a CBM.
Figure 5B:
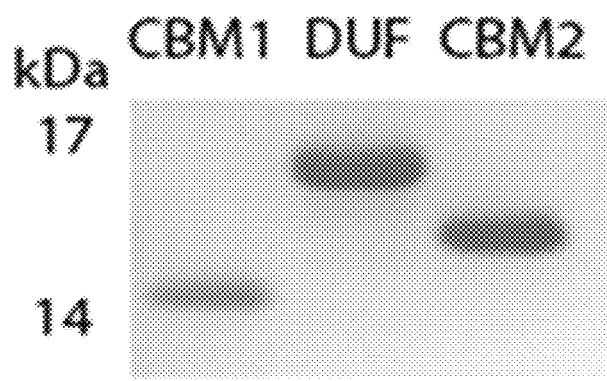

To characterize the enzymes' structure, the architecture of the dikinases was first analyzed. The sequences of the dikinases were analyzed using bioinformatic tools. The dikinase primary sequences from multiple species were analyzed to predict sequence conservation, secondary structure, regions of disorder, and regions of hydrophobicity in order to define the optimal constructs for recombinant protein expression of Cm-GWD. At-GWD and PWD have been reported to have cTP, one or two CBM domains, and a dikinase domain (FIG. 4). Cm-GWD has two CBM domains and a dikinase domain, and it also has a region approximately 100 amino acids long that is predicted to be rich in sheet-like secondary structure between the two CBM domains (FIG. 4). Given its size and predicted structure, this region was defined as a Domain of Unknown Function (DUF, FIG. 4). Further analysis of the sequence of this domain revealed conserved aromatic residues in positions analogous to those of a CBM domain, and therefore this region may encode a previously unrecognized CBM domain. To test this, multiple constructs of the DUF domain with different N- and C-termini were designed. These constructs yielded high-level expression of soluble and stable protein (FIG. 5A). Indeed, expression was as good or better than the individual CBM1 and CBM2 domains (FIG. 5B).

Figure 5C:
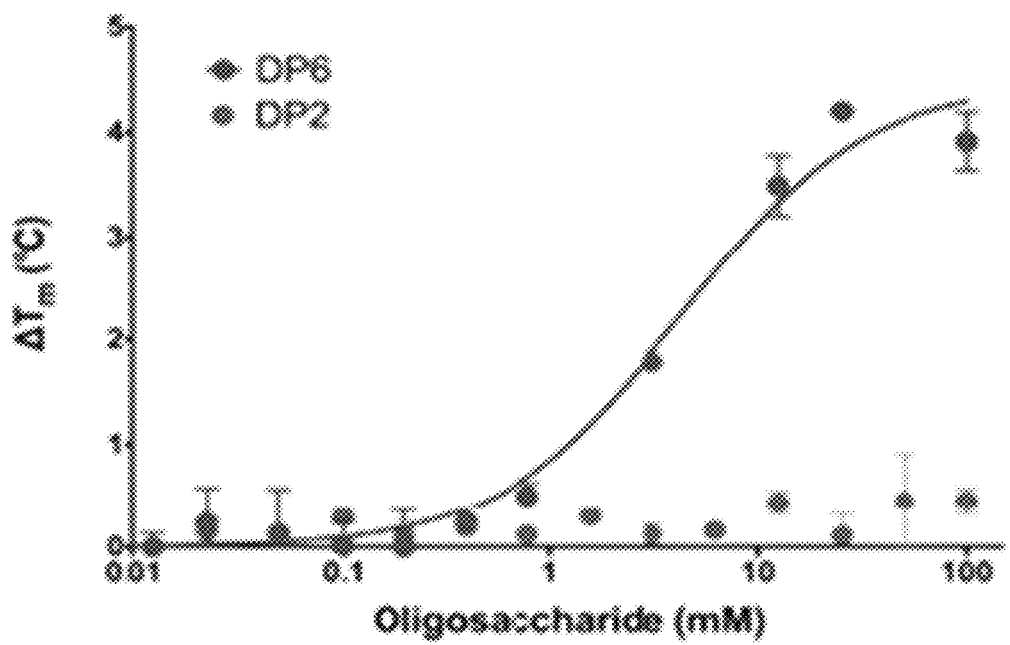

The binding of purified proteins to oligosaccharides was measured using a differential scanning fluorimetry (DSF)-based thermal shift assay. This assay has the advantage of allowing comparisons between chemically defined oligosaccharides, based on differences in the apparent dissociation constant ($K_d$). As a proof of principle, the binding of the Cm-GWD DUF to the oligosaccharide maltohexaose and to maltose was measured, as a negative control. The DUF domain was found to be very stable, with a melting temperature ($T_m$=59°) C. The change in $T_m$ was monitored with increasing concentration of oligosaccharide (FIG. 5C). A significant, dose dependent binding to maltohexaose with a $K_d$=7 mM was observed, consistent with the binding affinity reported for many CBM domains. No stabilization with maltose was observed, indicating that this is a specific effect. These data demonstrate that Cm-GWD contains a previously unrecognized CBM domain in its N-terminus.

To determine the structural basis for the function of dikinases, X-ray crystallography was combined on limited domain constructs with Small Angle X-ray Scattering (SAXS) on larger constructs. The former technique has proven very fruitful in the instant inventors' study of glucan phosphatases. SEC-SAXS was utilized, which provides critical global structure information and has the advantages of being a solution-based technique and works in cases with global conformational heterogeneity, a hallmark of most large multi-domain proteins.

Figure 6A:
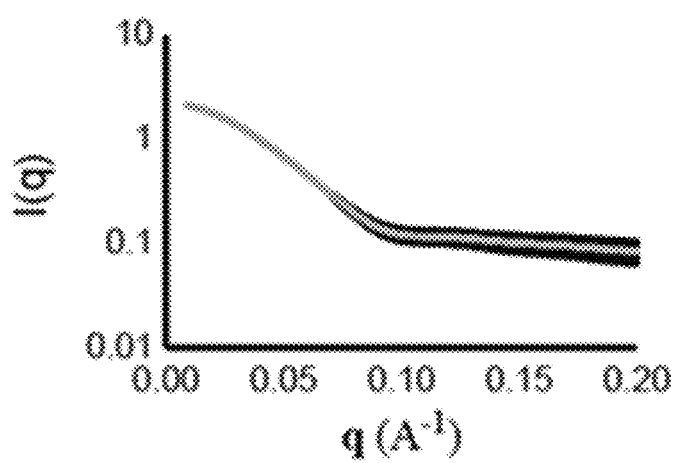
FIGS. 6A-C include graphs and images showing SEC-SAXS analysis of Cm-GWD. (A) includes a graph showing a scattering curve of Cm-GWD. (B) includes a graph showing pair-distance distribution of Cm-GWD. (C) includes an image showing an Ab initio model of Cm-GWD with the computed surface in blue mesh.
Figure 6B:
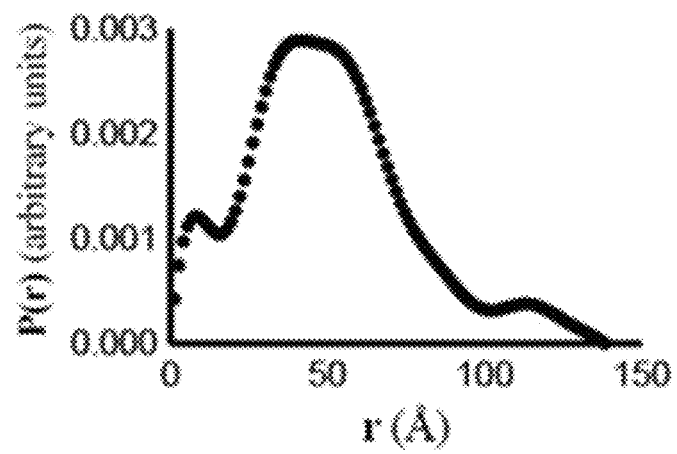
Figure 6C:
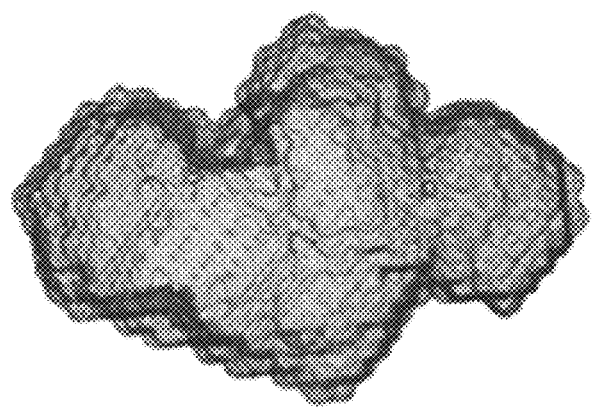

As a proof of principle, Cm-GWD (residues 511-1572), containing the final CBM and the catalytic dikinase domain, shown to be an active dikinase above, at the BioCAT beamline of the APS was analyzed. Cm-GWD was loaded on a Superose 6 10/300 at 4 mg/mL. Scattering data were continuously collected across the peak elution volume and then reduced and analyzed (FIG. 6A). The distance distribution plot reveals a shape characteristic of a multi-domain protein (FIG. 6B). Porod volumes, derived from P(R) curves, allowed unambiguous assignment of the molecular species deduced from gel filtration, with MW=114 kDa, (expected monomer=119 kDa). Multiple low-resolution molecular envelopes were generated using DAMMIF and a consensus model built with the DAMAVER suite. The model revealed a large globular shaped domain with two lobes and a deep intervening grove as well as an accessory smaller domain (FIG. 6C). The smaller domain (FIG. 6C, right) is consistent in size and shape with that of a CBM. This information serves as an important solution-based compliment to high-resolution structural analysis, and provides critical structural information on large and conformationally labile species.

To date, 30 expression constructs for Cm-GWD have been tested, of which 17 have produced soluble and stable protein. Constructs have been identified that express each of the individual CBM domains, as well as the DUF-CBM, discussed above (FIG. 9C). Expression yields for these constructs ranges from 2-30 mg/1 L of *E. coli* using a 2-step purification. Additionally, N-terminal truncation constructs have been produced and purified. Expression yields for these constructs ranges from 2-30 mg/1 L of *E. coli* using a 2-step purification.

Example 4

This Example demonstrates the utility of GWD for starch degradation and processing. As discussed above, starch is employed in a variety of industrial settings. Amylases have been optimized at the cost of millions of dollars; however, they are still unable to degrade starch on their own, and therefore harsh chemical treatments and extreme heat are used to degrade starch. This Example focuses on developing and harnessing glucan dikinases to maximize starch degradation in vitro.

Figure 7:
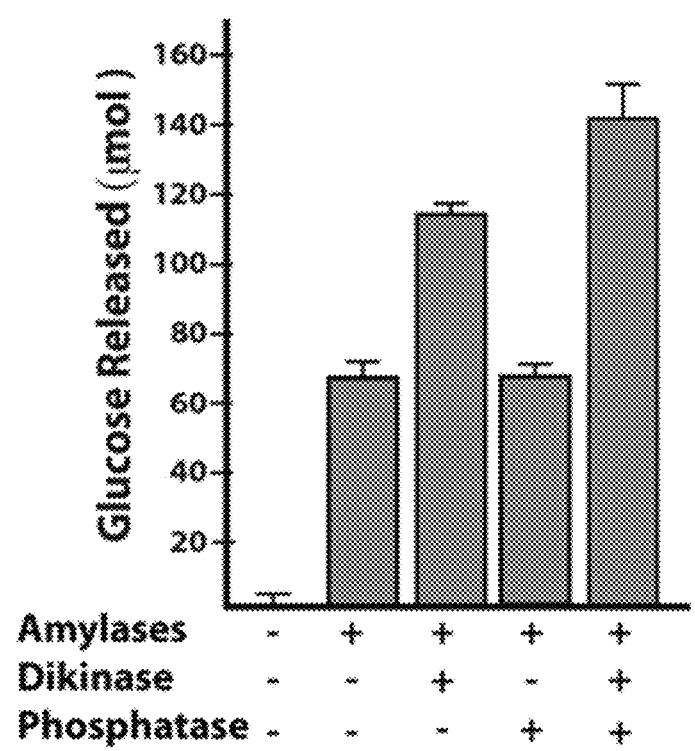
FIG. 7 includes a plot showing the glucose released for native *Arabidopsis* starch that was incubated at 25° C. for 60 minutes with combinations of amylases (BAM+ISA), dikinase (At-GWD), or phosphatase (At-SEX4), undigested starch was pelleted with a high-speed spin, the supernatant sugars were hydrolyzed via acid hydrolysis and glucose content was measured.

To observe how GWDs can be utilized to enhance starch utilization, native *Arabidopsis* starch was first treated with combinations of BAM3, ISA3, St-GWD, and At-SEX4. a high-speed spin was performed to remove the undigested starch, any remaining oligo-saccharides were hydrolyzed, and glucose released into the supernatant was measured (FIG. 7). Glucose was only released upon addition of amylases. The addition of St-GWD almost doubled glucose release. Addition of the glucan phosphatase SEX4 did not enhance glucose release on its own, but did further enhance glucose release when used with St-GWD, indicating utilization of the full starch phosphorylation cycle provides added benefit, more than doubling glucose release. These data provide a novel method to degrade starch that could impact both industrial processing and biofuel feedstock generation.

These data demonstrate that reversible starch phosphorylation increases the efficiency of amylases in vitro. Without being bound by theory or mechanism, there may be a temporospatial element to starch degradation that impacts in vitro degradation.

Example 5

Figure 9A:
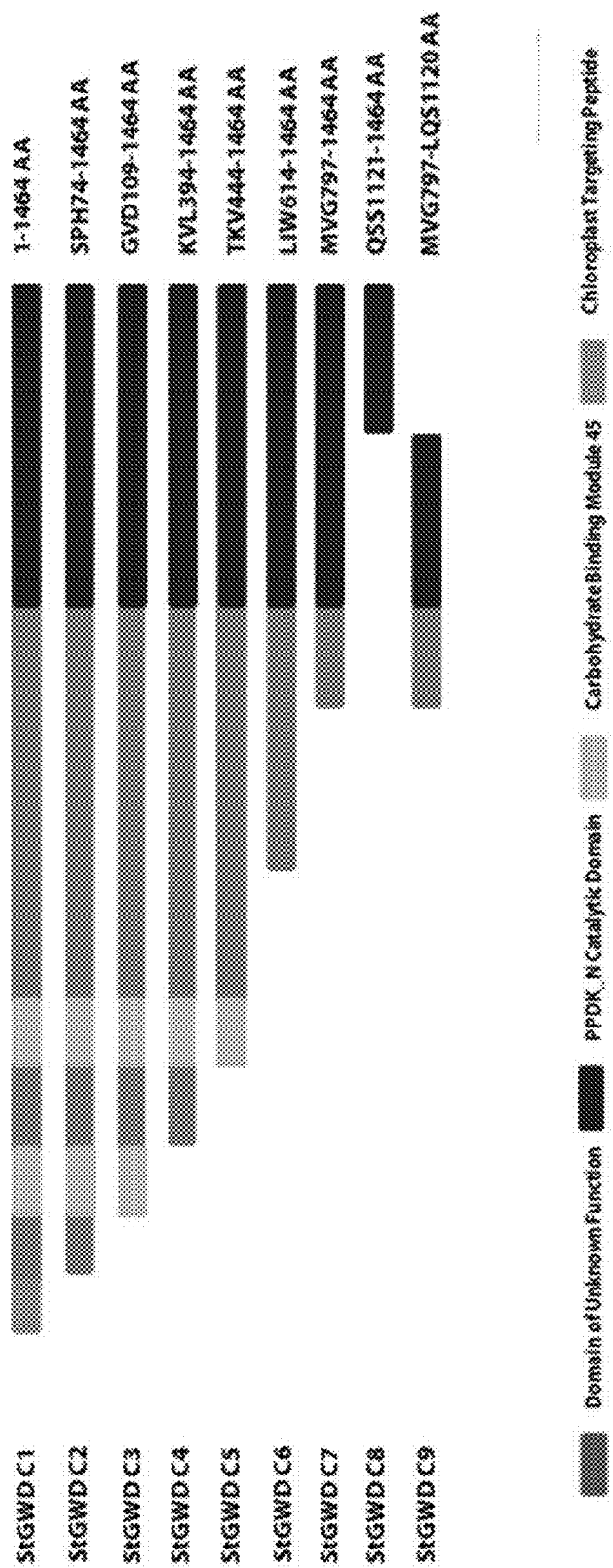
FIGS. 9A-D include images showing GWD constructs from *Solanum tuberosum* (St) and *Cyanidioschyzon merolae* (Cm). (A) shows a schematic of full-length StGWD along with subsequent truncations. (B) shows SDS-PAGE of SEC-purified StGWD proteins. (C) shows a schematic of full-length CmGWD along with subsequent truncations. (D) shows SDS-PAGE of SEC-purified CmGWD proteins.

Multiple GWD orthologs were cloned in an attempt to identify a GWD that is amenable to in vitro manipulation. To define the optimal constructs for recombinant protein expression, GWD primary sequences were analyzed from multiple species to predict: domain boundaries, secondary structure, regions of disorder, and regions of hydrophobicity. Similar methodologies successfully guided the instant inventors' cloning strategies to determine the structures of SEX4, LSF2, and laforin. Based on these data, the full-length GWD gene was cloned as well as engineering multiple truncations that remove the amino- and/or carboxy-terminus of the protein (Table 1, corresponding to FIG. 9). One of the orthologs that was cloned was the full-length *Solanum tuberosum* GWD (StGWD) gene as well as multiple truncations that remove different regions of the chloroplast Targeting Peptide (cTP) (FIG. 9A), which is predicted to be disordered. Additionally, constructs that begin at each predicted StGWD domain boundary were generated (FIG. 9A, Table 1).

TABLE 1

| Description | Construct from FIG. 9 | Amino Acids |
|---|---|---|
| StGWD constructs | | |
| StGWD Full length | C1 | amino acids 1-1464 |
| StGWD SPH74 | C2 | amino acids 74-1464 |
| StGWD GDV109 | C3 | amino acids 109-1464 |
| StGWD KVL394 | C4 | amino acids 394-1464 |
| StGWD TKV444 | C5 | amino acids 444-1464 |
| StGWD LIW614 | C6 | amino acids 614-1464 |
| StGWD MVG797 | C7 | amino acids 797-1464 |
| StGWD QSS1121 | C8 | amino acids 1121-1464 |
| StGWD HIS | C9 | amino acids 797-1120 |
| CmGWD constructs | | |
| CmGWD Full Length | C1 | amino acids 1-1572 |
| CmGWD KSL114 | C2 | amino acids 114-1572) |

TABLE 1-continued

| Description | Construct from FIG. 9 | Amino Acids |
| --- | --- | --- |
| CmGWD GHL345 | C3 | amino acids 345-1572 |
| CmGWD TIL511 | C4 | amino acids 511-1572 |
| CmGWD NVF820 | C5 | amino acids 820-1572 |
| CmGWD DUF | C6 | amino acids 345-469 |

Figure 9B:
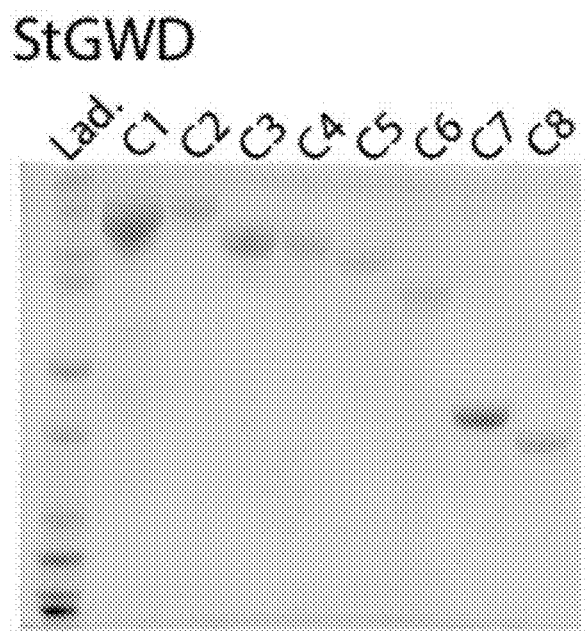
Figure 9C:
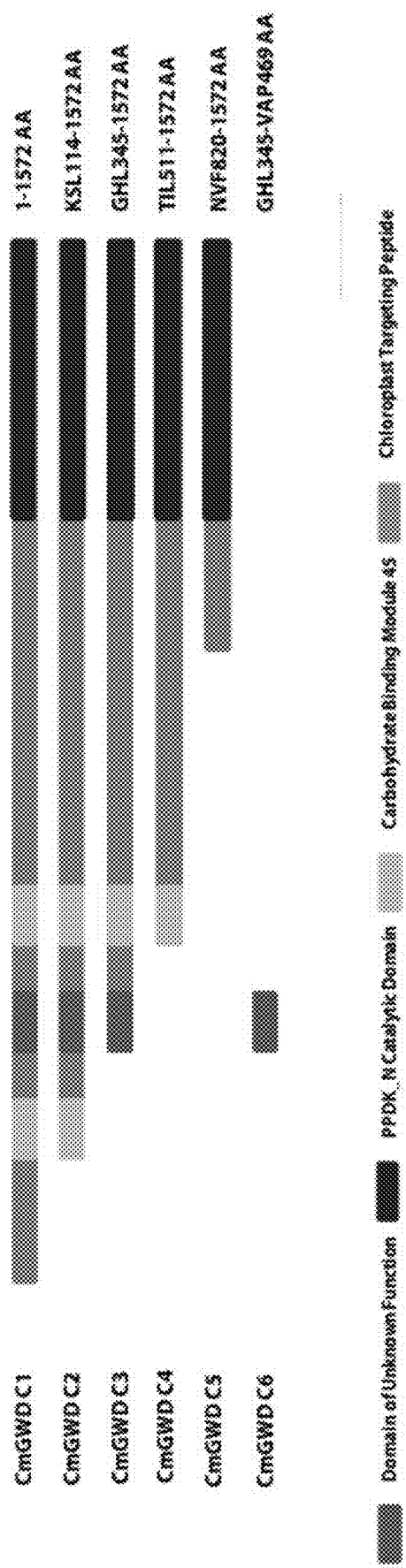
Figure 9D:
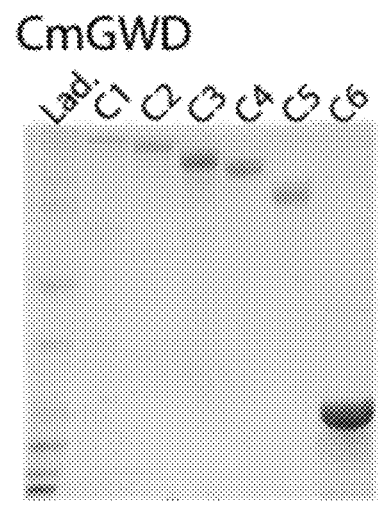
Figure 10A:
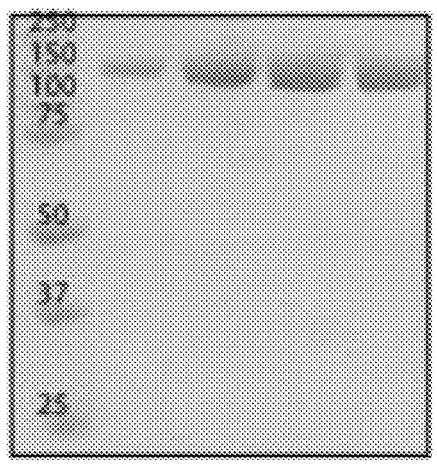
FIGS. 10A-D includes graphs and images showing StGWD-H992A purification where St-GWD was purified using a 3-step purification scheme. (A) shows SDS-PAGE of increasing amounts of St-GWD. (B) shows a SEC chromatogram of St-GWD. The protein elutes as a monomer or dimer. (C) shows native gel electrophoresis of St-GWD SEC fractions. (D) shows a graphs illustrating full-length GWD (St-GWD) and ΔcTP-GWD activity against gwd−/− *Arabidopsis* starch (left) and ΔcTP-GWD activity against different glucans.
Figure 10B:
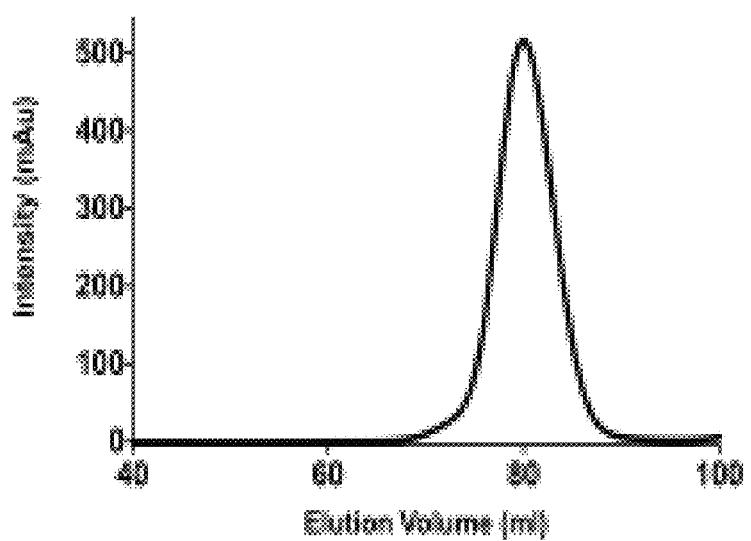
Figure 10C:
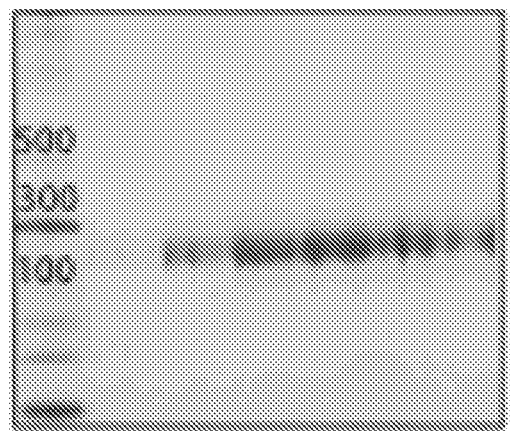
Figure 10D:
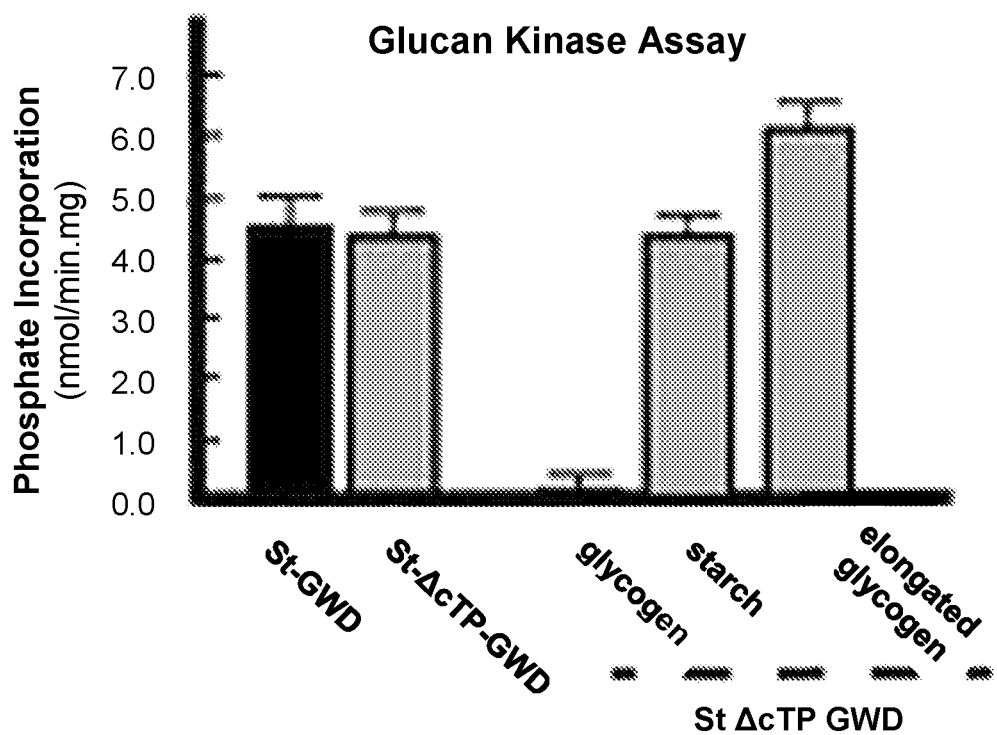

In addition, these constructs were purified using a 3-step purification scheme to sufficient purity for enzymatic assays (FIGS. 9B,D & 10A). Constructs that express each of the individual domains were identified, as well as constructs just lacking the cTP. Expression yields for these constructs ranged from 2-65 mg/1 L of E. coli using a 3-step purification. One of the most promising St-GWD constructs allowed the instant inventors to purify 60-65 mg of >95% pure St-GWD per liter of E. coli using a 3-step purification protocol (FIGS. 10A & 10B). Importantly, the purified protein was concentrated to 18 mg/ml and the protein was stable at 4° C. for >1 WEEK. Full-length St-GWD exclusively phosphorylates C6 hydroxyls of starch glucose moieties. Additionally, detailed biochemistry has been reported regarding the kinetics of how efficiently GWD phosphorylates potato starch, amylopectin, amylose, and glycogen. ΔcTP-St-GWD has a specific activity similar to full-length StGWD (FIG. 10D).

A truncated CmGWD construct (residues 511-1572) was also produced, which encodes the second predicted CBM and catalytic dikinase domain, to determine its specific activity. The activity of this protein was measured, and it was found to be an active glucan dikinase (FIG. 3). Importantly, the observed activity critically depends on His1162, since CmGWD H1162A lacked activity. CmGWD H1162 is analogous to the catalytic domain histidine identified in plant GWD as critical for enzyme activity (4). Strikingly, a construct encoding the catalytic domain alone had no measurable activity. This result demonstrates that the CBM and catalytic domains cooperate together to produce an active specific glucan dikinase.

Example 6

Given the instant inventors' robust results in phosphorylating starch and ability to define the multiple domains within dikinase proteins, they next sought to generate chimera proteins to phosphorylate other carbohydrates. The goal in this work was to produce an engineered protein that could phosphorylate glycogen, cellulose, or another carbohydrate. The idea being, that if a substance like cellulose could be modified with phosphorylation then it would be less recalcitrant to degradation.

First, the sequences of the dikinases and CBMs known to bind other carbohydrates were analyzed using bioinformatic tools. The dikinase and CBM primary sequences from multiple species were analyzed to predict sequence conservation, secondary structure, regions of disorder, and regions of hydrophobicity in order to define the optimal constructs for recombinant protein expression of engineered proteins.

Figure 11A:
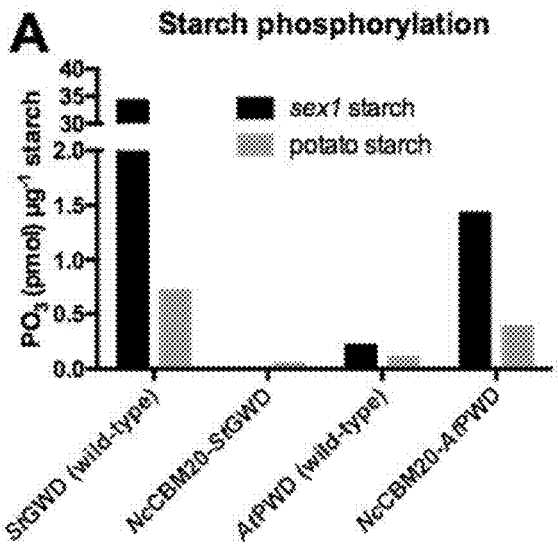
FIGS. 11A-D show graphs of Phosphorylation of starch and cellulose by engineered, chimeric CBM-dikinases. (A) Phosphate incorporation into phosphate-less *Arabidopsis* (sex1-3) starch or potato starch by wild-type StGWD and AtPWD, and engineered NcCBM20-StGWD and NcCBM20-AtPWD. (B) Wild-type AtPWD phosphorylates sex1-3 starch pretreated with NcCBM20-AtPWD to a greater extent than starch pretreated with wild-type StGWD. (C) Phosphorylation of cellulose by the four engineered chimeric enzymes. (D) Overall comparison of all chimeric enzyme activities. The level of phosphorylation of cellulose is comparable to that of starch.
Figure 11B:
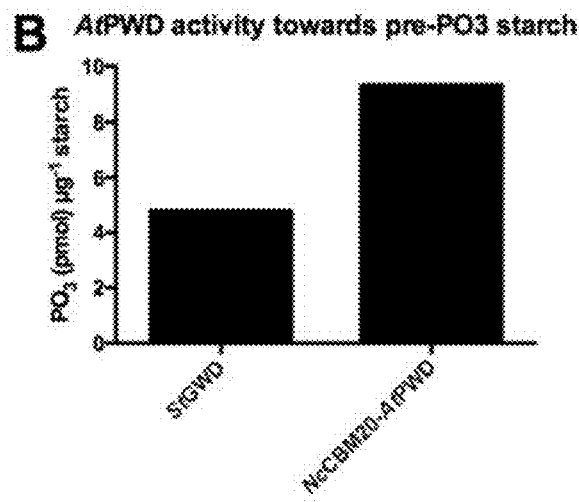

As proof of principle that an engineered glucan, water dikinase comprising an exotic CBM would be functional, the CBM20 from the starch monooxygenase NCU08746 from the fungus Neurospora crassa (33) was fused N-terminally to the dikinase domain of either GWD or PWD, generating NcCBM20-StGWD and NcCBM20-AtPWD, respectively. CBM20s bind (partially-)soluble glucose polymers such as glycogen and starch, and PWD comprises a homologous CBM20. The NcCBM20-AtPWD chimera robustly phosphorylated starch (FIG. 11A), which also served to prime wild-type AtPWD (FIG. 11B). This result is important because the PWD dikinase domain was thought to only phosphorylate starch after a priming phosphorylation by GWD. Herein is demonstrated that the PWD dikinase domain can phosphorylate starch before this priming if it is engineered with a different CBM.

Figure 11C:
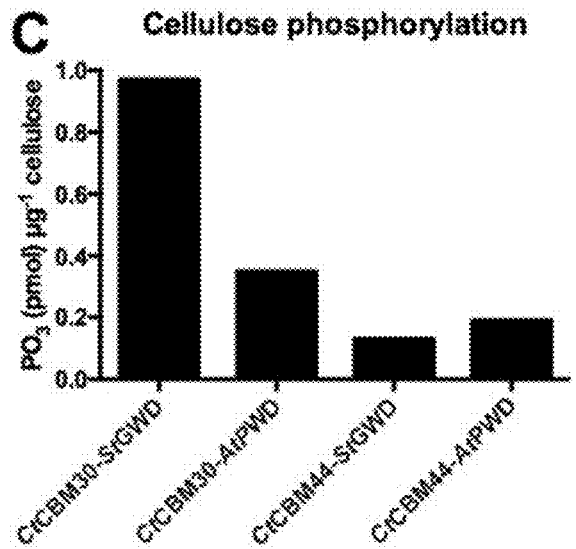
Figure 11D:
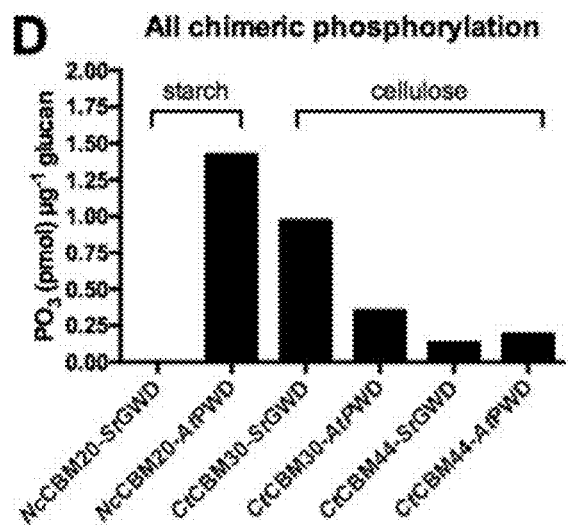

Next, it was tested whether phosphorylation could be directed towards cellulose, the most abundant polymer on earth, by building chimeras comprising cellulose-binding CBMs. Both the CBM30 and CBM44 were chosen from the cellulase CelJ of the thermophilic, gram-positive bacterium Clostridium thermocellum, which bind cellulose with high affinity. The engineered protein containing CtCBM30 and CtCBM44 was purified. The starch-phosphorylation assay was modified to develop an assay for measure phosphorylation of cellulose, which was obtained from Sigma-Avicel PH-101. To measure dikinase activity, the cellulose was incubated with the engineered chimeric dikinase in question along with $^{33}$P-β-ATP, the $^{33}$P-β-ATP and enzyme were washed out, and radio-label incorporation into the cellulose was measured. It was found that the CtCBM30-StGWD engineered protein robustly phosphorylated cellulose with the other engineered proteins also showing lower levels of cellulose phosphorylation (FIG. 11C). Cumulatively, six engineered proteins have been generated that are able to phosphorylate either starch or cellulose (FIG. 11D; SEQ ID NOs: 47-58) Thus, these data demonstrate that the protein engineering methodology disclosed herein works and is currently being utilized to expand on these results.

Given the success with engineering chimeric enzymes to phosphorylate starch and cellulose, the engineering approach will be expanded to phosphorylate other carbohydrates. Plant, fungal, and algal organic matter are comprised of diverse polysaccharides, in addition to starch and cellulose, including lignin, xylan, hemicelluloses, mannan, and chitin, which each present challenges to ex vivo degradation. A similar approach will be employed to append CBMs that specifically bind particular polysaccharides to the GWD and PWD dikinase domains and test phosphorylation of isolated carbohydrates as well as whole-cell extracts.

Example 7

Native Arabidopsis starch was treated with combinations of BAM3, ISA3, StGWD, and AtSEX4, performed a high-speed spin to remove the undigested starch, hydrolyzed any remaining oligo-saccharides, and measured glucose released into the supernatant (FIG. 7). Glucose was only released upon addition of amylases, as expected. Strikingly, the addition of AtGWD almost doubled glucose release. Addition of the glucan phosphatase SEX4 did not enhance glucose release on its own, but did further enhance glucose release when used with AtGWD, indicating utilization of the full starch phosphorylation cycle provides added benefit, more than doubling glucose release. These data provide a novel method to degrade starch that could impact both industrial processing and biofuel feedstock generation.

These data demonstrate that reversible starch phosphorylation increases the efficiency of amylases in vitro. Additionally, these studies were extended to develop the use of glucan dikinases for starch processing and utilization. First, the ratios of amylase, glucan dikinase, and glucan phosphatase that are most efficient were established. The interplay between different enzyme families is not well understood, and thus the concentration and ratio of these enzymes may be key to efficient starch degradation in vitro. Second, the combination of enzymes is most efficient was defined. In plants, there are two dikinases, two glucan phosphatases, and two amylases have been tested to date, but have yet to identify the optimal combination of enzymes for promoting starch degradation. CmGWD and the glucan phosphatase from *C. merolae*, CmLaforin, in combination with the other enzymes will be explored. Third, the optimal order of enzyme addition to the reaction mixture was defined. The in planta work suggests that there is a necessary temporospatial element to starch degradation that likely also impact in vitro degradation. Fourth, while current protocol uses a batch approach to starch degradation, the enzymes may be more efficient when added sequentially.

Example 8

Starch physiochemical properties differentially effect the efficiency of glucan kinases. While thus far reference has been made to "starch," "starch" is very heterogeneous: its physicochemical properties, composition with respect to amylose versus amylopectin, amount of phosphorylation, and molecular structure all vary greatly depending on the source of starch. For example, potato starch granules are 3-5 fold larger, they have a smooth surface, and are rounded. Conversely, corn starch is smaller, possess a rough surface, and contain edges and pores. These properties greatly affect starch gelatinization and viscosity, and thus impact manufacturing. Starch isolated from different sources are broadly categorized as A-type and B-type allomorphs. The A-type allomorph, typical of cereal starches, is more compact and the helical chains are packed in a monoclinic lattice. The B-type allomorph, found in potato and *Arabidopsis*, contains helical chains packed in a hexagonal lattice with 36 water molecules. Therefore, the ability of the different dikinases to enhance degradation of starch from *Arabidopsis*, potato, corn, cassava, rice, and wheat will be tested. Answering these questions yielded both further insights into the role of reversible starch phosphorylation in starch degradation in planta and provided a powerful model to enhance in vitro starch degradation.

Employing glucan kinases to enhance the degradation of cellulose and other carbohydrates was also explored. The addition of glucan kinases and phosphatases has been shown to enhance the amylytic digestion of starch in vivo. It is now contended that the kinases engineered to phosphorylate other diverse polysaccharides, such as cellulose, will enhance their degradation. Cellulose is digested by cellulase enzymes from microorganisms, mostly fungi and bacteria. Cellulose, however, like starch, is partially water-insoluble, with the majority of cellulose strands present in crystalline fibres that are inaccessible to the degradative cellulases, which can attack cellulose strands only once the strands have become soluble. Thus, testing whether phosphorylation of cellulose by the instant chimeric enzymes can enhance its digestion in a similar manner as done for in vitro starch digestion was conducted. Also, the extension of this to other diverse carbohydrates that are traditionally recalcitrant to degradation, such as lignin, xylan, hemicelluloses, pectins, mannan, and chitin was performed.

Discussion

There is an increasing understanding of the importance of reversible starch phosphorylation in nature. Yet, there are critical outstanding questions regarding the specific enzymatic function and activity of the enzymes involved, and how these enzymes can be harnessed. As disclosed herein, tools have been generated to define the enzymology, architecture, structure, and specific function of glucan dikinases. Enhancing starch degradation by harnessing glucan dikinase and glucan phosphatase activities can be achieved utilizing the disclosure herein. The model of enhanced starch degradation can be extended to enhance the degradation of other diverse polysaccharides that share a similar recalcitrance to enzymatic degradation due to their insoluble nature. As demonstrated, glucan dikinases have been engineered to phosphorylate insoluble cellulose, which will next combine phosphorylation with enzymatic degradation with the goal of enhancing enzymatic cellulosic breakdown and thus minimizing the use of harsh chemical and thermal treatments.

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a polypeptide" includes a plurality of such polypeptides, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references, including those listed below, are incorporated herein by reference.

REFERENCES

1. Blennow A, Engelsen S B. Helix-breaking news: fighting crystalline starch energy deposits in the cell. Trends Plant Sci. 2010; 15(4):236-40. PubMed PMID: 20149714.

2. Zeeman S C, Kossmann J, Smith A M. Starch: Its Metabolism, Evolution, and Biotechnological Modification in Plants. Annu Rev Plant Biol. 2010; 61:209-34. PubMed PMID: 20192737.
3. Ritte G, Heydenreich M, Mahlow S, Haebel S, Kotting O, Steup M. Phosphorylation of C6- and C3-positions of glucosyl residues in starch is catalysed by distinct dikinases. FEBS Lett. 2006; 580(20):4872-6. PubMed PMID: 16914145.
4. Ritte G, Lloyd J R, Eckermann N, Rottmann A, Kossmann J, Steup M. The starch-related R1 protein is an alpha-glucan, water dikinase. Proc Natl Acad Sci USA. 2002; 99(10):7166-71. PubMed PMID: 12011472.
5. Kotting O, Pusch K, Tiessen A, Geigenberger P, Steup M, Ritte G. Identification of a novel enzyme required for starch metabolism in *Arabidopsis* leaves. The phosphoglucan, water dikinase. Plant Physiol. 2005; 137(1):242-52. PubMed PMID: 15618411.
6. Kotting O, Santelia D, Edner C, Eicke S, Marthaler T, Gentry M S, Comparot-Moss S, Chen J, Smith A M, Steup M, Ritte G, Zeeman S C. STARCH-EXCESS4 Is a Laforin-Like Phosphoglucan Phosphatase Required for Starch Degradation in *Arabidopsis thaliana*. Plant Cell. 2009; 21(1):334-46. PubMed PMID: 19141707.
7. Meekins D A, Guo H F, Husodo S, Paasch B C, Bridges T M, Santelia D, Kotting O, Vander Kooi C W, Gentry M S. Structure of the *Arabidopsis* glucan phosphatase like sex four2 reveals a unique mechanism for starch dephosphorylation. Plant Cell. 2013; 25(6):2302-14. PubMed PMID: 23832589; PubMed Central PMCID: PMC3723627.
8. Santelia D, Kotting O, Seung D, Schubert M, Thalmann M, Bischof S, Meekins D A, Lutz A, Patron N, Gentry M S, Allain F H, Zeeman S C. The phosphoglucan phosphatase like sex Four2 dephosphorylates starch at the C3-position in *Arabidopsis*. Plant Cell. 2011; 23(11): 4096-111. PubMed PMID: 22100529; PubMed Central PMCID: PMC3246334.
9. Ral J P, Bowerman A F, Li Z, Sirault X, Furbank R, Pritchard J R, Bloemsma M, Cavanagh C R, Howitt C A, Morell M K. Down-regulation of Glucan, Water-Dikinase activity in wheat endosperm increases vegetative biomass and yield. Plant biotechnology journal. 2012. PubMed PMID: 22672098.
10. Weise S E, Aung K, Jarou Z J, Mehrshahi P, Li Z, Hardy A C, Carr D J, Sharkey T D. Engineering starch accumulation by manipulation of phosphate metabolism of starch. Plant biotechnology journal. 2012; 10(5):545-54. PubMed PMID: 22321580.
11. Caspar T, Lin T-P, Kakefuda G, Benbow L, Preiss J, Somerville C. Mutants of *Arabidopsis* with Altered Regulation of Starch Degradation. Plant Physiol. 1991; 95(4): 1181-8.
12. Lorberth R, Ritte G, Willmitzer L, Kossmann J. Inhibition of a starch-granule-bound protein leads to modified starch and repression of cold sweetening. Nat Biotechnol. 1998; 16(5):473-7. PubMed PMID: 9592398.
13. Yu T S, Kofler H, Hausler R E, Hille D, Flugge U I, Zeeman S C, Smith A M, Kossmann J, Lloyd J, Ritte G, Steup M, Lue W L, Chen J, Weber A. The *Arabidopsis* sex1 mutant is defective in the R1 protein, a general regulator of starch degradation in plants, and not in the chloroplast hexose transporter. Plant Cell. 2001; 13(8): 1907-18. PubMed PMID: 11487701.
14. Mikkelsen R, Mutenda K E, Mant A, Schurmann P, Blennow A. Alpha-glucan, water dikinase (GWD): a plastidic enzyme with redox-regulated and coordinated catalytic activity and binding affinity. Proc Natl Acad Sci USA. 2005; 102(5):1785-90. PubMed PMID: 15665090.
15. Ritte G, Steup M, Kossmann J, Lloyd J R. Determination of the starch-phosphorylating enzyme activity in plant extracts. Planta. 2003; 216(5):798-801. PubMed PMID: 12624767.
16. Hejazi M, Fettke J, Paris O, Steup M. The two plastidial starch-related dikinases sequentially phosphorylate glucosyl residues at the surface of both the A- and B-type allomorphs of crystallized maltodextrins but the mode of action differs. Plant physiology. 2009; 150(2):962-76. PubMed PMID: 19395406; PubMed Central PMCID: PMC2689988.
17. Hejazi M, Fettke J, Haebel S, Edner C, Paris O, Frohberg C, Steup M, Ritte G. Glucan, water dikinase phosphorylates crystalline maltodextrins and thereby initiates solubilization. Plant J. 2008; 55(2):323-34. PubMed PMID: 18419779.
18. Gentry M S, Pace R M. Conservation of the glucan phosphatase laforin is linked to rates of molecular evolution and the glycogen metabolism of the organism. BMC Evol Biol. 2009; 9(1):138. PubMed PMID: 19545434.
19. Gentry M S, Dowen R H, 3rd, Worby C A, Mattoo S, Ecker J R, Dixon J E. The phosphatase laforin crosses evolutionary boundaries and links carbohydrate metabolism to neuronal disease. J Cell Biol. 2007; 178(3):477-88. PubMed PMID: 17646401.
20. Singh J, Kaur L, McCarthy O J. Factors influencing the physico-chemical, morphological, thermal and rheological properties of some chemically modified starches for food applications—A review. Food Hydrocolloids. 2007; 21(1):1-22.
21. Malcata F X. Microalgae and biofuels: a promising partnership? Trends in biotechnology. 2011; 29(11):542-9. PubMed PMID: 21724282.
22. Sayaslan A. Wet-milling of wheat flour: industrial processes and small-scale test methods. LWT—Food Science and Technology. 2004; 37(5):499-515.
23. Robyt J F, Choe J-y, Fox J D, Hahn R S, Fuchs E B. Acid modification of starch granules in alcohols: reactions in mixtures of two alcohols combined in different ratios. Carbohydrate Research. 1996; 283(0): 141-50.
24. Transparency-Market-Research. Biofuel Enzymes Market-Global Industry Size, Market Share, Trends, Analysis and Forecast, 2012-2018 2012. Available from: http://www.transparencymarketresearch.com/biofuel-enzymes-market.html.
25. Kelly R M, Dijkhuizen L, Leemhuis H. Starch and α-glucan acting enzymes, modulating their properties by directed evolution. Journal of Biotechnology. 2009; 140 (3-4):184-93.
26. Meekins D A, Raththagala M, Husodo S, White C J, Guo H F, Kotting O, Vander Kooi C W, Gentry M S. Phosphoglucan-bound structure of starch phosphatase Starch Excess4 reveals the mechanism for C6 specificity. Proc Natl Acad Sci USA. 2014; 111(20):7272-7. PubMed PMID: 24799671.
27. Baunsgaard L, Lutken H, Mikkelsen R, Glaring M A, Pham T T, Blennow A. A novel isoform of glucan, water dikinase phosphorylates pre-phosphorylated alpha-glucans and is involved in starch degradation in *Arabidopsis*. Plant J. 2005; 41(4):595-605. PubMed PMID: 15686522.
28. Vander Kooi C W, Taylor A O, Pace R M, Meekins D A, Guo H F, Kim Y, Gentry M S. Structural basis for the 29. Dukhande V V, Rogers D M, Roma-Mateo C, Donderis J, Marina A, Taylor A O, Sanz P, Gentry M S. Laforin, a dual specificity phosphatase involved in Lafora disease, is present mainly as monomeric form with full phosphatase activity. PLoS One. 2011; 6(8):e24040. PubMed PMID: 21887368; PubMed Central PMCID: PMC3162602.
30. Worby C A, Gentry M S, Dixon J E. Laforin: A dual specificity phosphatase that dephosphorylates complex carbohydrates. J Biol Chem. 2006; 281(41):30412-8.
31. Brewer M K, Husodo S, Dukhande V V, Johnson M B, Gentry M S. Expression, purification and characterization of soluble red rooster laforin as a fusion protein in *Escherichia coli*. BMC biochemistry. 2014; 15:8. PubMed PMID: 24690255.
32. Castanheira P, Moreira S, Gama M, Faro C. *Escherichia coli* expression, refolding and characterization of human laforin. Protein expression and purification. 2010; 71(2): 195-9. PubMed PMID: 20152902.
33. Moreira S, Castanheira P, Casal M, Faro C, Gama M. Expression of the functional carbohydrate-binding module (CBM) of human laforin. Protein expression and purification. 2010; 74(2):169-74. PubMed PMID: 20600946.
34. Volkov V V, Svergun D I. Uniqueness of ab initio shape determination in small-angle scattering. Journal of Applied Crystallography. 2003; 36:860-4. PubMed PMID: ISI: 000182284400105.
35. Edner C, Li J, Albrecht T, Mahlow S, Hejazi M, Hussain H, Kaplan F, Guy C, Smith S M, Steup M, Ritte G. Glucan, water dikinase activity stimulates breakdown of starch granules by plastidial beta-amylases. Plant Physiol. 2007; 145(1):17-28. PubMed PMID: 17631522.
36. Srichuwong S, Jane J L. Physicochemical properties of starch affected by molecular composition and structures: a review. Food Sci Technol. 2007; 16(5):663-74.
37. Hoover R. Composition, molecular structure, and physicochemical properties of tuber and root starches: a review. Carbohydrate Polymers. 2001; 45(3):253-67.
38. Imberty A, Chanzy H, Perez S, Buleon A, Tran V. The double-helical nature of the crystalline part of A-starch. J Mol Biol. 1988; 201(2):365-78. PubMed PMID: 3418703.
39. Seetharaman K, Bertoft E. Perspectives on the history of research on starch Part II: On the discovery of the constitution of diastase. Starch-Starke. 2012; 64(10):765-9. PubMed PMID: ISI:000309459300003.
40. Seetharaman K, Bertoft E. Perspectives on the history of research on starch Part I: On the linkages in starch. Starch-Starke. 2012; 64(9):677-82. PubMed PMID: ISI: 000308400800004.
41. U.S. Provisional Patent Application No. 61/673,479 to Gentry et al., filed Jul. 19, 2012.
42. U.S. Pat. No. 9,410,133 to Gentry et al., issued Aug. 9, 2016.
43. U.S. Provisional Patent Application No. 61/825,440 to Gentry et al., filed May 20, 2013.
44. U.S. Pat. No. 9,222,114 to Gentry et al., issued Dec. 29, 2015.45.
45. Vu V V, Beeson W T, Span E A, Farquhar E R, Marietta, M A. A family of starch-active polysaccharide monooxygenases. Proceedings of the National Academy of Sciences. 2014; 111(38).
46. Walker J A, Takasuka T E, Deng K, Bianchetti C M, Udell H S, Prom B M, Fox B G. Multifunctional cellulase catalysis targeted by fusion to different carbohydrate-binding modules. Biotechnology for Biofuels, 2015; 8(1).
47. Kumar R, Singh S, Singh O V. Bioconversion of lignocellulosic biomass: biochemical and molecular perspectives. Journal of Industrial Microbiology & Biotechnology 2008; (35.5): 377-91.

What is claimed is:

1. A fragment of a non-native glucan kinase polypeptide comprising:
    an isolated polypeptide including a sequence selected from the group consisting of a fragment of SEQ ID NO: 2, a fragment of SEQ ID NO:22, and combinations thereof;
    wherein SEQ ID NO: 2 and SEQ ID NO: 22 are wild-type sequences;
    wherein the fragment is selected from the group consisting of SEQ ID NO: 4, 6, 8, 10, 12, 14, 16, 18, 20, 24, 26, 28, 30, 32, 34, 36, 38, 40, 42, 44, and 46; and
    wherein the fragment has glucan dikinase activity.

2. The polypeptide of claim 1, wherein the polypeptide is a thermophile.

3. The polypeptide of claim 2, wherein the polypeptide is stable at least at a 3.0 pH to about 8.0 pH.

4. The polypeptide of claim 2, wherein the polypeptide is stable at least at a temperature of about 10° C. to about 75° C.

5. The polypeptide of claim 4, wherein the polypeptide is stable at least at a temperature of about 37° C. to about 75° C.

6. The polypeptide of claim 1, wherein the polypeptide is a non-native Cyanidioschyzon merolae GWD (Cm-GWD) polypeptide.

7. The polypeptide of claim 1, wherein the polypeptide is a non-native Solanum tuberosum GWD (St-GWD) polypeptide.

8. A method for processing starch, comprising:
    providing a fragment of a non-native glucan kinase polypeptide according to claim 1;
    exposing a starch to the glucan kinase polypeptide; and
    collecting the starch that has been exposed to the glucan kinase polypeptide.

9. The method of claim 8, wherein the glucan dikinase kinase polypeptide includes a sequence selected from the group consisting of SEQ ID NO: 2, 4, 6, 8, 10, 12, 14, 16, 18, 20, 24, 26, 28, 30, 32, 34, 36, 38, 40, 42, 44, and 46.

10. The method of claim 8, further comprising, before the collecting step, exposing the starch to a dikinase, an amylase, or both.

11. The method of claim 8, wherein the step of providing the glucan kinase polypeptide includes providing an organism expressing the glucan kinase polypeptide.

12. The method of claim 11, wherein the step of exposing the starch to the glucan kinase polypeptide occurs in the organism.

13. The method of claim 11, wherein the organism is a plant.

\* \* \* \* \*